(12) United States Patent
Cha et al.

(10) Patent No.: US 10,903,431 B2
(45) Date of Patent: Jan. 26, 2021

(54) COMPOUND AND ORGANIC ELECTRONIC DEVICE COMPRISING SAME

(71) Applicant: LG Chem, Ltd., Seoul (KR)

(72) Inventors: Yongbum Cha, Daejeon (KR); Wanpyo Hong, Daejeon (KR)

(73) Assignee: LG Chem, Ltd.

( * ) Notice: Subject to any disclaimer, the term of this patent is extended or adjusted under 35 U.S.C. 154(b) by 328 days.

(21) Appl. No.: 15/760,447

(22) PCT Filed: Sep. 22, 2016

(86) PCT No.: PCT/KR2016/010562
§ 371 (c)(1),
(2) Date: Mar. 15, 2018

(87) PCT Pub. No.: WO2017/052212
PCT Pub. Date: Mar. 30, 2017

(65) Prior Publication Data
US 2018/0277767 A1  Sep. 27, 2018

(30) Foreign Application Priority Data

Sep. 24, 2015  (KR) .................. 10-2015-0135898
Aug. 29, 2016  (KR) .................. 10-2016-0110164

(51) Int. Cl.
*H01L 51/00* (2006.01)
*C07D 401/04* (2006.01)
(Continued)

(52) U.S. Cl.
CPC ........ *H01L 51/0072* (2013.01); *C07D 209/80* (2013.01); *C07D 209/82* (2013.01); *C07D 209/86* (2013.01); *C07D 401/04* (2013.01); *C07D 401/10* (2013.01); *C07D 403/04* (2013.01); *C07D 403/10* (2013.01); *C07D 403/14* (2013.01); *C07D 405/04* (2013.01); *C07D 405/12* (2013.01); *C07D 405/14* (2013.01); *C07D 409/04* (2013.01); *C07D 409/12* (2013.01); *C07D 409/14* (2013.01);
(Continued)

(58) Field of Classification Search
None
See application file for complete search history.

(56) References Cited

U.S. PATENT DOCUMENTS 3,291,771 A     12/1966  Altermatt
2004/0251816 A1  12/2004  Leo et al.
(Continued)

FOREIGN PATENT DOCUMENTS

GB       932533 A      7/1963
JP    2011222831 A    11/2011
(Continued)

OTHER PUBLICATIONS

Extended European Search Report including Written Opinion for Application No. EP16848937.5 dated Jun. 4, 2018.
(Continued)

*Primary Examiner* — Robert S Loewe
(74) *Attorney, Agent, or Firm* — Lerner, David, Littenberg, Krumholz & Mentlik, LLP

(57) ABSTRACT

The present application relates to a compound and an organic electronic device including the same.

20 Claims, 1 Drawing Sheet

(51) Int. Cl.
| | |
|---|---|
| *C09K 11/06* | (2006.01) |
| *C07D 403/04* | (2006.01) |
| *C07D 403/10* | (2006.01) |
| *C07D 405/04* | (2006.01) |
| *C07D 409/04* | (2006.01) |
| *C07D 487/04* | (2006.01) |
| *C07D 209/82* | (2006.01) |
| *H01L 51/50* | (2006.01) |
| *C07D 209/80* | (2006.01) |
| *C07D 209/86* | (2006.01) |
| *C07D 401/10* | (2006.01) |
| *C07D 403/14* | (2006.01) |
| *C07D 405/12* | (2006.01) |
| *C07D 405/14* | (2006.01) |
| *C07D 409/12* | (2006.01) |
| *C07D 409/14* | (2006.01) |
| *C07F 7/08* | (2006.01) |
| *C09K 11/02* | (2006.01) |

(52) U.S. Cl.
CPC .......... *C07D 487/04* (2013.01); *C07F 7/0812* (2013.01); *C09K 11/025* (2013.01); *C09K 11/06* (2013.01); *H01L 51/006* (2013.01); *H01L 51/009* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0073* (2013.01); *H01L 51/0074* (2013.01); *H01L 51/0094* (2013.01); *H01L 51/50* (2013.01); *C09K 2211/1007* (2013.01); *C09K 2211/1011* (2013.01); *C09K 2211/1014* (2013.01); *C09K 2211/188* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *Y02E 10/549* (2013.01)

(56) References Cited

U.S. PATENT DOCUMENTS

| | | |
|---|---|---|
| 2012/0181922 A1 | 7/2012 | Kawamura et al. |
| 2015/0188057 A1 | 7/2015 | Itoi et al. |
| 2015/0255726 A1 | 9/2015 | Kawamura et al. |
| 2018/0269405 A1* | 9/2018 | Mun .................. C07D 403/04 |

FOREIGN PATENT DOCUMENTS

| | | |
|---|---|---|
| JP | 2015128115 A | 7/2015 |
| KR | 20140120090 A | 10/2014 |
| WO | 2003012890 A2 | 2/2003 |
| WO | 03059014 A1 | 7/2003 |
| WO | 2014196580 A1 | 12/2014 |
| WO | 2017052099 A1 | 3/2017 |
| WO | 2017109722 A1 | 6/2017 |

OTHER PUBLICATIONS

Search report from International Application No. PCT/KR2016/010562, dated Jan. 2, 2017.

Hirano, K., et al., "Gold (I)-Catalyzed Polycyclizations of Polyenyne-Type Anilines Based on Hydroamination and Consecutive Hydroarylation Cascade." The Journal of Organic Chemistry, Sep. 27, 2011, vol. 76, pp. 9068-9080.

Thang, D. C., et al., "Carcinogenic Nitrogen Compounds Park LXXXI, Steric Control in Heterocyclic Cyclisations with 6-subsituted Chrysenes." Journal of the Chemical Society, Perkin Transations 1, Received Jan. 27, 1972, pp. 1932-1934.

Chemical Abstract Compounds, STN Express; RN 1337987-52-6 (Entered STN: Oct. 20, 2011); RN 1337987-29-7 (Entered STN: Oct. 20, 2011); RN 42726-29-4 (Entered STN: Nov. 16, 1984); RN 42725-70-2 (Entered STN: Nov. 16, 1984); RN 24369-21-9 (Entered STN: Nov. 16, 1984).

* cited by examiner

[Figure 1]
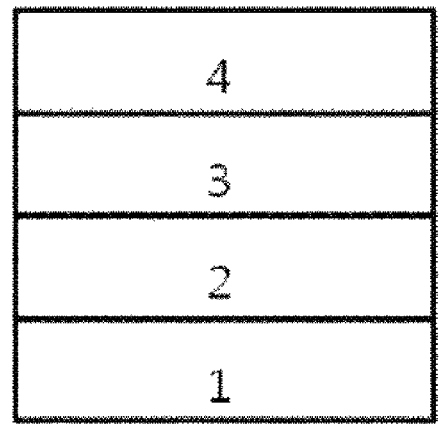
[Figure 2]
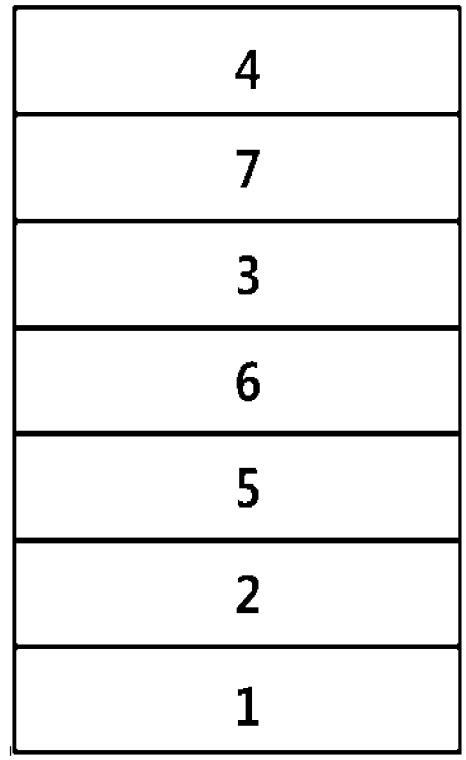

COMPOUND AND ORGANIC ELECTRONIC DEVICE COMPRISING SAME

CROSS-REFERENCE TO RELATED APPLICATIONS

This application is a national phase entry under 35 U.S.C. § 371 of International Application No. PCT/KR2016/010562, which claims priority from Korean Patent Application Nos. 10-2015-0135898 and 10-2016-0110164 filed in the Korean Intellectual Property Office on Sep. 24, 2015 and Aug. 29, 2016, respectively, the entire contents of which are incorporated herein by reference.

TECHNICAL FIELD

The present application relates to a compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon typically has a structure including a positive electrode, a negative electrode, and an organic material layer disposed therebetween. Here, the organic material layer may have a multi-layered structure composed of different materials in order to enhance the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

Such an organic light emitting device has been known to have characteristics such as self-emission, high luminance, high efficiency, a low driving voltage, a wide viewing angle, high contrast, and quick responsiveness.

In an organic light emitting device, materials used as an organic material layer may be classified into a light emitting material and a charge transport material, for example, a hole injection material, a hole transport material, an electron transport material, an electron injection material, and the like depending on the function. Further, the light emitting materials may be divided into blue, green, and red light emitting materials depending on the light emitting color, and into yellow and orange light emitting materials required for implementing a much better natural color. Meanwhile, when only one material is used as the light emitting material, there occur problems in that the maximum light emitting wavelength moves to a long wavelength due to the interaction between molecules, color purity deteriorates, or the efficiency of the device is reduced due to a light emission diminution effect, and accordingly, a host/dopant-based material may be used as the light emitting material in order to increase color purity and increase light emitting efficiency through the energy transfer.

In order for an organic light emitting device to sufficiently exhibit the above-described excellent characteristics, first, materials which form an organic material layer in the device, for example, a hole injection material, a hole transport material, a light emitting material, an electron transport material, an electron injection material, and the like need to be supported by stable and efficient materials, but stable and efficient materials for an organic material layer for an organic light emitting device have not been sufficiently developed up to now. Therefore, there is a continuous need for developing a new material, and the need for developing such materials also applies to the above-described other organic electronic devices.

DETAILED DESCRIPTION OF THE INVENTION

Technical Problem

The present application has been made in an effort to provide a novel compound and an organic electronic device including the same.

Technical Solution

The present application provides a compound represented by the following Chemical Formula 1.

[Chemical Formula 1]

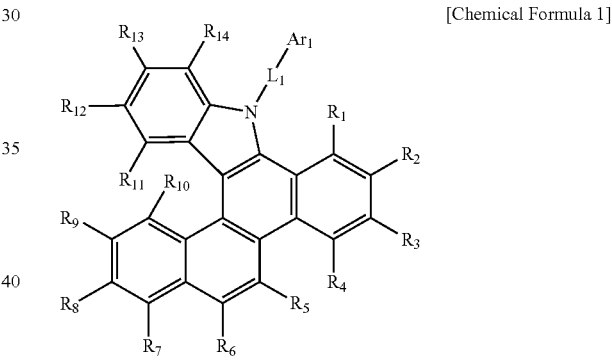

In Chemical Formula 1, $L_1$ is a substituted or unsubstituted arylene group; or a substituted or unsubstituted divalent heterocyclic group, $Ar_1$ is hydrogen; deuterium; a halogen group; a cyano group; a substituted or unsubstituted alkyl group; a substituted or unsubstituted aryl group; a substituted or unsubstituted heterocyclic group; a substituted or unsubstituted amine group; or a substituted or unsubstituted silyl group, $R_1$ to $R_4$ and $R_7$ to $R_{10}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, $R_{11}$ to $R_{14}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring, and $R_5$ and $R_6$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring.

Further, the present application provides an organic electronic device including: a first electrode; a second electrode provided to face the first electrode; and one or more organic material layers provided between the first electrode and the second electrode, in which one or more layers of the organic material layers include the above-described compound.

Advantageous Effects

The compound according to an exemplary embodiment of the present application is used for an organic electronic device including an organic light emitting device, and thus may lower the driving voltage of the organic electronic device and improve the light efficiency, and enhance lifetime characteristics of the device by thermal stability of the compound.

DESCRIPTION OF DRAWINGS

FIG. 1 illustrates an example of an organic light emitting device in which a substrate 1, a positive electrode 2, a light emitting layer 3, and a negative electrode 4 are sequentially stacked.

FIG. 2 illustrates an example of an organic light emitting device in which a substrate 1, a positive electrode 2, a hole injection layer 5, a hole transport layer 6, a light emitting layer 3, an electron transport layer 7, and a negative electrode 4 are sequentially stacked.

1: Substrate
2: Positive electrode
3: Light emitting layer
4: Negative electrode
5: Hole injection layer
6: Hole transport layer
7: Electron transport layer

BEST MODE

Hereinafter, the present specification will be described in more detail.

The present specification provides the compound represented by Chemical Formula 1.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; an alkyl group; a cycloalkyl group; an alkenyl group; an amine group; a phosphoryl group; an aryl group; and a heterocyclic group, being substituted with a substituent to which two or more substituents among the substituents exemplified above are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branch-chained, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the group may be

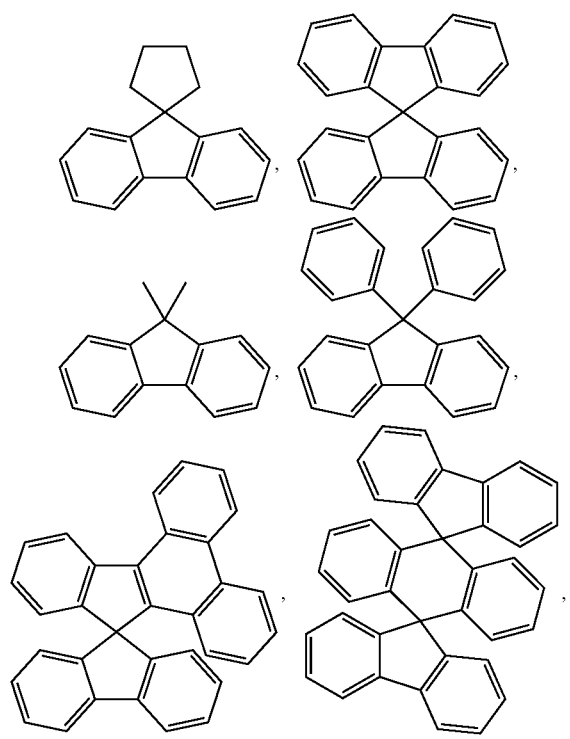

and the like, but is not limited thereto.

In the present specification, a heterocyclic group includes one or more of an atom other than carbon, that is, a heteroatom, and specifically, the heteroatom may include one or more atoms selected from the group consisting of O, N, Se, Si, and S, and the like. The number of carbon atoms of the heterocyclic group is not particularly limited, but is preferably 2 to 60. Examples of the heterocyclic group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

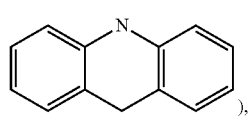 [SMILES: c1ccc2c(c1)Cc1ccccc1N2]), a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group, a benzosilole group, a dibenzosilole group, a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

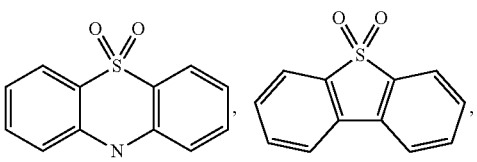

and the like.

In the present specification, the fused structure may be a structure in which an aromatic hydrocarbon ring is fused with the corresponding substituent. Examples of a fused ring of benzimidazole include

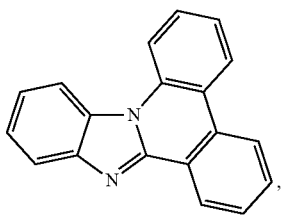

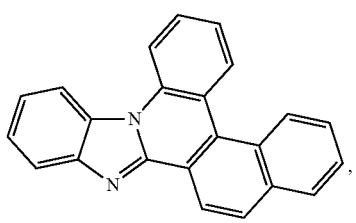

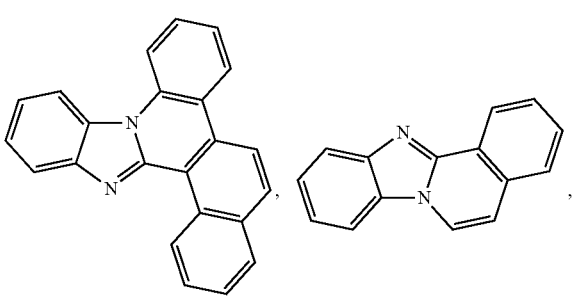

and the like, but are not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

According to an exemplary embodiment of the present application, $R_5$ and $R_6$ may combine with each other to be represented by the following Chemical Formula 2.

[Chemical Formula 2]

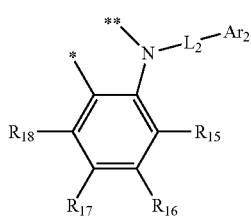

In Chemical Formula 2,

* and ** are a moiety bonded to a position of $R_5$ or $R_6$, $L_2$ is a substituted or unsubstituted arylene group; or a substituted or unsubstituted divalent heterocyclic group, $Ar_2$ is hydrogen; deuterium; a halogen group; a cyano group; a substituted or unsubstituted alkyl group; a substituted or unsubstituted aryl group; a substituted or unsubstituted heterocyclic group; or a substituted or unsubstituted silyl group, and $R_{15}$ to $R_{18}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring.

According to an exemplary embodiment of the present application, in Chemical Formulae 1 and 2, * and ** means a moiety to be bonded, and * and ** are bonded to moieties different from each other.

According to an exemplary embodiment of the present application, when $R_5$ and $R_6$ of Chemical Formula 1 are bonded to * and ** of Chemical Formula 2, $R_5$ and $R_6$ correspond one-to-one to each other, and a position to correspond to each other is not limited. For example, $R_5$ may be bonded to * and R6 may be bonded to , or $R_5$ may be bonded to  and $R_6$ may be bonded to *.

According to an exemplary embodiment of the present application, Chemical Formula 2 may be represented by any one of Chemical Formulae 2-1 to 2-3.

[Chemical Formula 2-1]

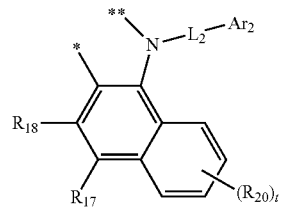

[Chemical Formula 2-2]

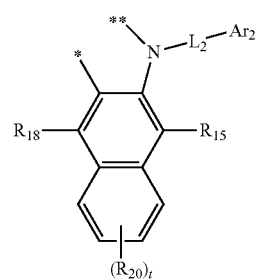

[Chemical Formula 2-3]

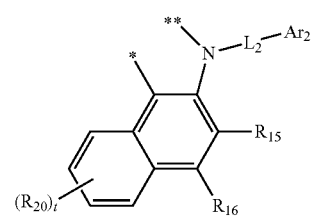

in Chemical Formulae 2-1 to 2-3,

* and ** are a moiety bonded to a position of $R_5$ or $R_6$, $L_2$ and $Ar_2$ are the same as those defined in Chemical Formula 2, $R_{15}$ to $R_{18}$ and $R_{20}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted aryl group; or a substituted or unsubstituted heterocyclic group, and t is an integer of 0 to 4, and when t is an integer of 2 or more, a plurality of $R_{20}$'s is the same as or different from each other.

According to an exemplary embodiment of the present application, Chemical Formula 1 is represented by the following Chemical Formula 3 or 4.

[Chemical Formula 3]

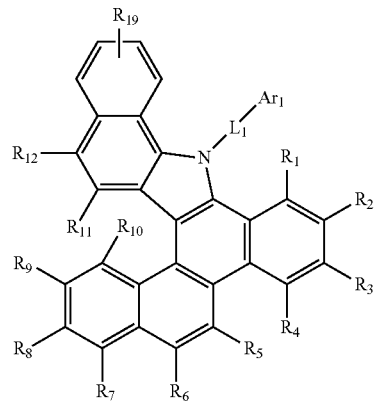

[Chemical Formula 4]

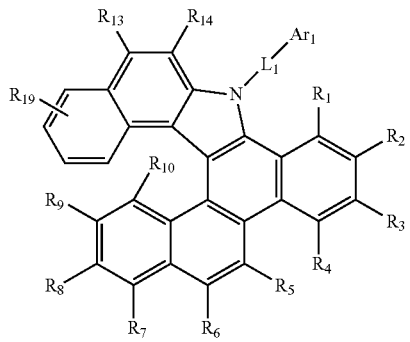

In Chemical Formulae 3 and 4, $L_1$, $Ar_1$, and $R_1$ to $R_{14}$ are the same as those defined in Chemical Formula 1, and $R_{19}$ is the same as the definition of $R_1$ of Chemical Formula 1.

According to an exemplary embodiment of the present application, Chemical Formula 1 is represented by any one of the following Chemical Formulae 1-1, 1-2, 3-1, 3-2, 4-1, and 4-2.

[Chemical Formula 1-1]

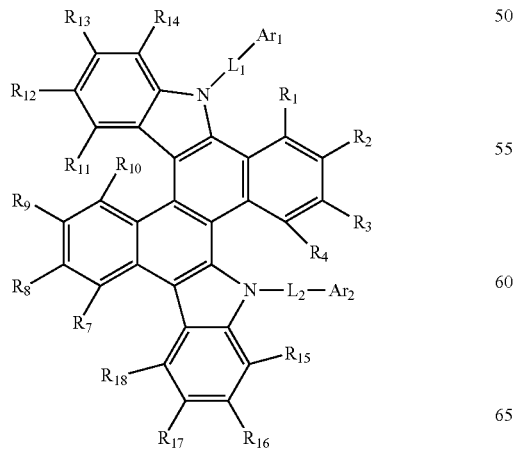

[Chemical Formula 1-2]

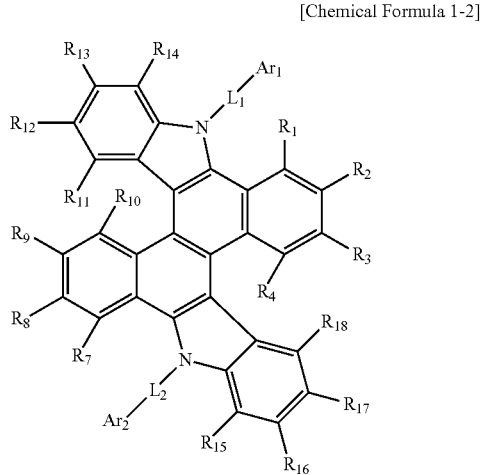

[Chemical Formula 3-1]

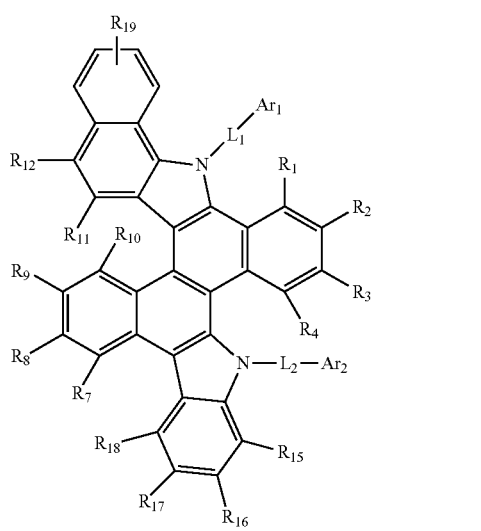

[Chemical Formula 3-2]

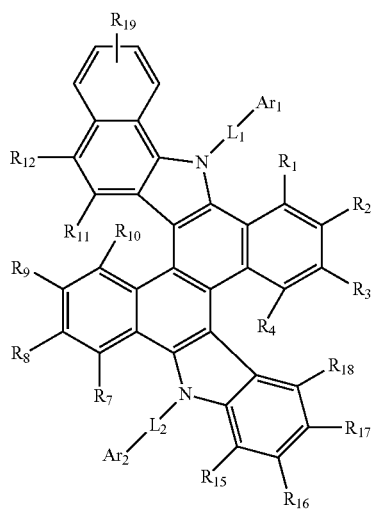

-continued

[Chemical Formula 4-1]

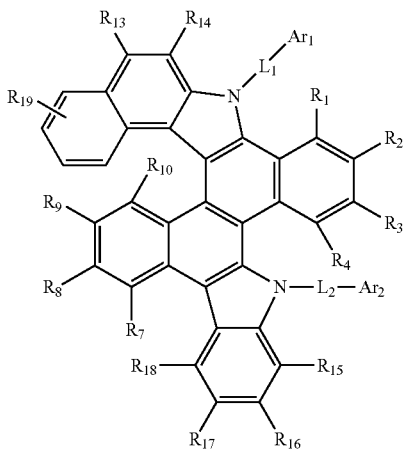

[Chemical Formula 4-2]

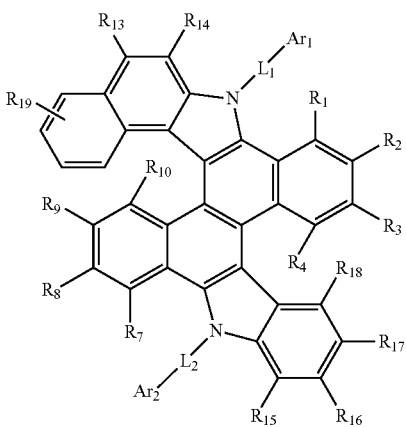

In Chemical Formulae 1-1, 1-2, 3-1, 3-2, 4-1, and 4-2, $L_1$, $L_2$, $Ar_1$, $Ar_2$, $R_1$ to $R_4$, and $R_7$ to $R_{18}$ are the same as those defined in Chemical Formulae 1 and 2, and $R_{19}$ is the same as the definition of $R_1$ of Chemical Formula 1.

According to an exemplary embodiment of the present application, $L_1$ is a substituted or unsubstituted phenylene group; a substituted or unsubstituted divalent biphenyl group; a substituted or unsubstituted naphthylene group; a substituted or unsubstituted pyridylene group; a substituted or unsubstituted pyrimidylene group; or a substituted or unsubstituted triazinylene group.

According to an exemplary embodiment of the present application, $R_6$ is -$L_3$-$Ar_3$, $L_3$ is a direct bond; a substituted or unsubstituted arylene group; or a substituted or unsubstituted divalent heterocyclic group, and $Ar_3$ is hydrogen; deuterium; a halogen group; a cyano group; a substituted or unsubstituted alkyl group; a substituted or unsubstituted aryl group; a substituted or unsubstituted amine group; a substituted or unsubstituted heterocyclic group; or a substituted or unsubstituted silyl group.

According to an exemplary embodiment of the present application, $R_{12}$ is -$L_4$-$Ar_4$, $L_4$ is a direct bond; a substituted or unsubstituted arylene group; or a substituted or unsubstituted divalent heterocyclic group, and $Ar_4$ is hydrogen; deuterium; a halogen group; a cyano group; a substituted or unsubstituted alkyl group; a substituted or unsubstituted aryl group; a substituted or unsubstituted amine group; a substituted or unsubstituted heterocyclic group; or a substituted or unsubstituted silyl group.

According to an exemplary embodiment of the present application, $L_4$ is a direct bond; a phenylene group; a divalent biphenyl group; a pyridylene group; a pyrimidylene group; or a triazinylene group.

According to an exemplary embodiment of the present application, $Ar_4$ is hydrogen; deuterium; a halogen group; a cyano group; a substituted or unsubstituted alkyl group; a substituted or unsubstituted aryl group; a substituted or unsubstituted amine group; a substituted or unsubstituted heterocyclic group; or a substituted or unsubstituted silyl group.

According to an exemplary embodiment of the present application, $Ar_4$ is hydrogen; deuterium; a halogen group; a cyano group; a substituted or unsubstituted alkyl group; or a substituted or unsubstituted aryl group.

According to an exemplary embodiment of the present application, $Ar_4$ is hydrogen; deuterium; a halogen group; a cyano group; a methyl group; a phenyl group; a biphenyl group; or a naphthyl group.

According to an exemplary embodiment of the present application, $Ar_1$ to $Ar_3$ are the same as or different from each other, and are each independently a substituted or unsubstituted $C_6$ to $C_{20}$ aryl group; a substituted or unsubstituted $C_2$ to $C_{20}$ heterocyclic group; or a substituted or unsubstituted amine group.

According to an exemplary embodiment of the present application, in $Ar_1$ to $Ar_3$, the aryl group is a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group.

According to an exemplary embodiment of the present application, in $Ar_1$ to $Ar_3$, the aryl group is a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group, and the substituted or unsubstituted means being unsubstituted or substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group.

According to an exemplary embodiment of the present application, in $Ar_1$ to $Ar_3$, the aryl group is a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group, and the substituted or unsubstituted means being unsubstituted or substituted with at least one selected from the group consisting of deuterium; a halogen group; a methyl group; a t-butyl group; a cyano group; a phenyl group; a biphenyl group; a naphthyl group; an anthracenyl group; a phenanthrenyl group; a pyridyl group; a pyrimidyl group; and a triazinyl group.

According to an exemplary embodiment of the present application, in $Ar_1$ to $Ar_3$, the heterocyclic group is a substituted or unsubstituted pyridyl group; a substituted or unsubstituted pyrimidyl group; a substituted or unsubstituted triazinyl group; a substituted or unsubstituted thiophenyl group; a substituted or unsubstituted furanyl group; a substituted or unsubstituted benzofuranyl group; a substituted or unsubstituted benzothiophenyl group; a substituted or unsubstituted dibenzofuranyl group; a substituted or unsubstituted dibenzothiophenyl group; a substituted or unsubstituted carbazolyl group; a substituted or unsubstituted benzocarbazolyl group; a substituted or unsubstituted dibenzocarbazolyl group; a substituted or unsubstituted dibenzosilole group; a substituted or unsubstituted imidazolyl group; a substituted or unsubstituted benzimidazolyl group; a substituted or unsubstituted dibenzimidazolyl group; a substituted or unsubstituted thiazolyl group; a substituted or unsubstituted benzothiazolyl group; a substituted or unsubstituted oxazolyl group; a substituted or unsubstituted benzoxazolyl group; a substituted or unsubstituted phenanthrolinyl group; a substituted or unsubstituted phenothiazinyl group; a substituted or unsubstituted phenoxazinyl group; or a substituted or unsubstituted quinolinyl group, and the substituted or unsubstituted means being unsubstituted or substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group.

According to an exemplary embodiment of the present application, in $Ar_1$ to $Ar_3$, the heterocyclic group is a substituted or unsubstituted pyridyl group; a substituted or unsubstituted pyrimidyl group; a substituted or unsubstituted triazinyl group; a substituted or unsubstituted thiophenyl group; a substituted or unsubstituted furanyl group; a substituted or unsubstituted benzofuranyl group; a substituted or unsubstituted benzothiophenyl group; a substituted or unsubstituted dibenzofuranyl group; a substituted or unsubstituted dibenzothiophenyl group; a substituted or unsubstituted carbazolyl group; a substituted or unsubstituted benzocarbazolyl group; a substituted or unsubstituted dibenzocarbazolyl group; a substituted or unsubstituted dibenzosilole group; a substituted or unsubstituted imidazolyl group; a substituted or unsubstituted benzimidazolyl group; a substituted or unsubstituted dibenzimidazolyl group; a substituted or unsubstituted thiazolyl group; a substituted or unsubstituted benzothiazolyl group; a substituted or unsubstituted oxazolyl group; a substituted or unsubstituted benzoxazolyl group; a substituted or unsubstituted phenanthrolinyl group; a substituted or unsubstituted phenothiazinyl group; a substituted or unsubstituted phenoxazinyl group; or a substituted or unsubstituted quinolinyl group, and the substituted or unsubstituted means being unsubstituted or substituted with at least one selected from the group consisting of deuterium; a halogen group; a methyl group; a t-butyl group; a cyano group; a phenyl group; a biphenyl group; a naphthyl group; an anthracenyl group; a phenanthrenyl group; a pyridyl group; a pyrimidyl group; and a triazinyl group.

According to an exemplary embodiment of the present application, the amine group is represented by —NR'R", and R' and R" are the same as or different from each other, and may be each independently a substituted or unsubstituted $C_1$ to $C_{60}$ alkyl group; a substituted or unsubstituted $C_6$ to $C_{60}$ cycloalkyl group; a substituted or unsubstituted $C_6$ to $C_{60}$ aryl group; or a substituted or unsubstituted $C_2$ to $C_{60}$ heterocyclic group.

According to an exemplary embodiment of the present application, R' and R" are a substituted or unsubstituted $C_6$ to $C_{60}$ aryl group, and R' and R" may be the same as or different from each other.

According to an exemplary embodiment of the present application, R' and R" are a $C_6$ to $C_{60}$ aryl group which is unsubstituted or substituted with a $C_1$ to $C_{60}$ alkyl group, and R' and R" may be the same as or different from each other.

According to an exemplary embodiment of the present application, R' and R" are the same as or different from each other, and may be each independently a phenyl group, a biphenyl group, a naphthyl group, a terphenyl group, a fluorenyl group, or a dimethylfluorenyl group.

According to an exemplary embodiment of the present application, $R_1$ to $R_4$ and $R_7$ to $R_{10}$ are the same as or different from each other, and are each independently hydrogen; deuterium; a halogen group; a $C_1$ to $C_{10}$ alkyl group; or $C_6$ to $C_{20}$ aryl group.

According to an exemplary embodiment of the present application, $R_1$ to $R_4$ and $R_7$ to $R_{10}$ are the same as or different from each other, and are each independently hydrogen; deuterium; a halogen group; a methyl group; or a phenyl group.

According to an exemplary embodiment of the present application, $R_1$ to $R_4$ and $R_7$ to $R_{10}$ are hydrogen.

According to an exemplary embodiment of the present application, the compound represented by Chemical Formula 1 is any one selected from the structural formulae of the following Group 1.

[Group 1]

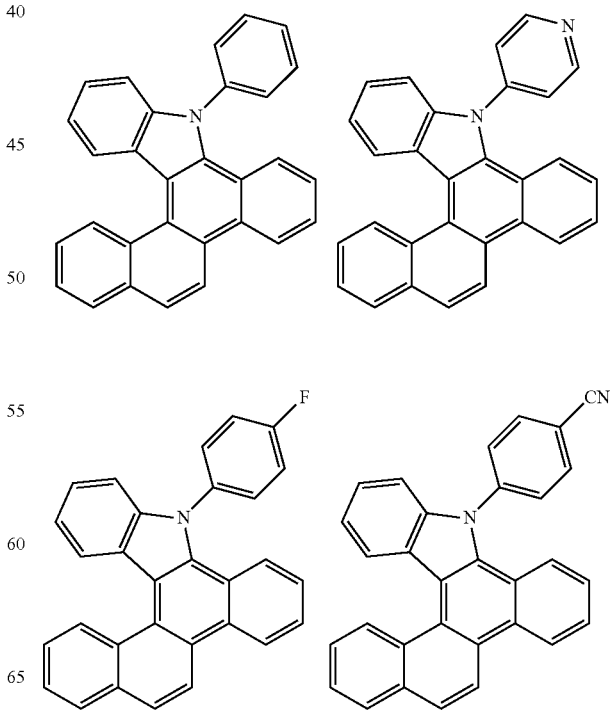

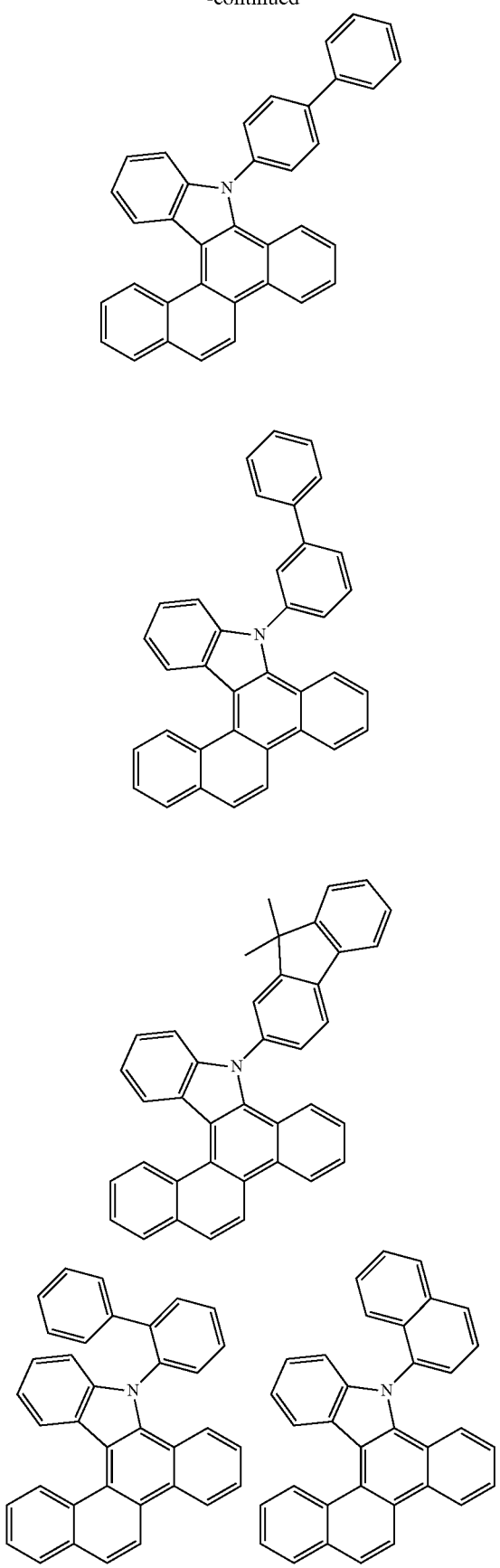

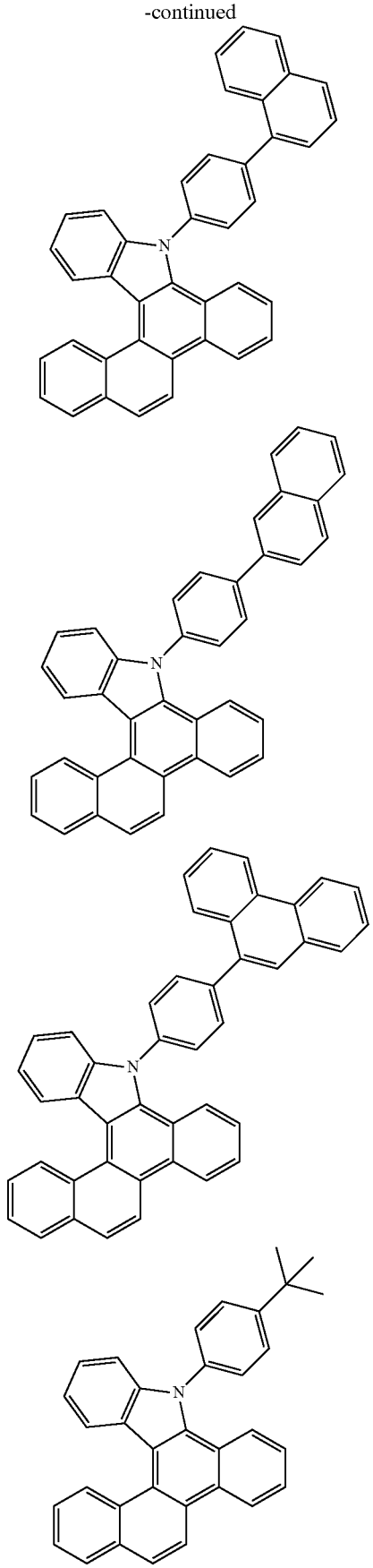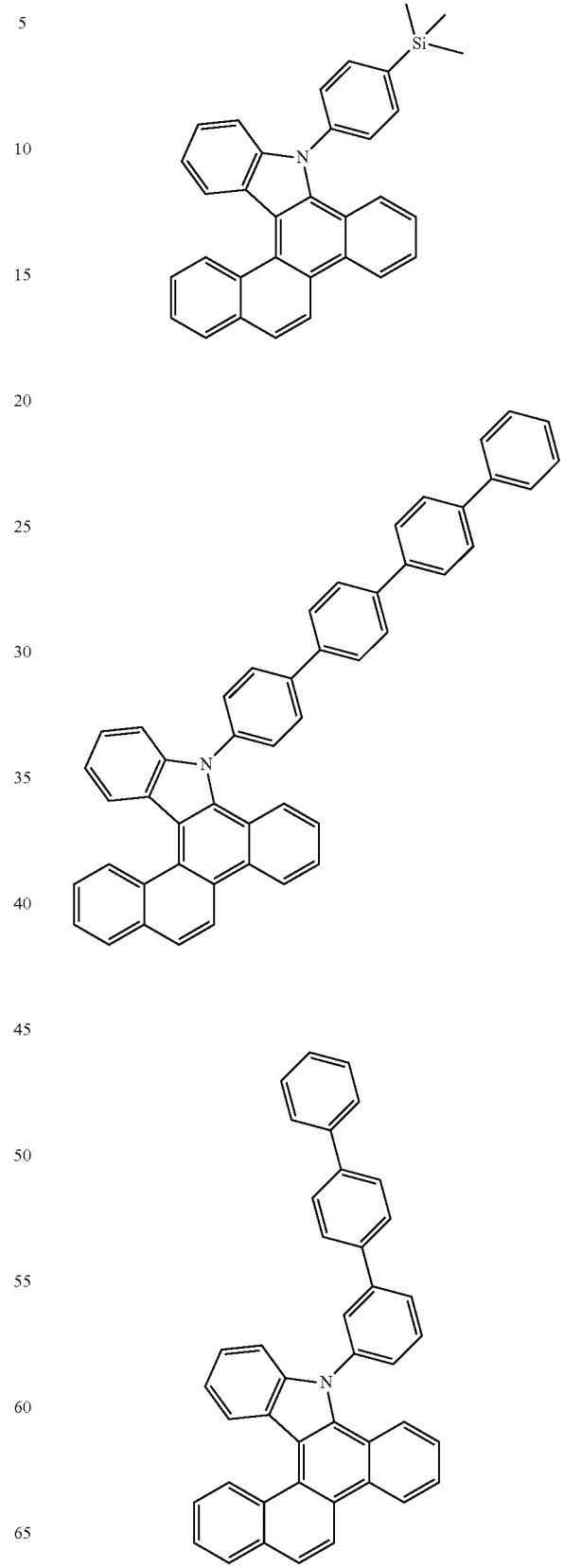

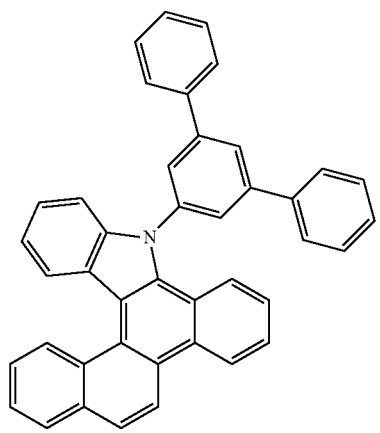
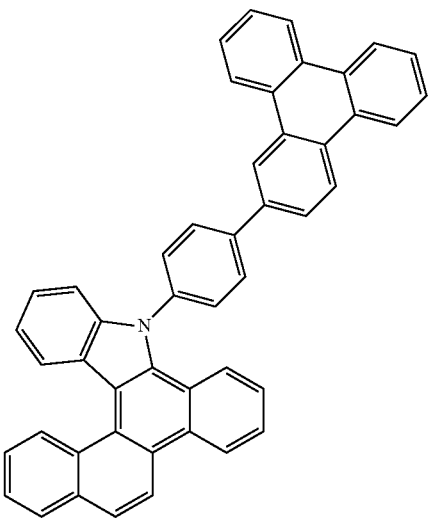
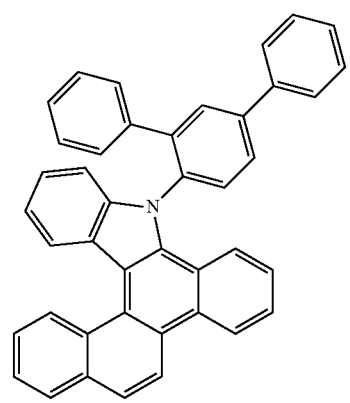
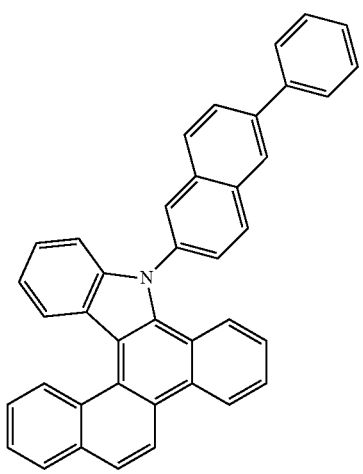
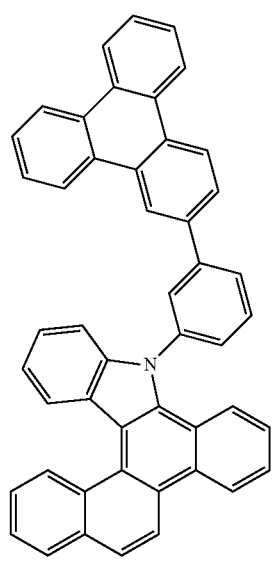
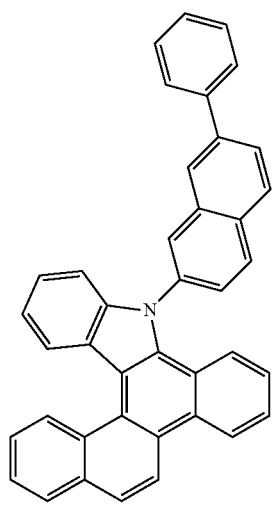

21
-continued
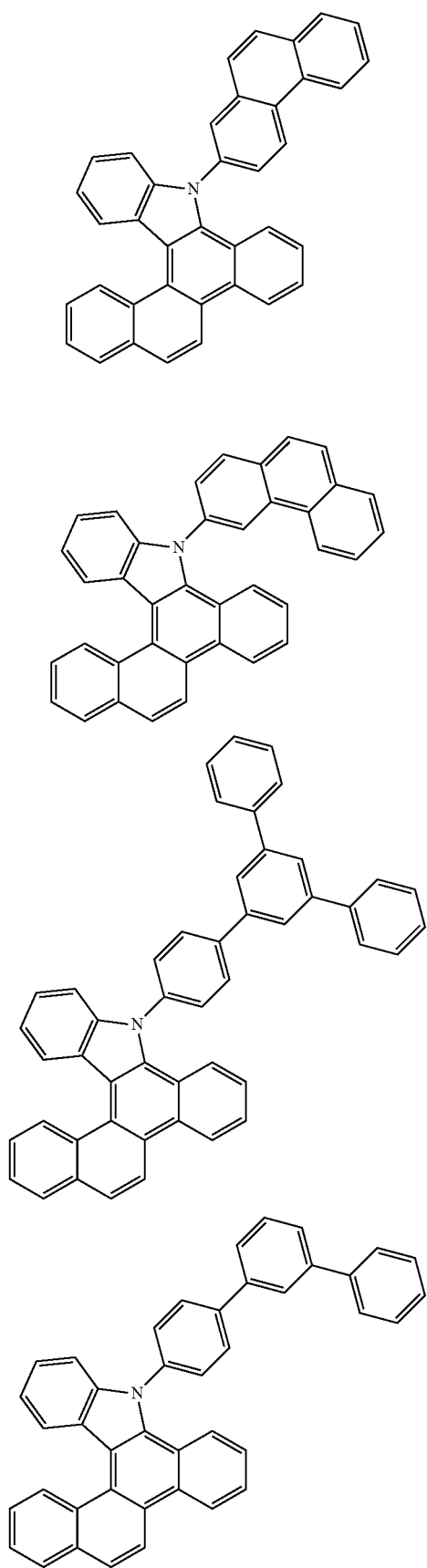
22
-continued
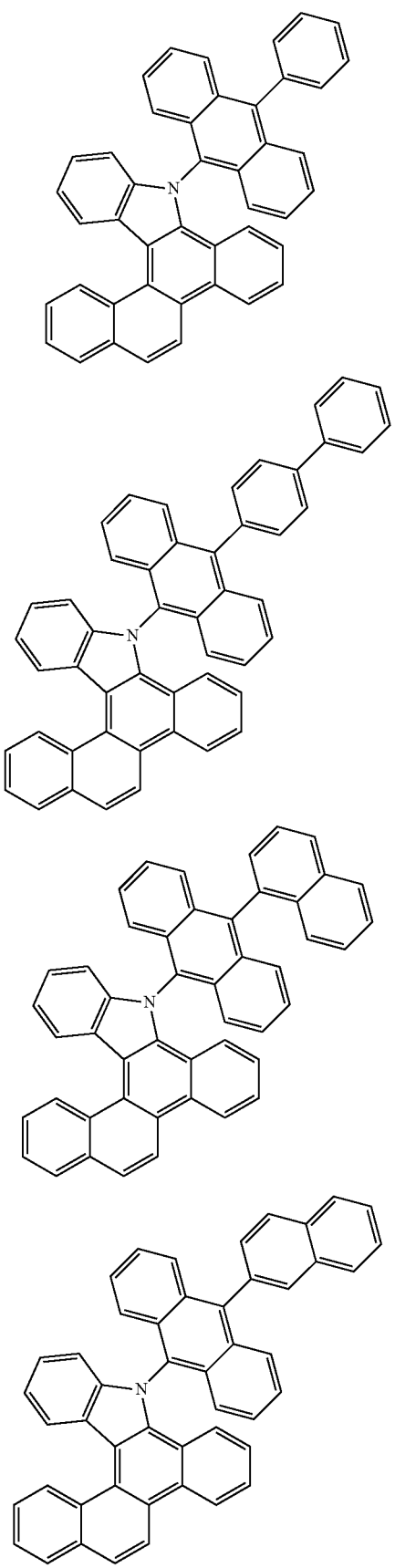

-continued
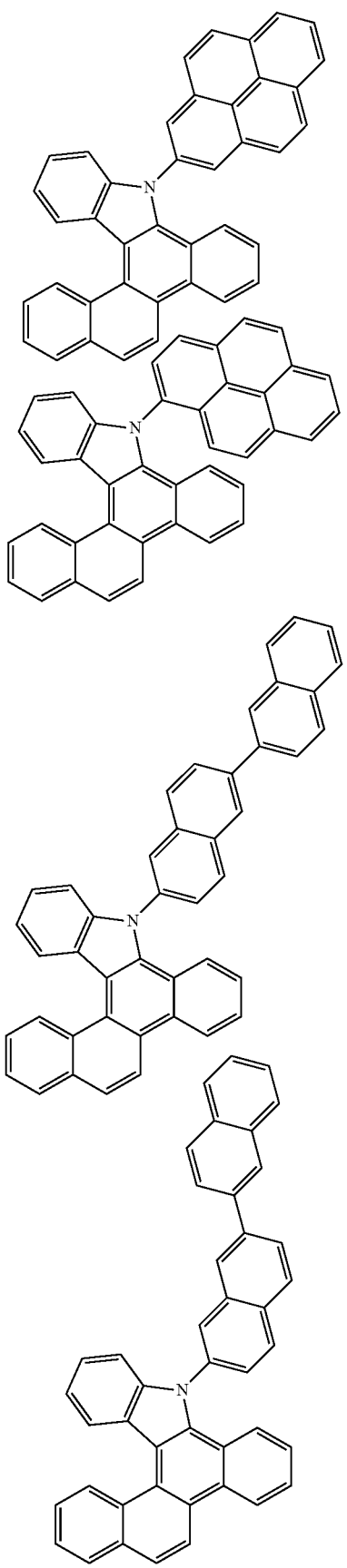
-continued
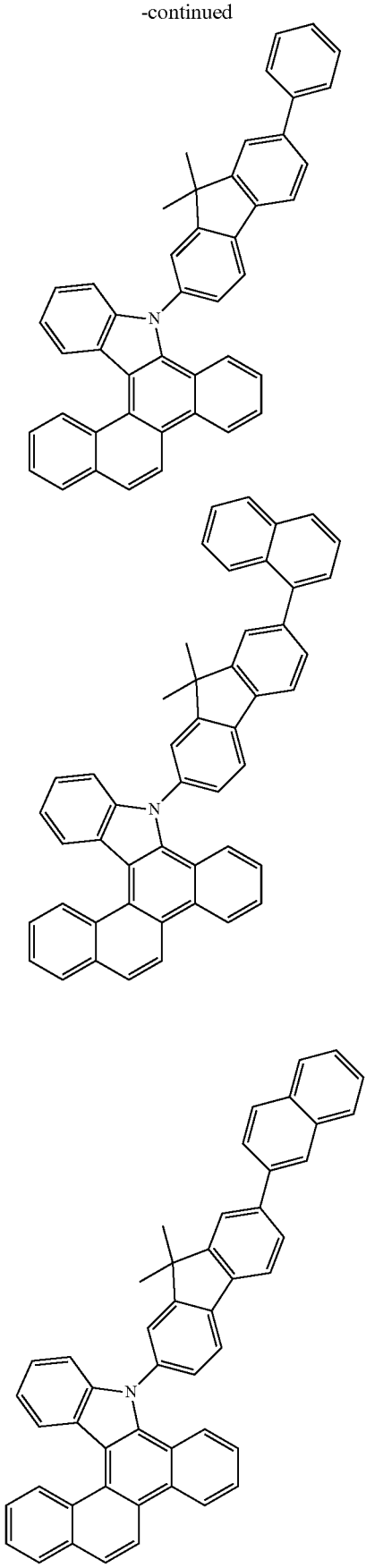

25
-continued
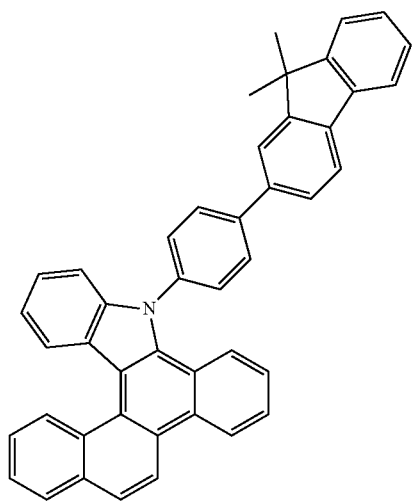
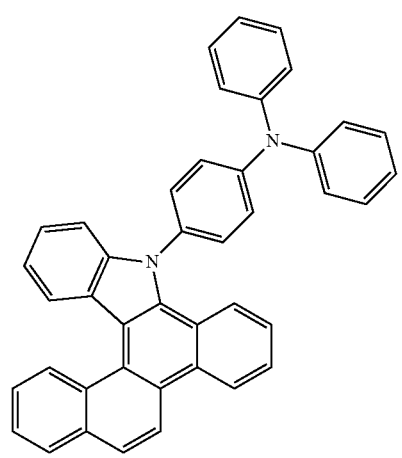
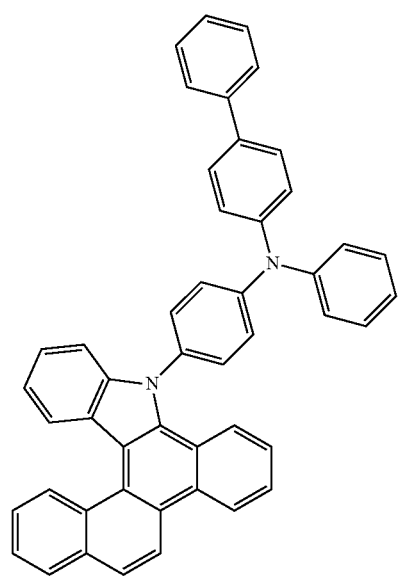
26
-continued
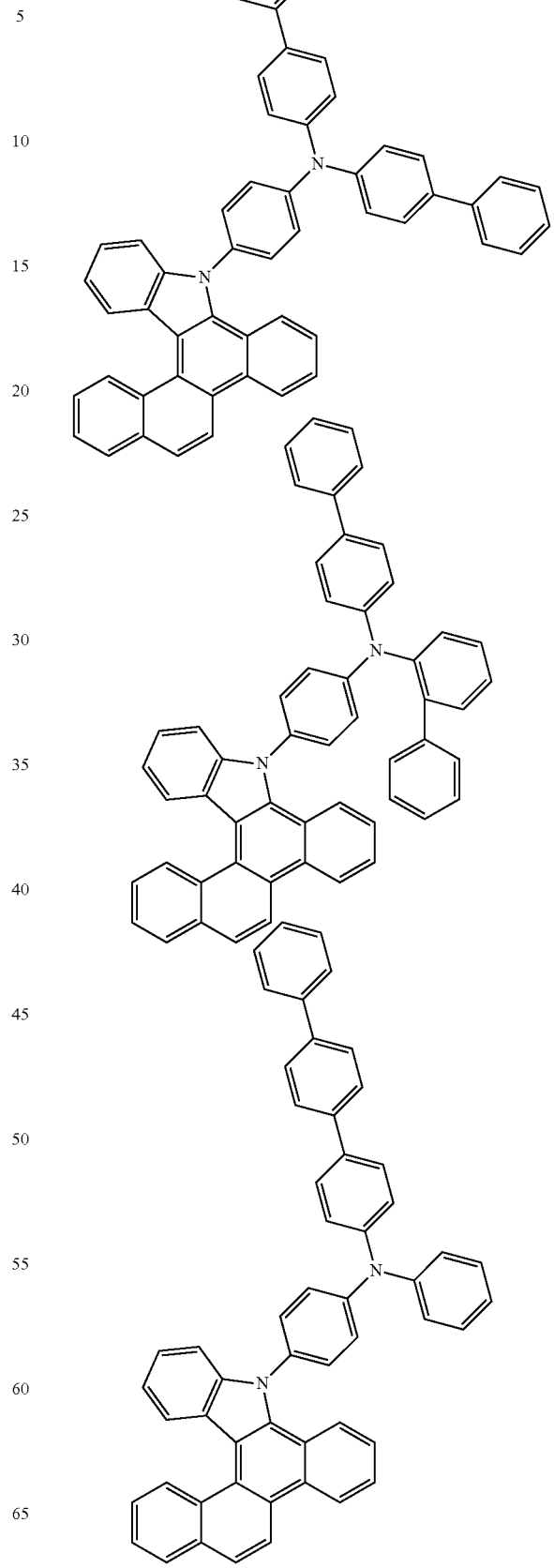

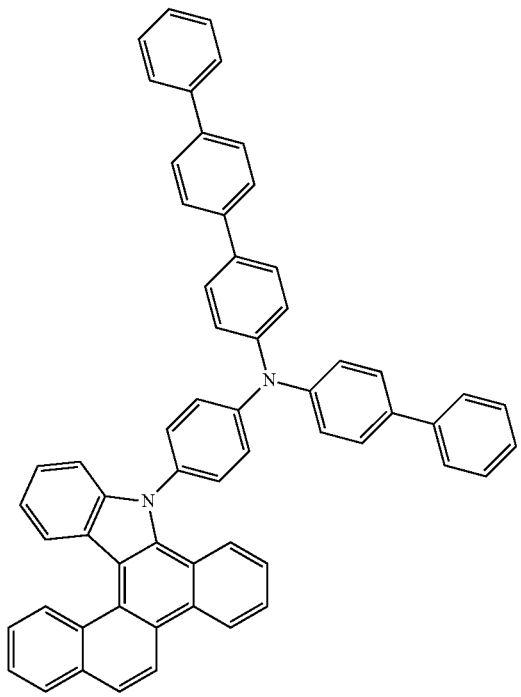
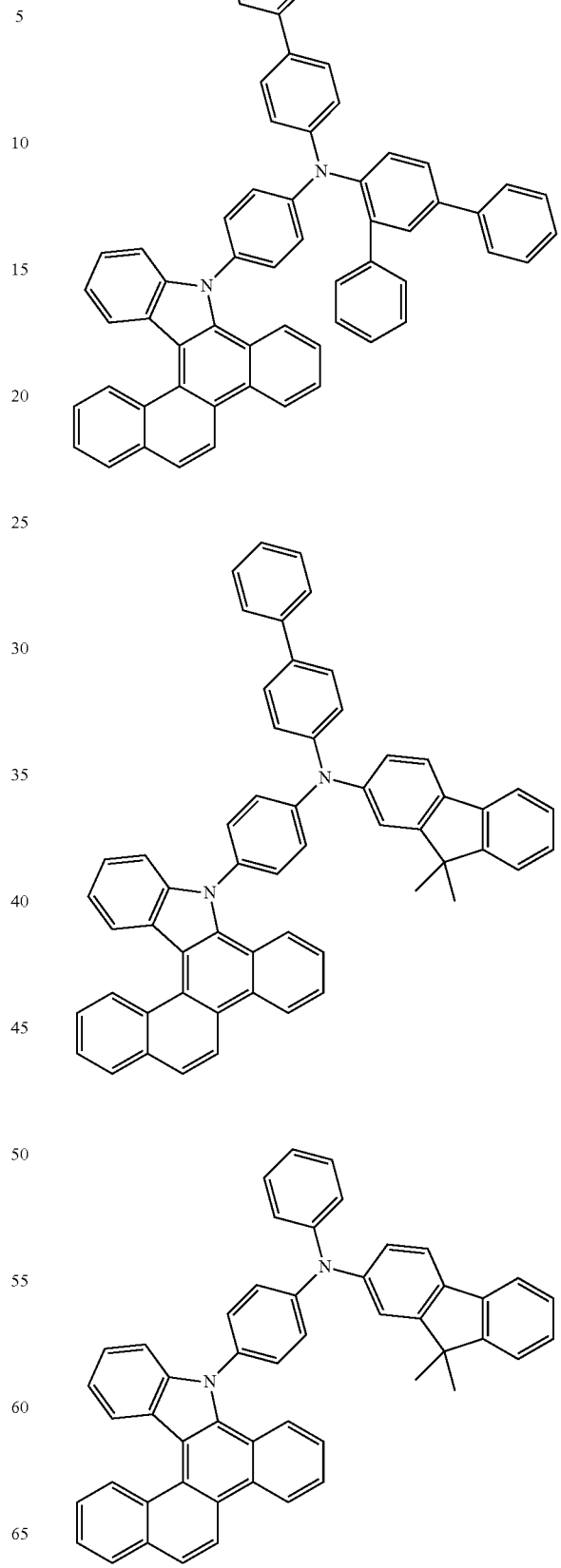

-continued
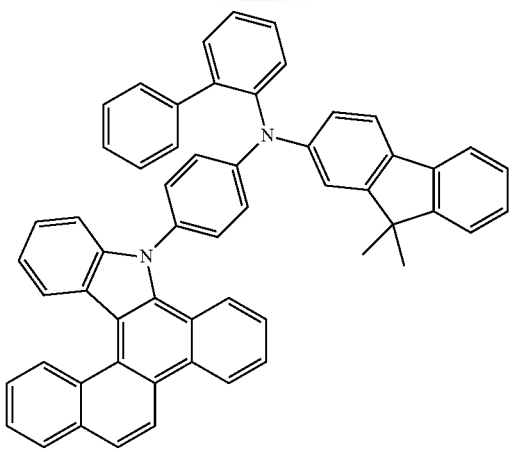
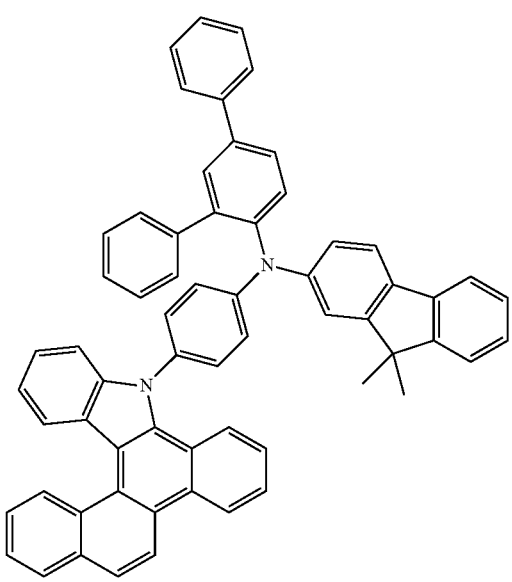
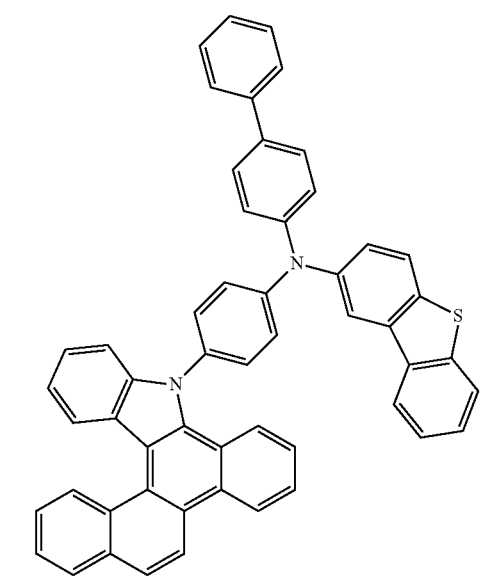
-continued
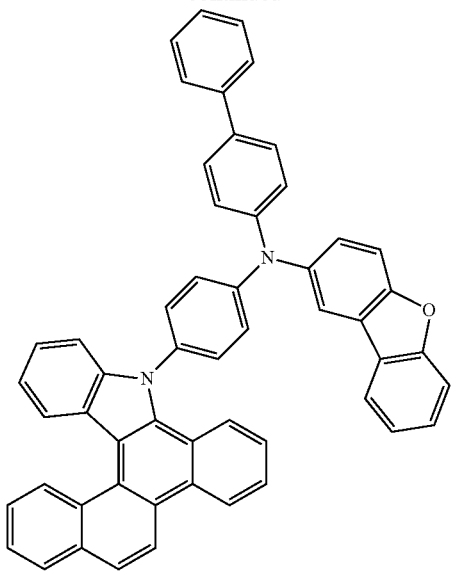
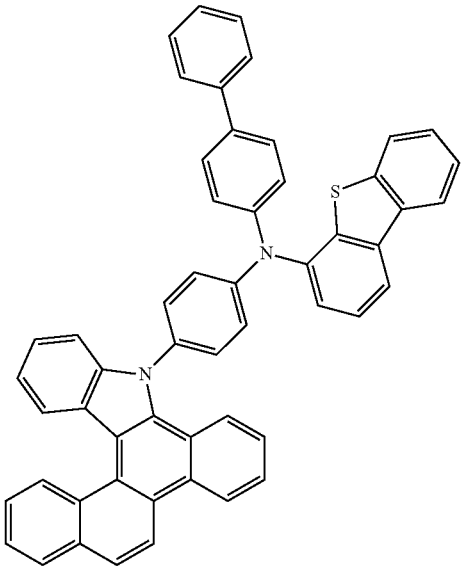
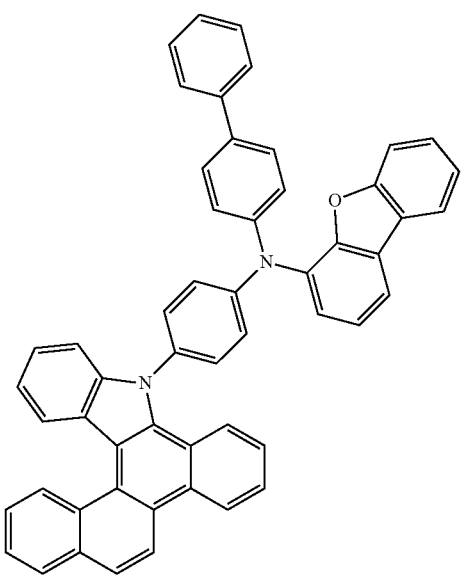

31
-continued
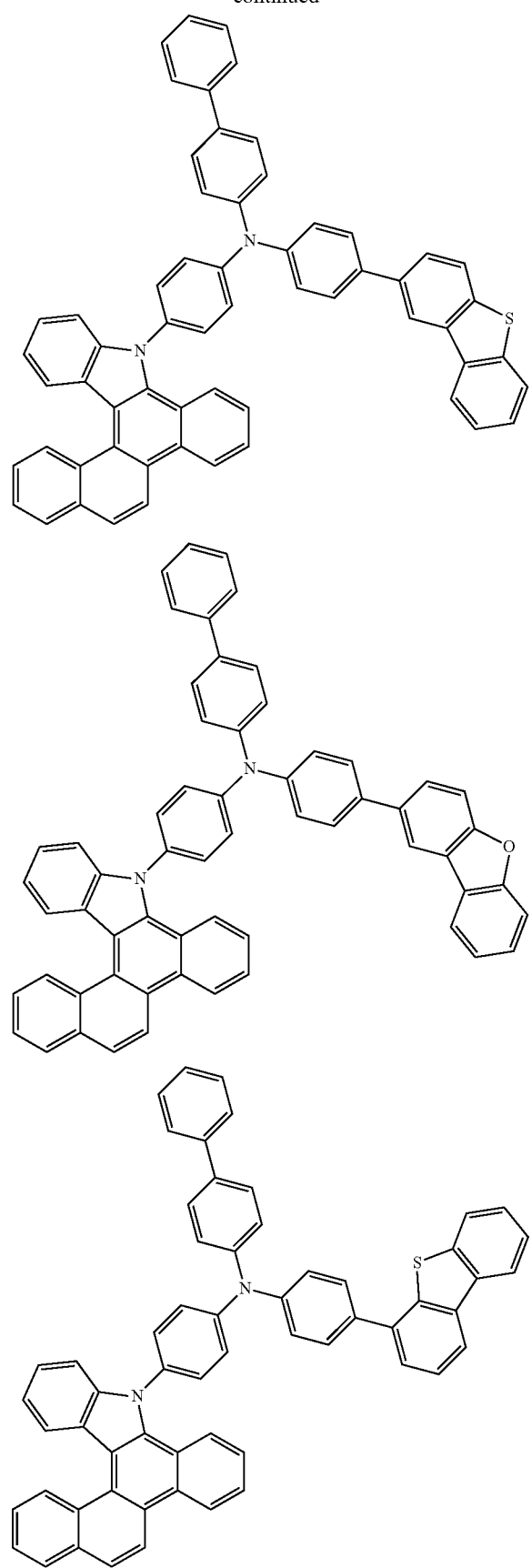
32
-continued
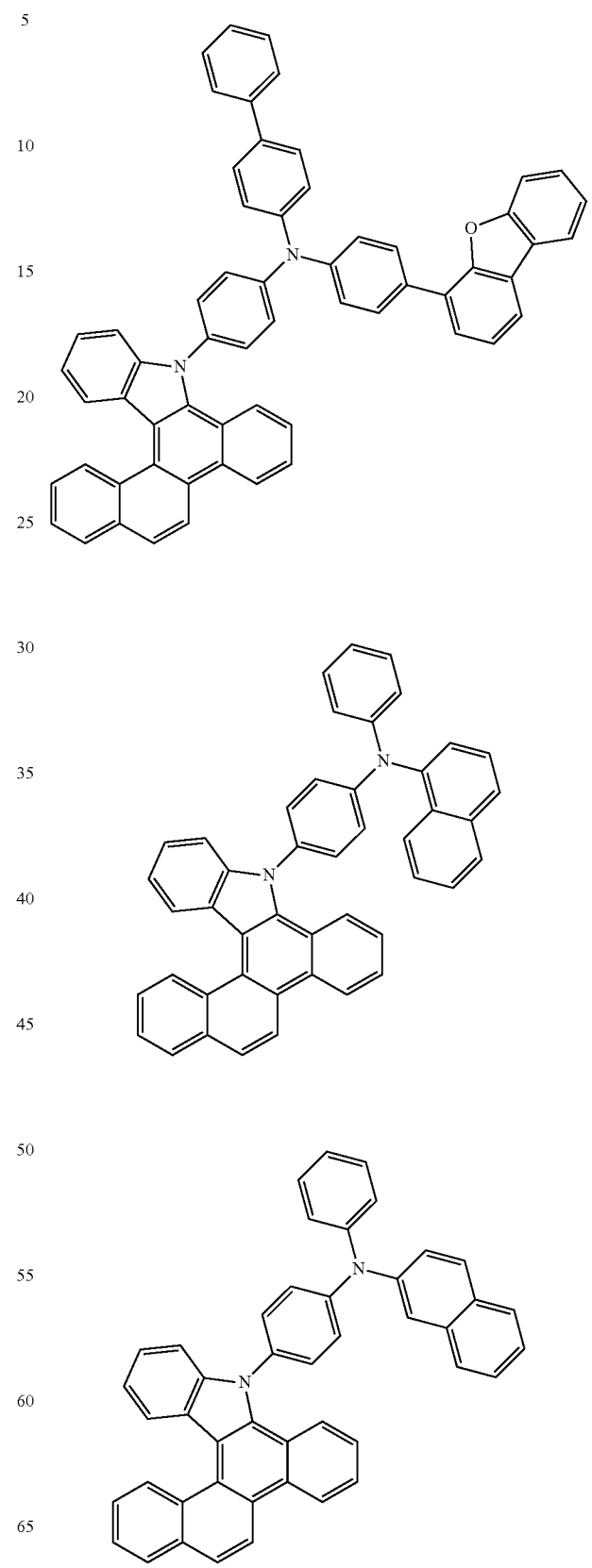

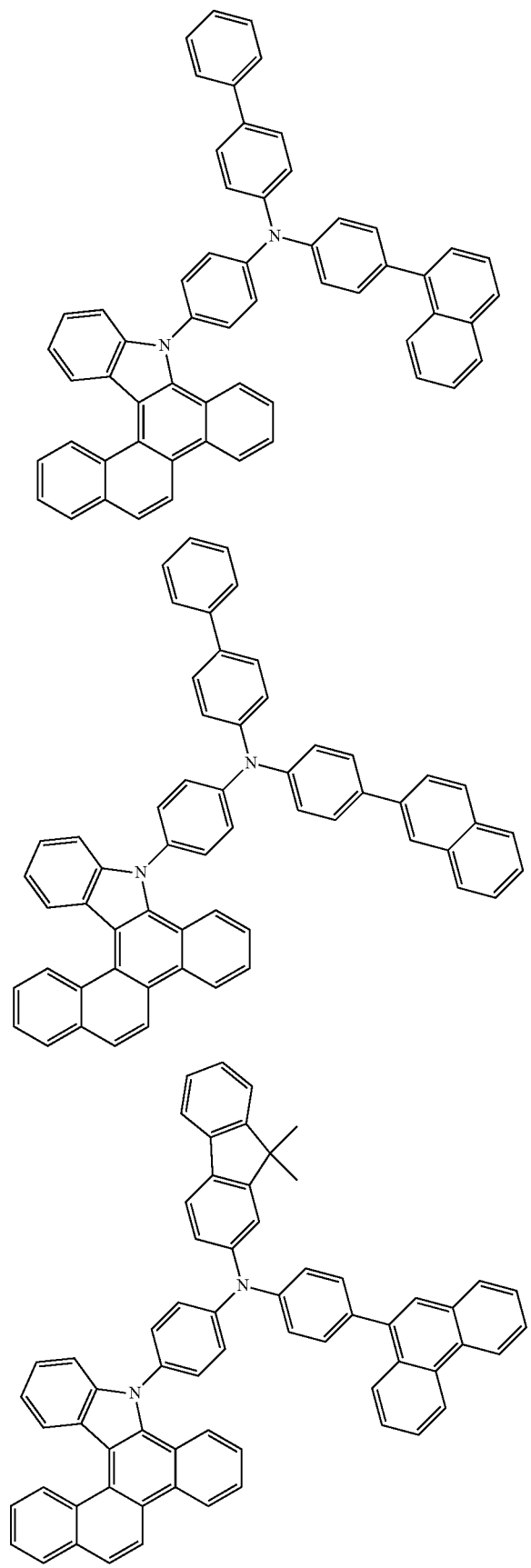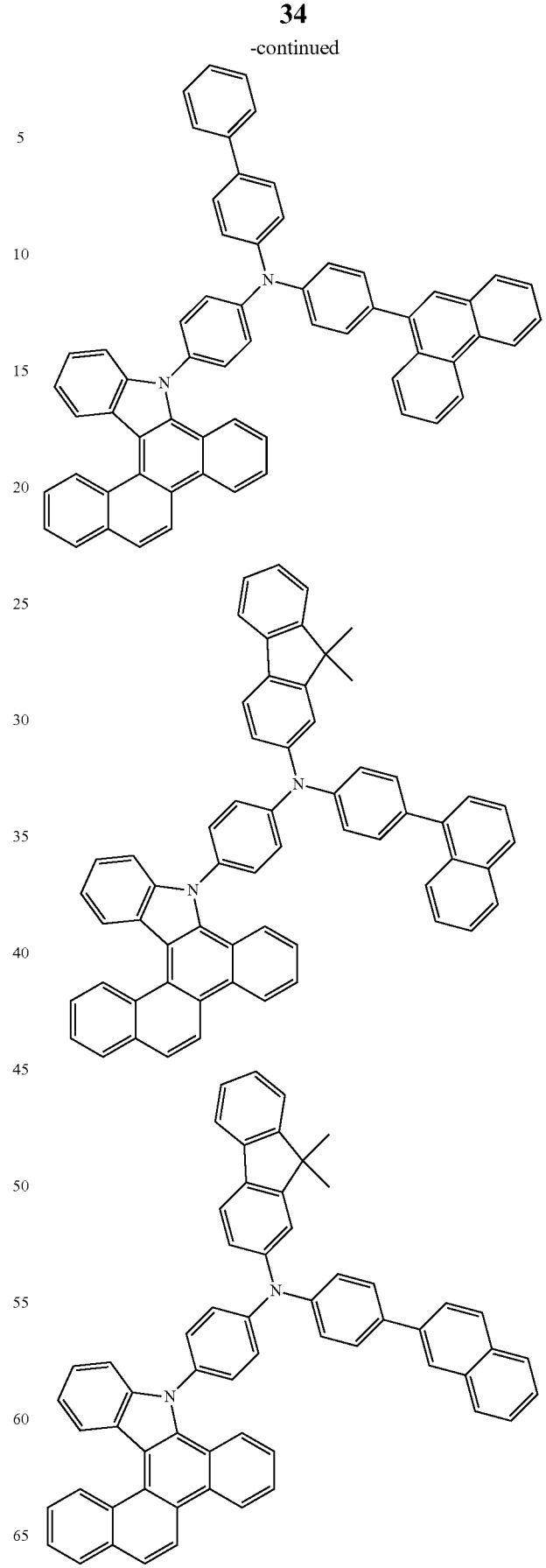

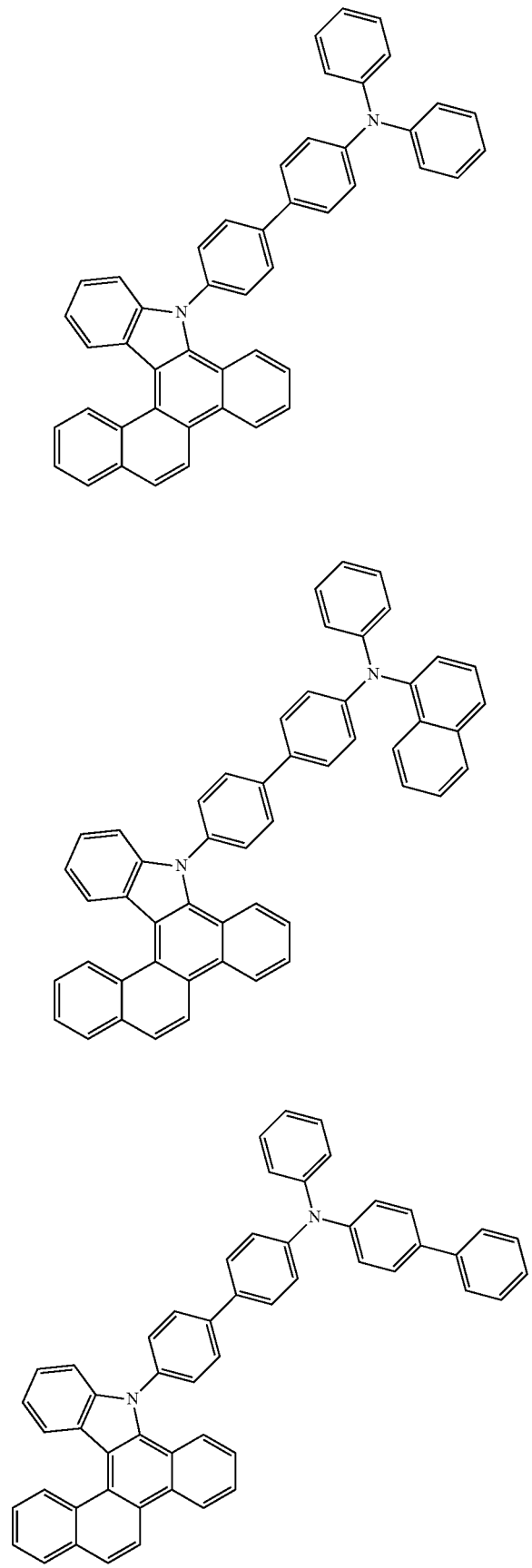
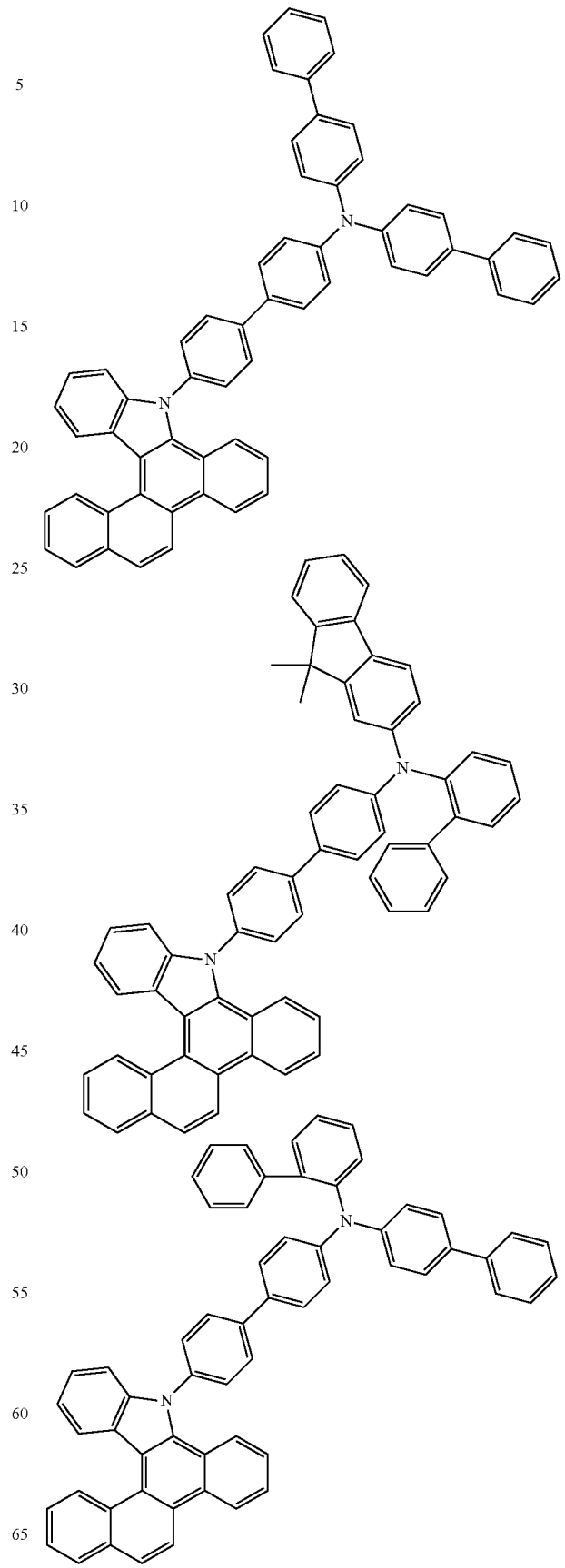

37
-continued
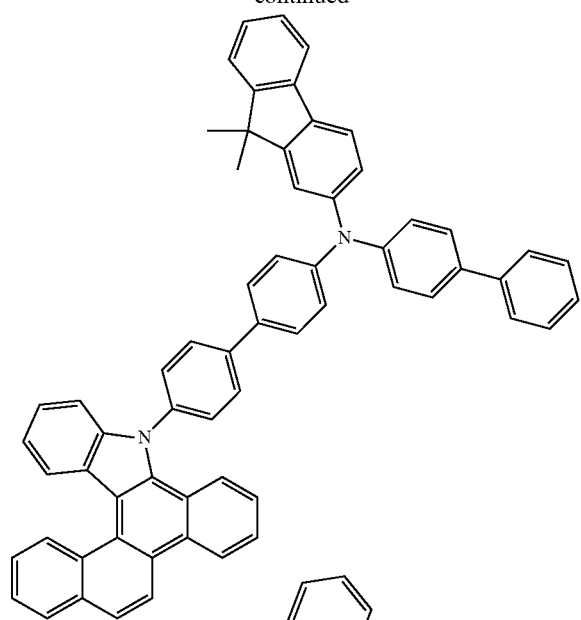
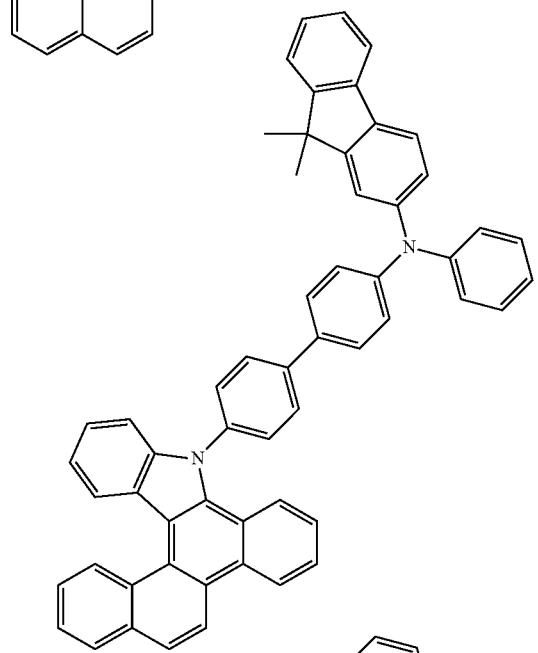
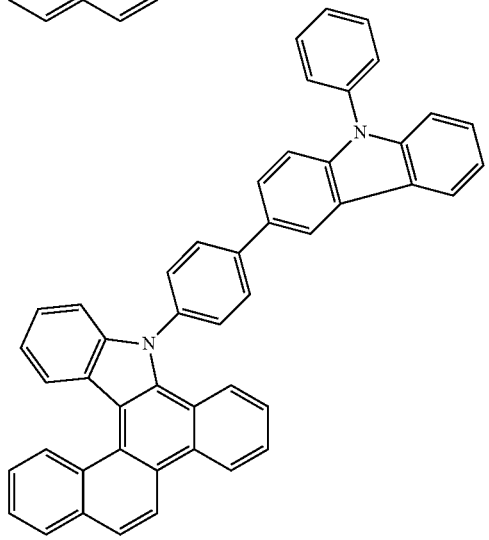
38
-continued
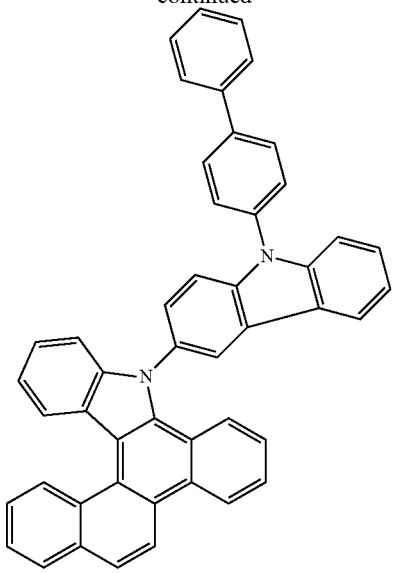
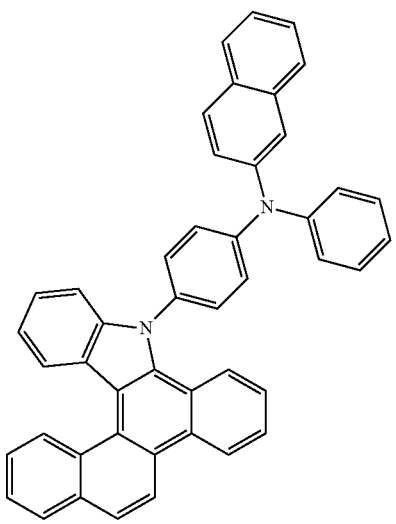
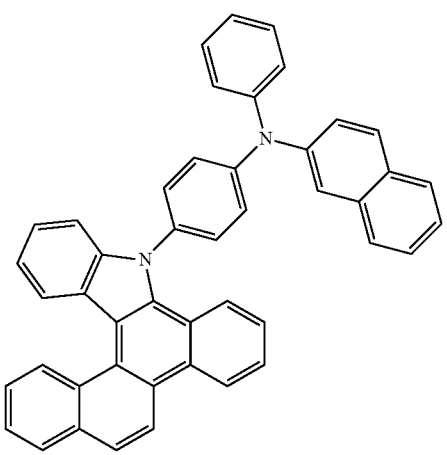

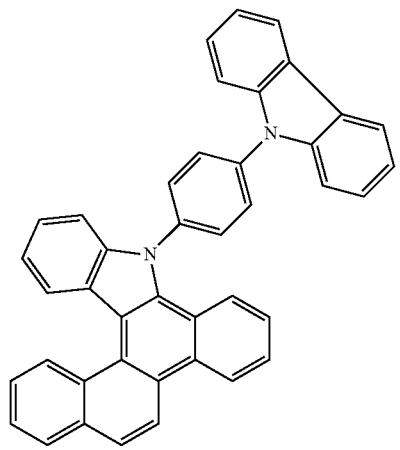
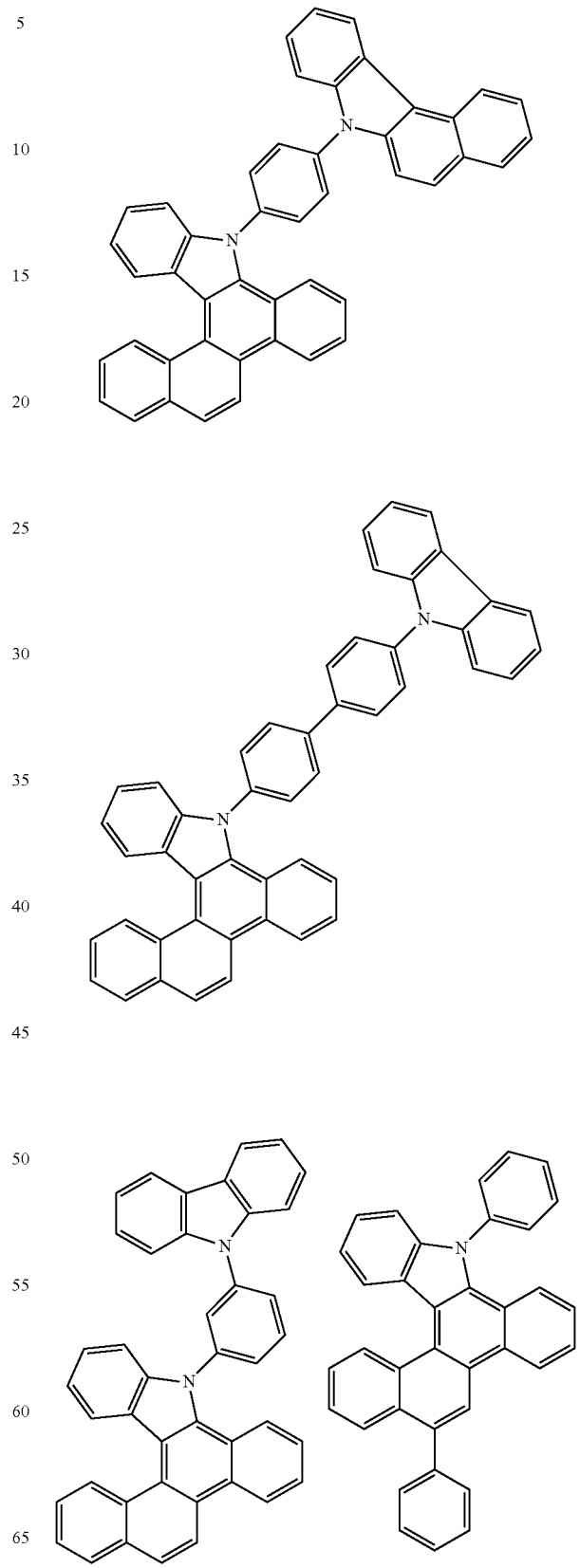

41
-continued
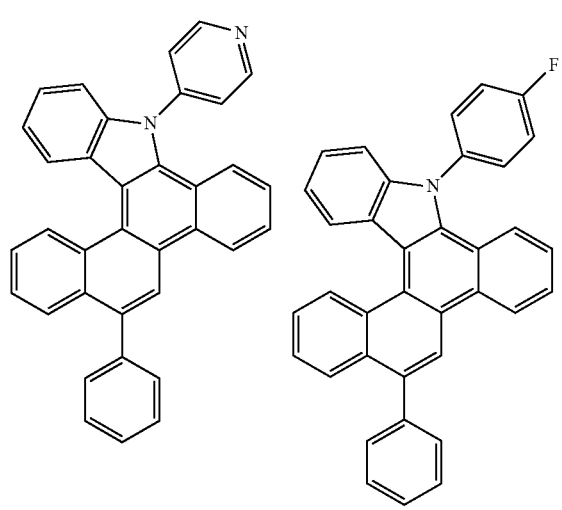
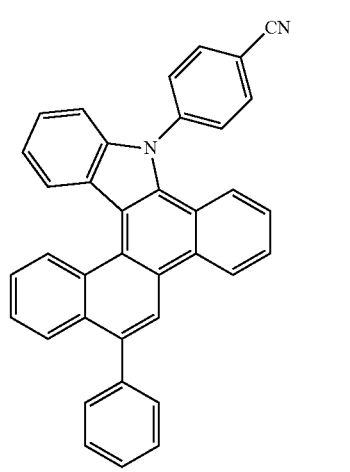
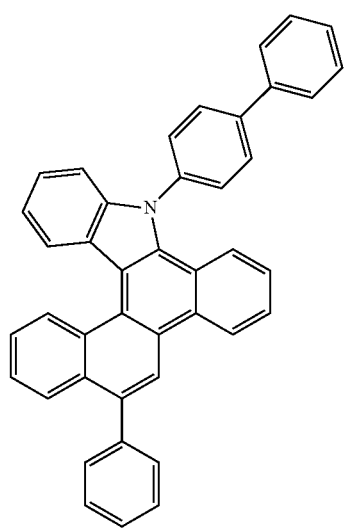
42
-continued
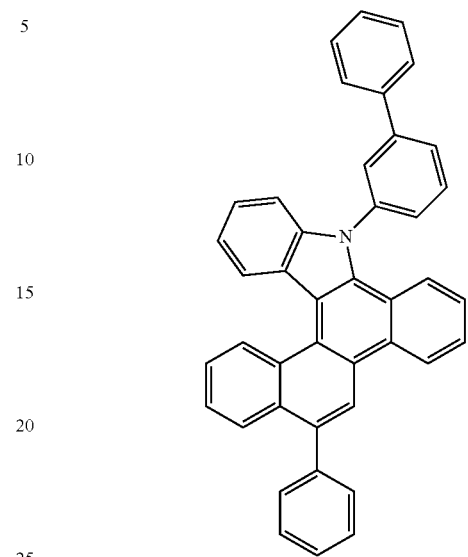
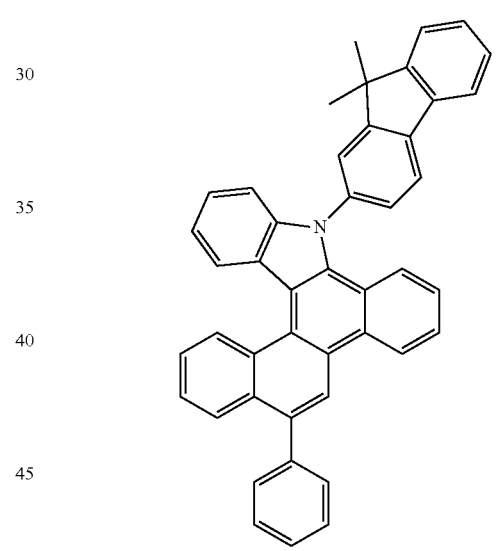
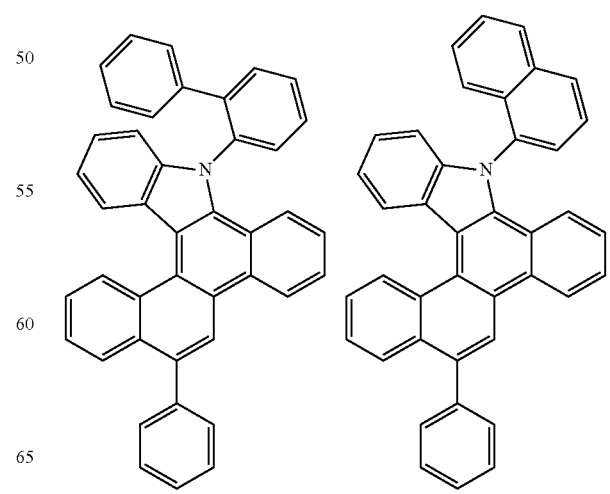

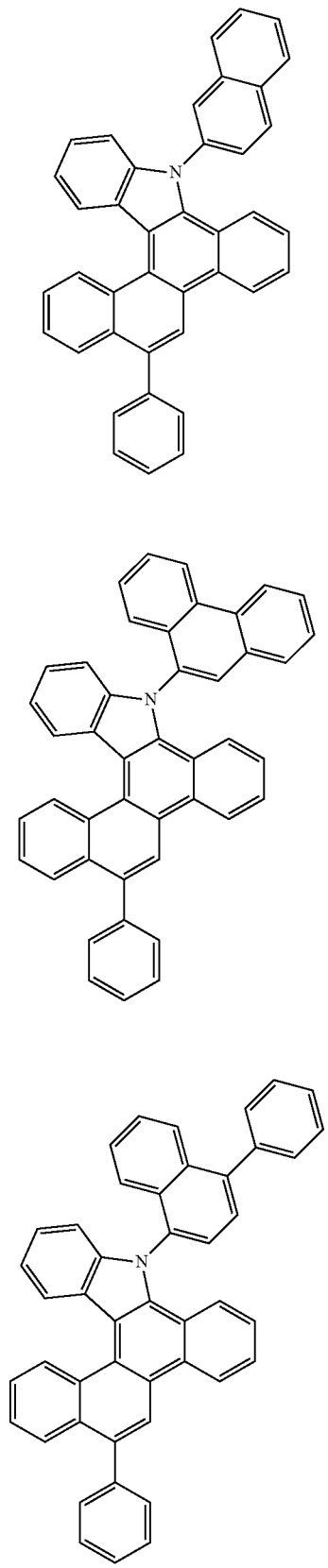
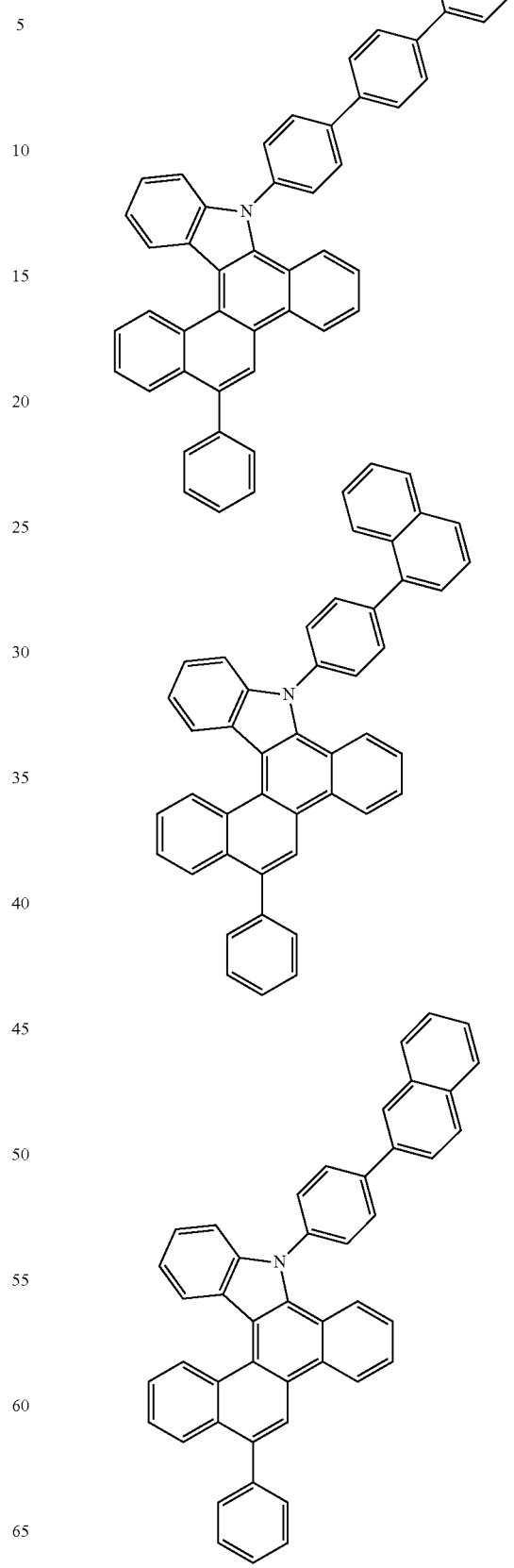

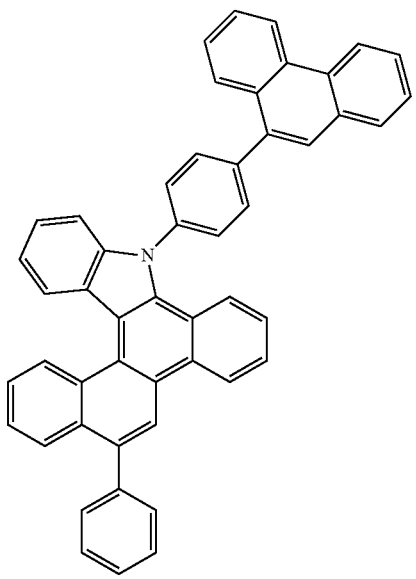

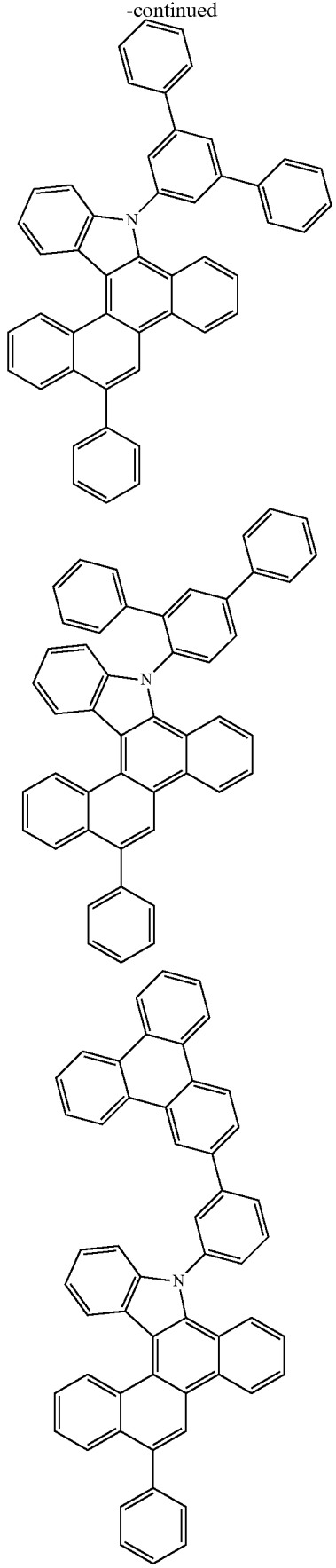
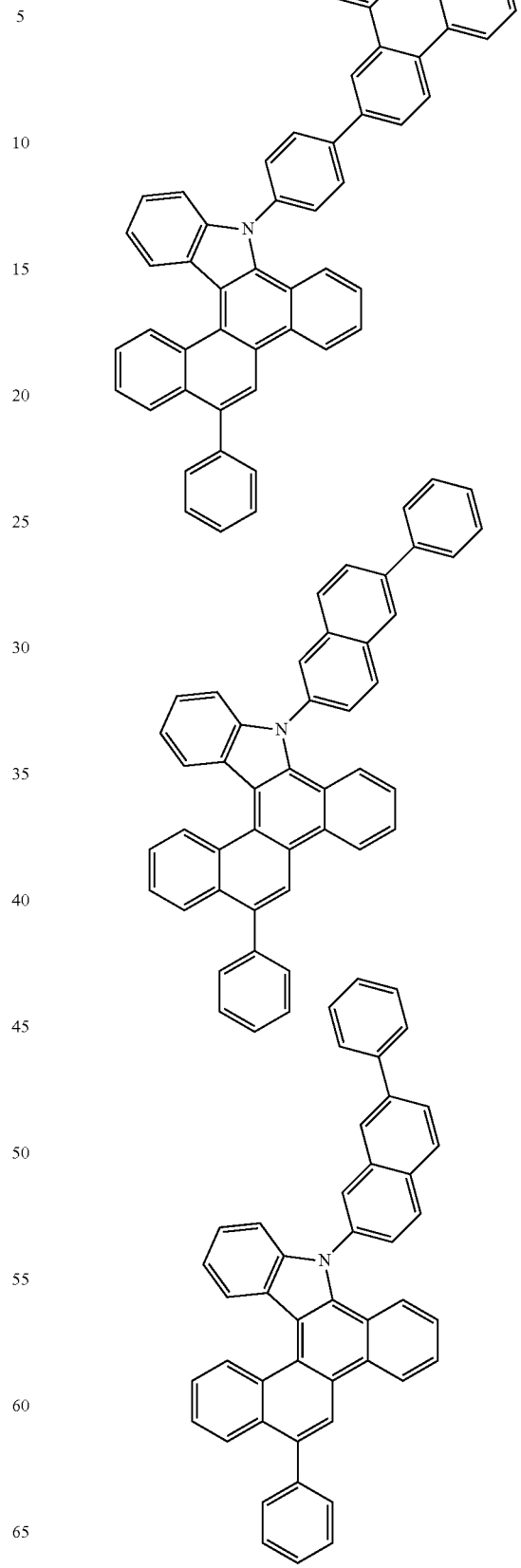

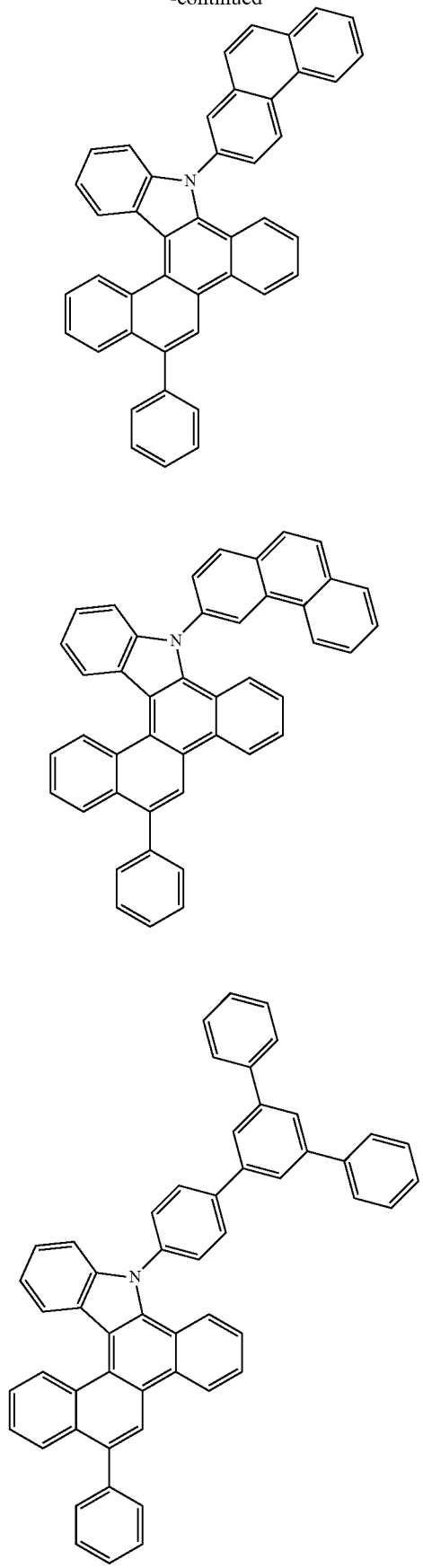
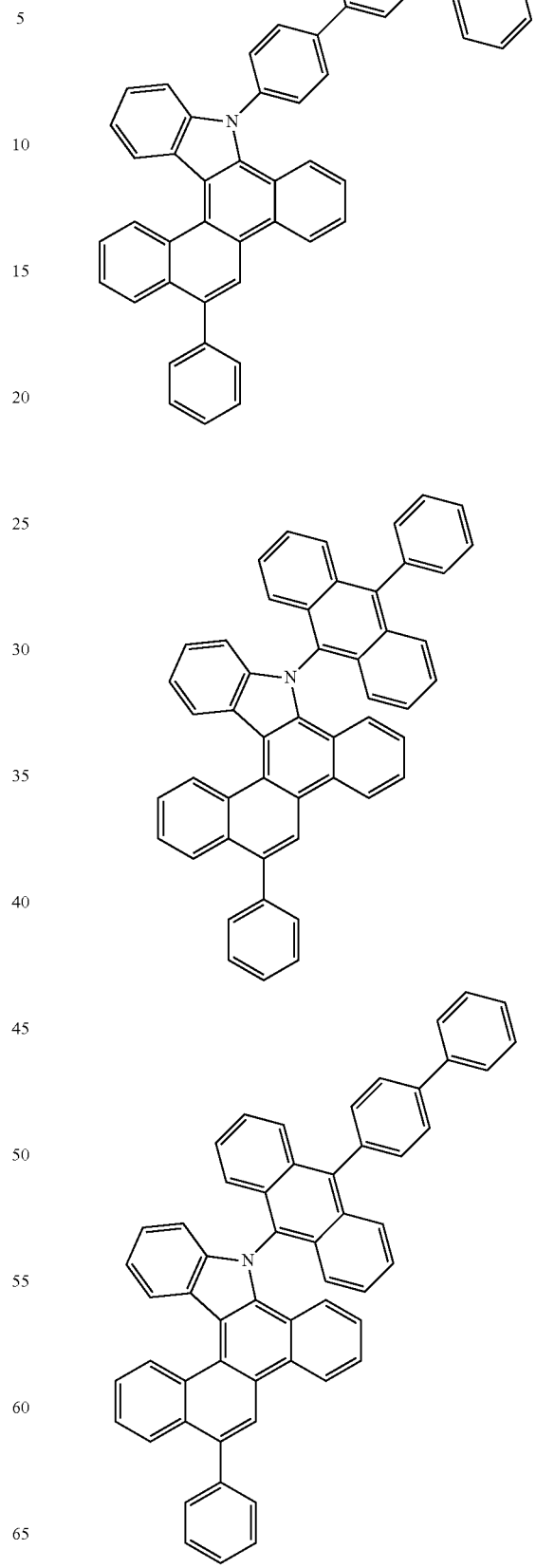

51
-continued
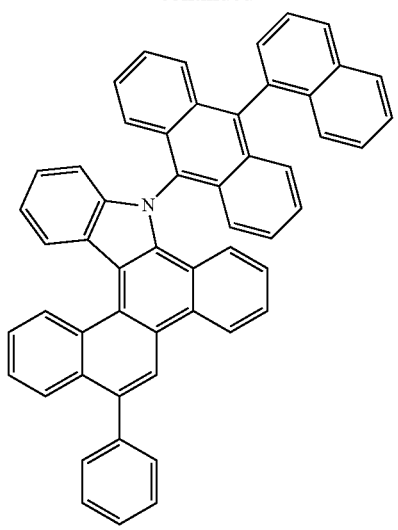 [SMILES: c1ccc(-c2cc3c4ccccc4c4c(c5ccccc5n4-c4c5ccccc5c(-c5cccc6ccccc56)c5ccccc45)c3c3ccccc23)cc1]
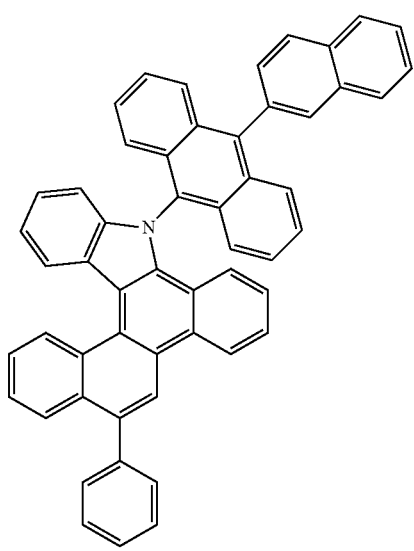
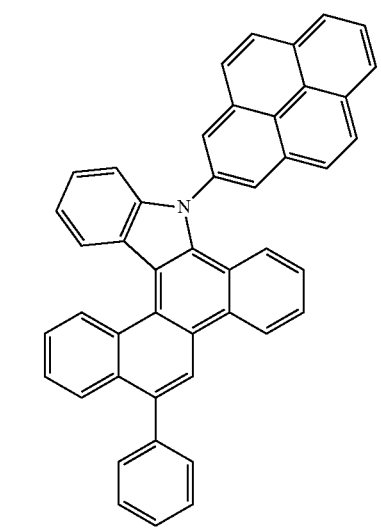
52
-continued
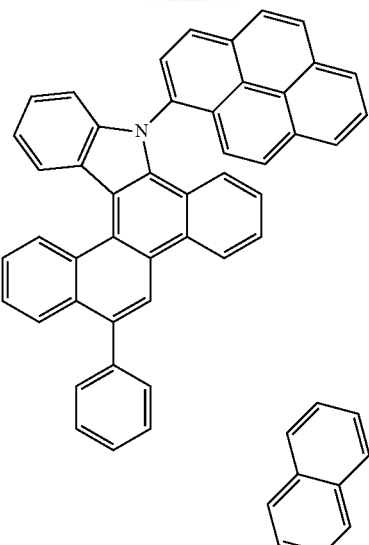
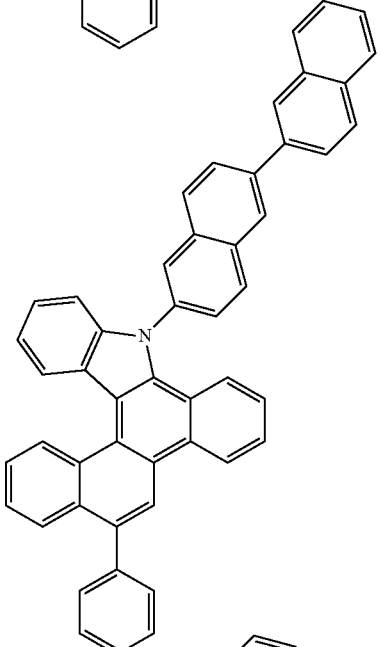
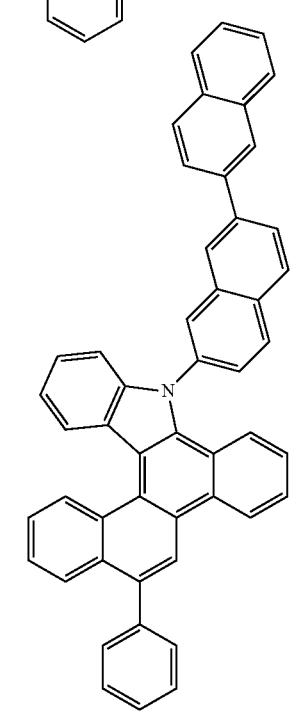

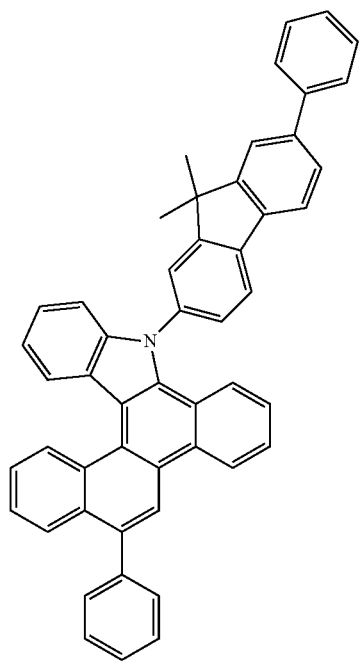
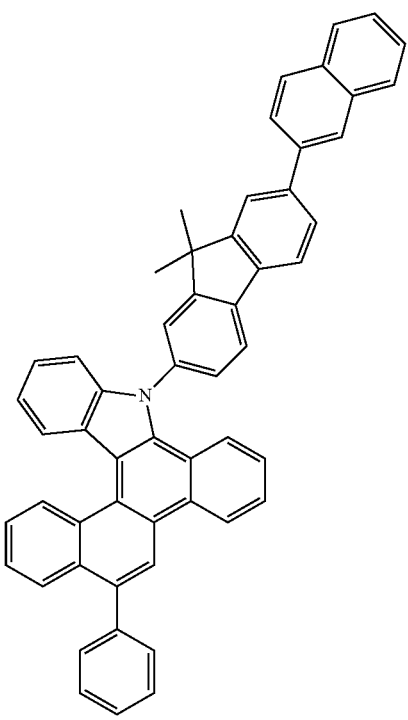
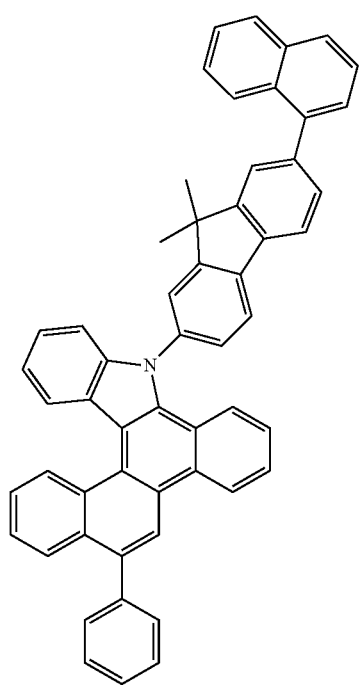 [SMILES: CC1(C)c2cc(-c3cccc4ccccc34)ccc2-c2ccc(-n3c4ccccc4c4c5c6ccccc6c(-c6ccccc6)cc5c5ccccc5c43)cc21]
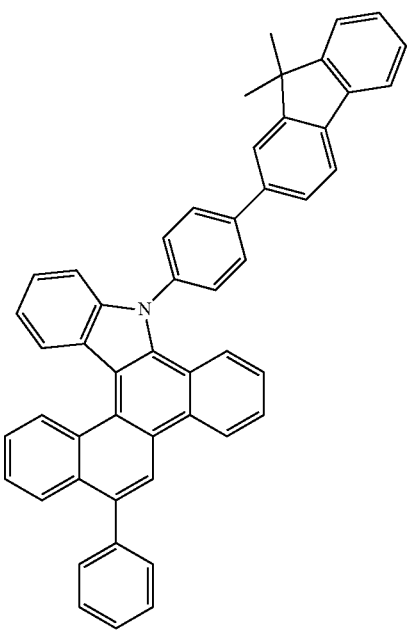

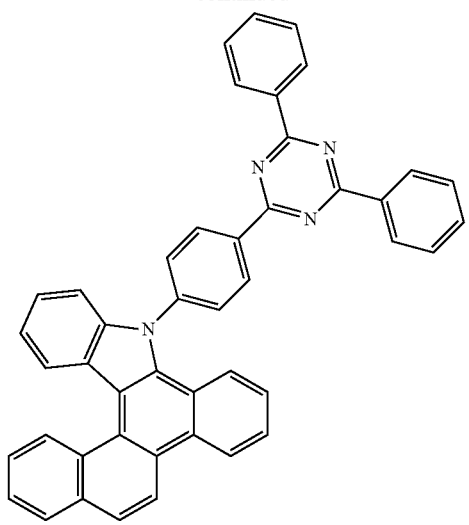
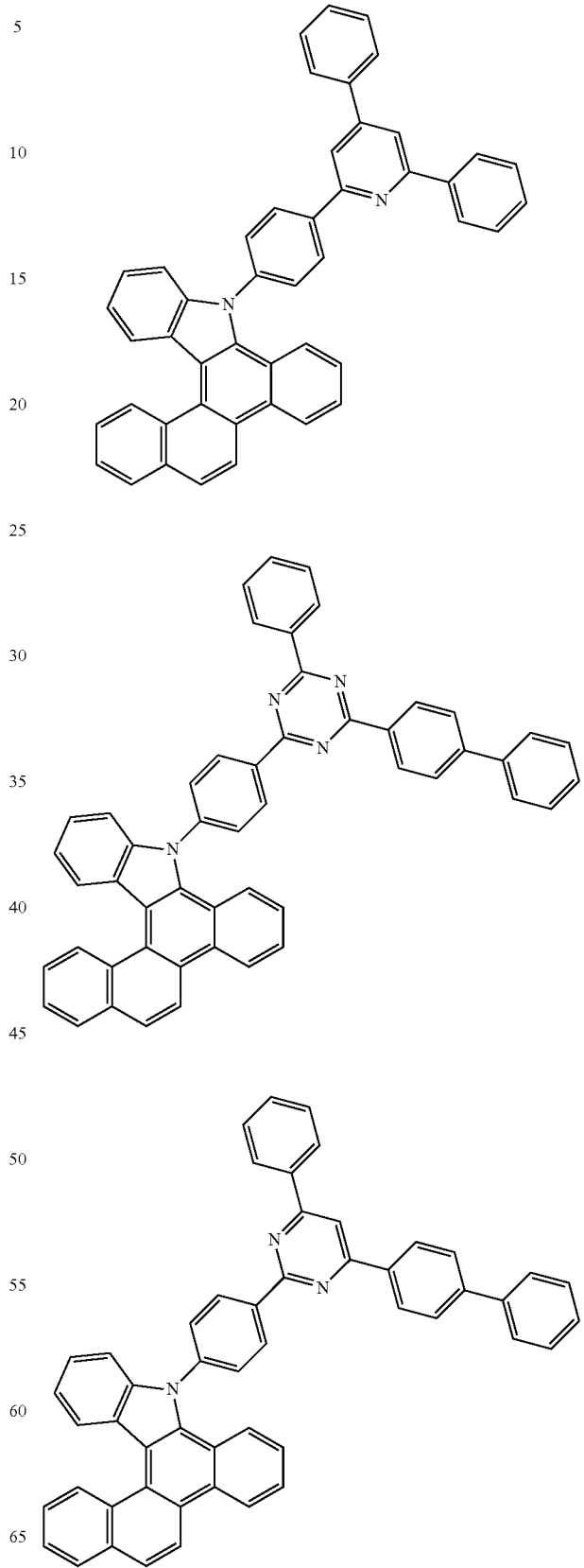

57
-continued
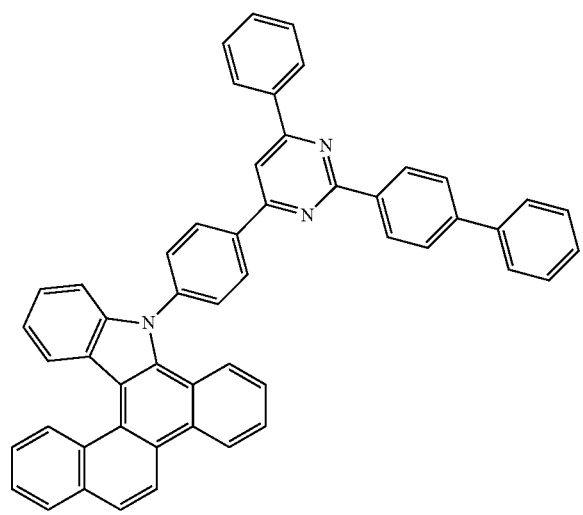
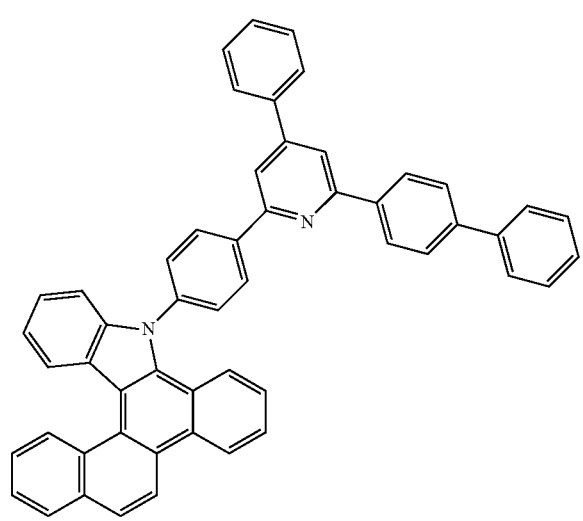
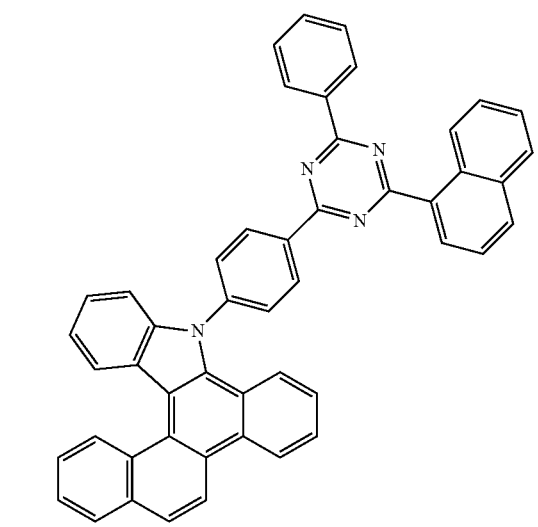
58
-continued
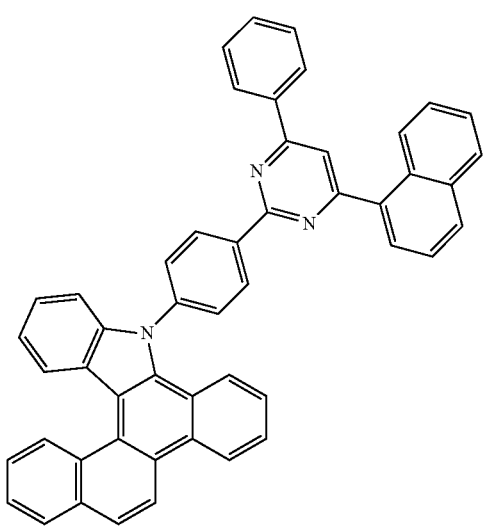
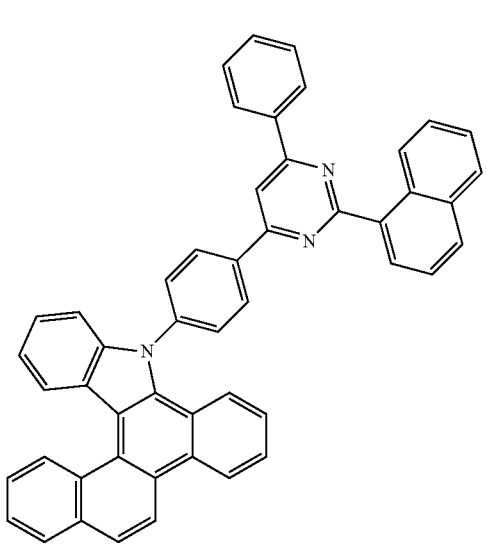
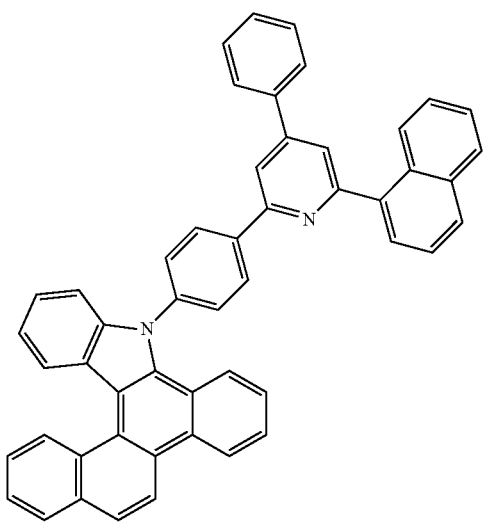

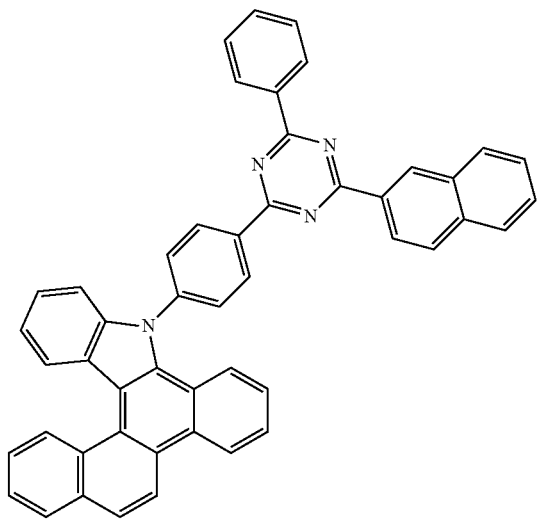
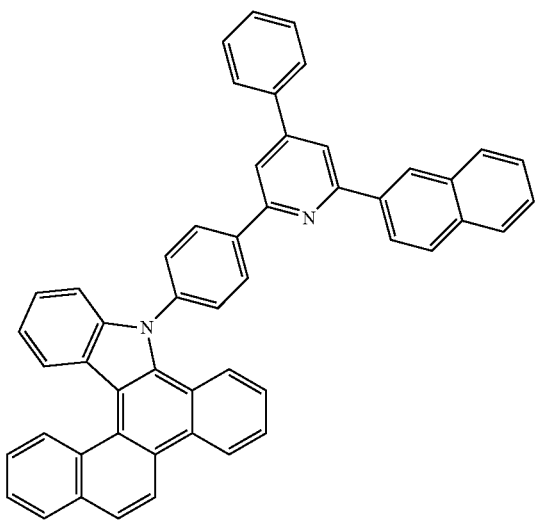
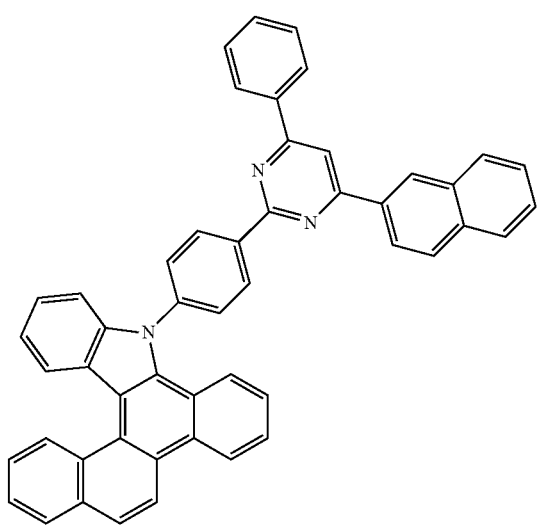
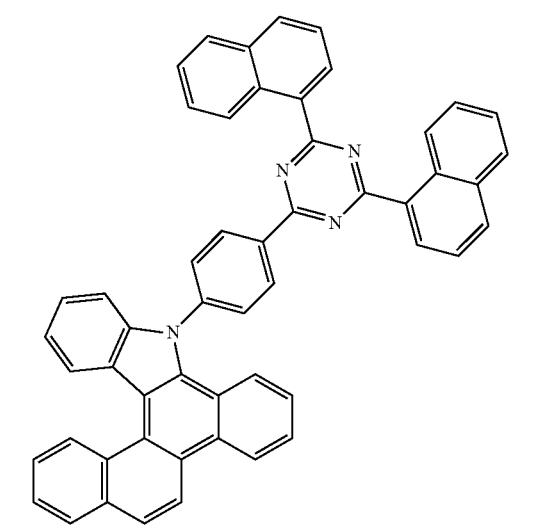
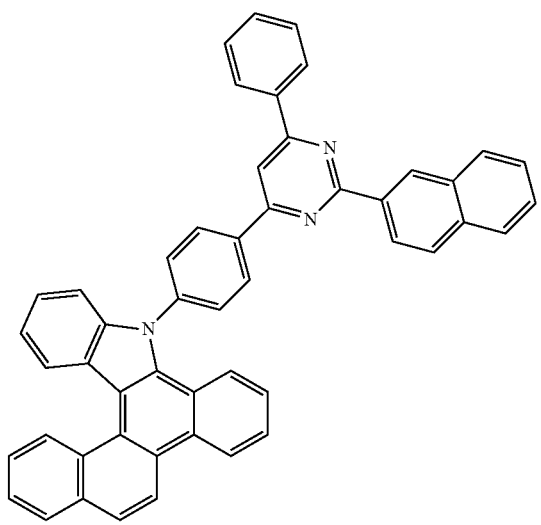
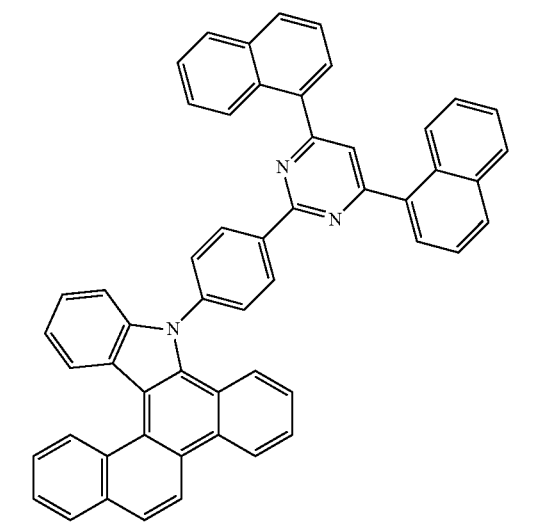

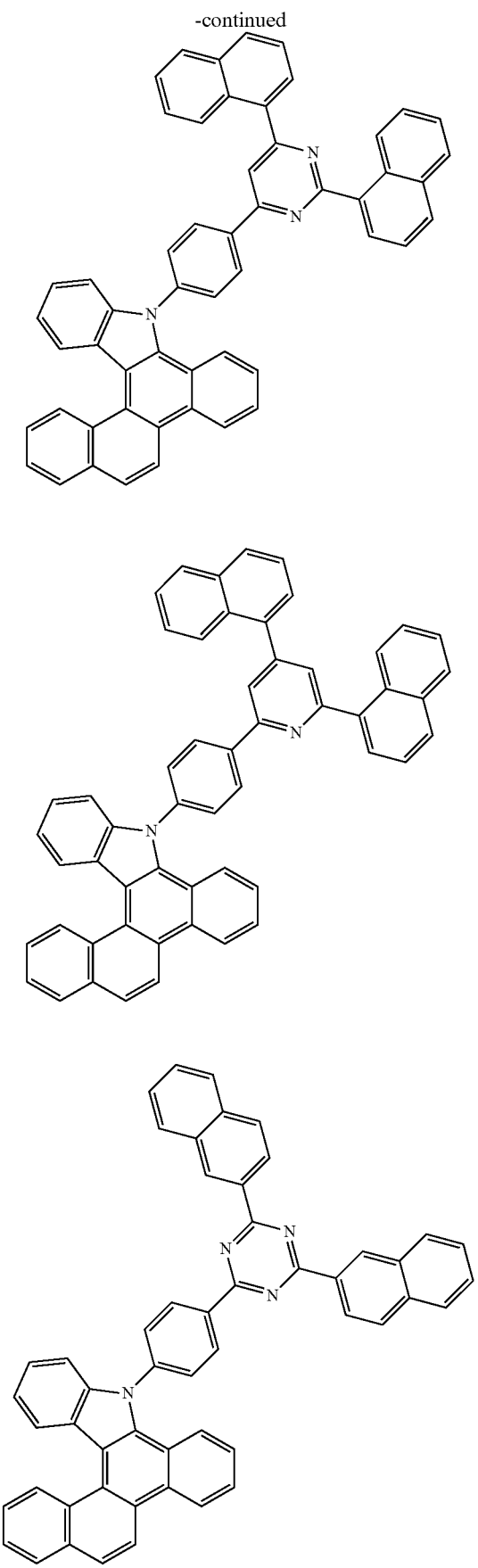
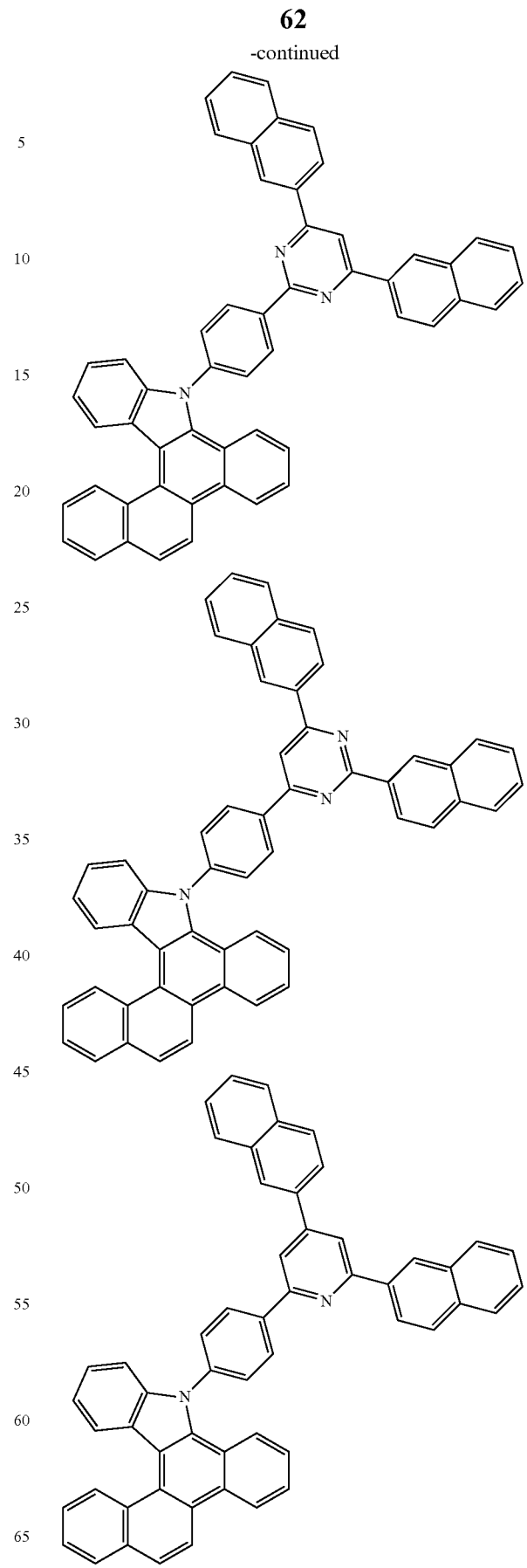

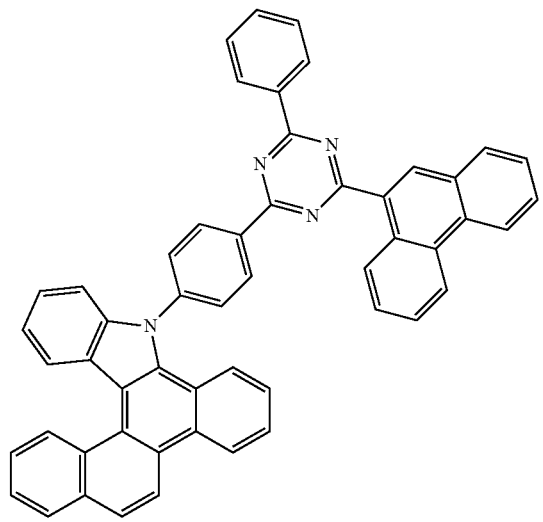
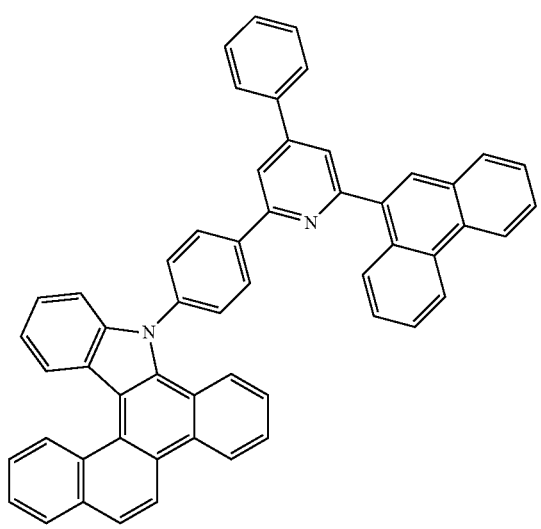
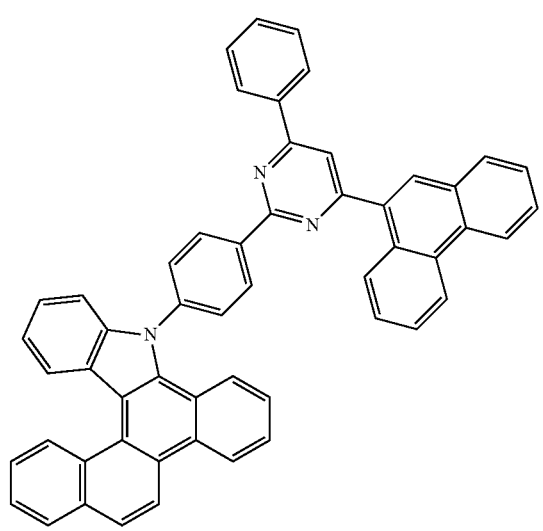
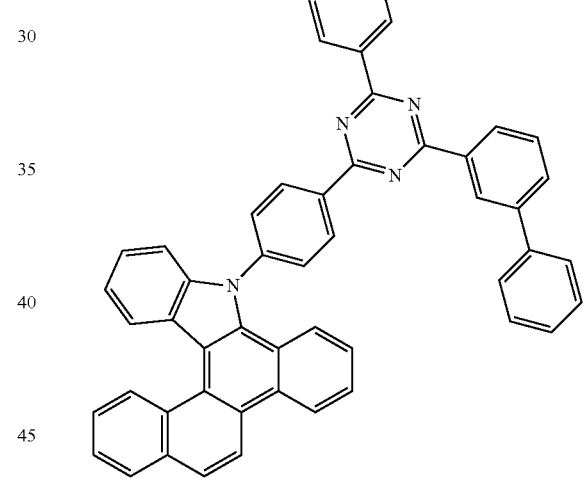
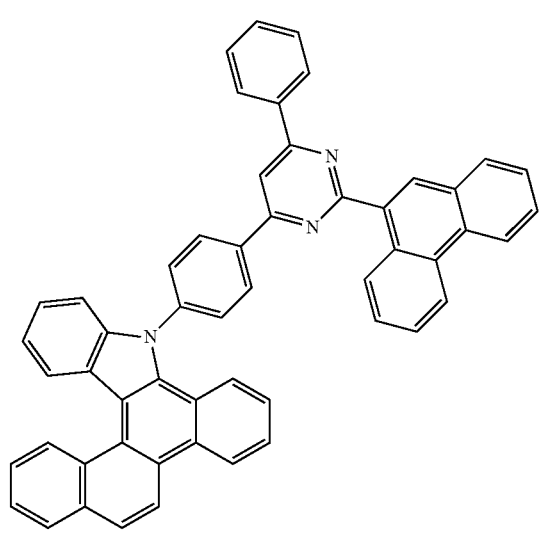
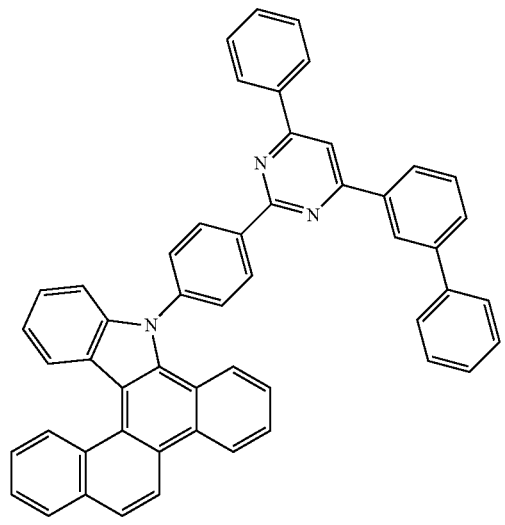

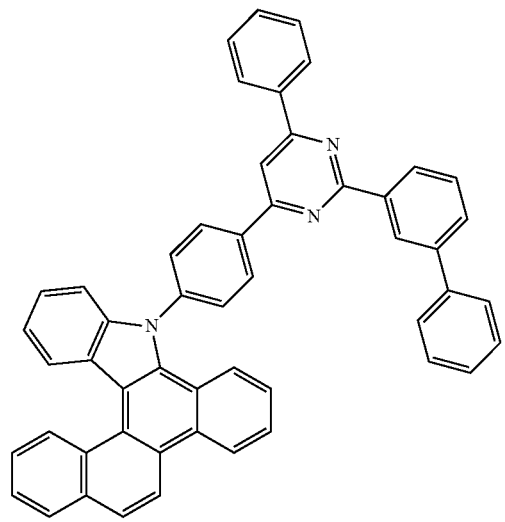
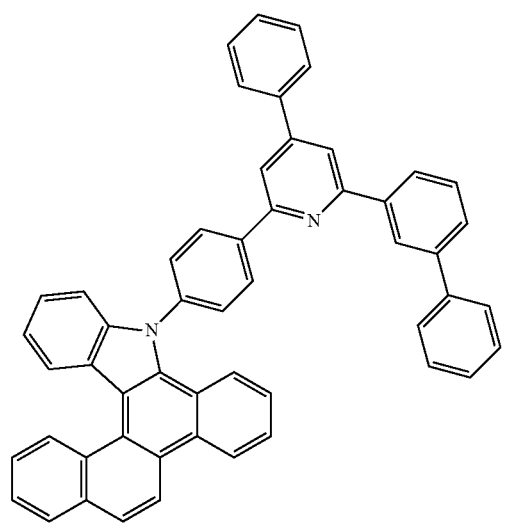
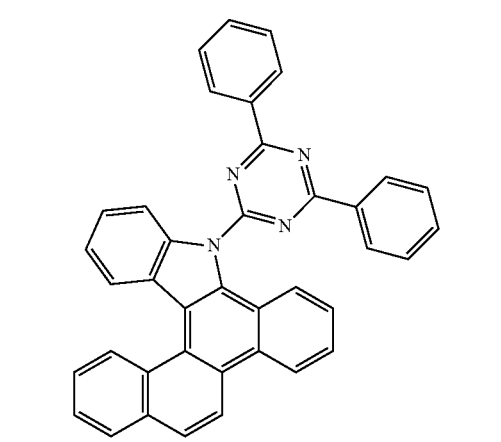
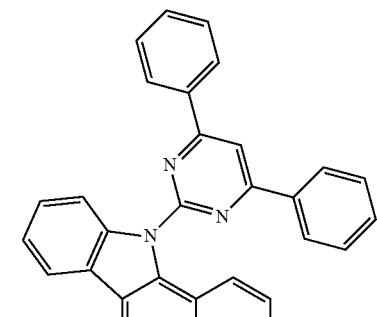
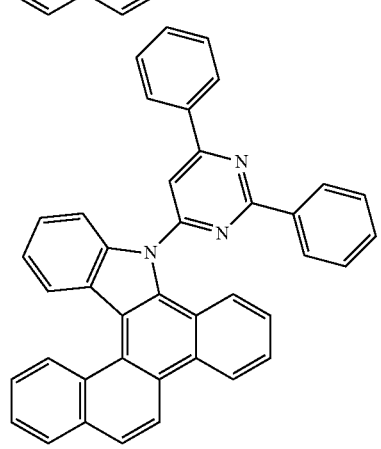
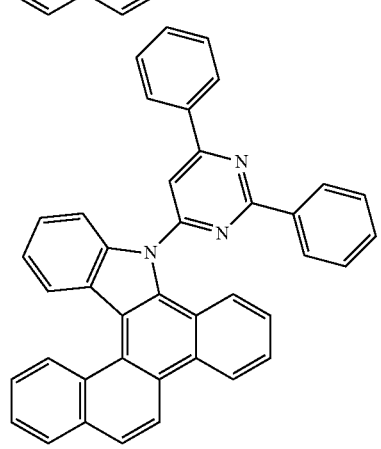
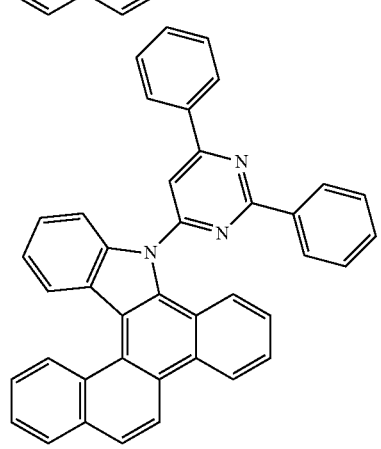

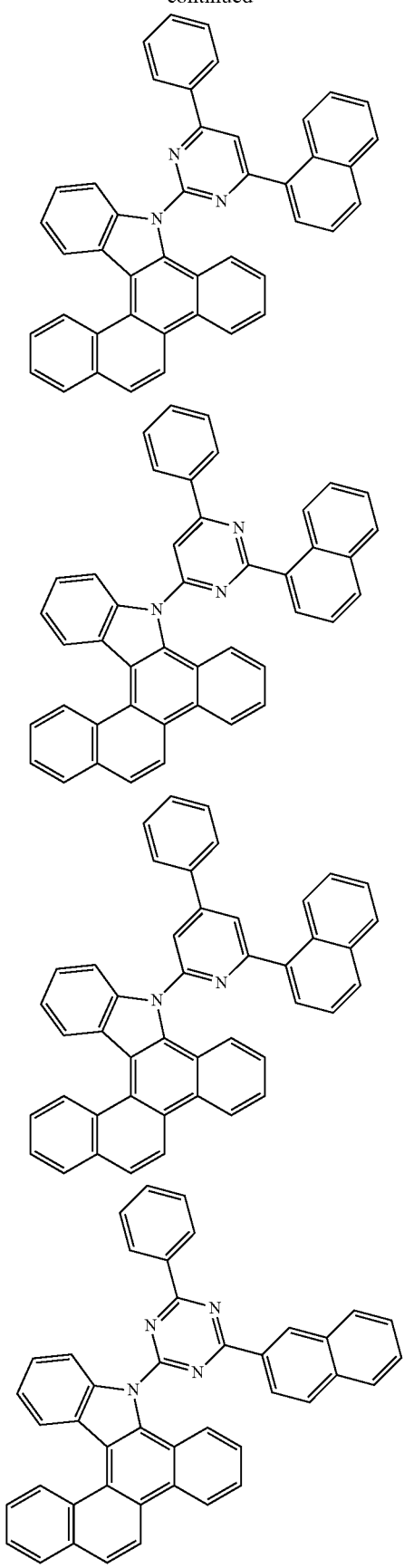
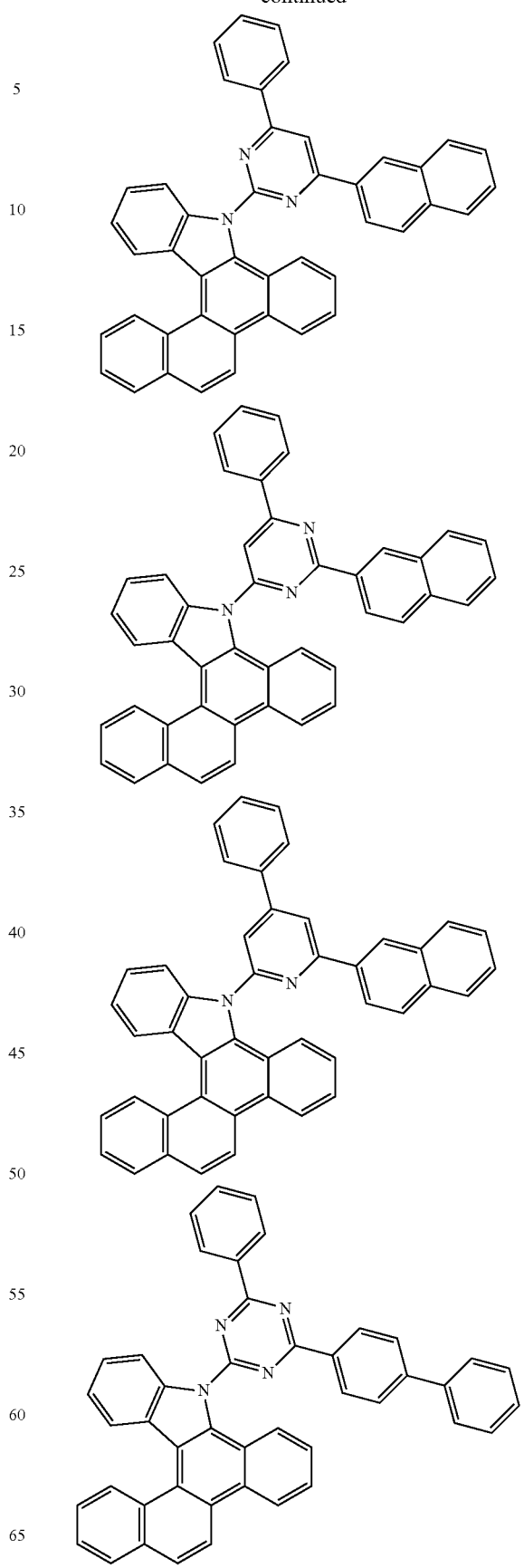

-continued
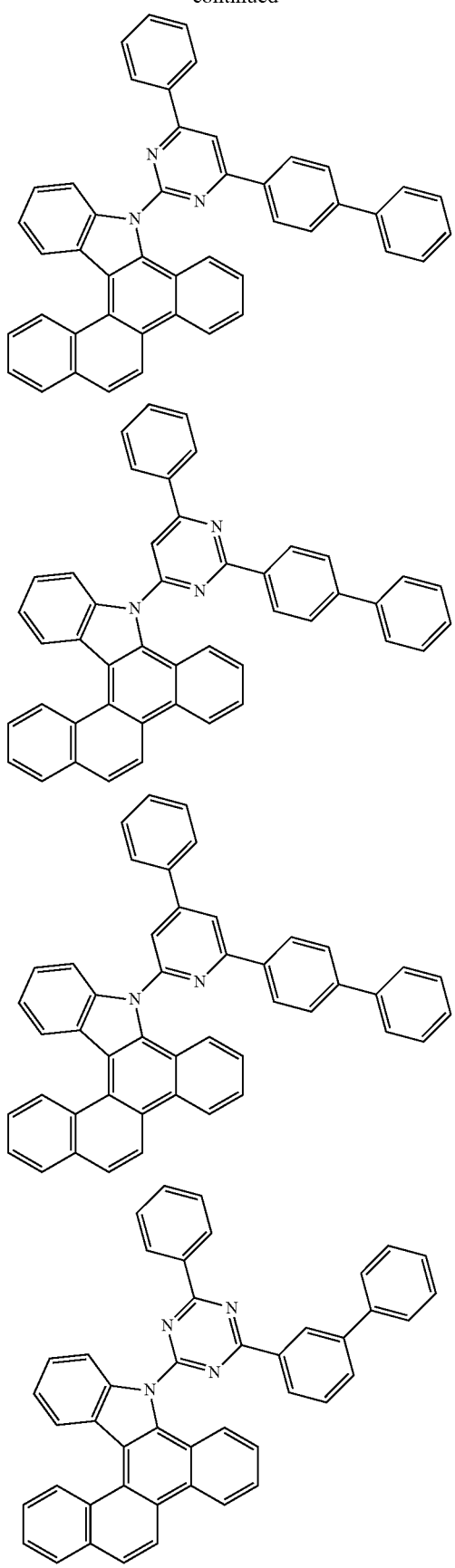
-continued
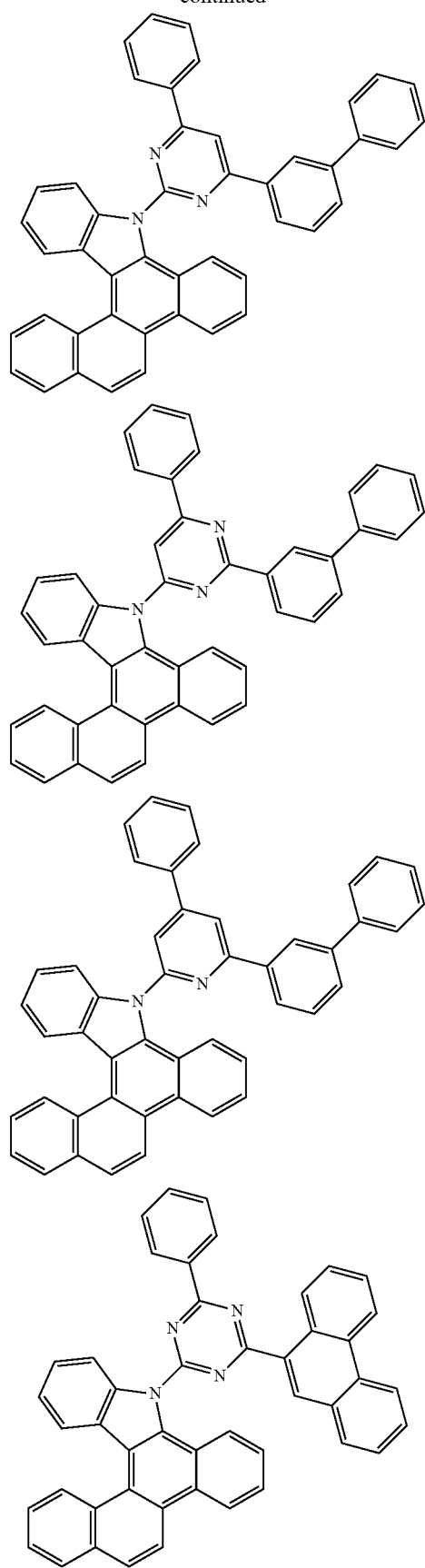

71
-continued
72
-continued
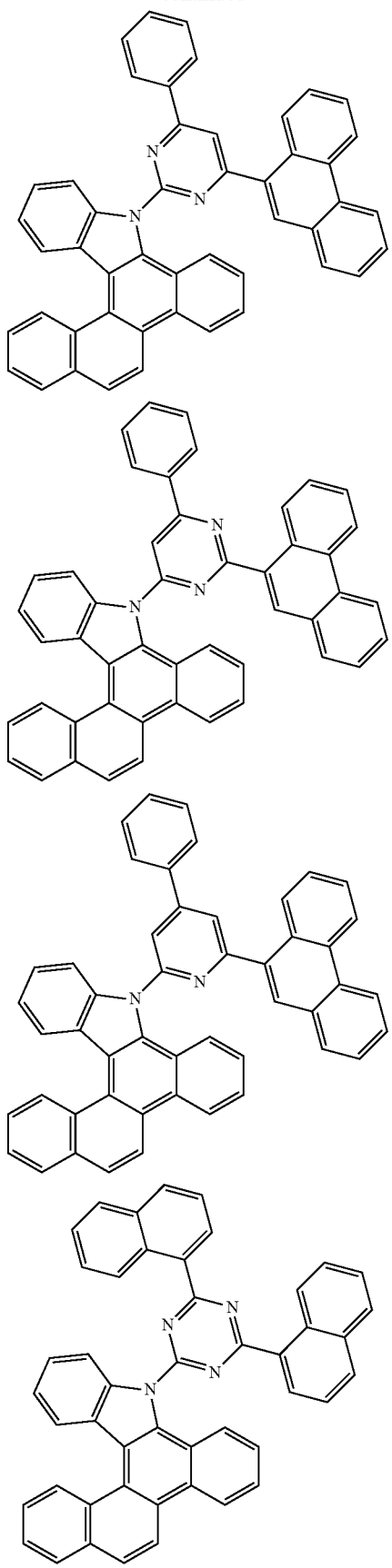
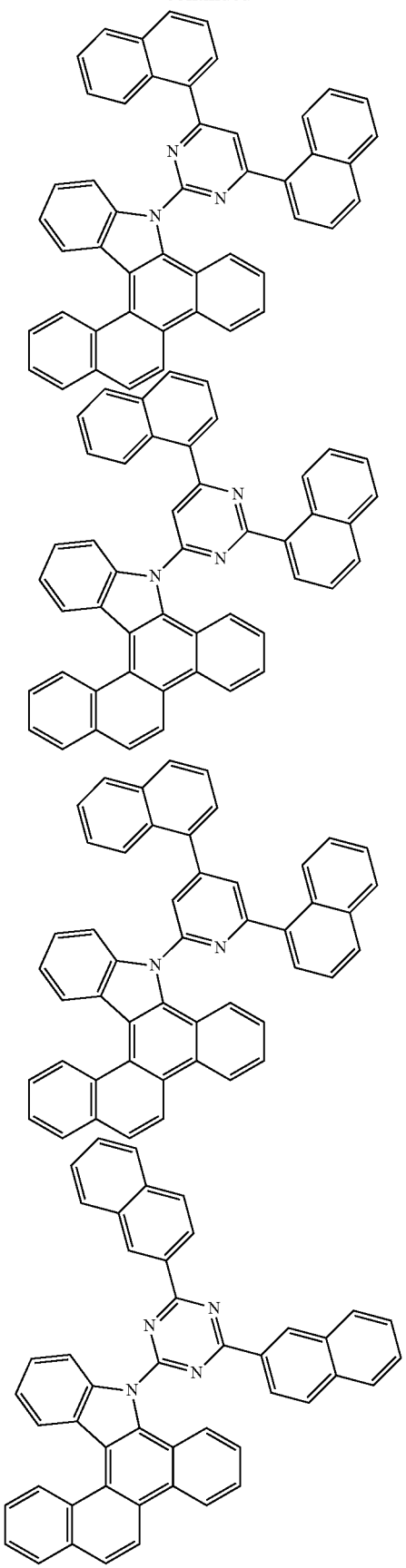

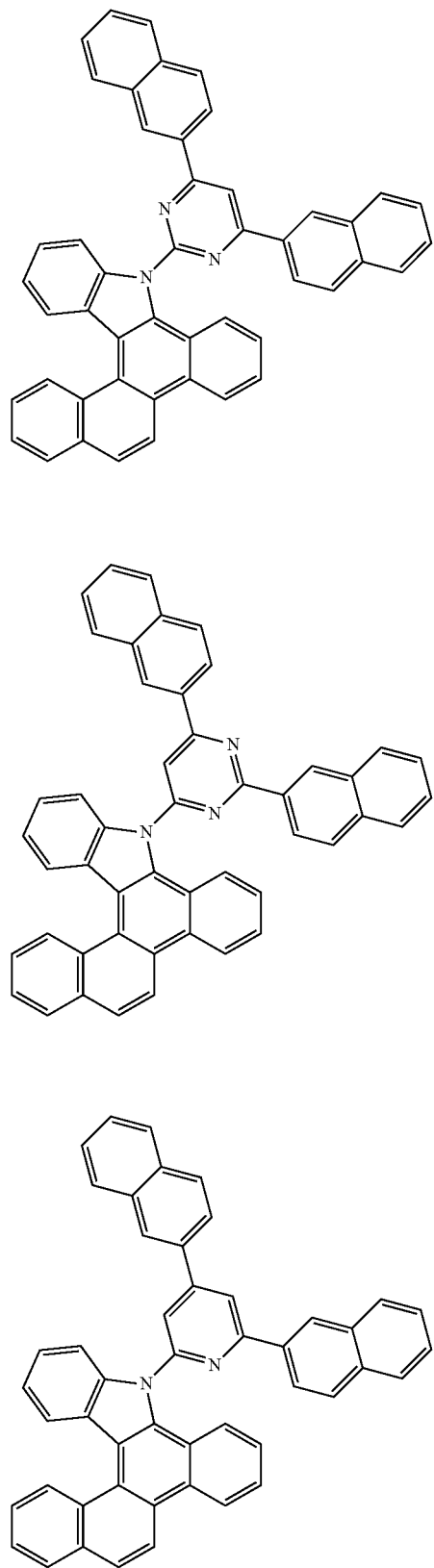
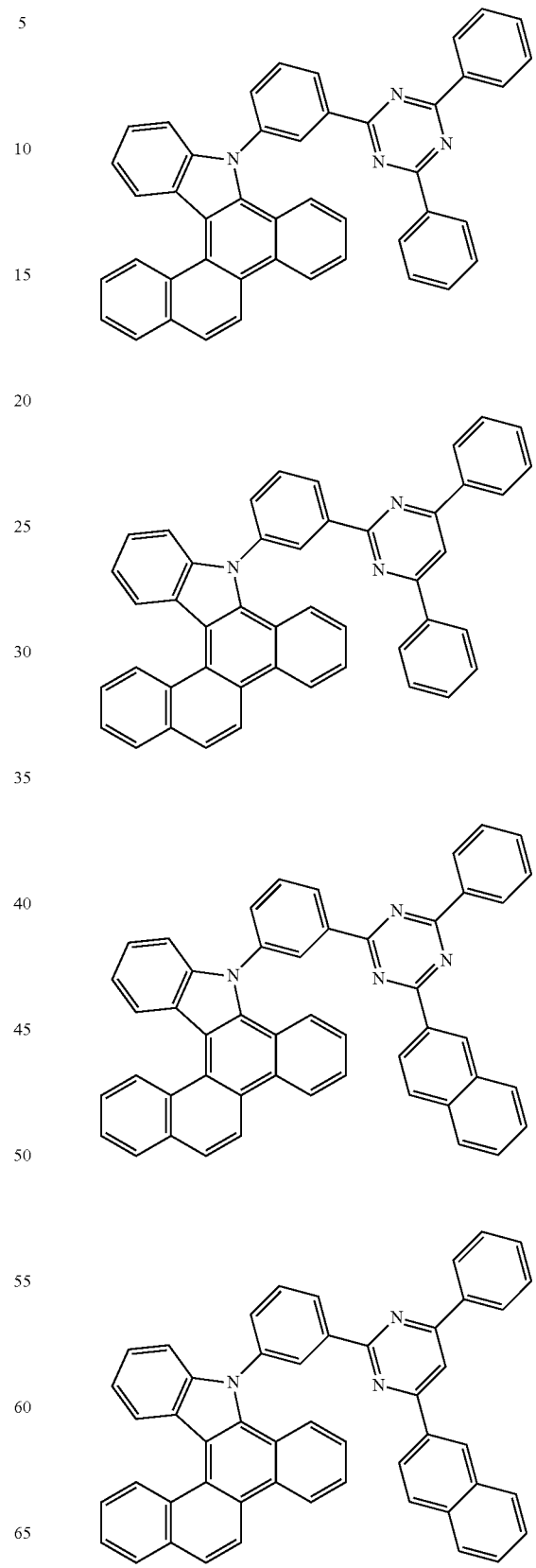

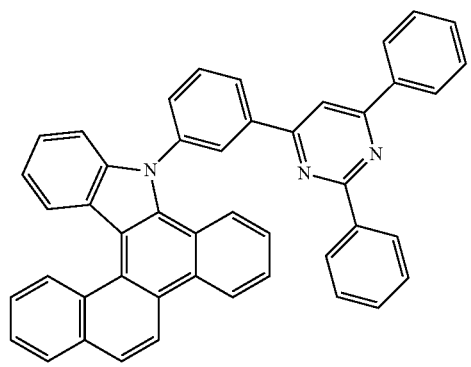
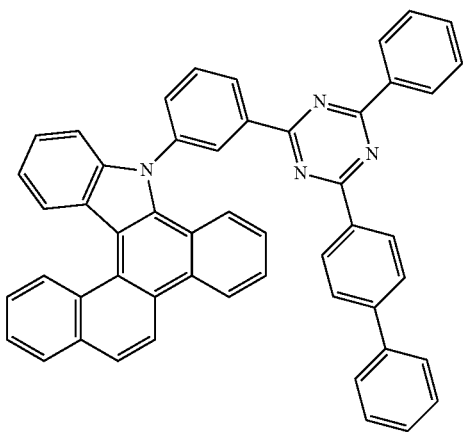
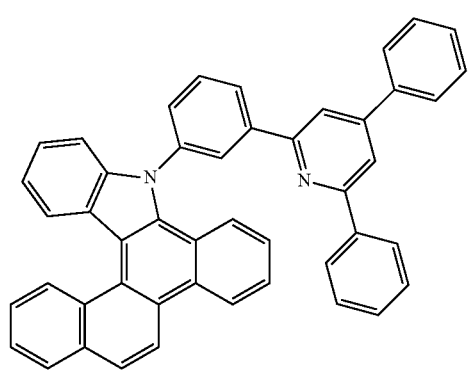
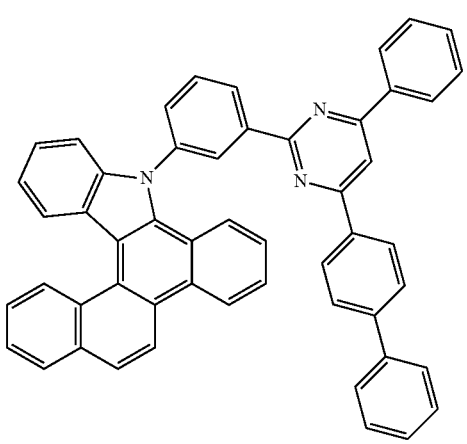
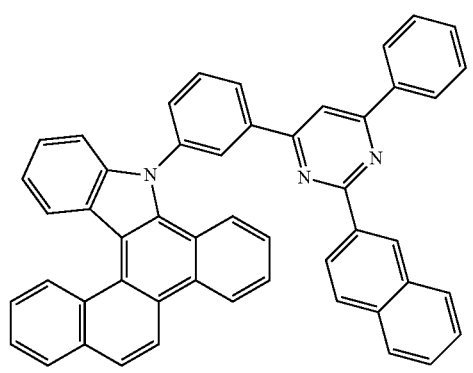
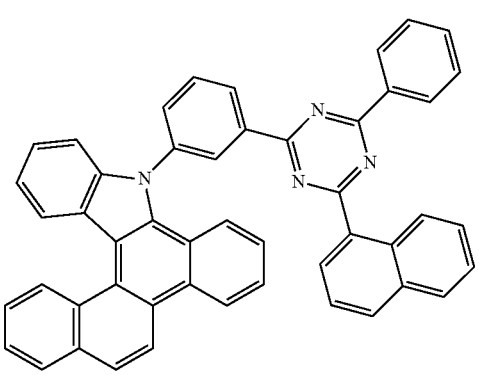
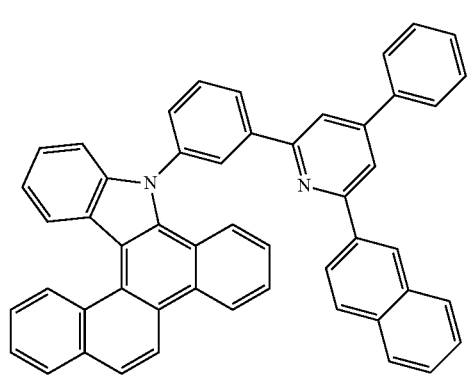
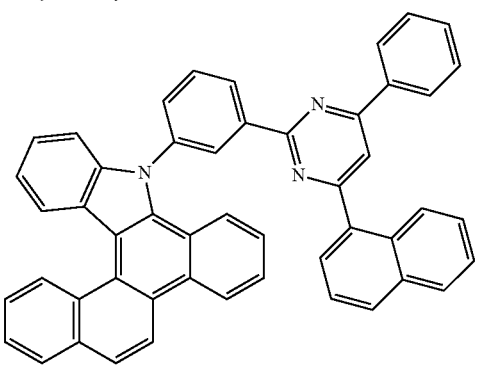

77
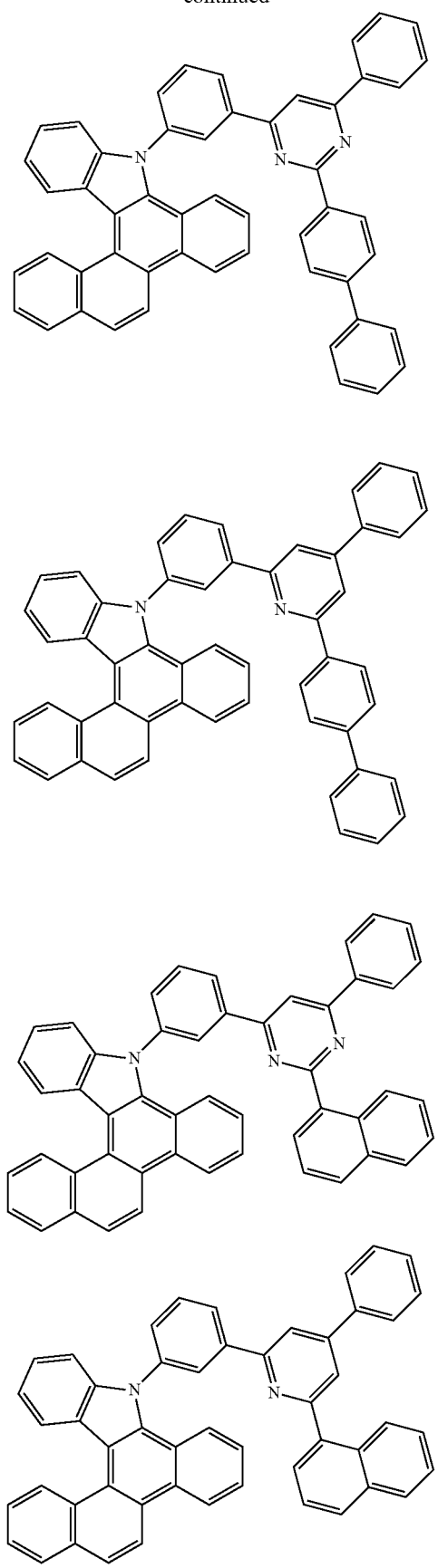
78
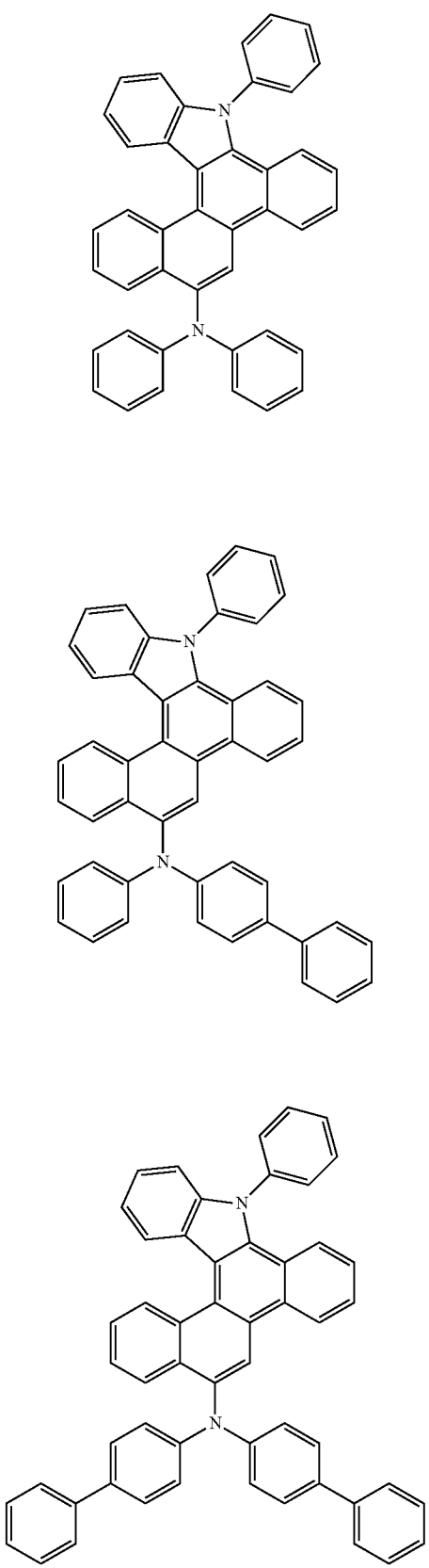

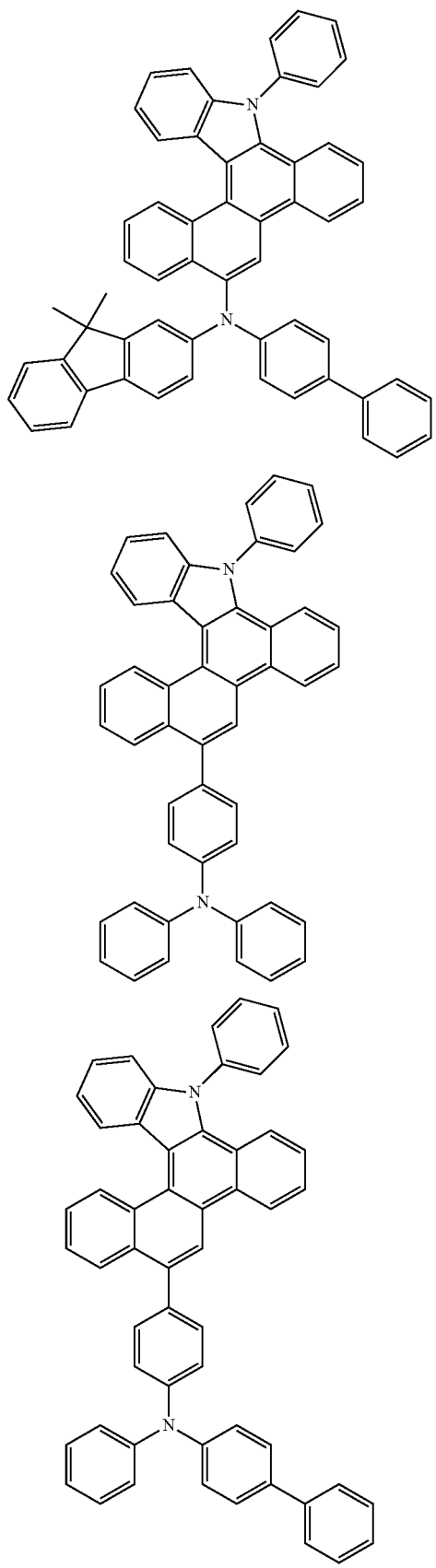
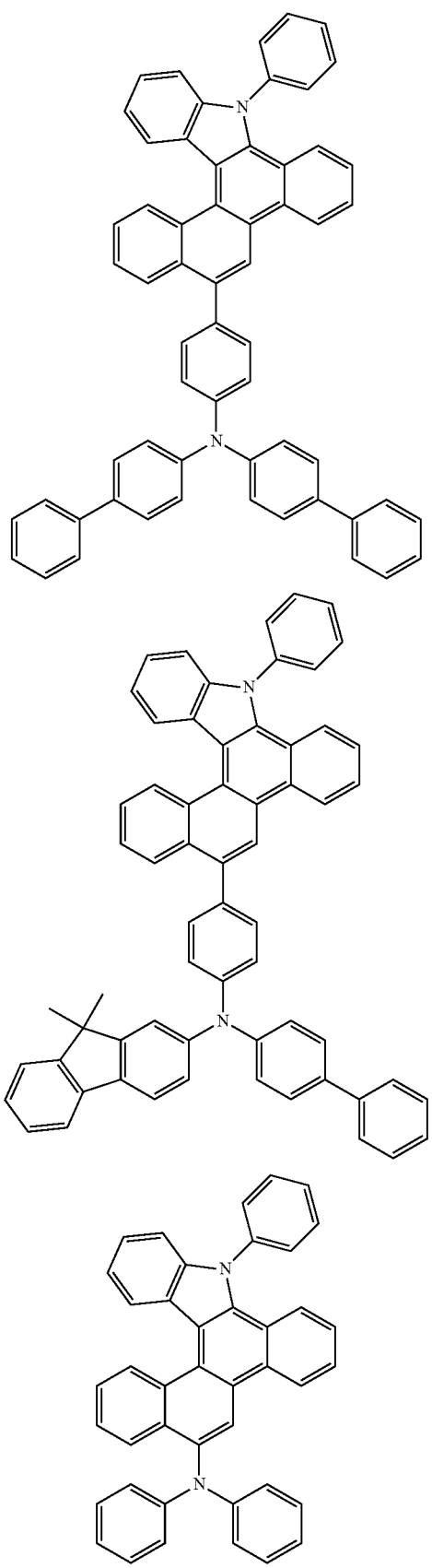 [SMILES: c1ccc(-c2ccc(N(c3ccc(-c4ccccc4)cc3)c3ccc(-c4cc5c6ccccc6c6c(c7ccccc7n6-c6ccccc6)c5c5ccccc45)cc3)cc2)cc1 ; CC1(C)c2ccccc2-c2ccc(N(c3ccc(-c4ccccc4)cc3)c3ccc(-c4cc5c6ccccc6c6c(c7ccccc7n6-c6ccccc6)c5c5ccccc45)cc3)cc21 ; c1ccc(N(c2ccccc2)c2cc3c4ccccc4c4c(c5ccccc5n4-c4ccccc4)c3c3ccccc23)cc1]

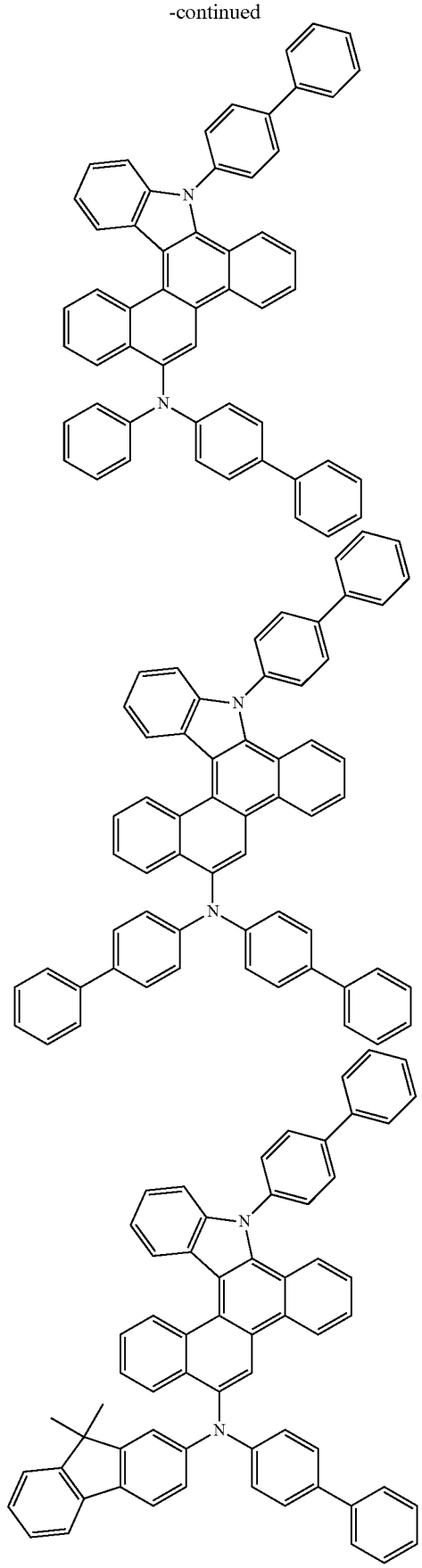
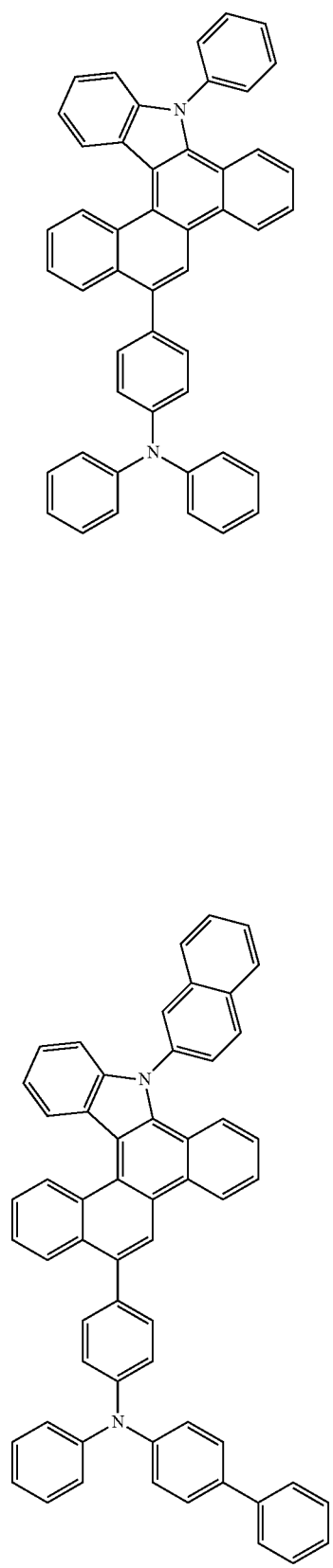

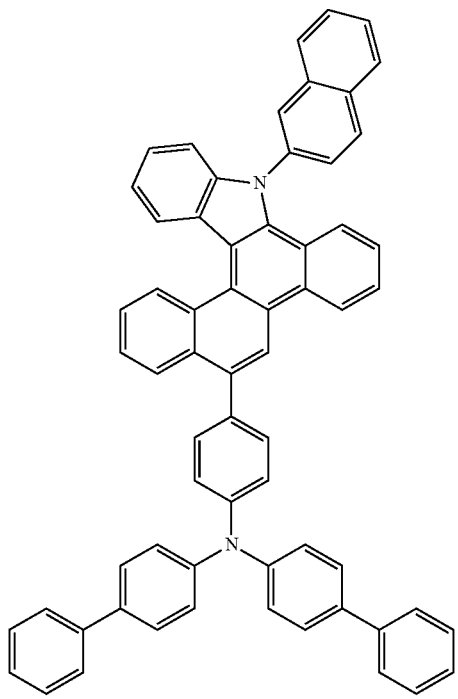
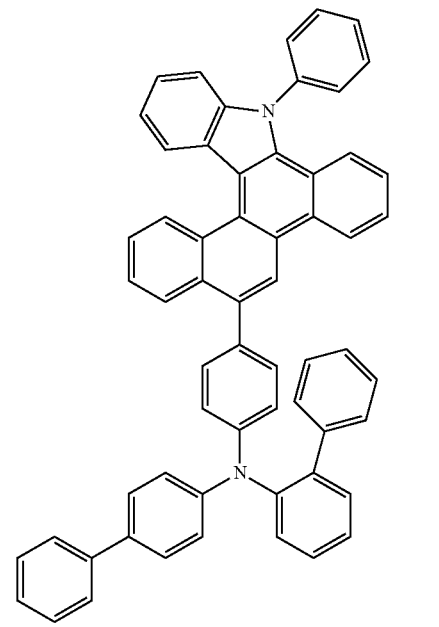
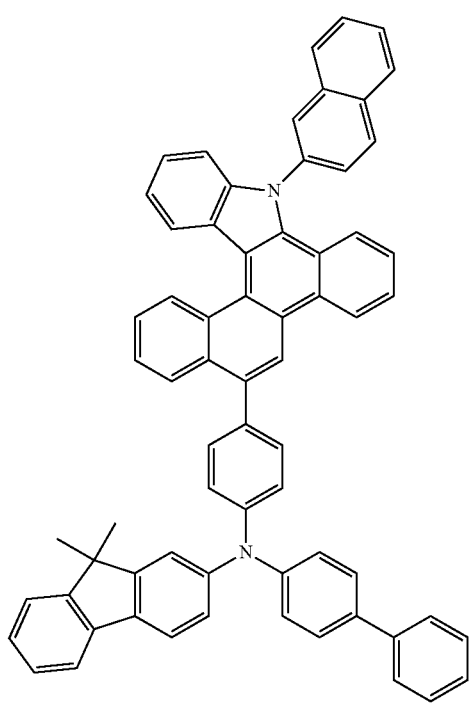
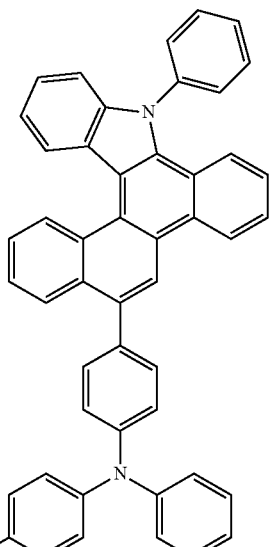

85
-continued
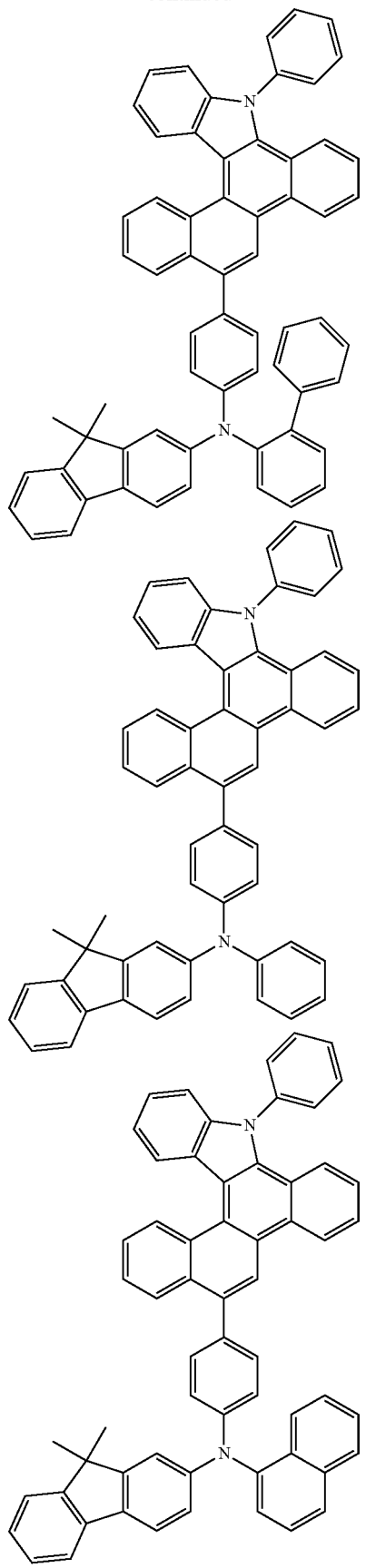
86
-continued
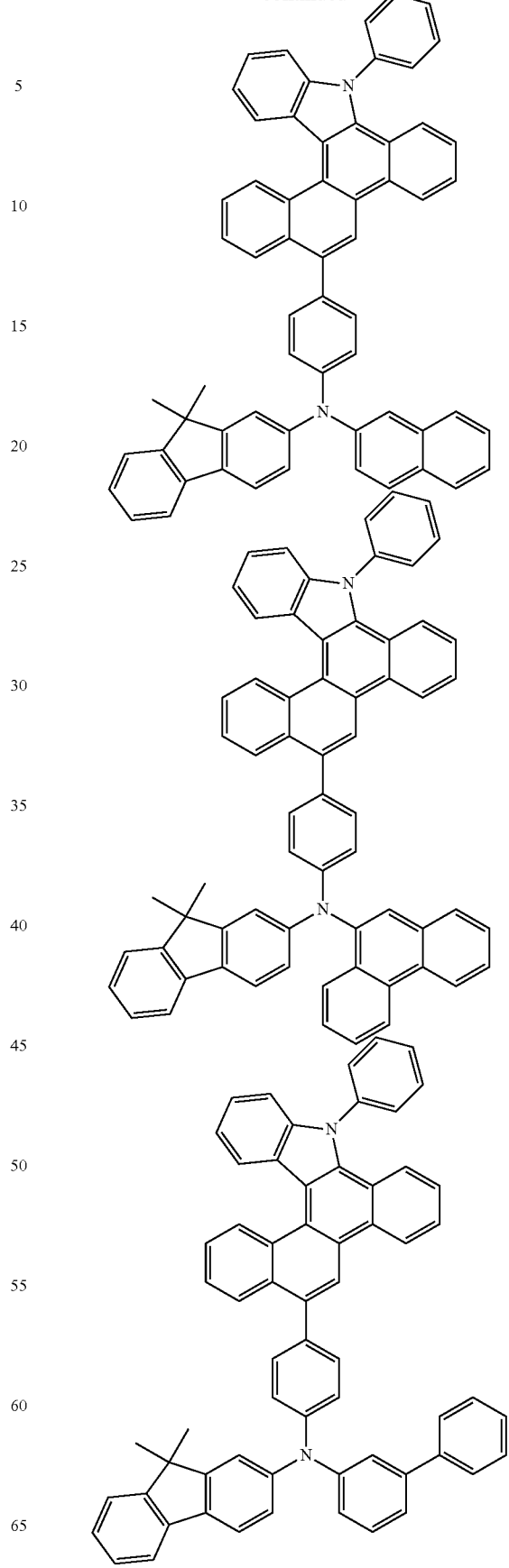

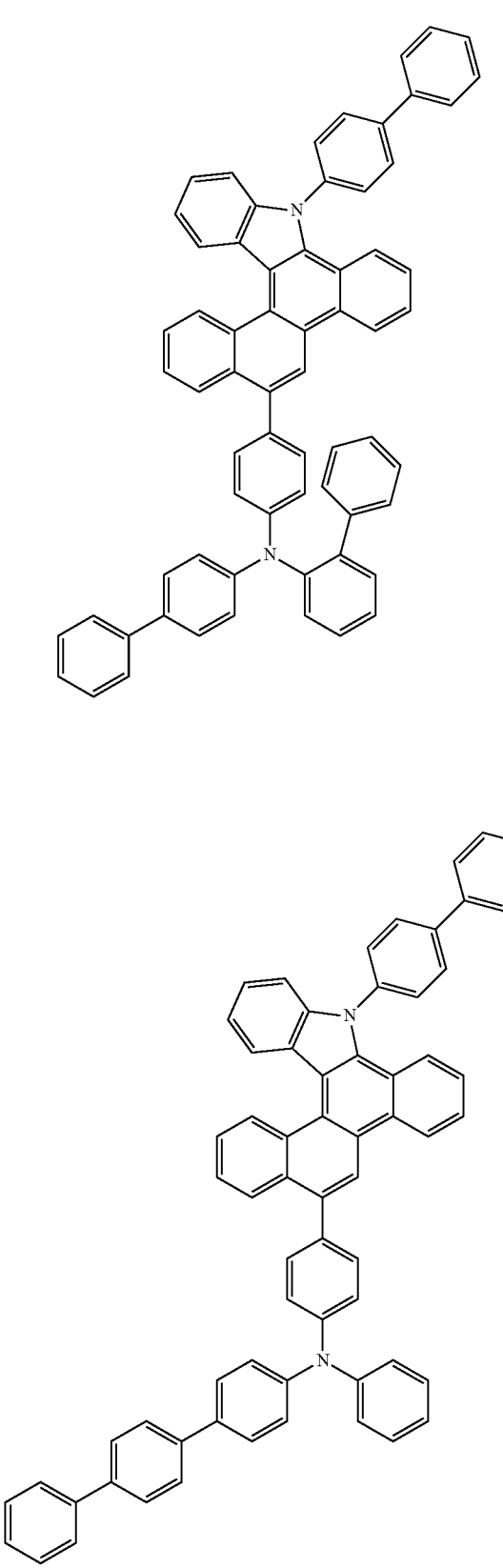
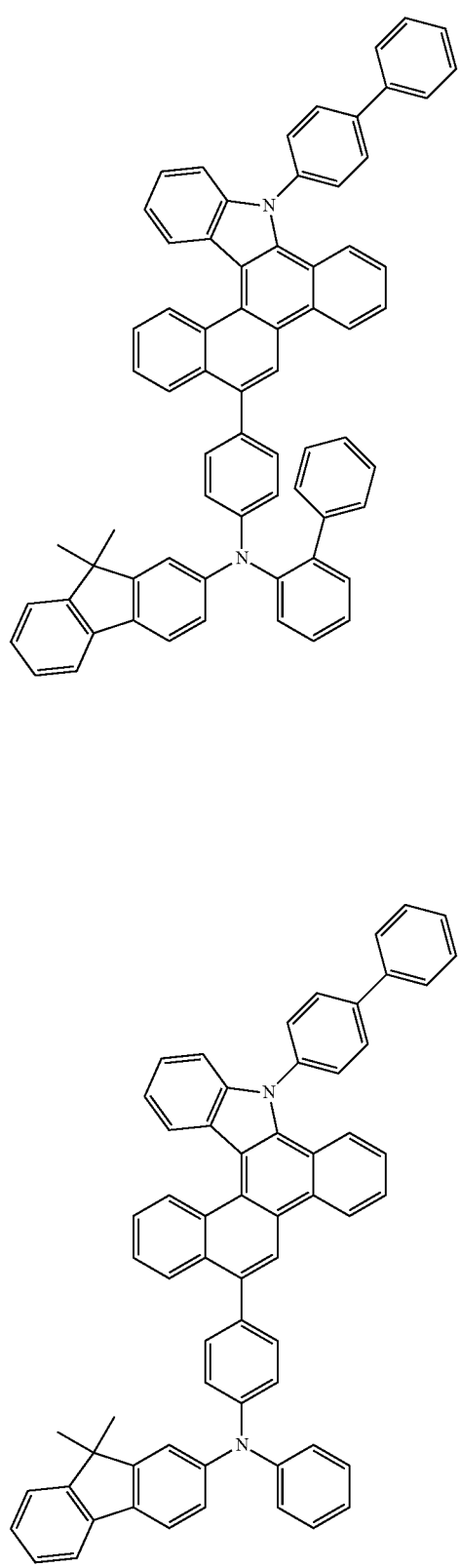

-continued
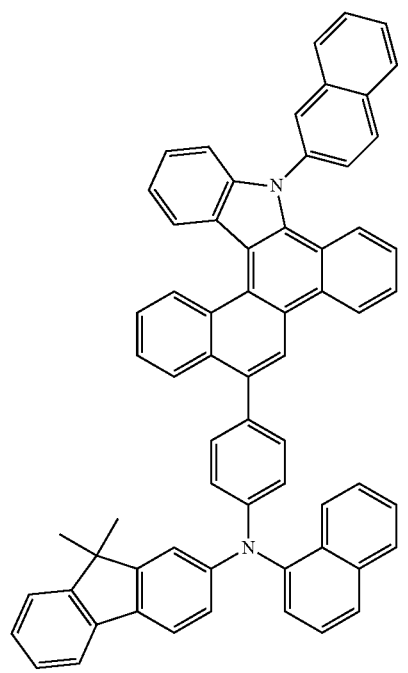
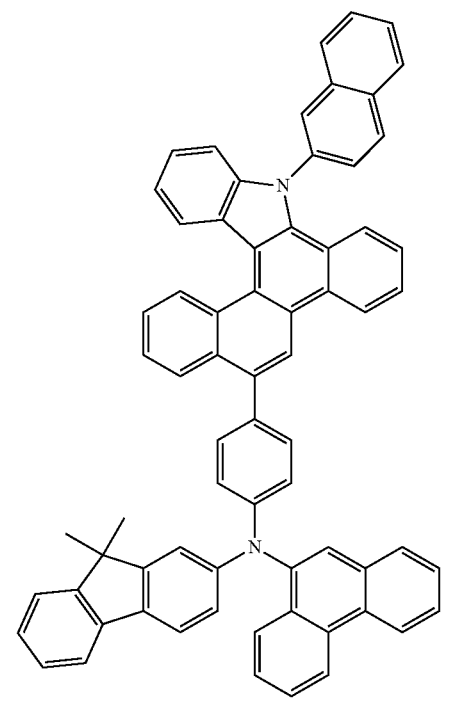
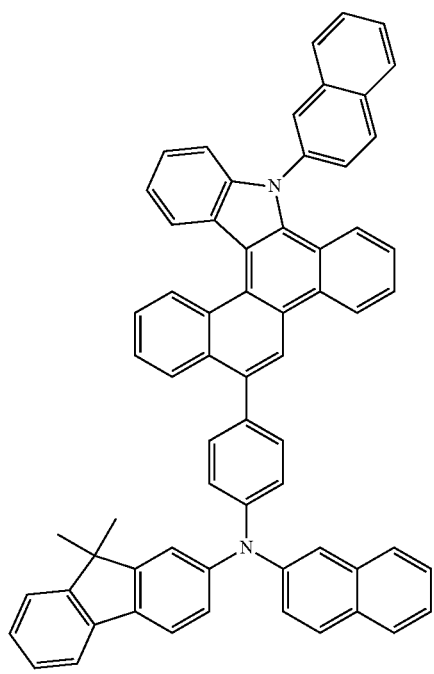
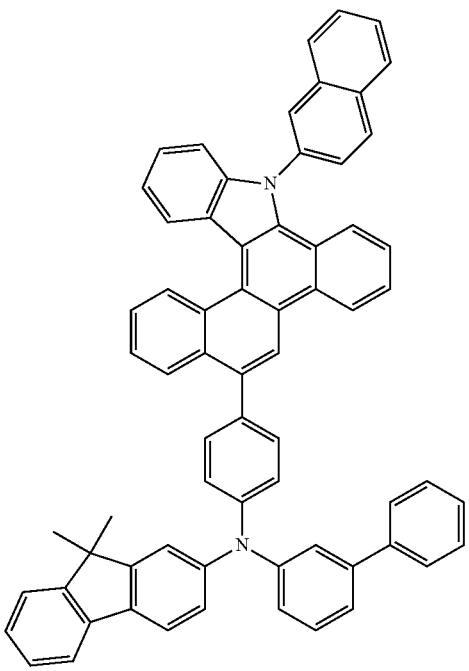

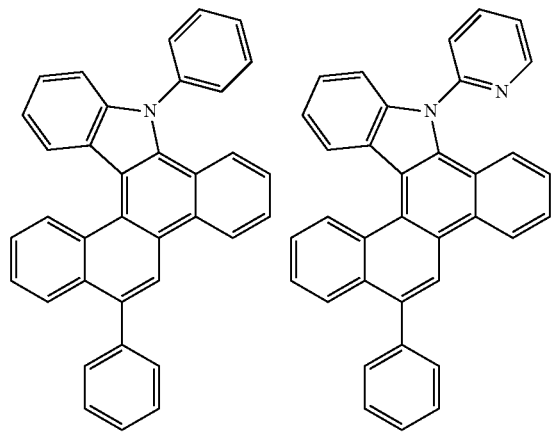
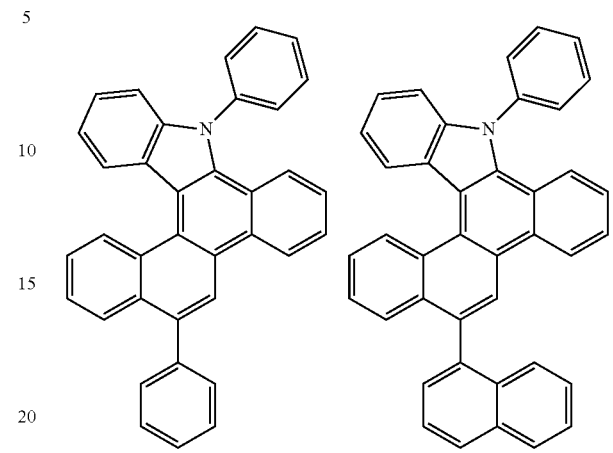
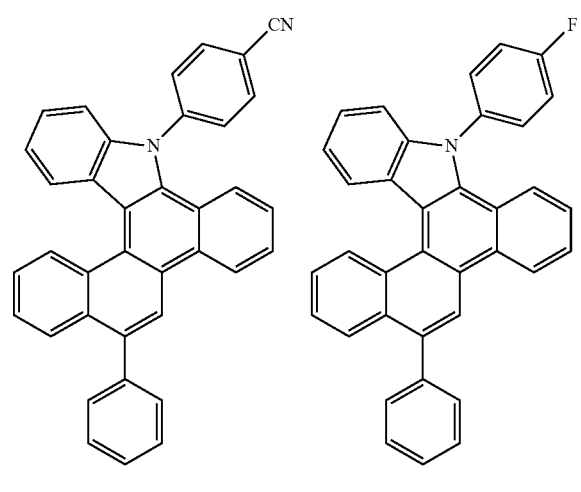
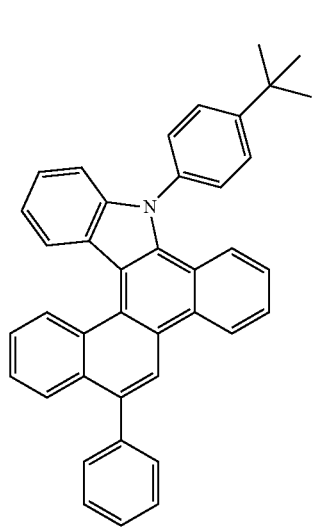

93
-continued
94
-continued
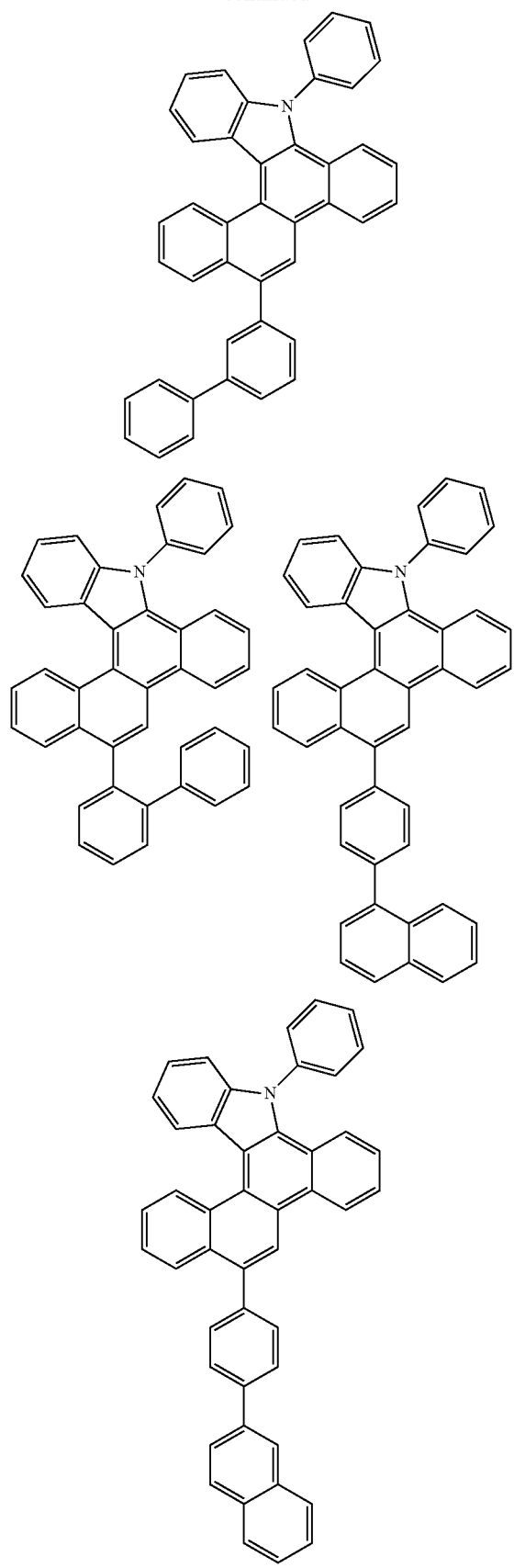
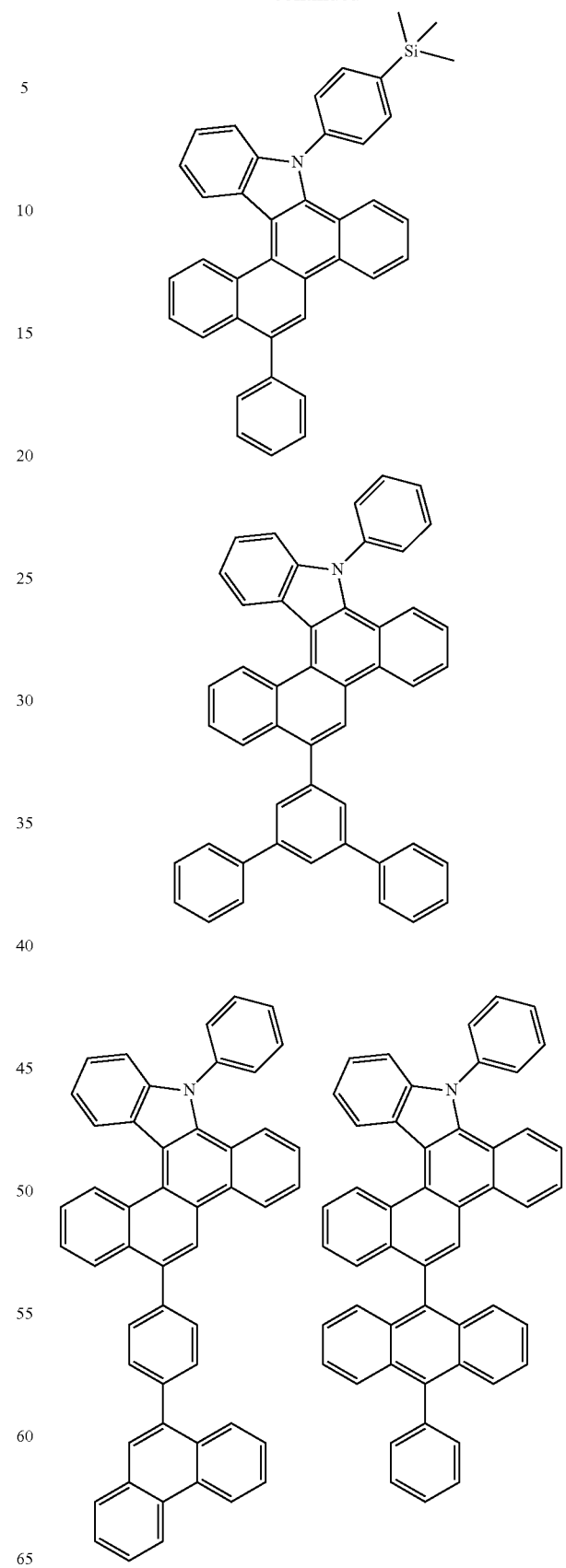

95
-continued
96
-continued
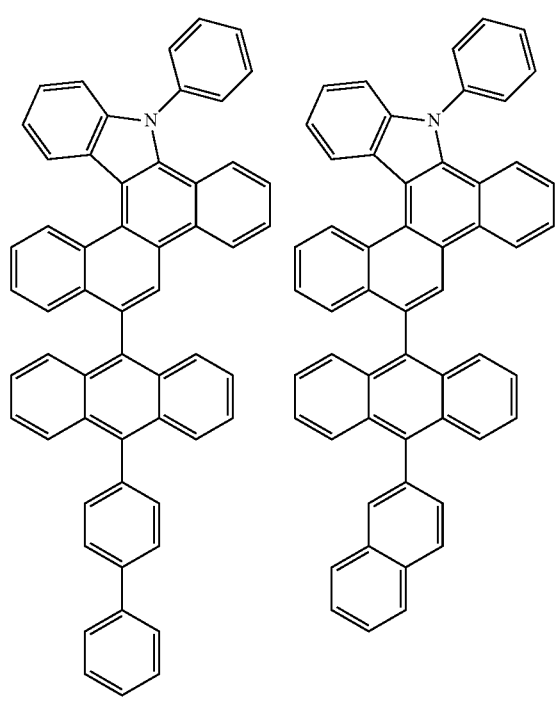
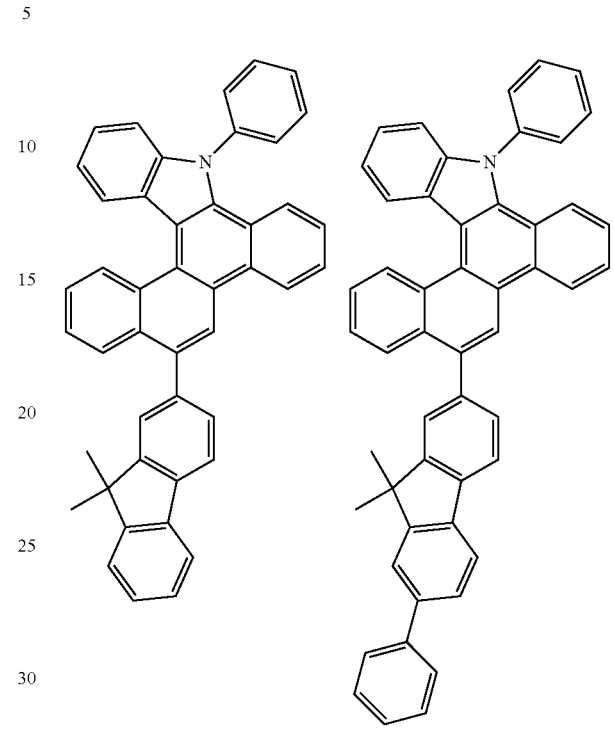
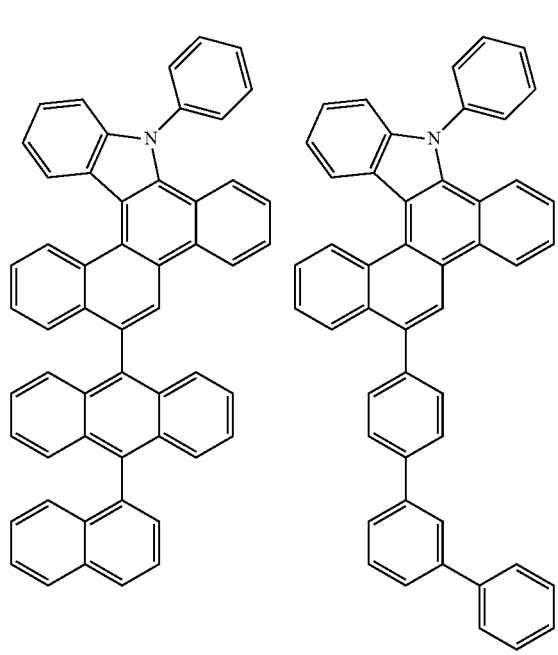

97
-continued
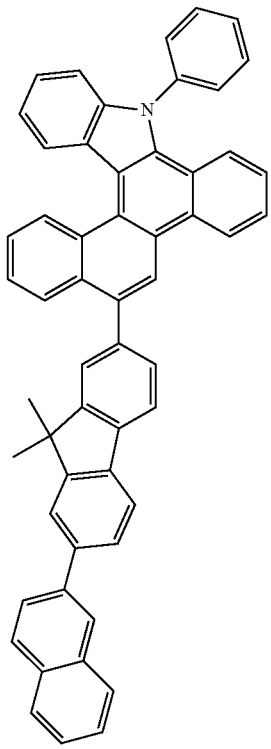
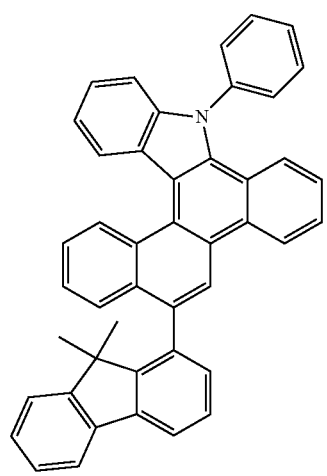
98
-continued
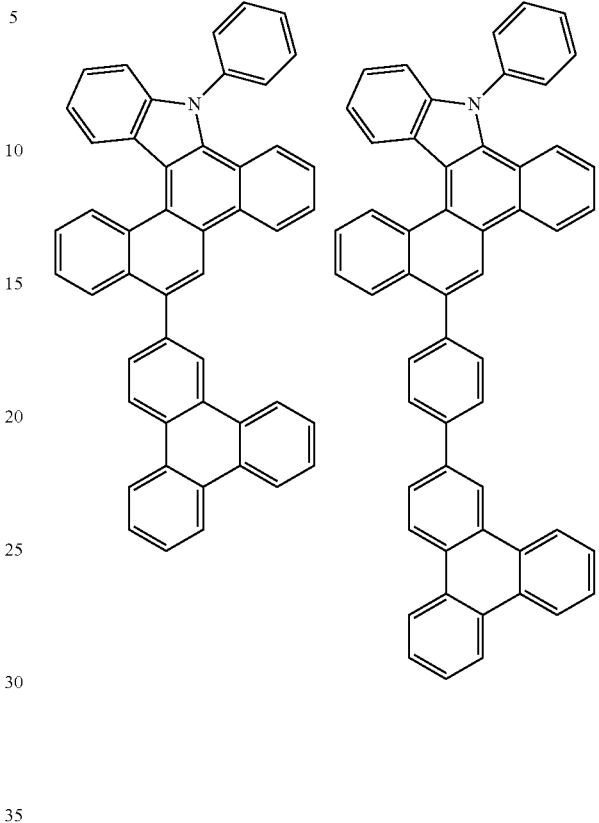
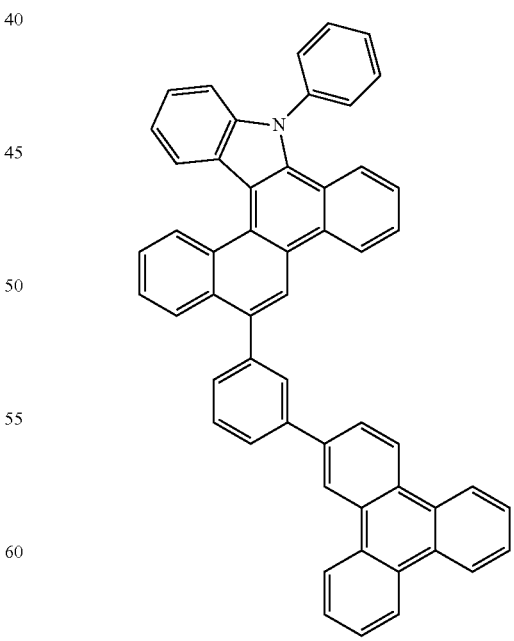

99
-continued
100
-continued
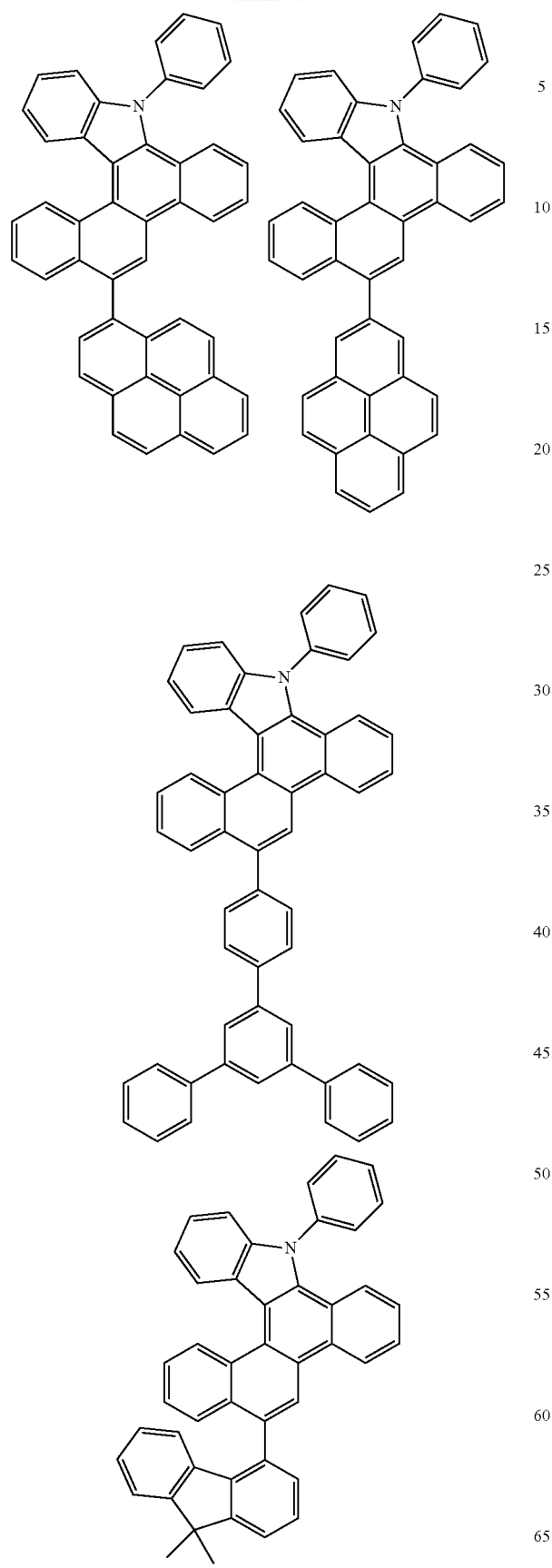

101
-continued
102
-continued
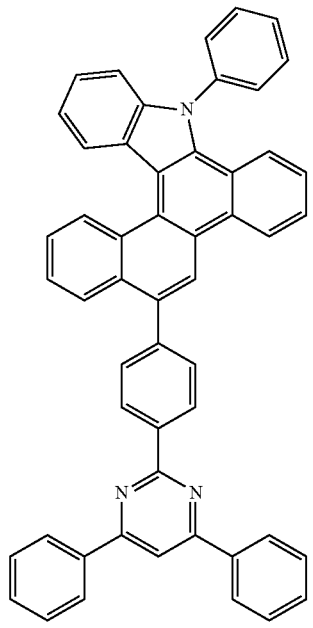
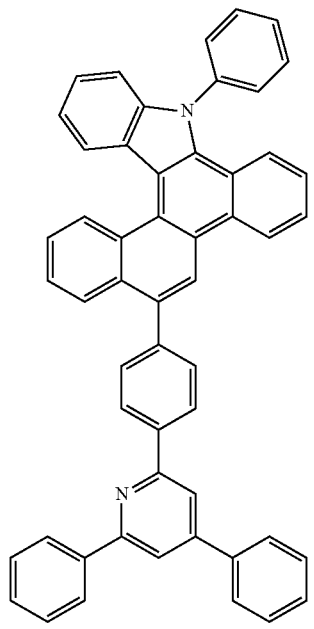
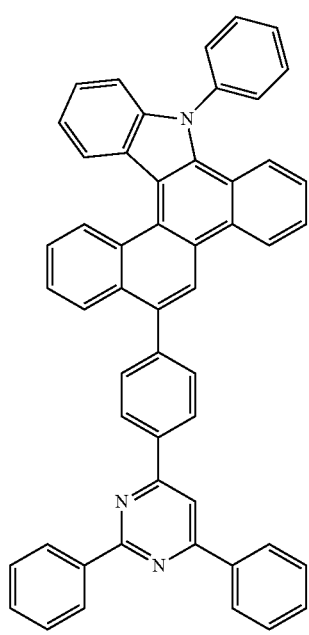
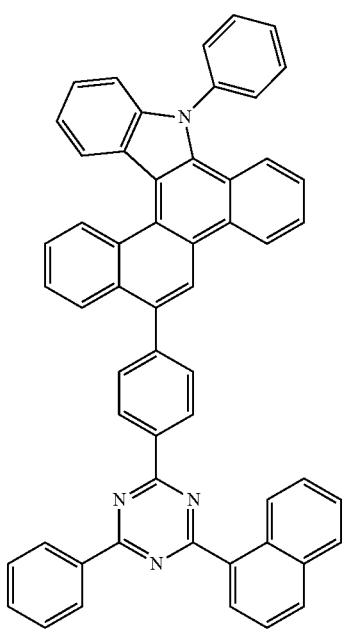

103
-continued
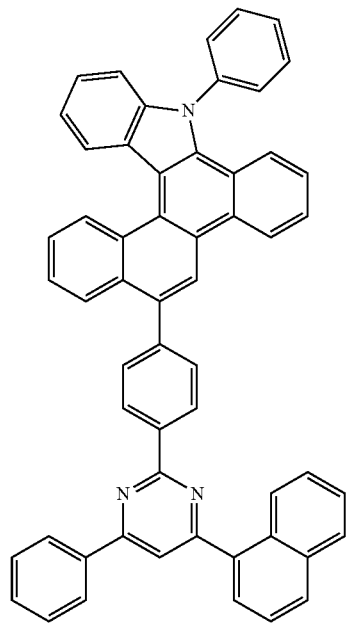
104
-continued
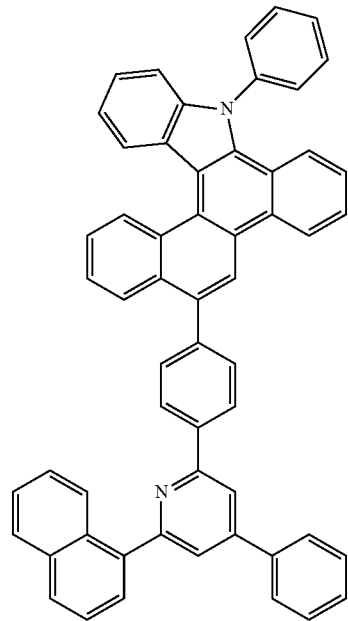
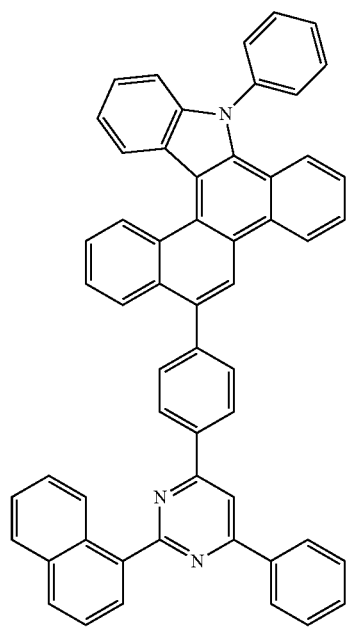
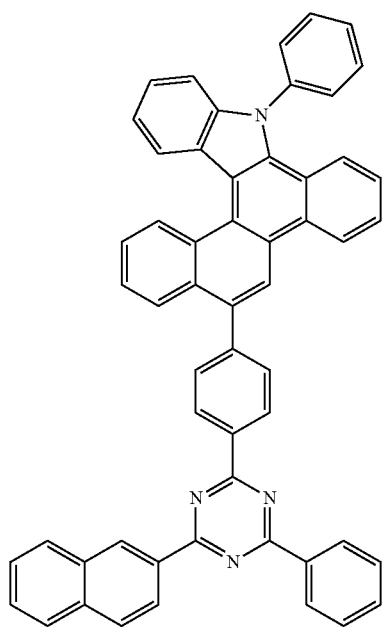

105
-continued
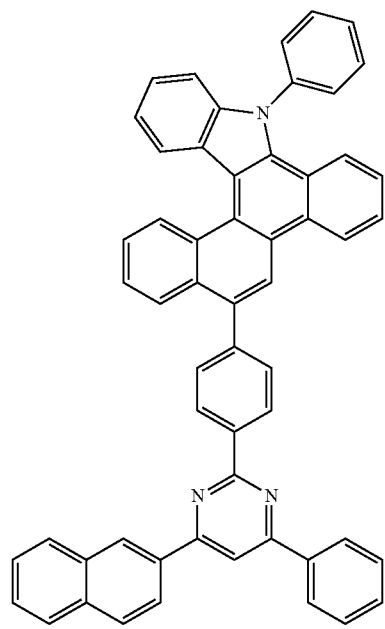
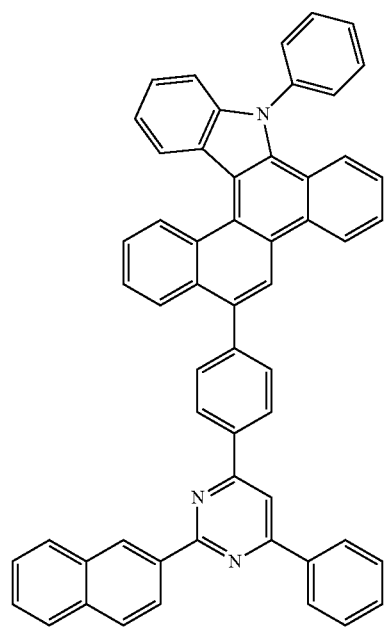
106
-continued
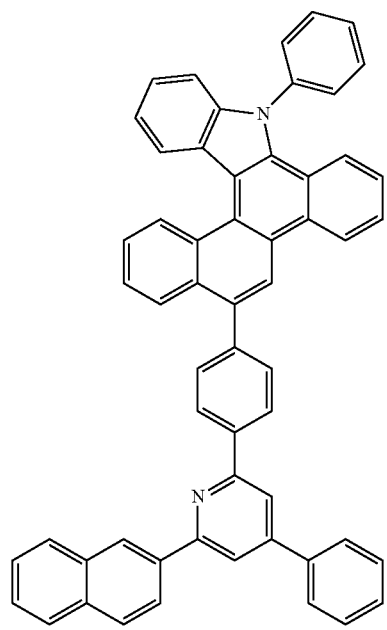
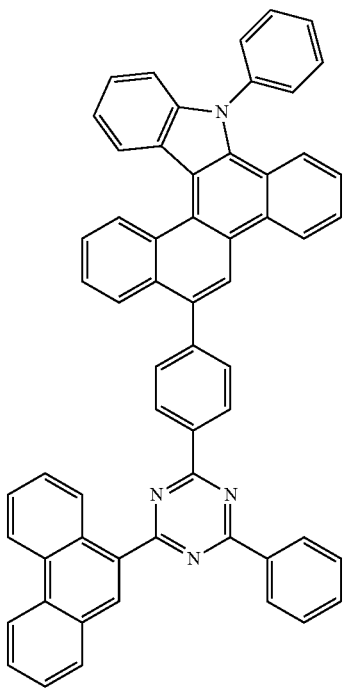

107
-continued
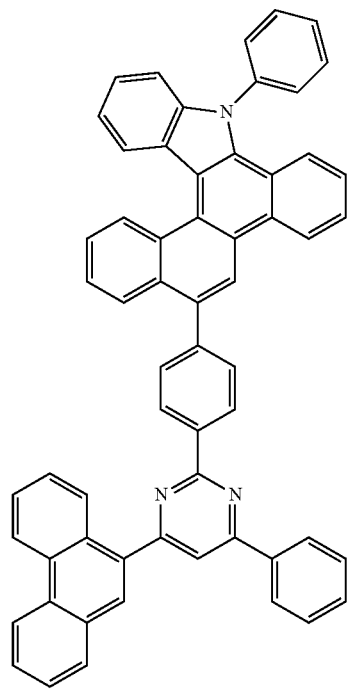
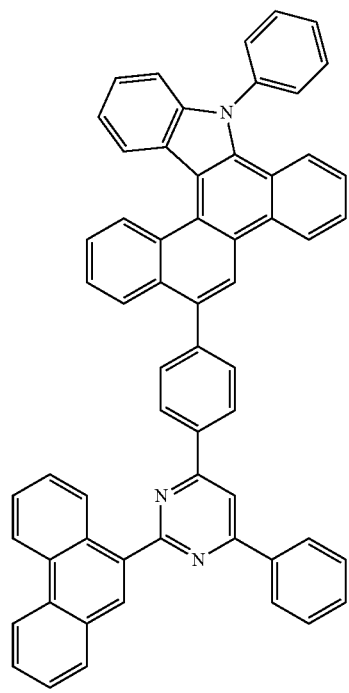
108
-continued
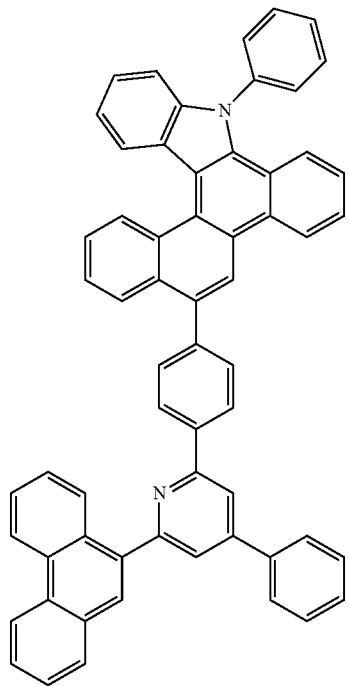 [SMILES: c1ccc(-c2cc(-c3ccc(-c4cc5c6ccccc6c6c(c7ccccc7n6-c6ccccc6)c5c5ccccc45)cc3)nc(-c3cc4ccccc4c4ccccc34)c2)cc1]
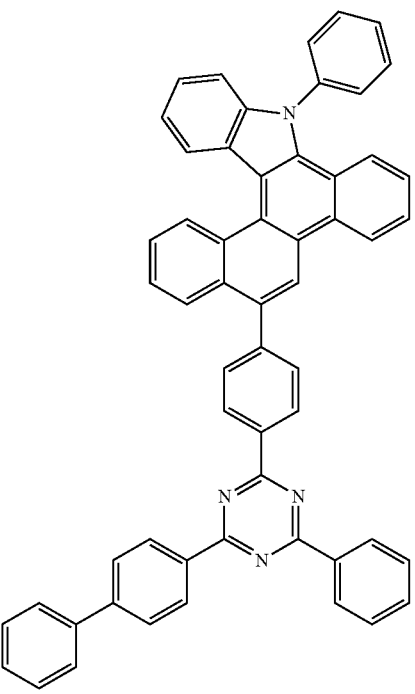

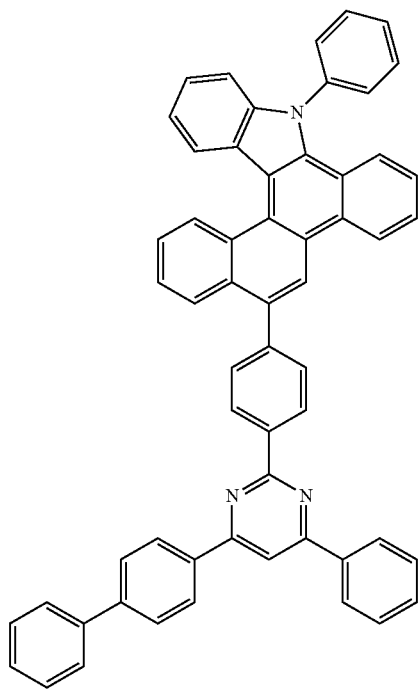
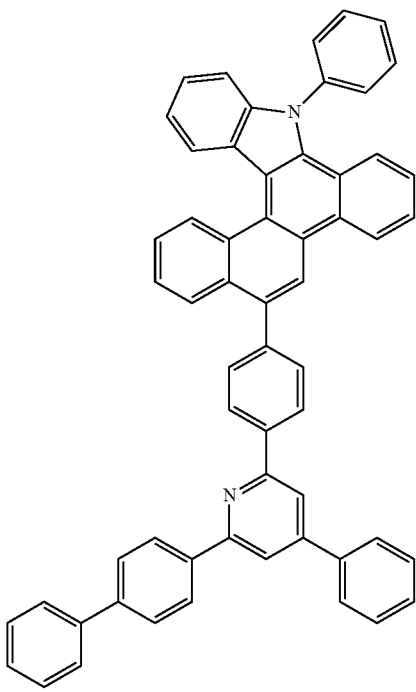
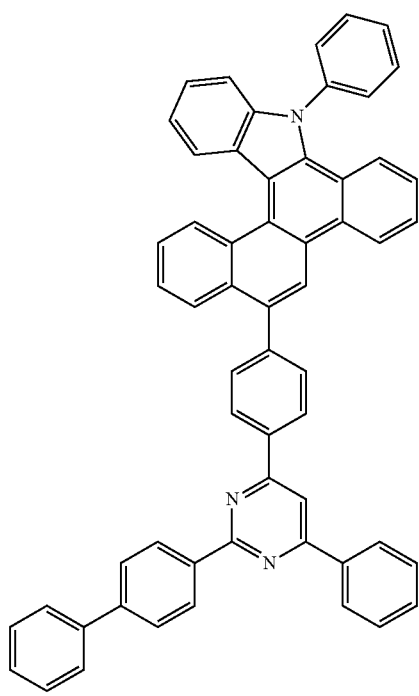
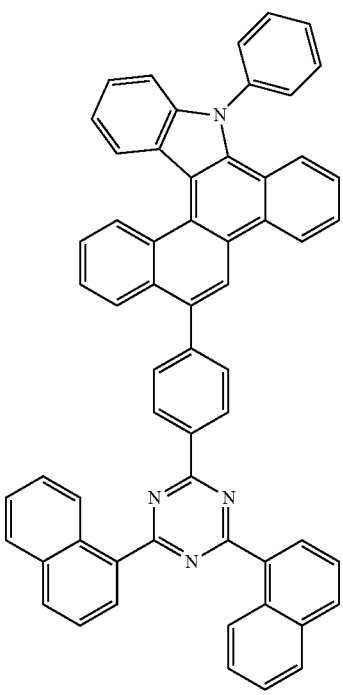

111
-continued
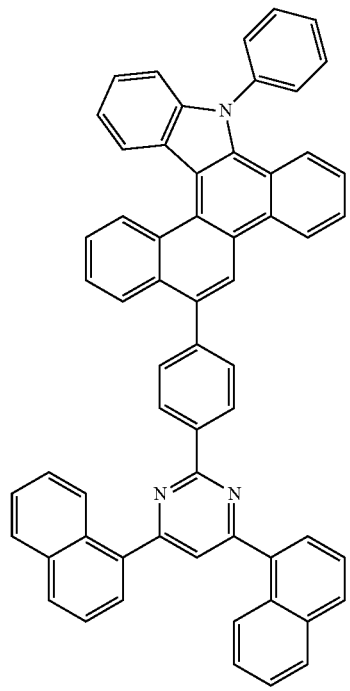
112
-continued
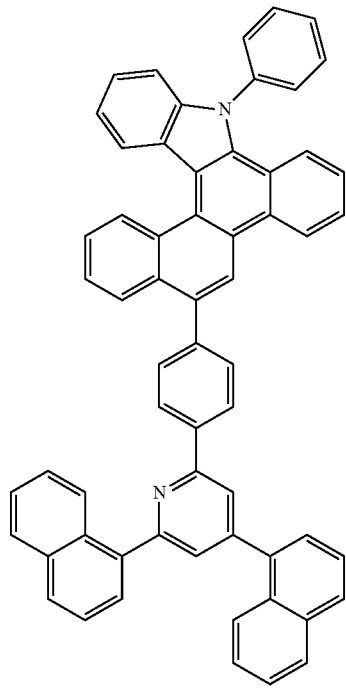
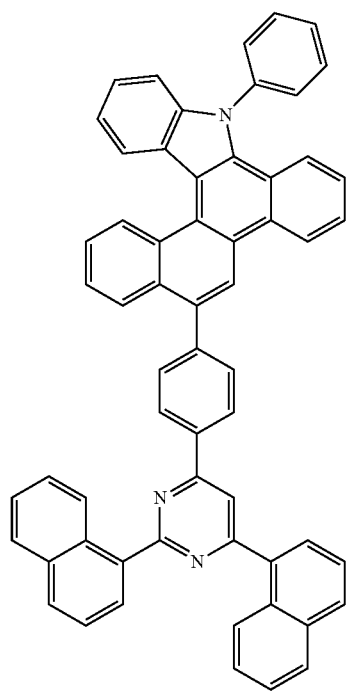
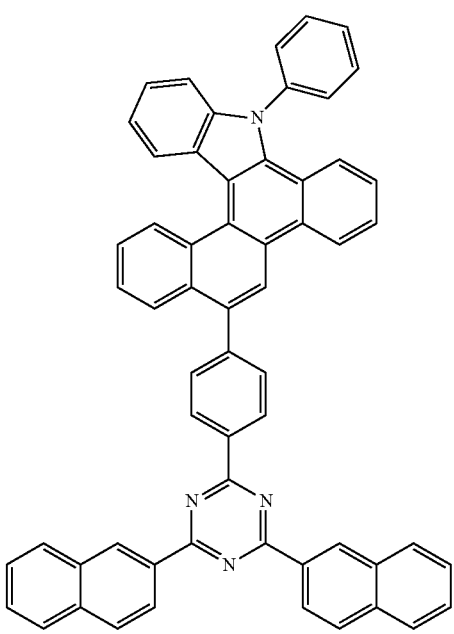

113
-continued
114
-continued
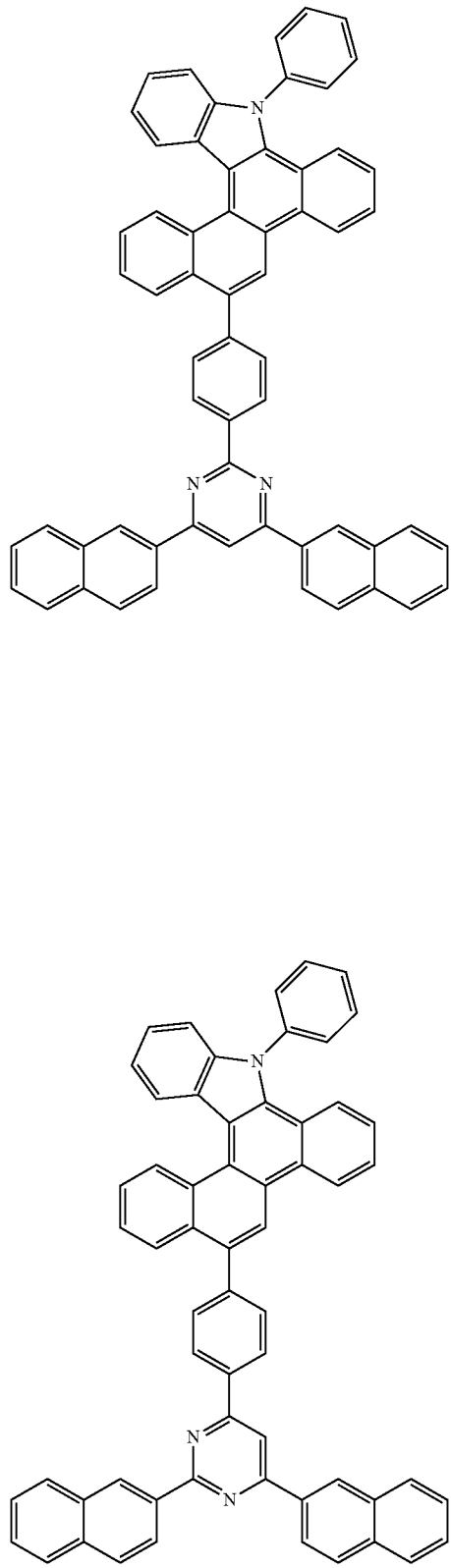
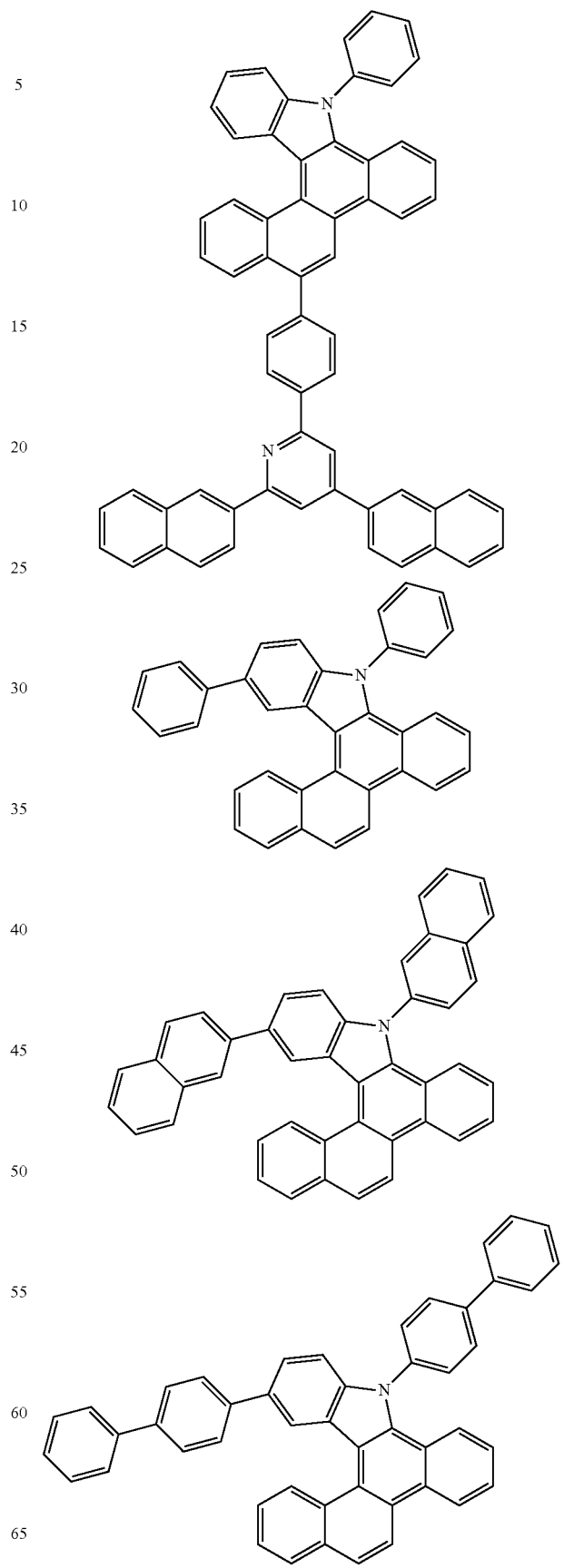

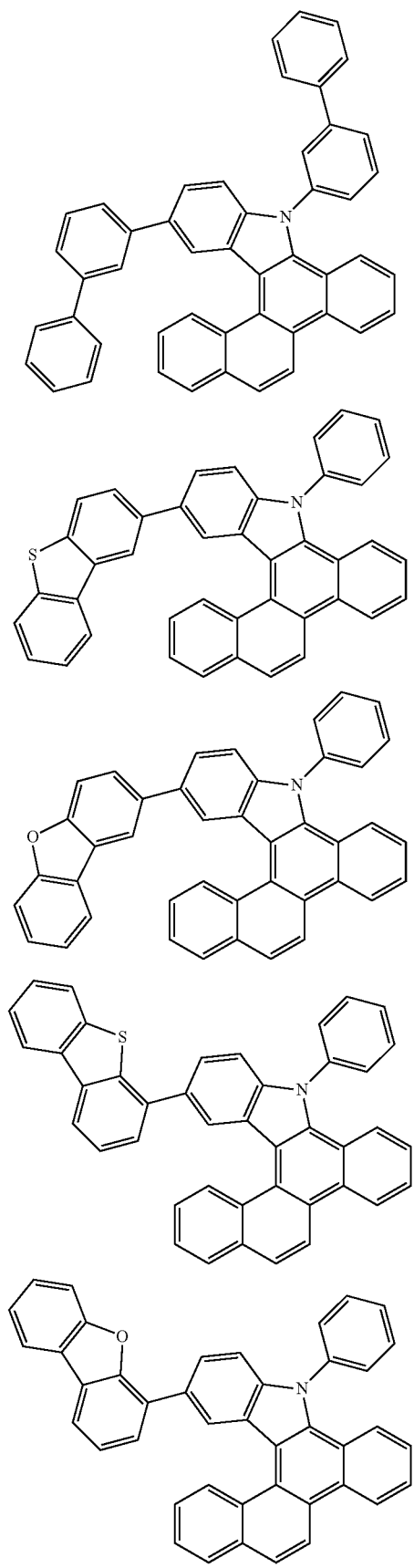
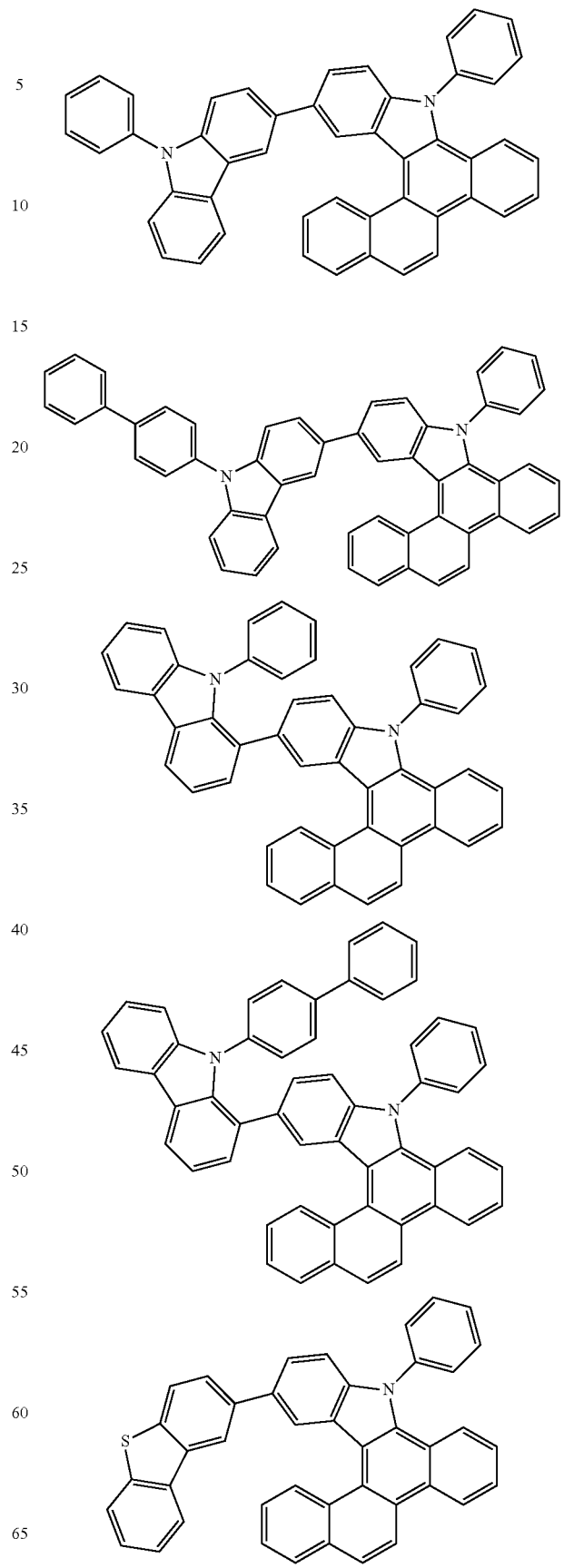

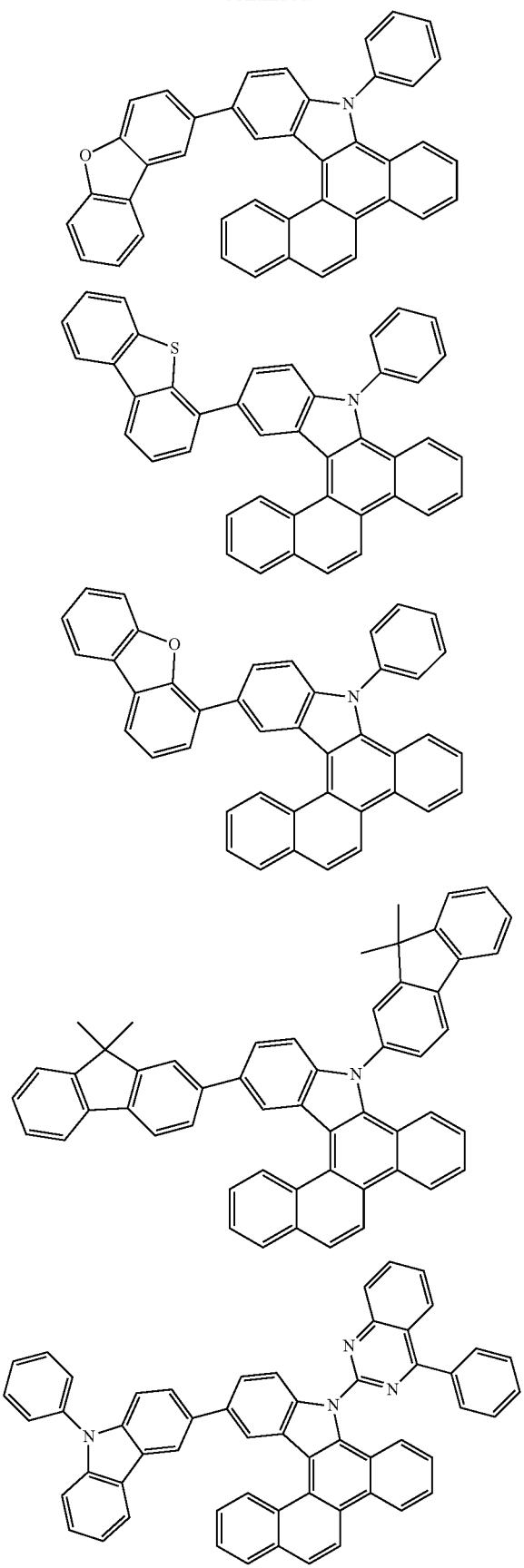
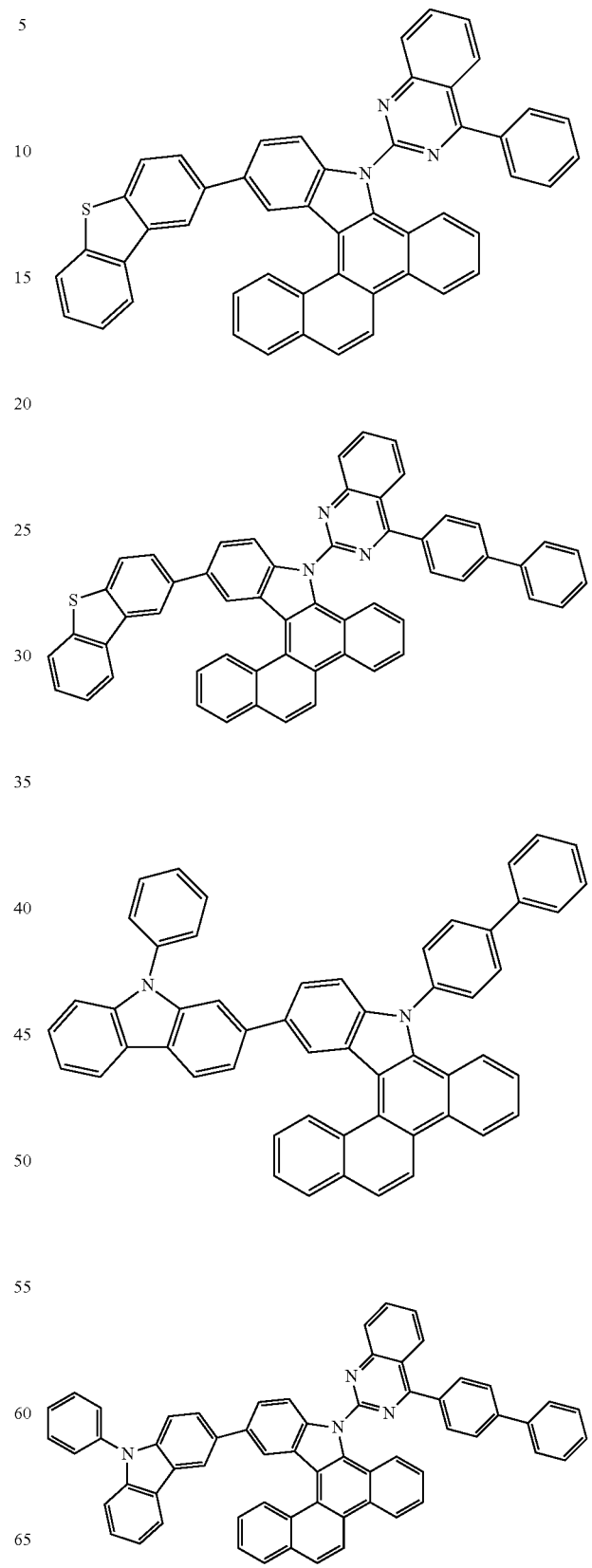

119
-continued
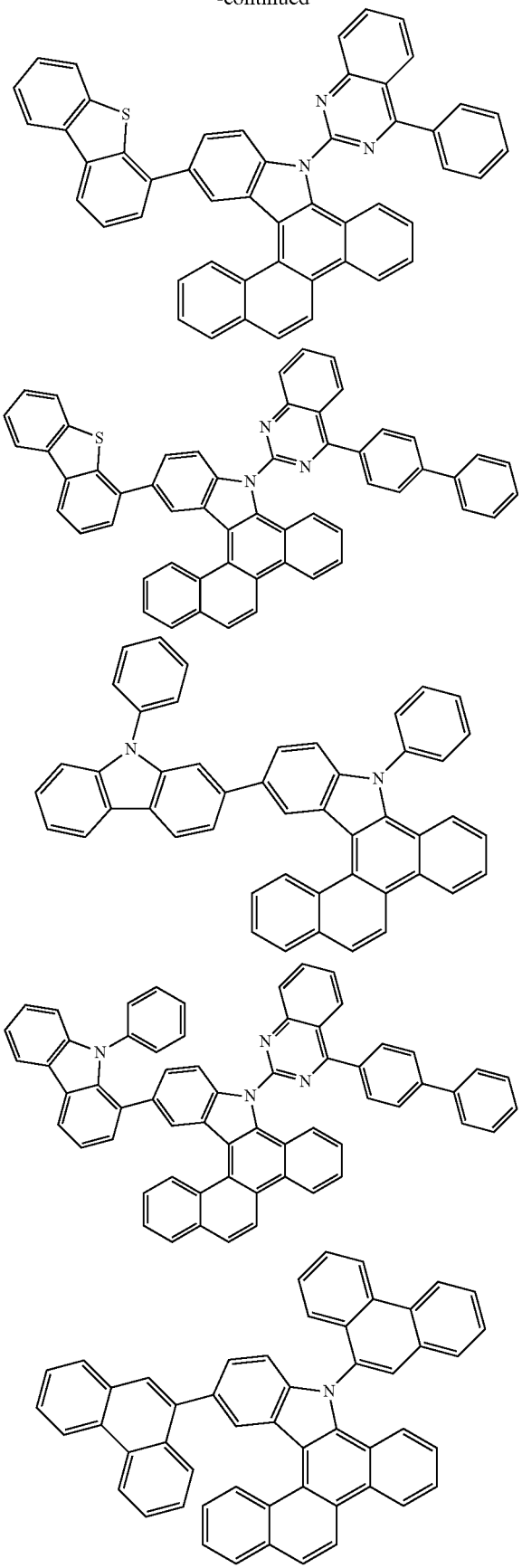
120
-continued
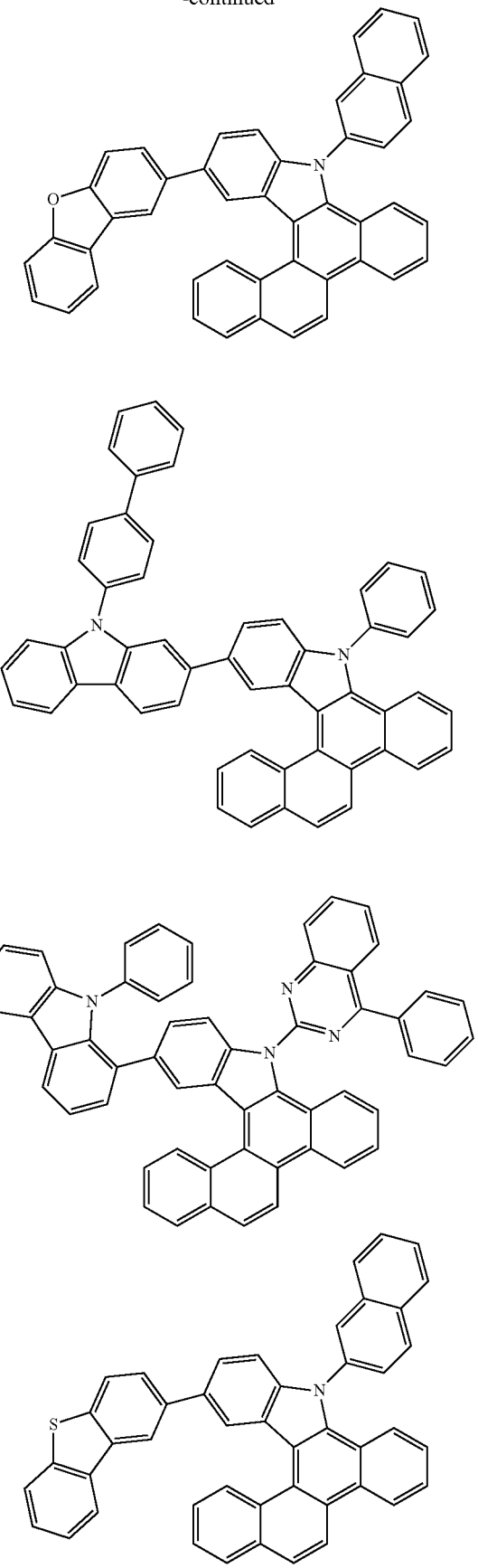

121
-continued
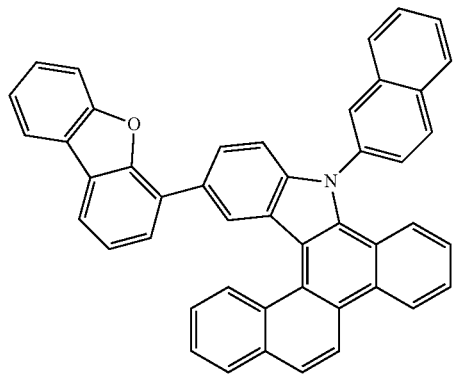
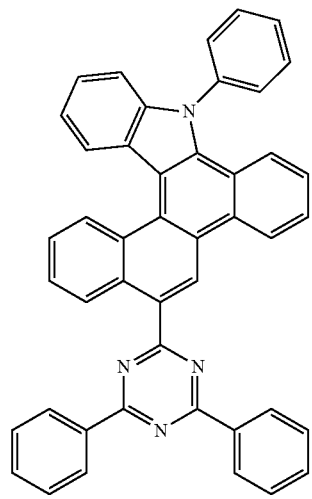
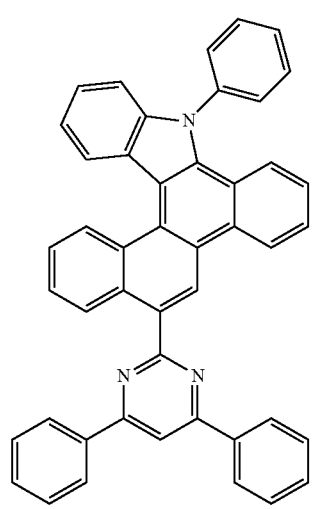
122
-continued
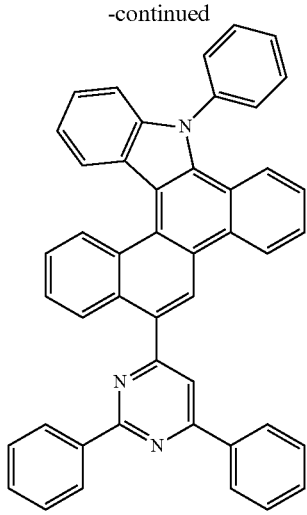
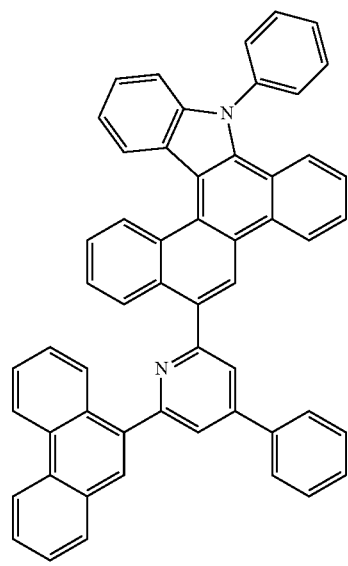
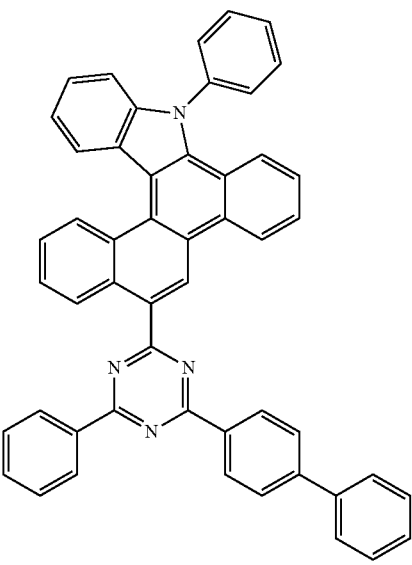

123
-continued
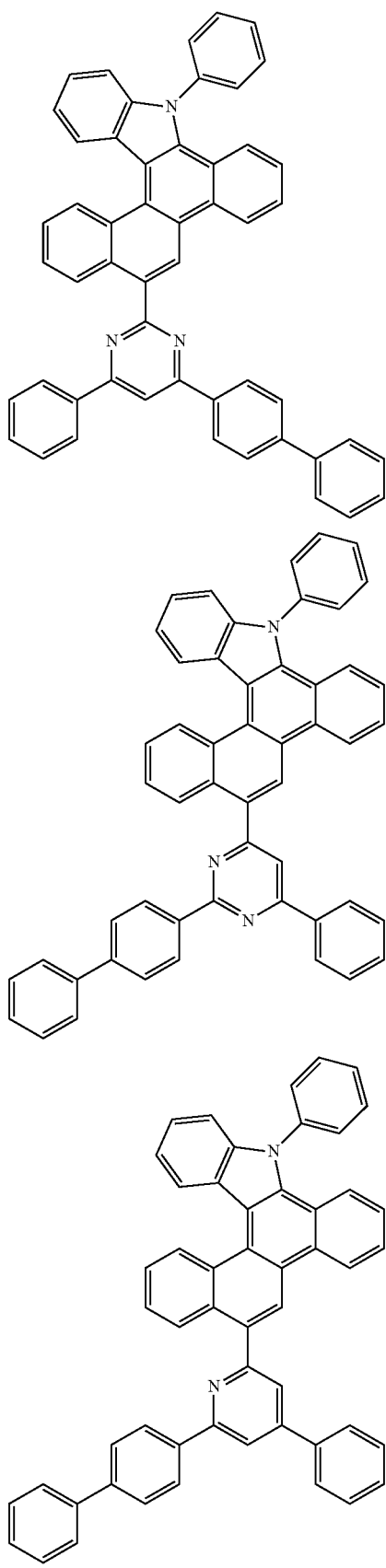
124
-continued
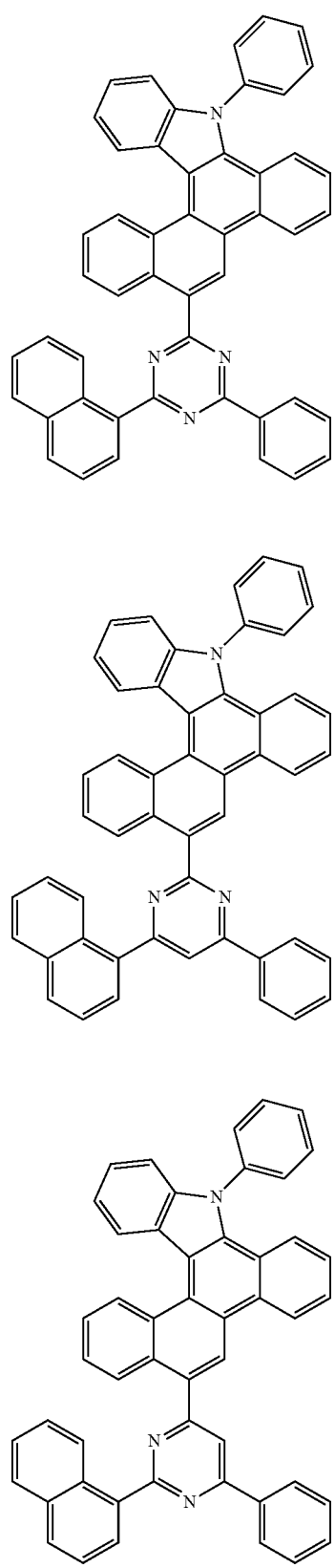

125
-continued
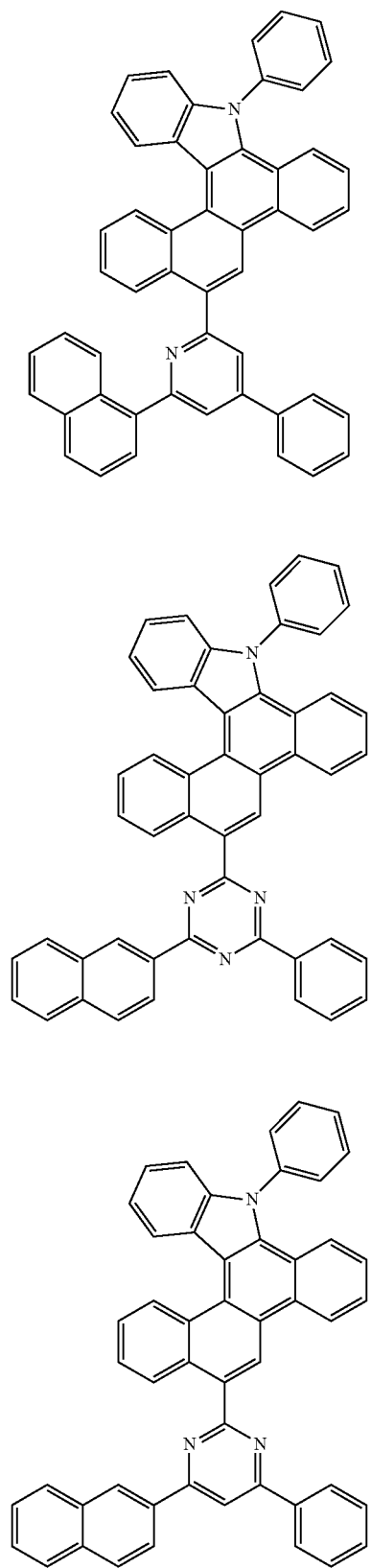
126
-continued
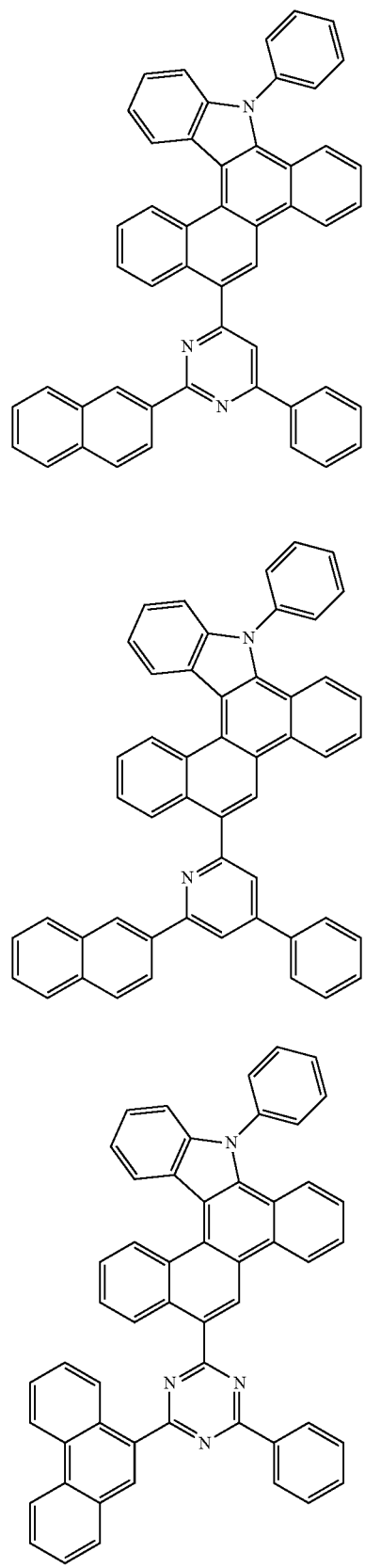

127
-continued
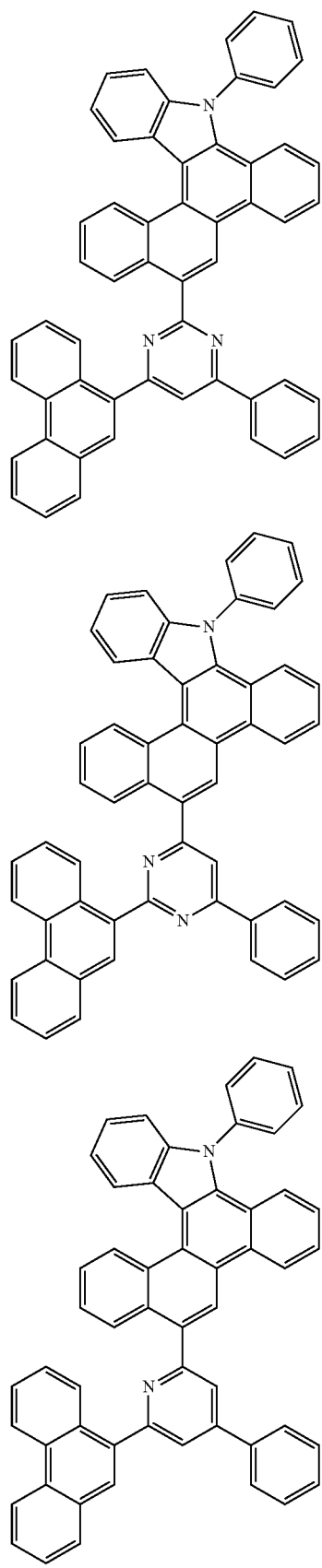 [SMILES: c1ccc(-c2nc(-c3cc4ccccc4c4ccccc34)nc(-c3cc4c5ccccc5c5c(c6ccccc6n5-c5ccccc5)c4c4ccccc34)n2)cc1 ; c1ccc(-c2cc(-c3cc4ccccc4c4ccccc34)nc(-c3cc4c5ccccc5c5c(c6ccccc6n5-c5ccccc5)c4c4ccccc34)n2)cc1 ; c1ccc(-c2cc(-c3cc4c5ccccc5c5c(c6ccccc6n5-c5ccccc5)c4c4ccccc34)nc(-c3cc4ccccc4c4ccccc34)n2)cc1]
128
-continued
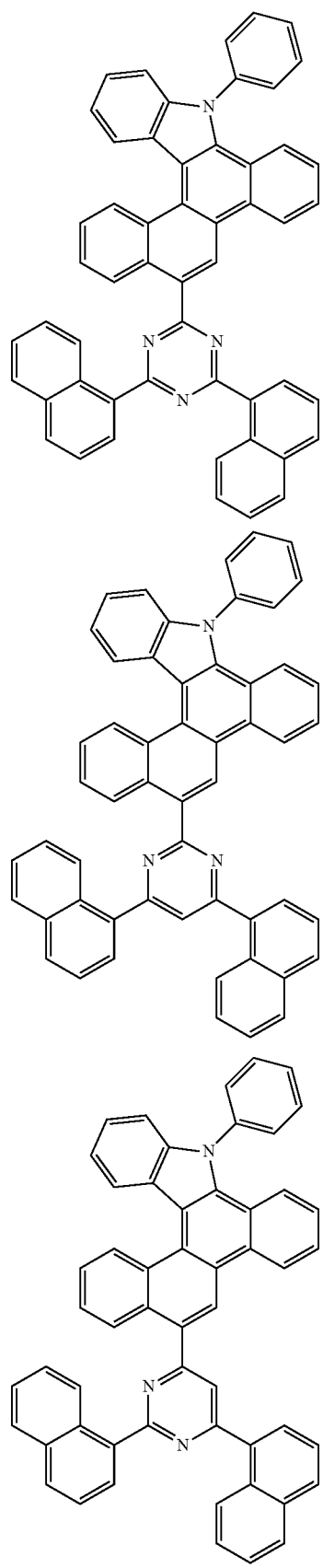

129
-continued
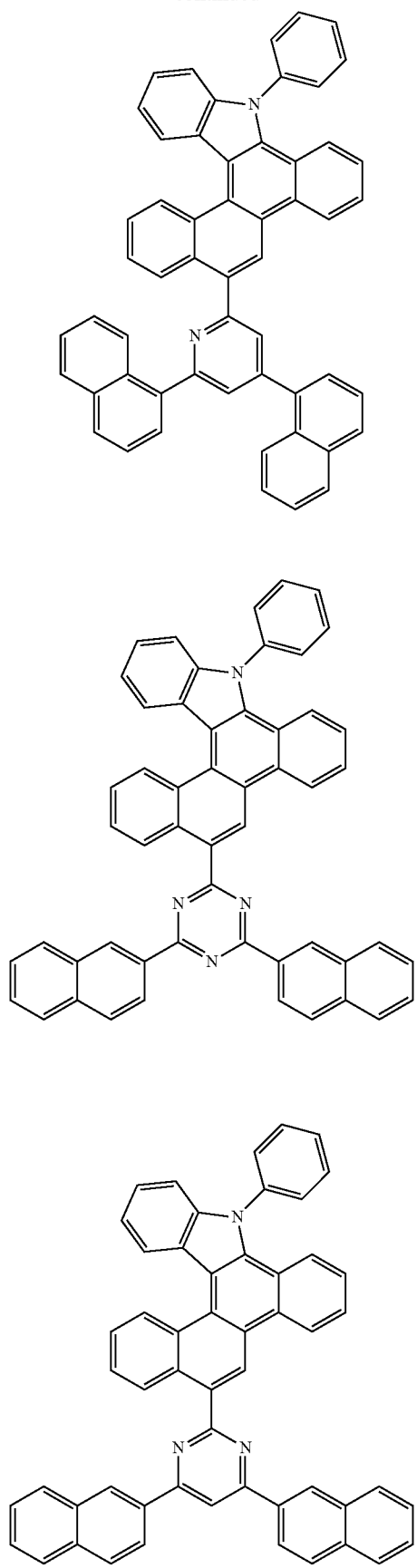
130
-continued
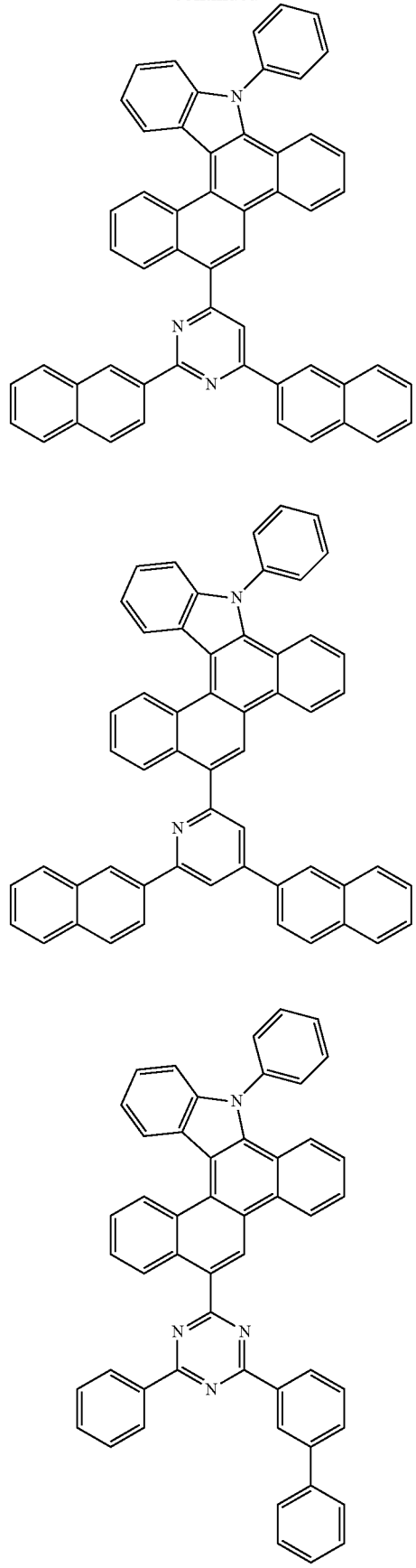

131
-continued
132
-continued
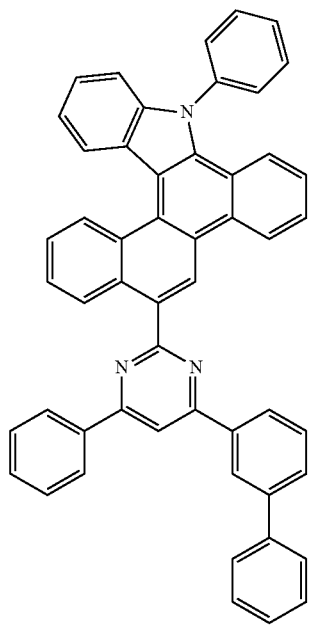
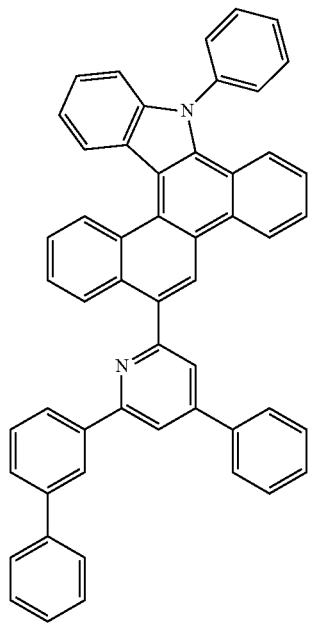
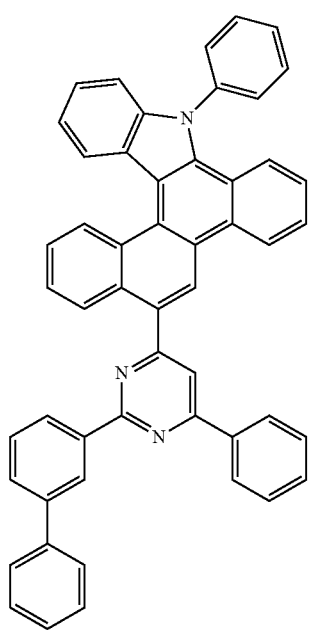
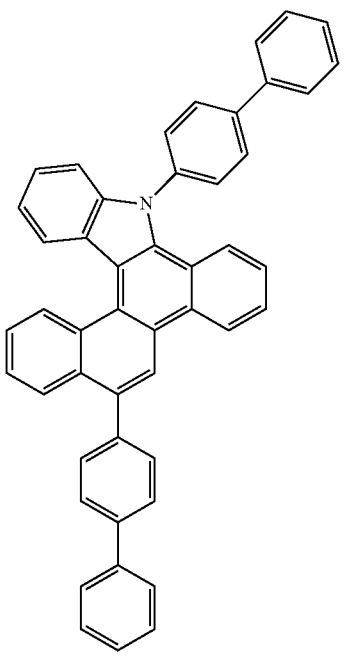

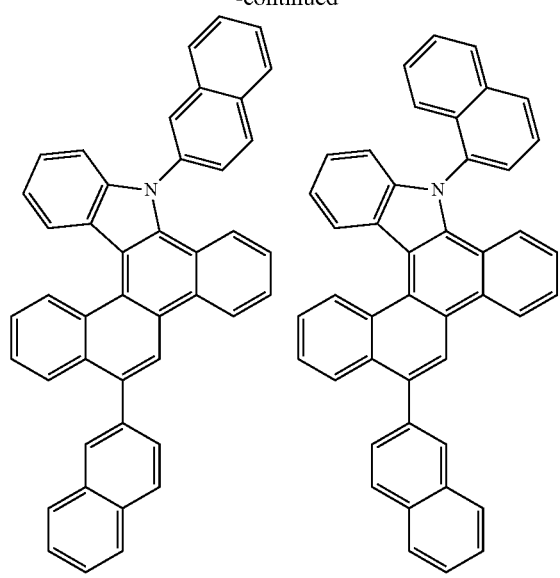
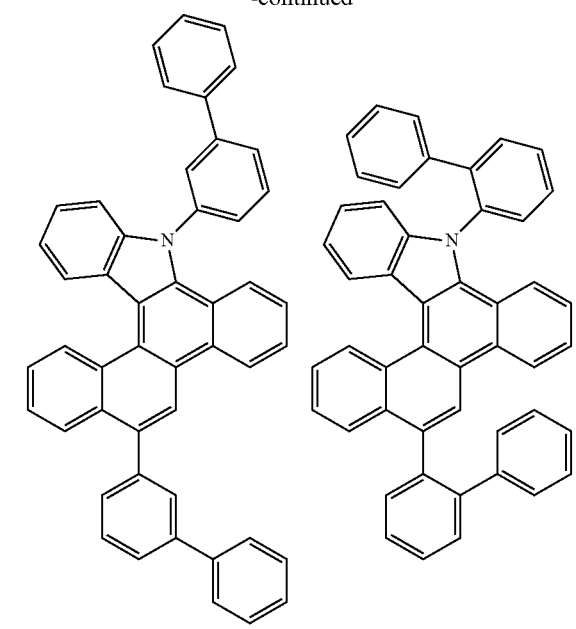
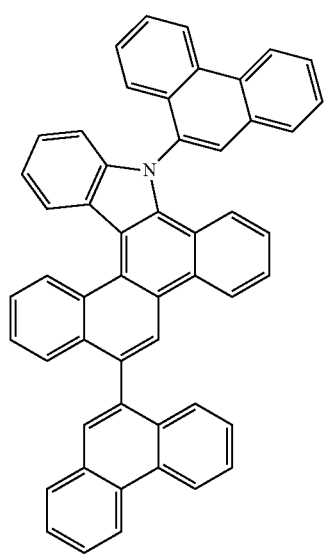
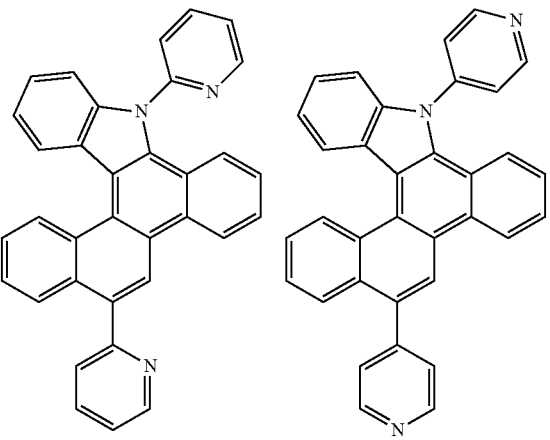
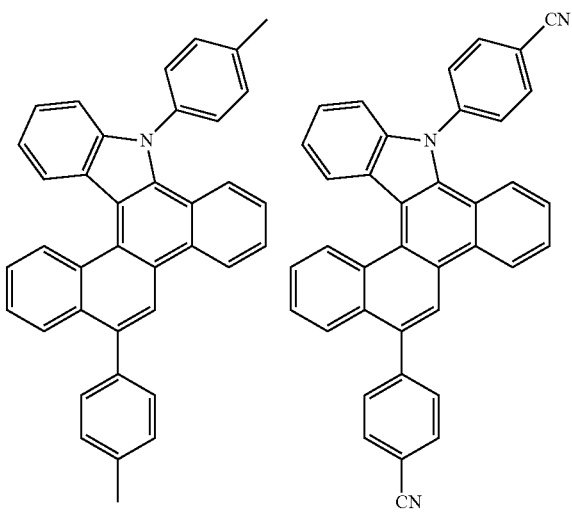
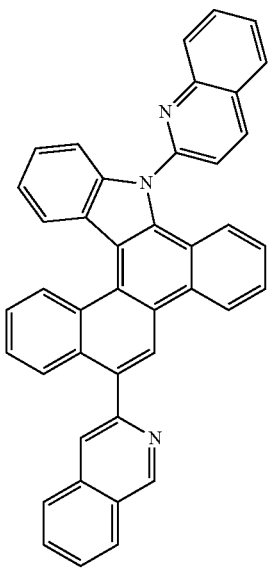

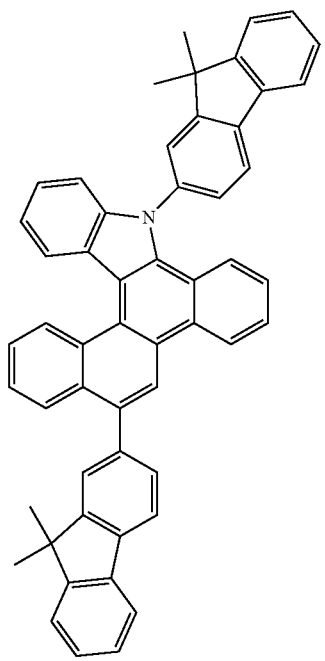
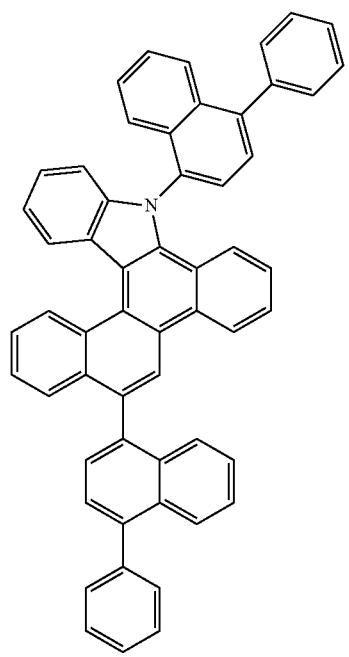
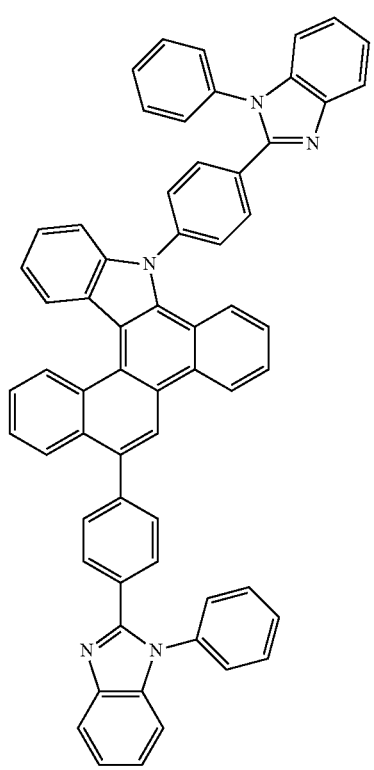
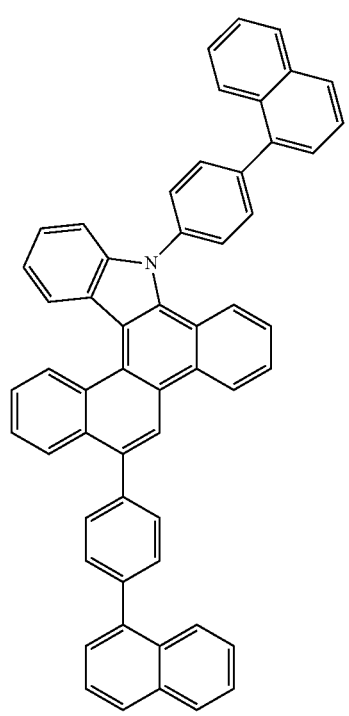

137
-continued
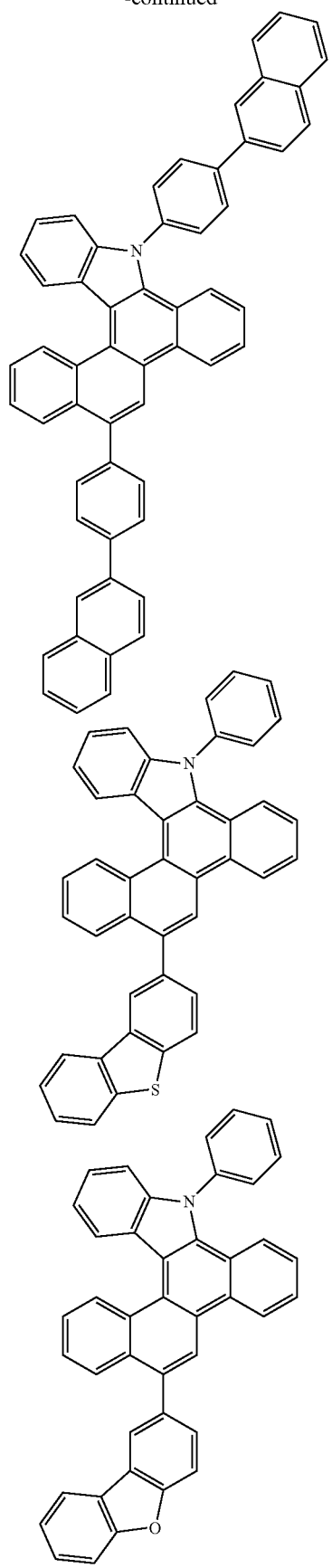
138
-continued
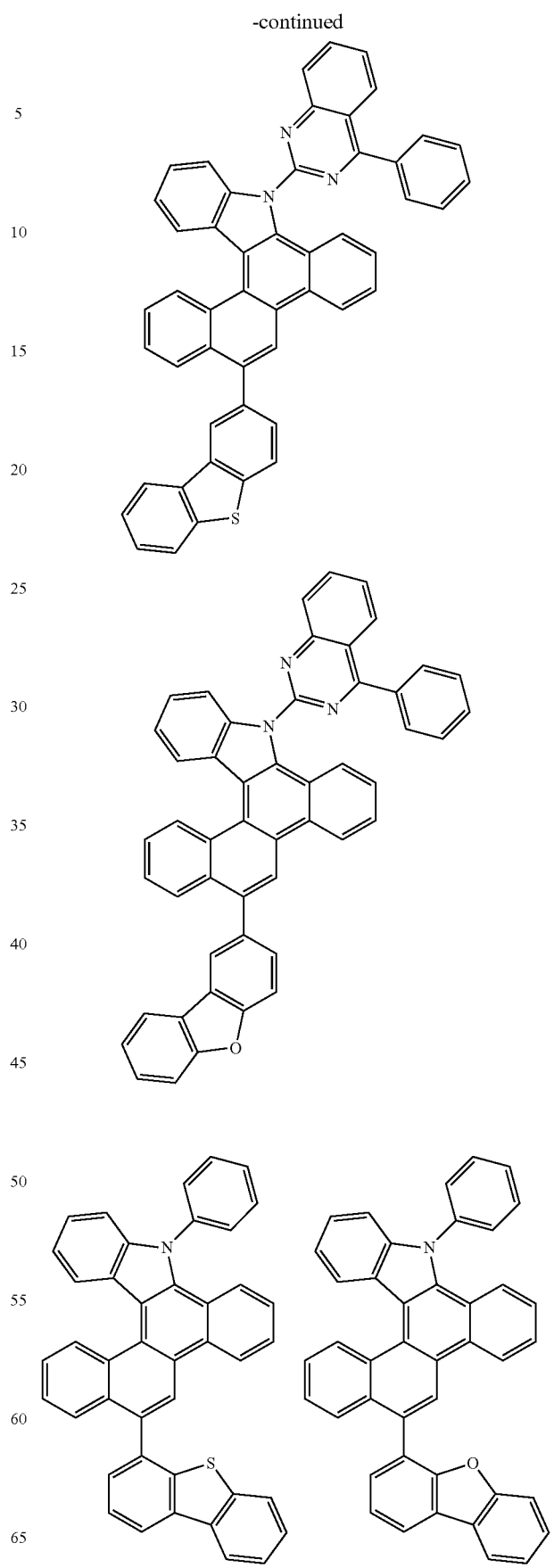

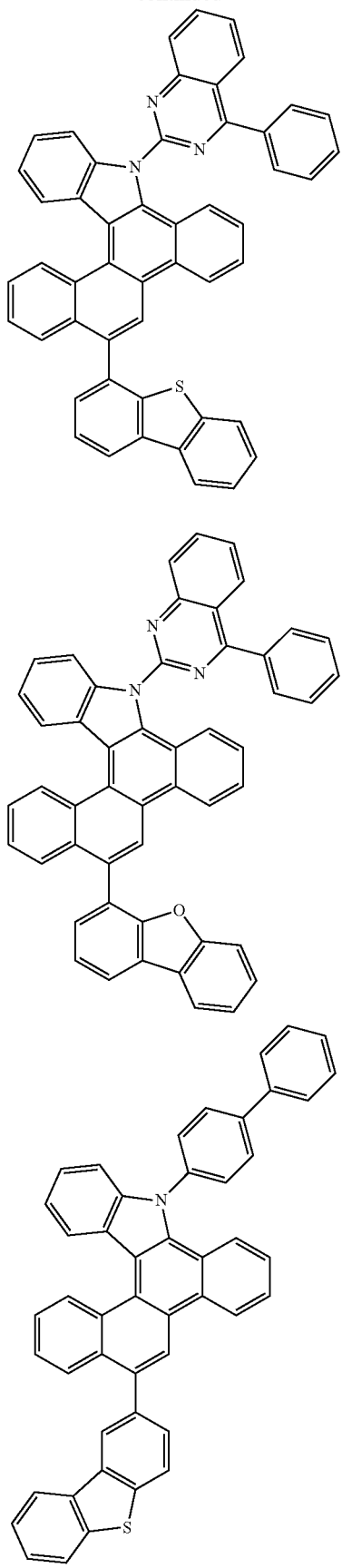
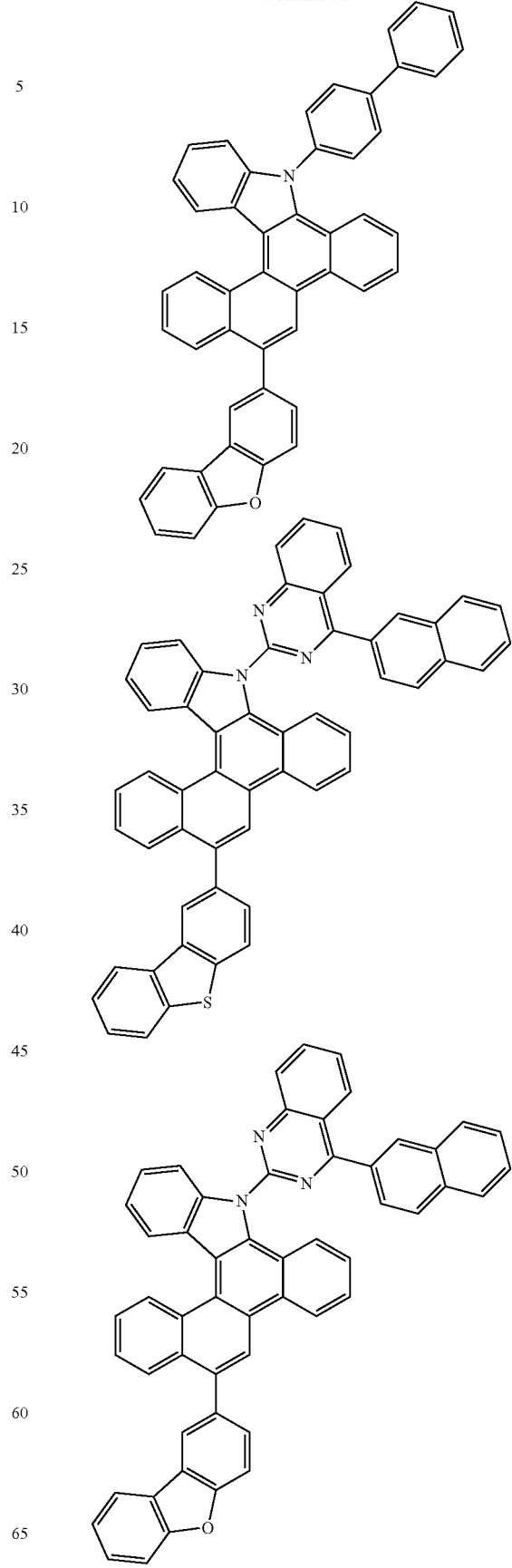

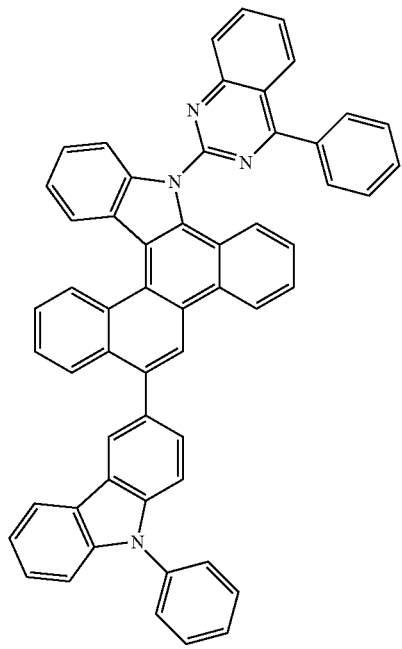
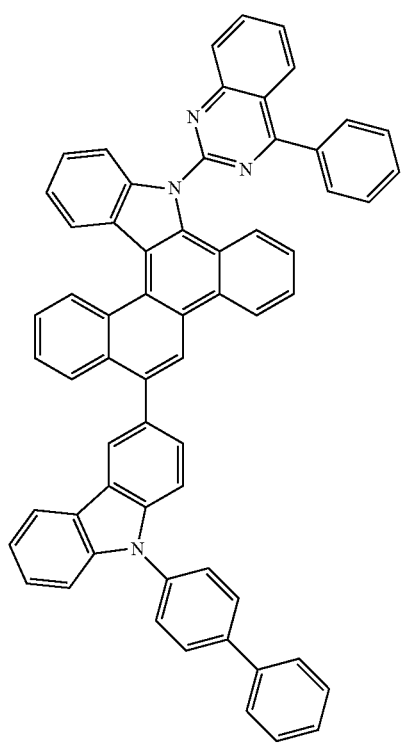
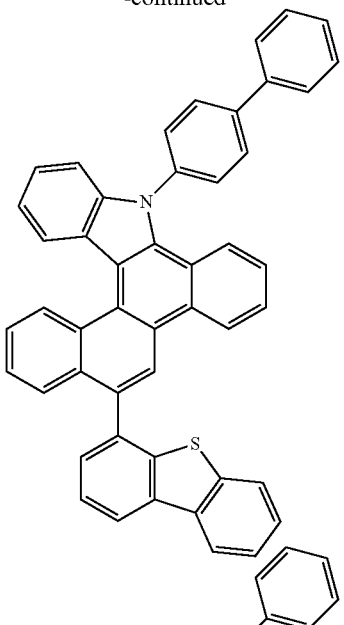
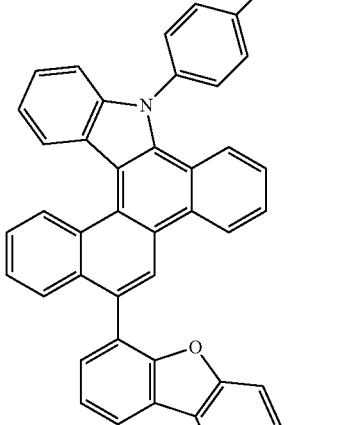
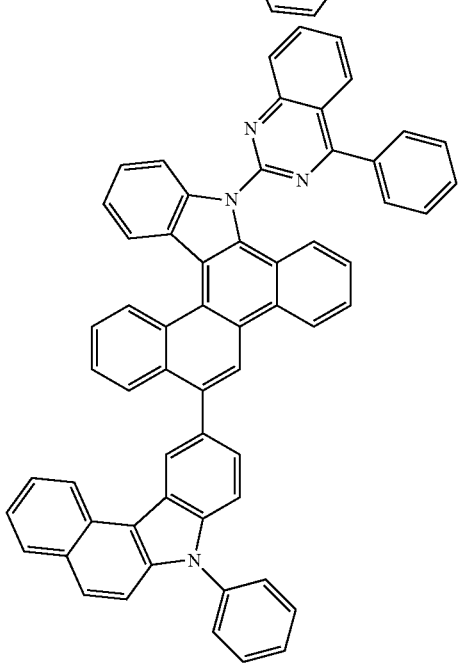

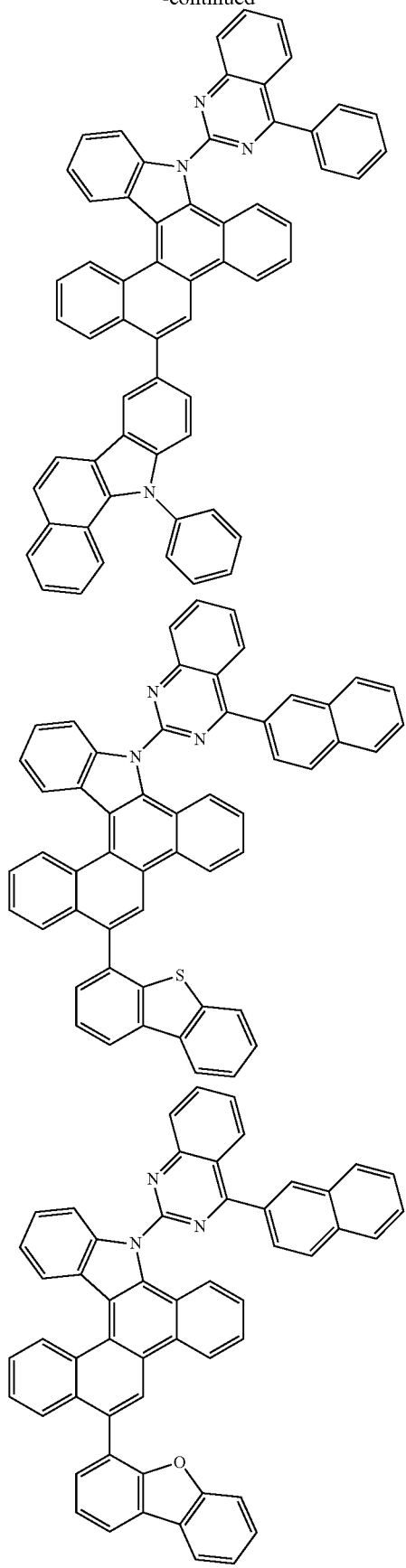
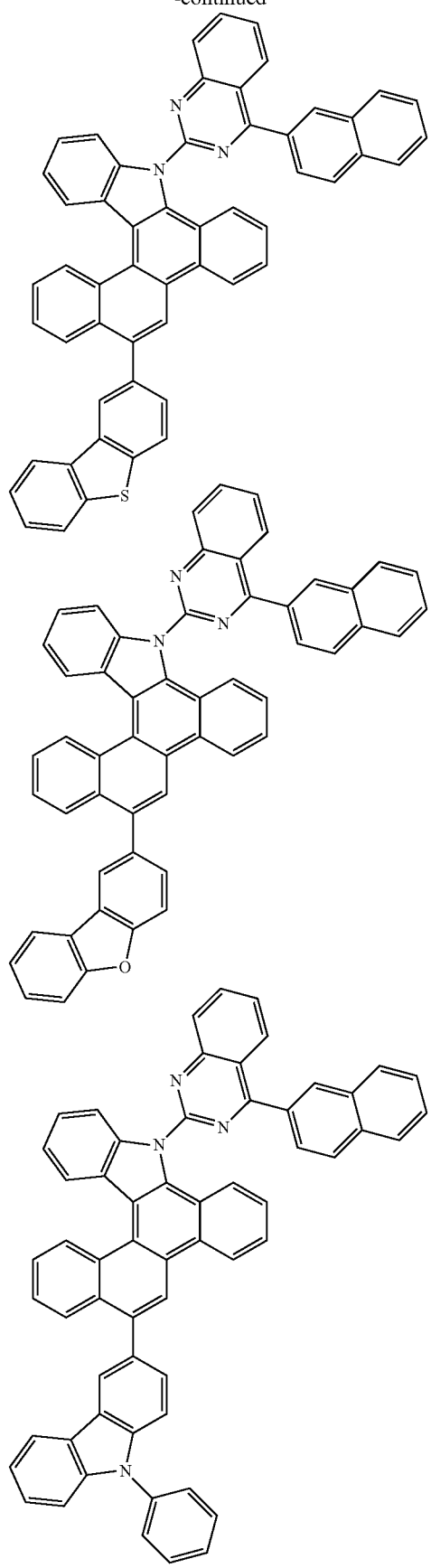

145
-continued
146
-continued
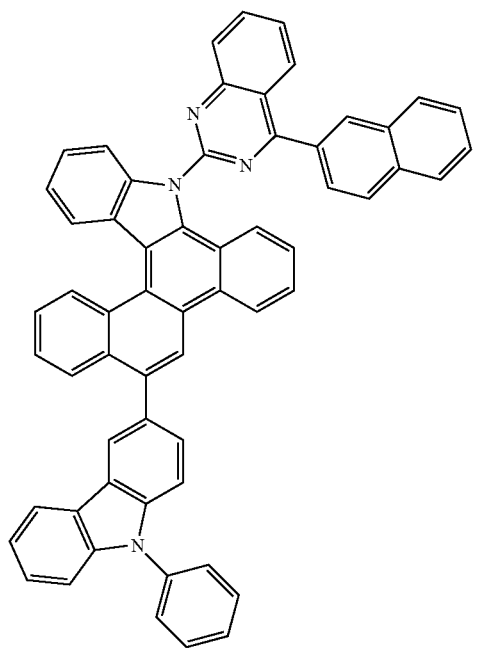
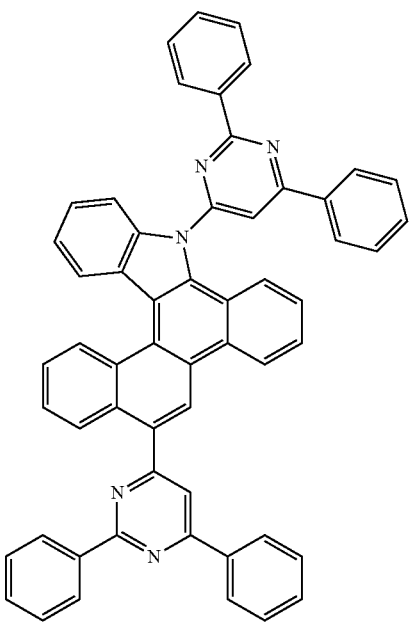
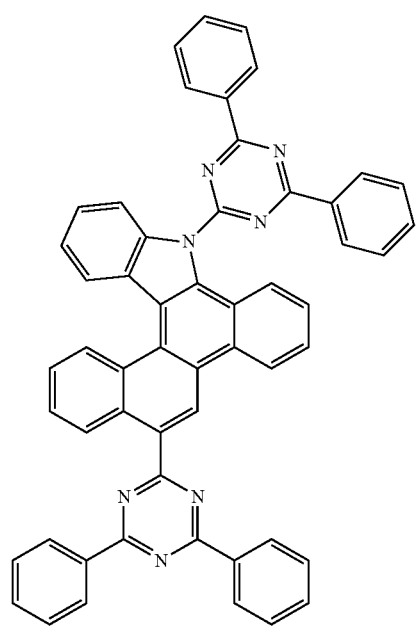

147
-continued
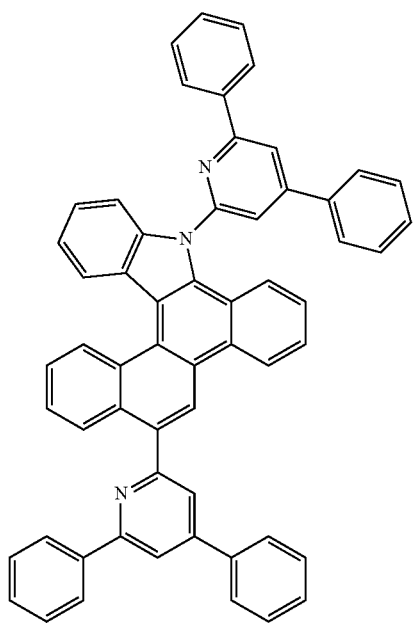
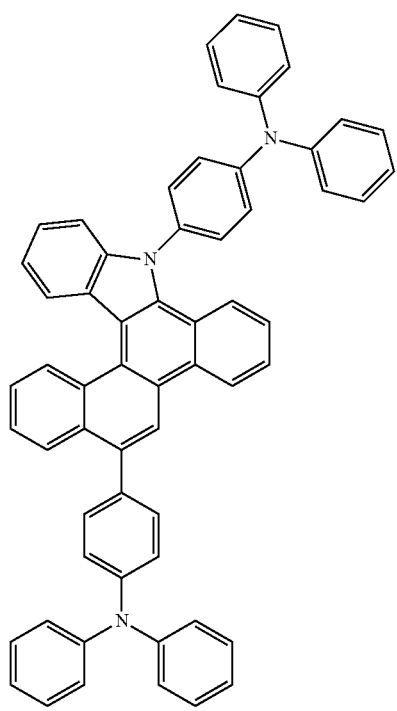
148
-continued
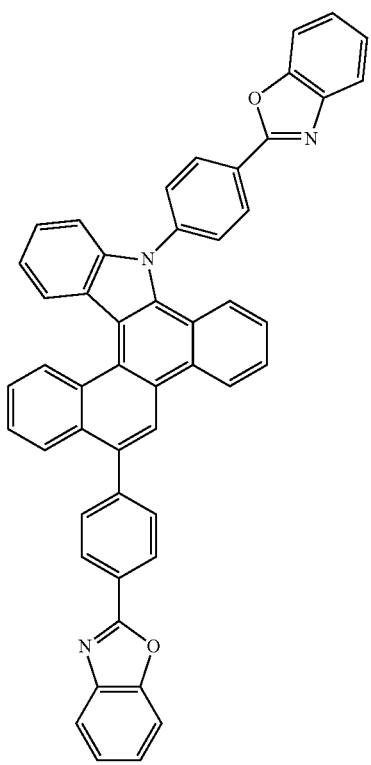
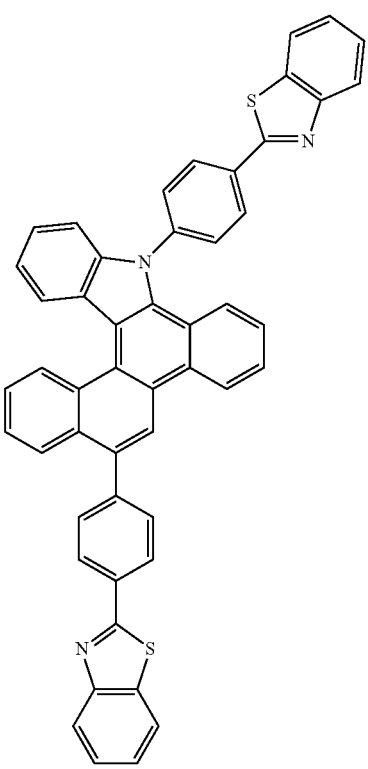

149
-continued
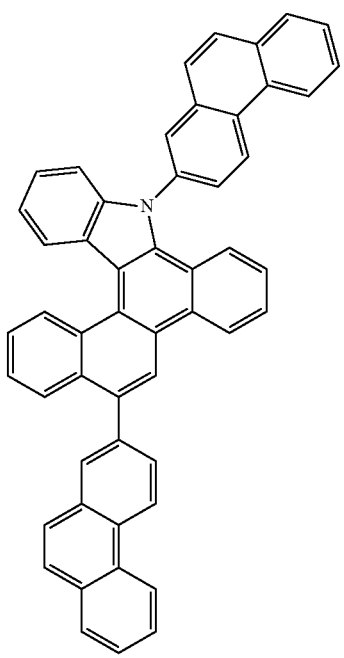
150
-continued
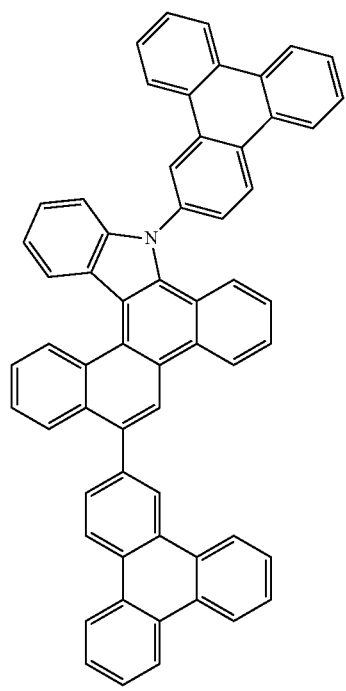
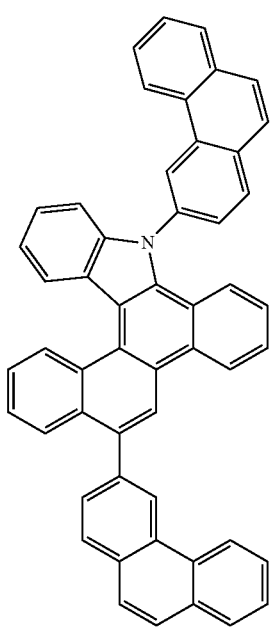
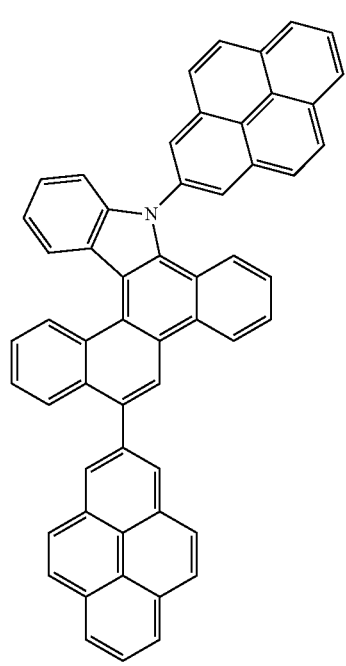

151
-continued
152
-continued
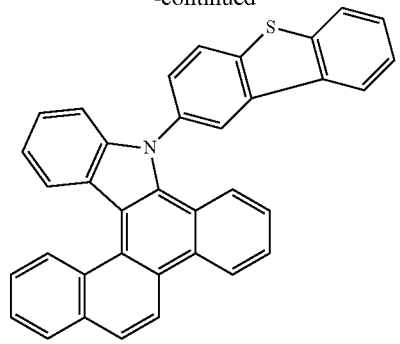
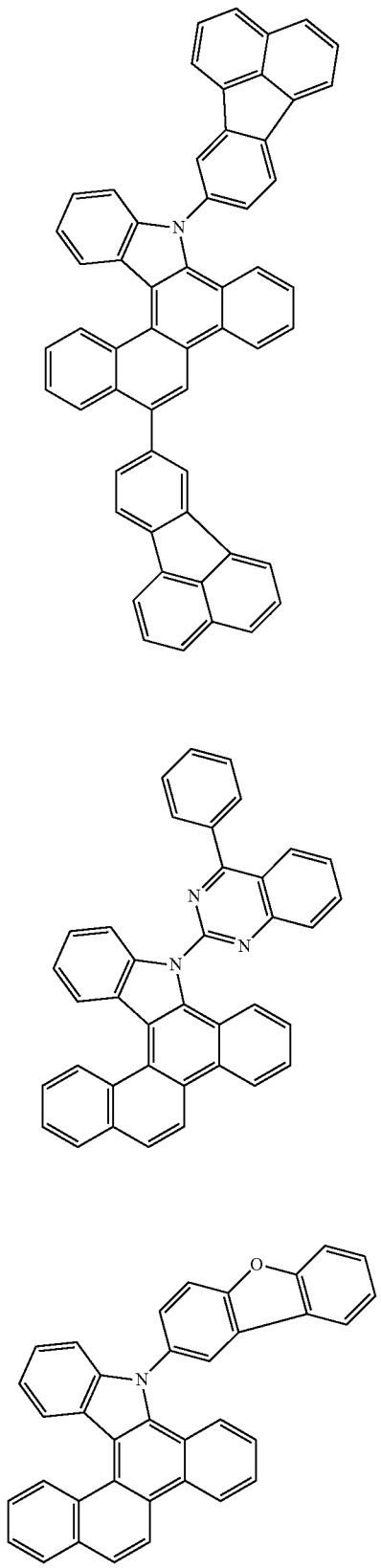
According to an exemplary embodiment of the present application, the compound represented by Chemical Formula 1 is any one selected from the structural formulae of the following Group 2.
[Group 2]
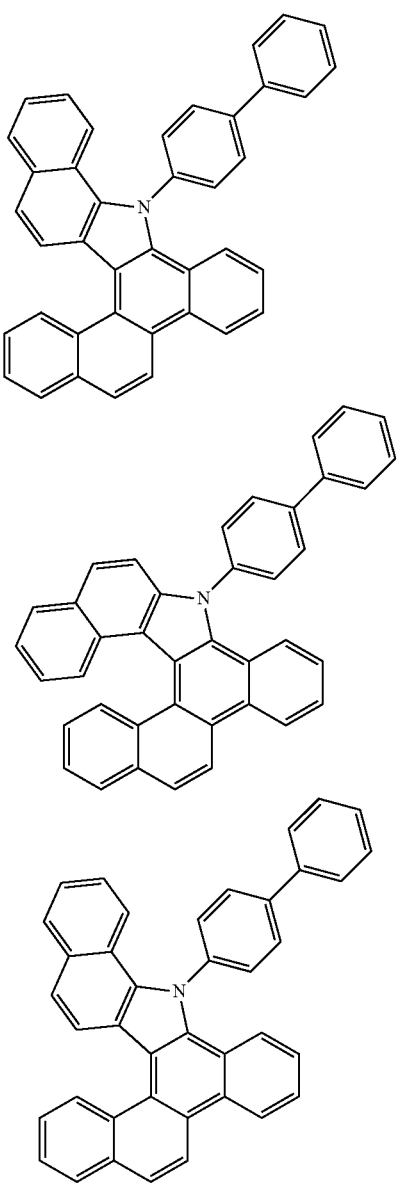

153
-continued
154
-continued
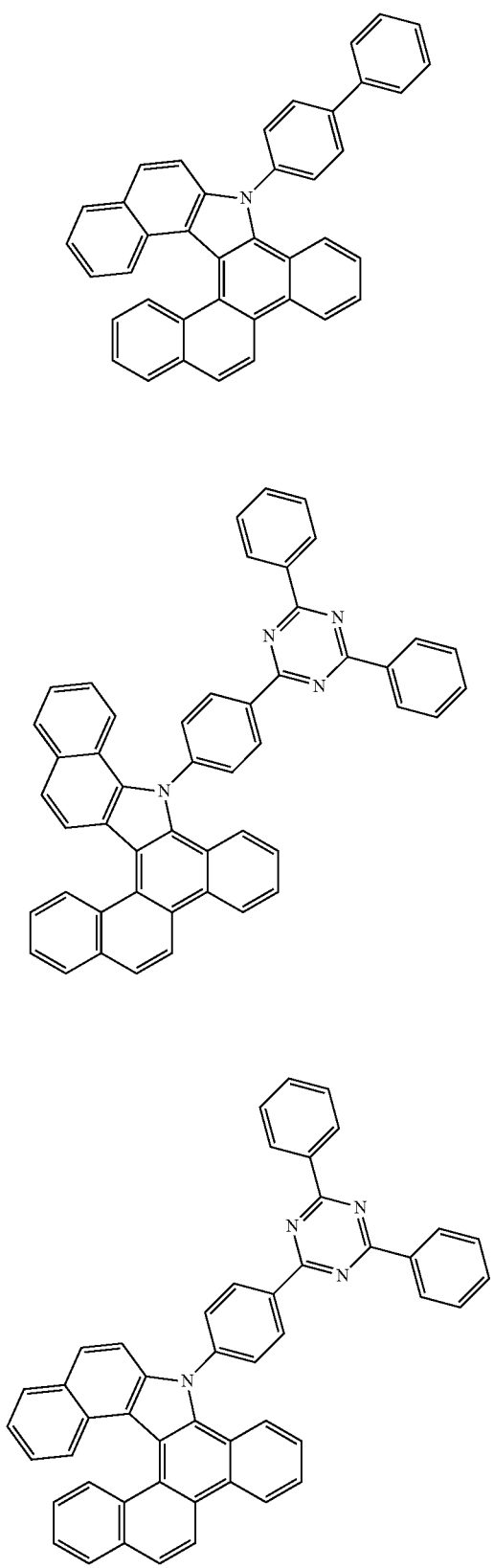
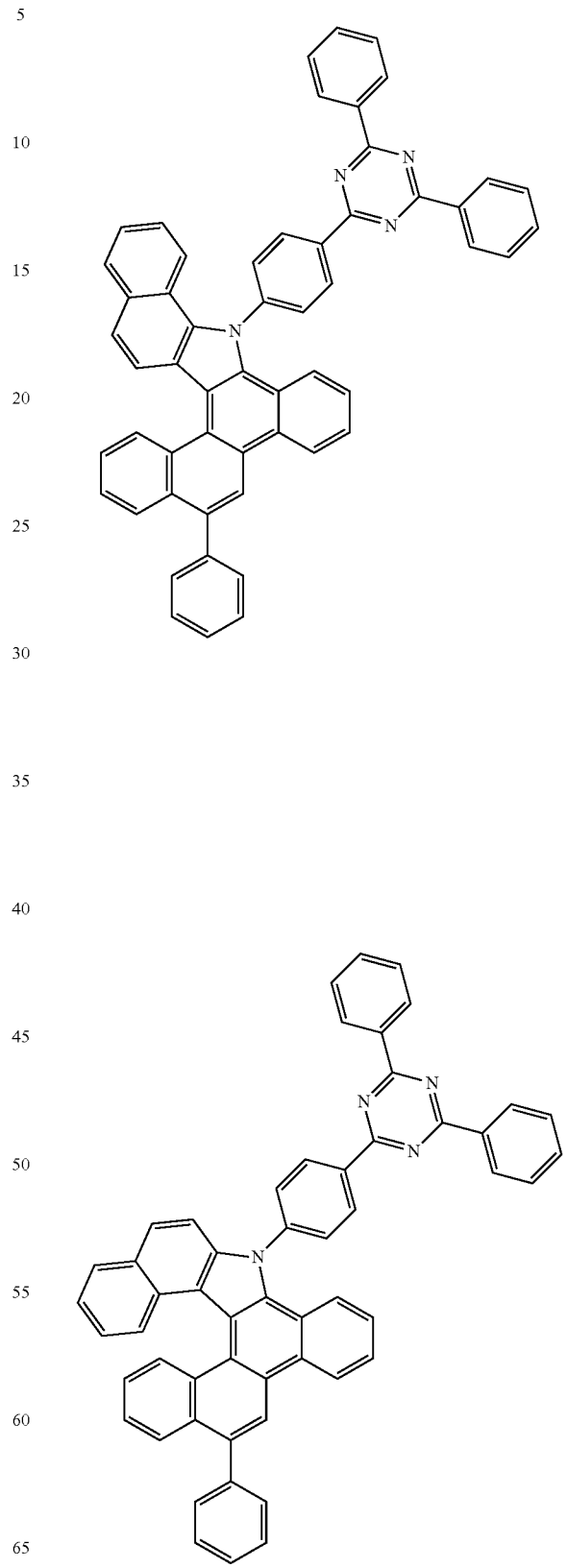

155
-continued
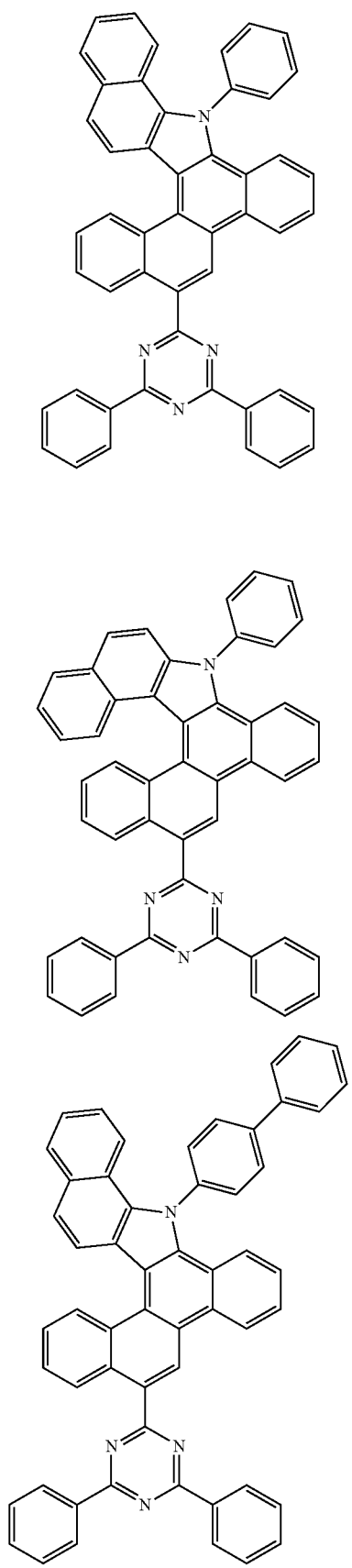
156
-continued
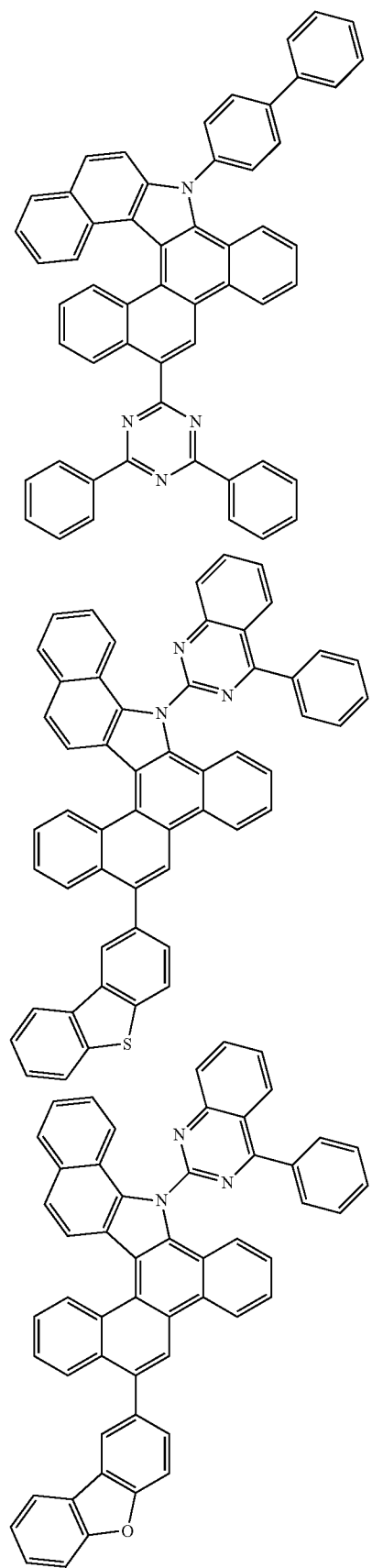

157
-continued
158
-continued
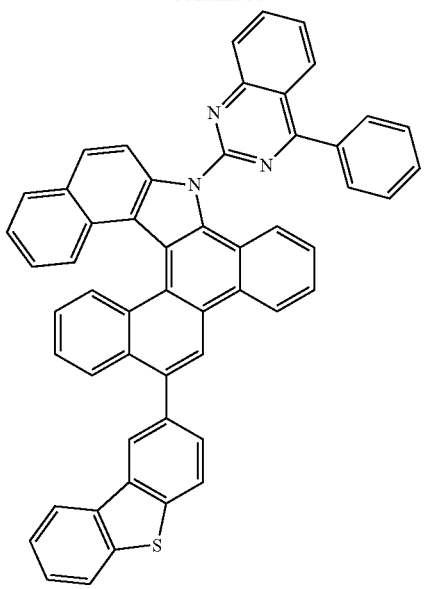
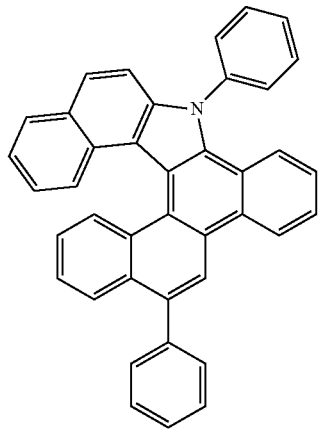
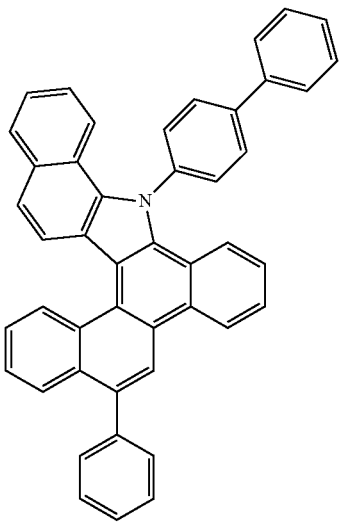
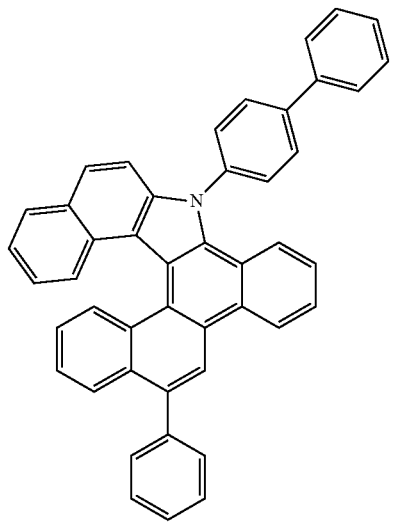

159
-continued
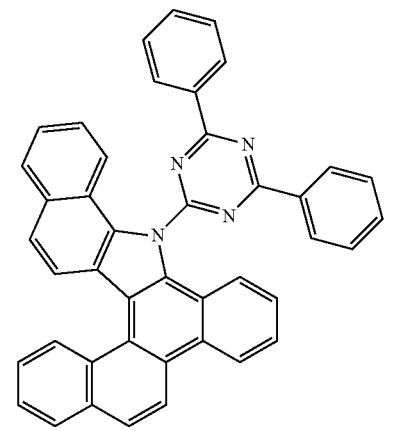
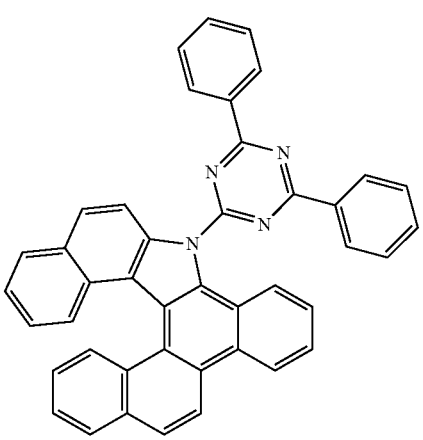
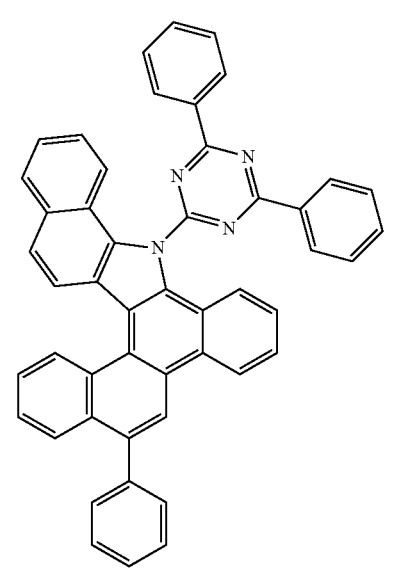
160
-continued
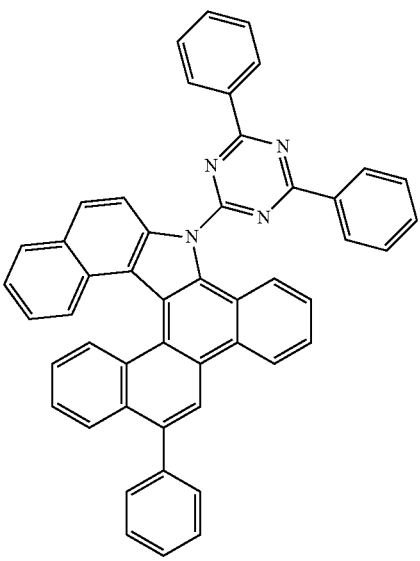
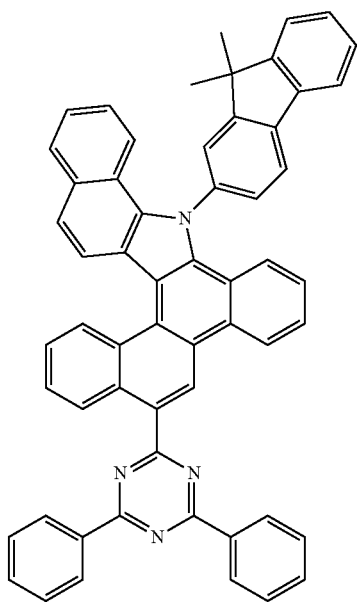

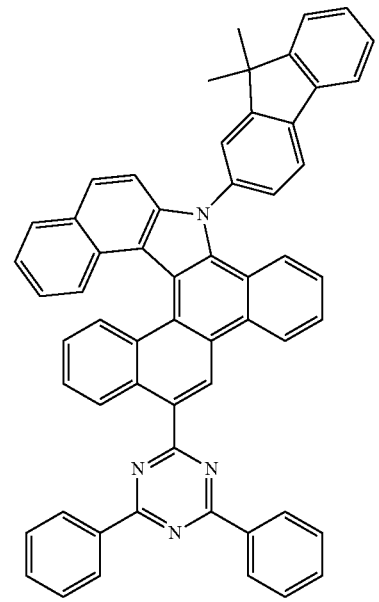

163
-continued
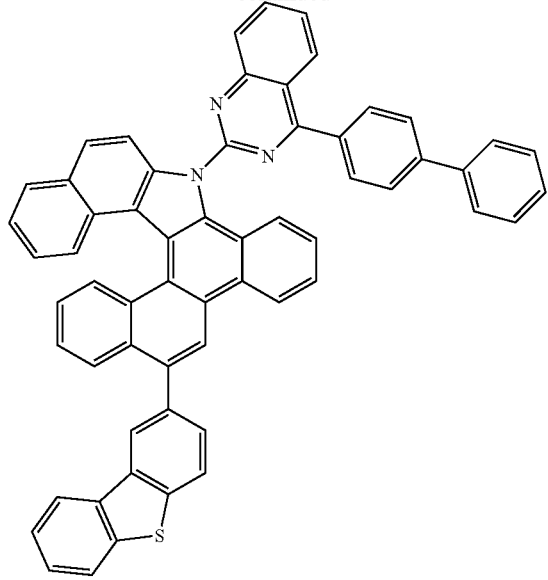
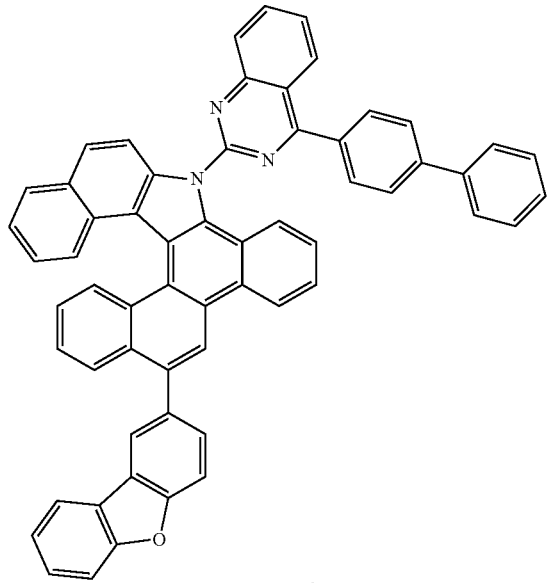
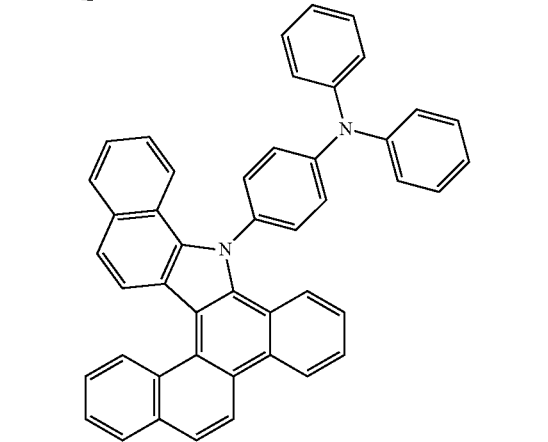
164
[Group 3]
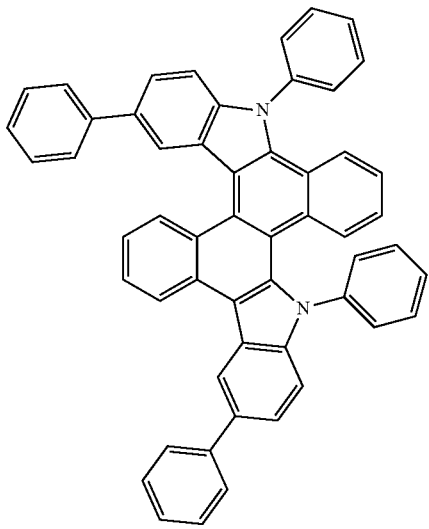
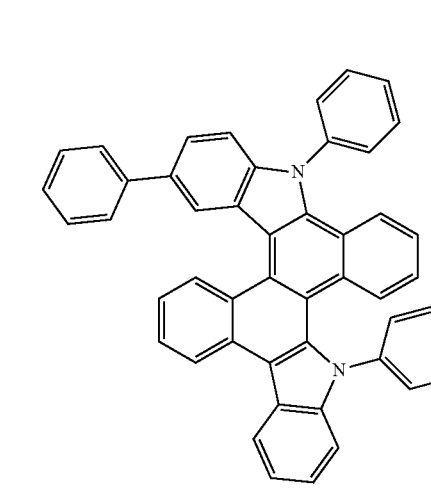
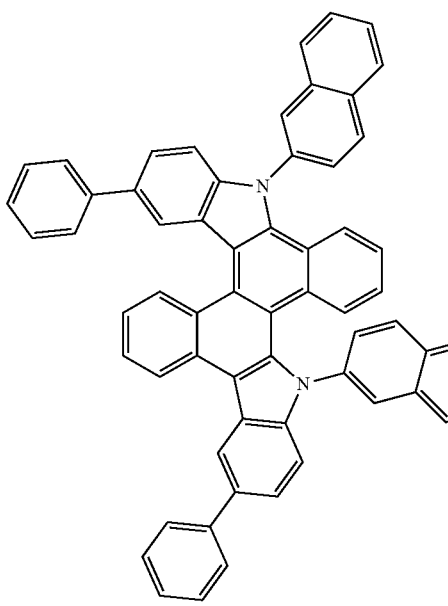
According to an exemplary embodiment of the present application, the compound represented by Chemical Formula 1 is any one selected from the structural formulae of the following Group 3.

-continued
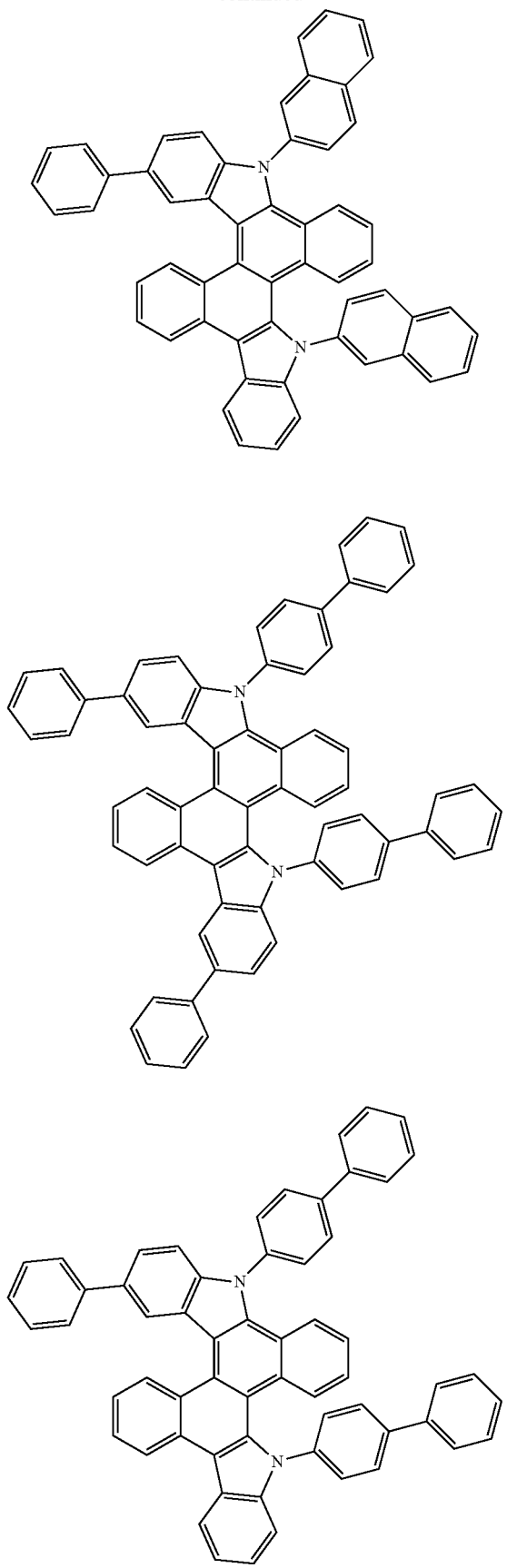
-continued
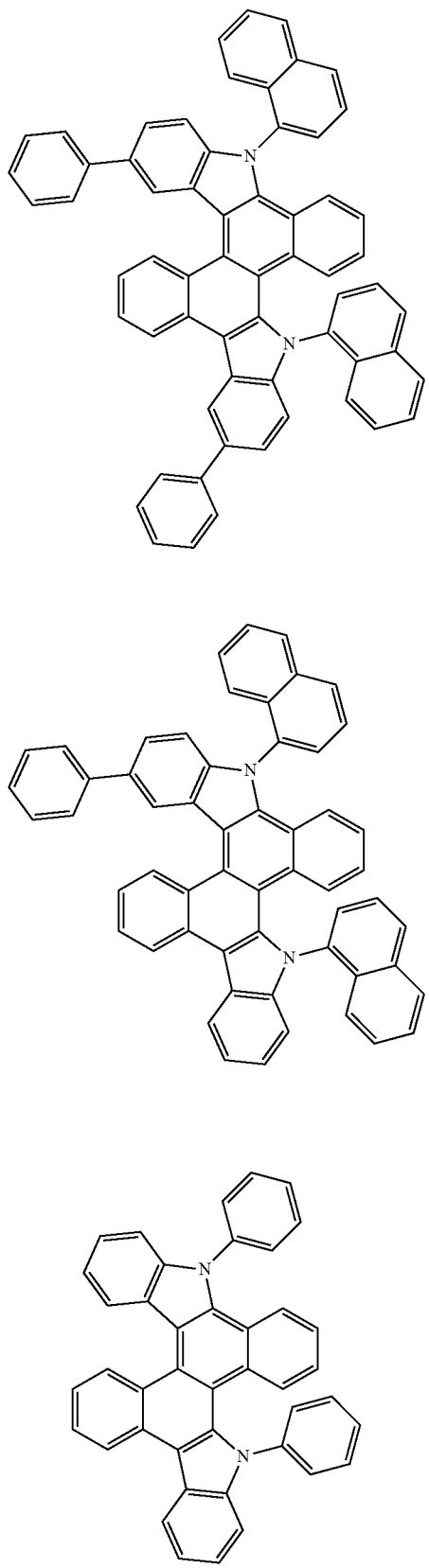

167
-continued
168
-continued
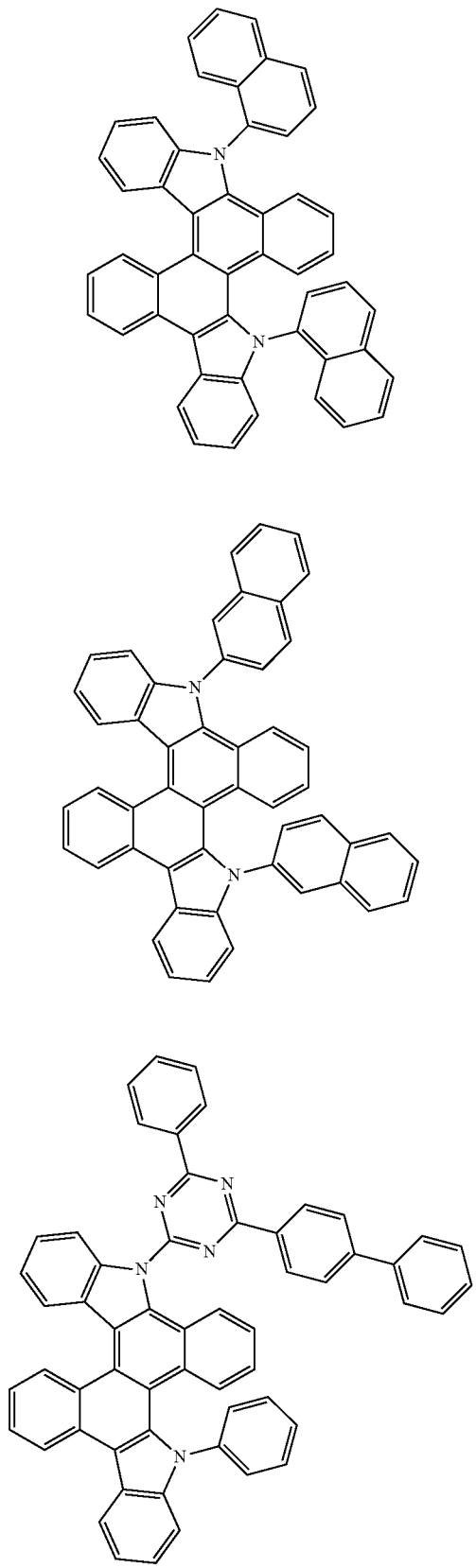 [SMILES: c1ccc2c(-n3c4ccccc4c4c5c6ccccc6c6c7ccccc7n(-c7cccc8ccccc78)c6c5c5ccccc5c43)cccc2c1 ; c1ccc2cc(-n3c4ccccc4c4c5c6ccccc6c6c7ccccc7n(-c7ccc8ccccc8c7)c6c5c5ccccc5c43)ccc2c1 ; c1ccc(-c2ccc(-c3nc(-c4ccccc4)nc(-n4c5ccccc5c5c6c7ccccc7c7c8ccccc8n(-c8ccccc8)c7c6c6ccccc6c54)n3)cc2)cc1]
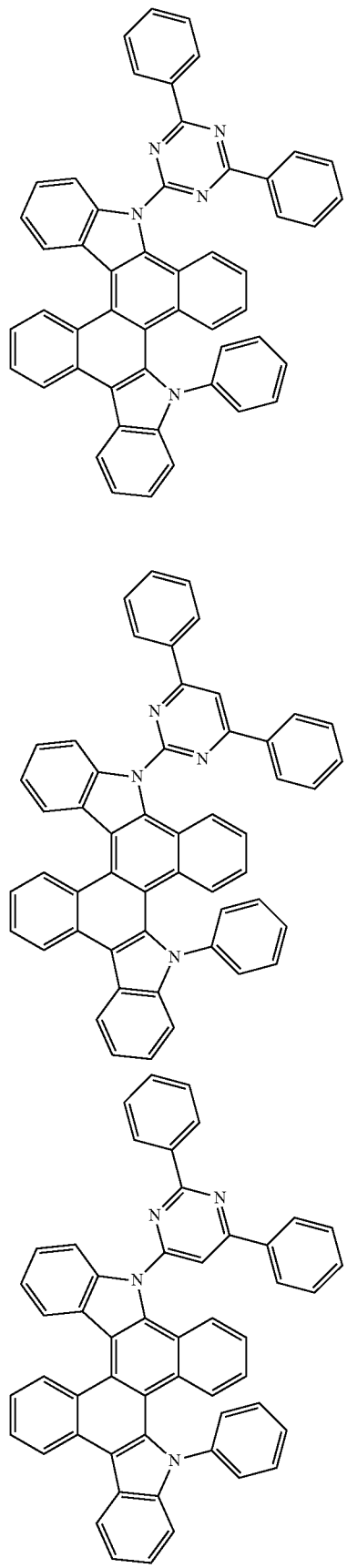

-continued
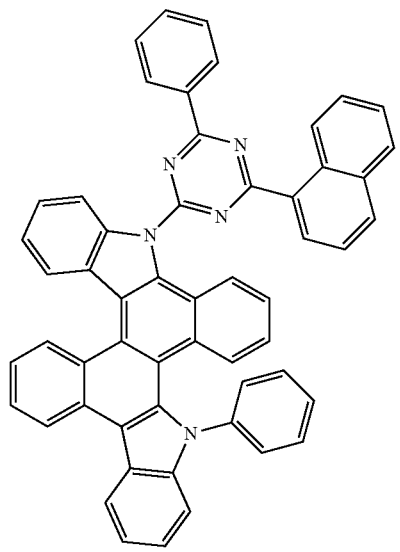
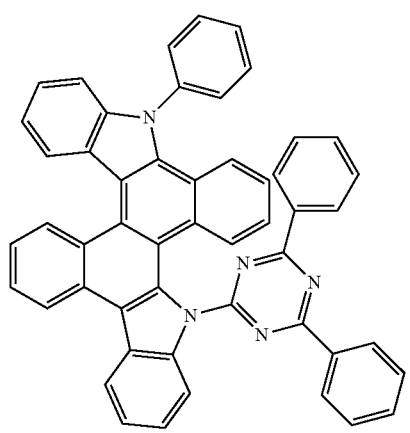
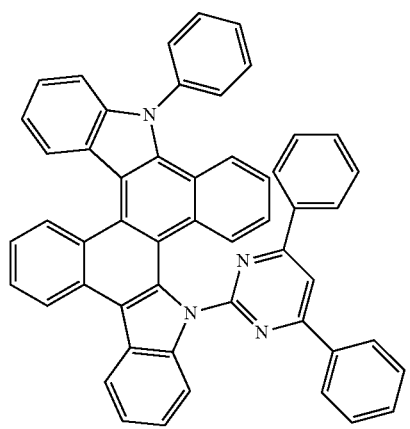
-continued
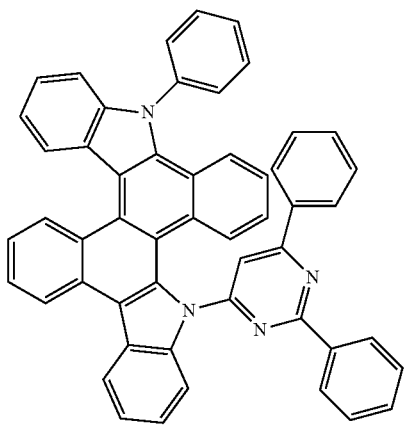
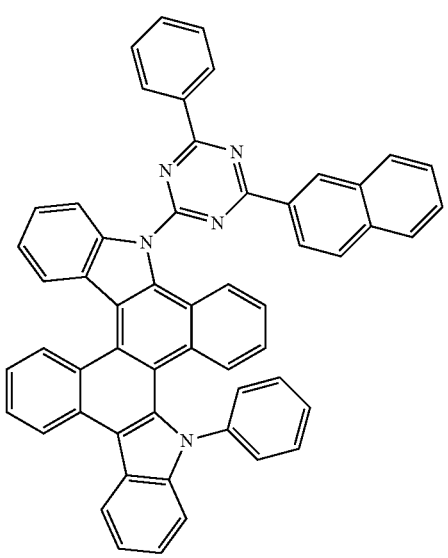
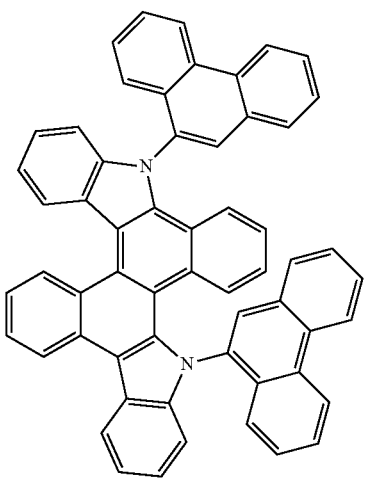

171
-continued
172
-continued
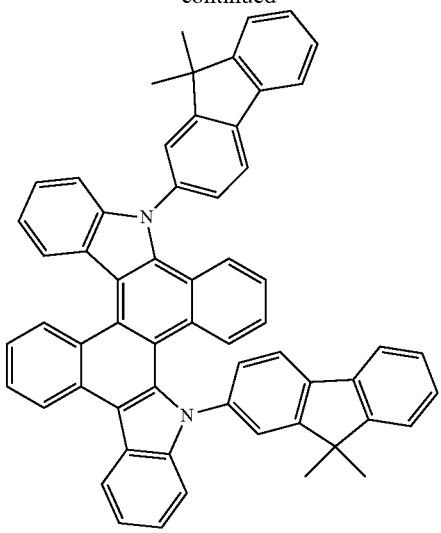
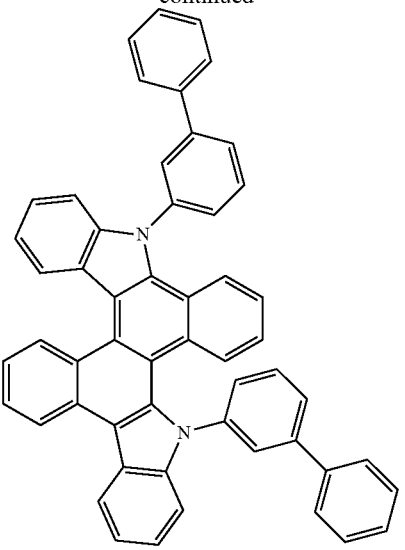
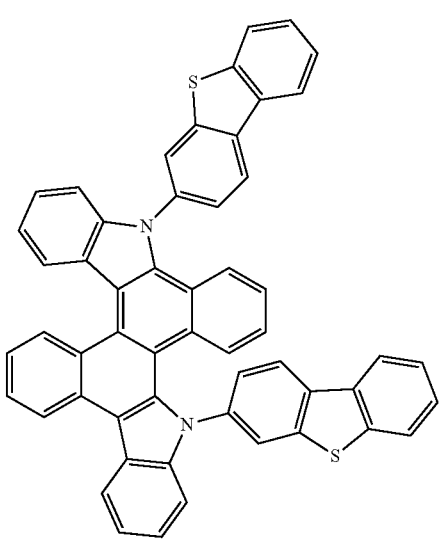
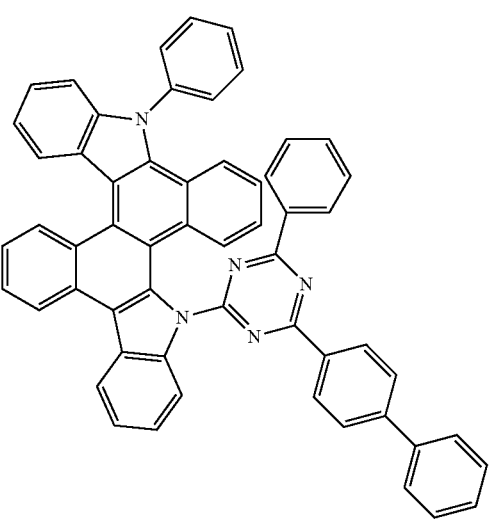

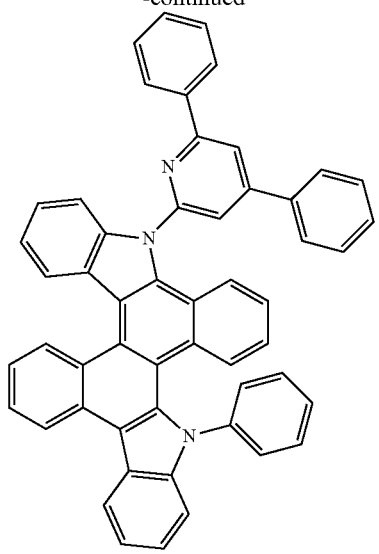
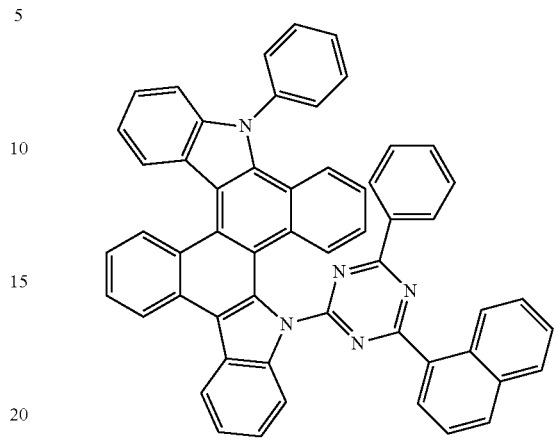
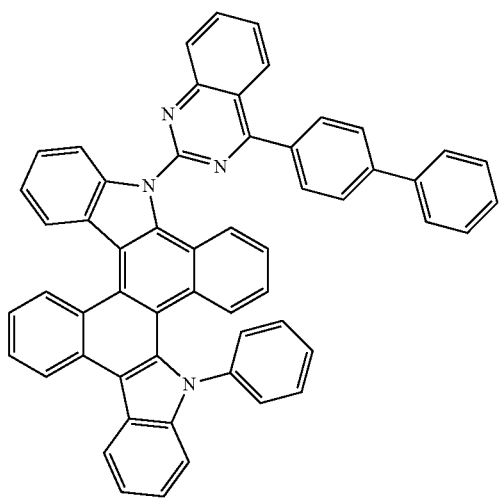
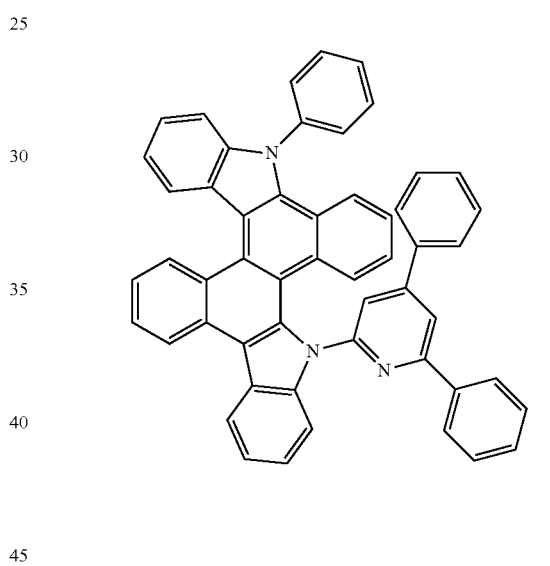
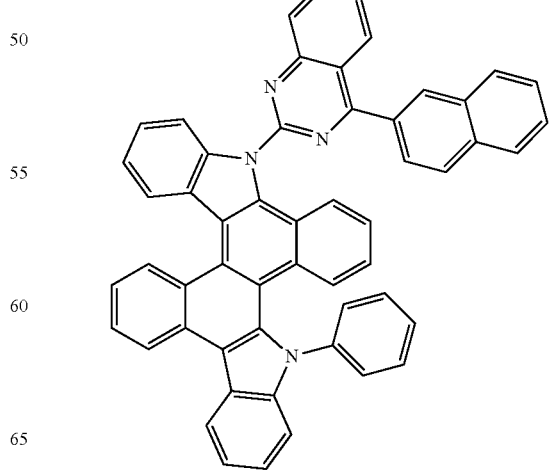

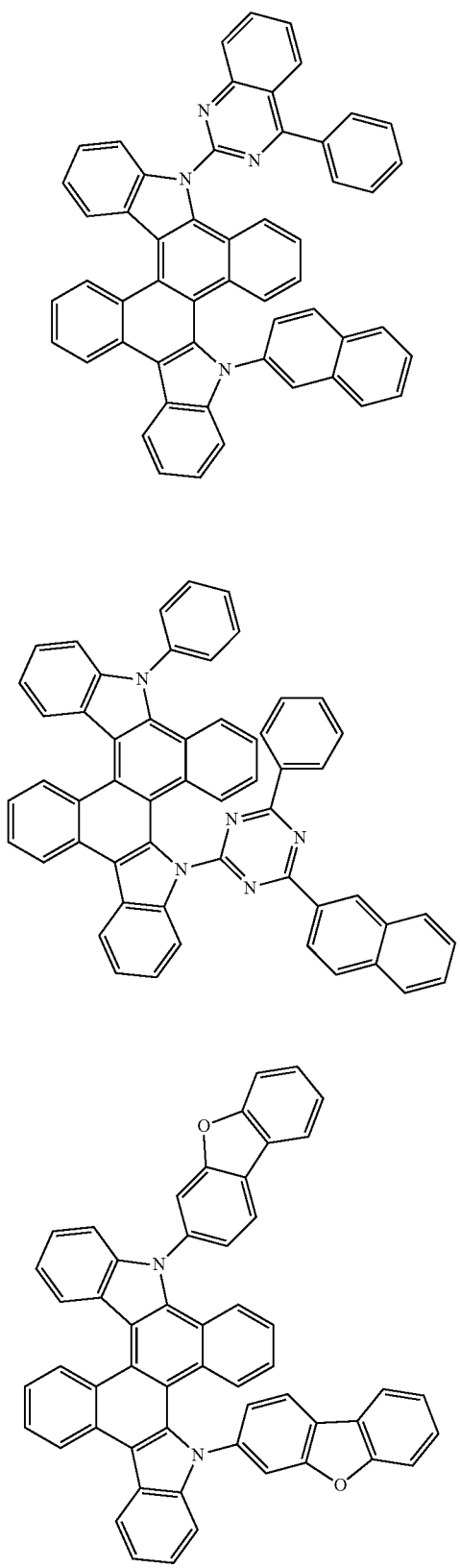
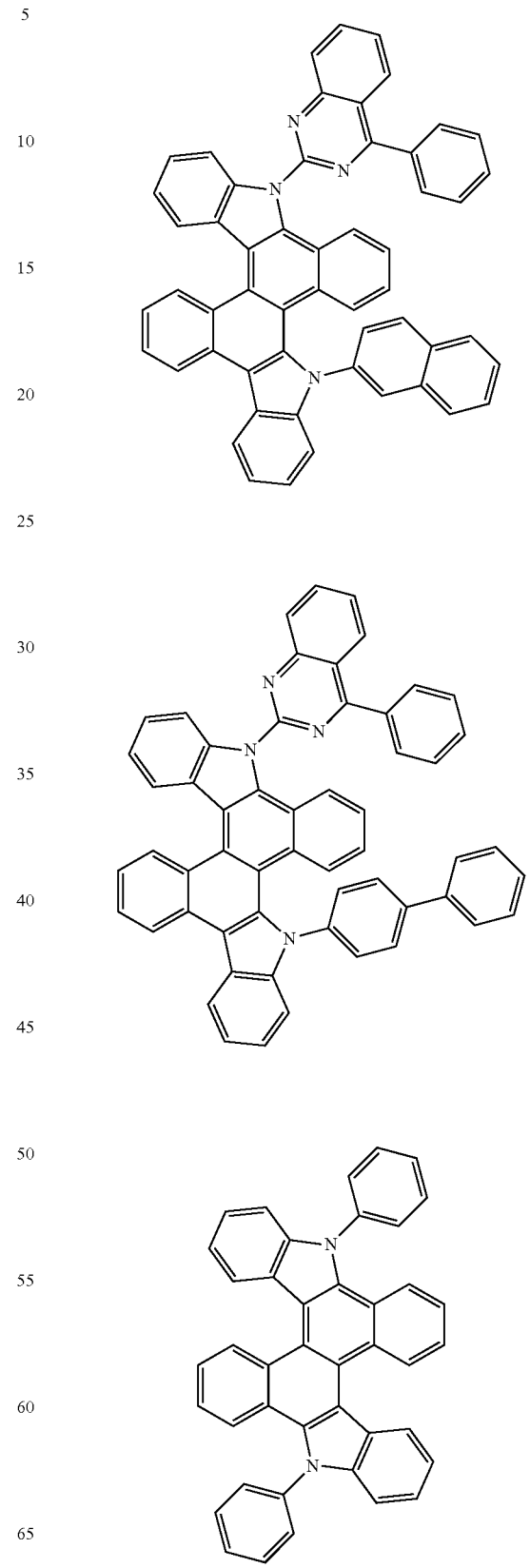

177
-continued
178
-continued
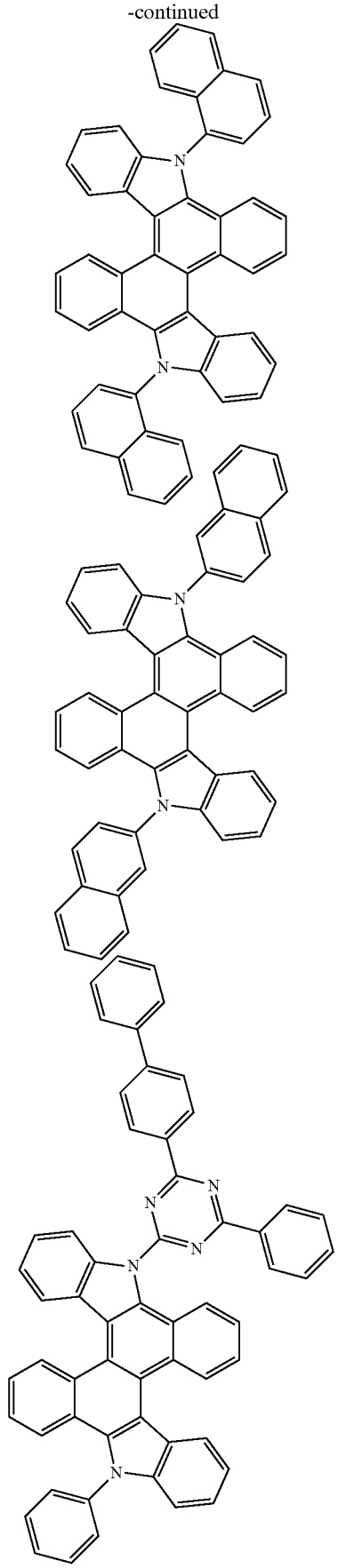
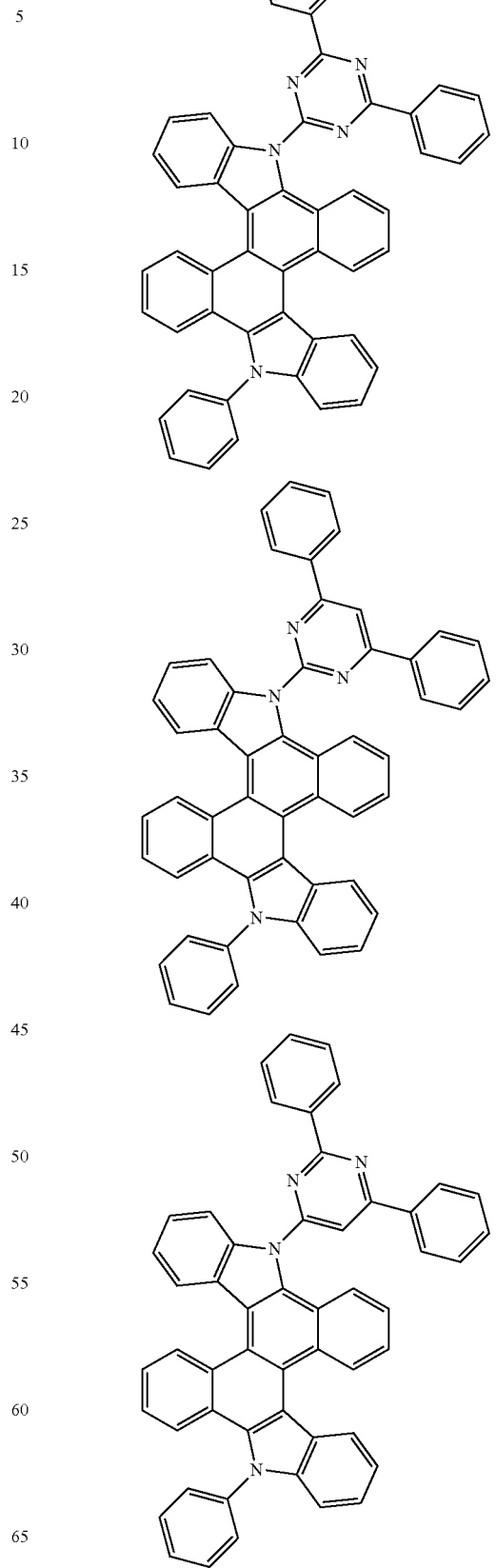

-continued
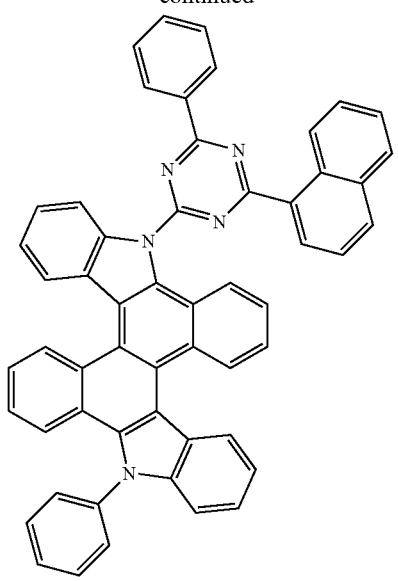
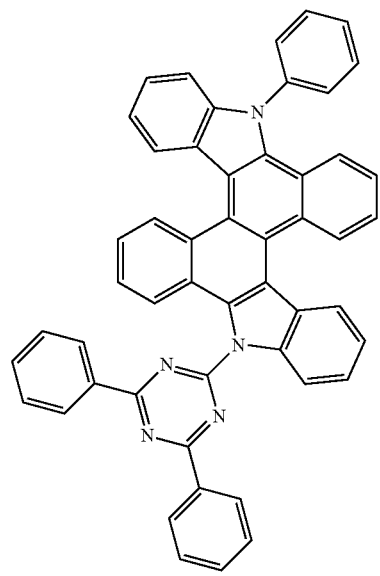
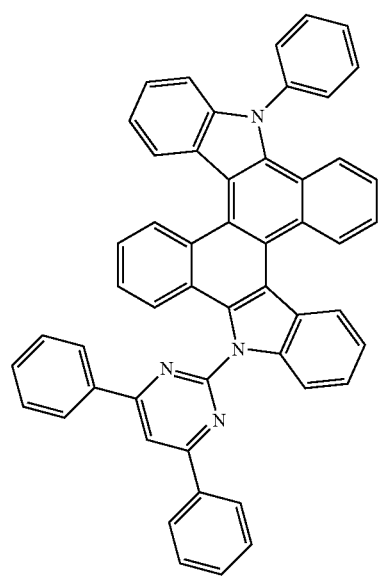
-continued
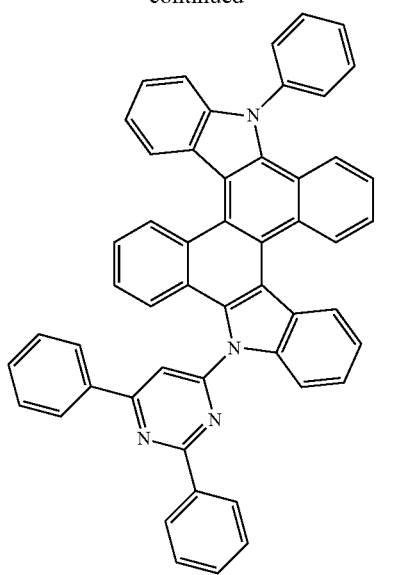
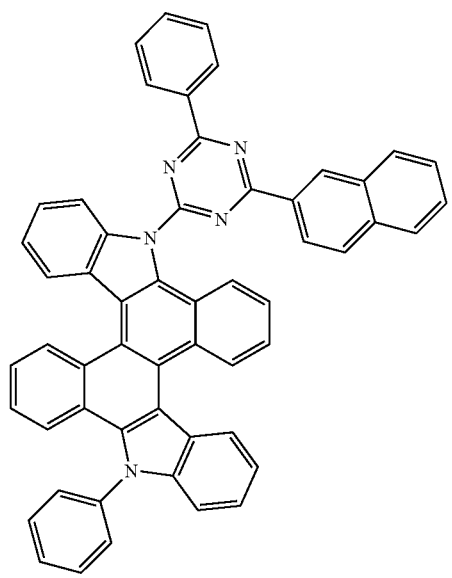
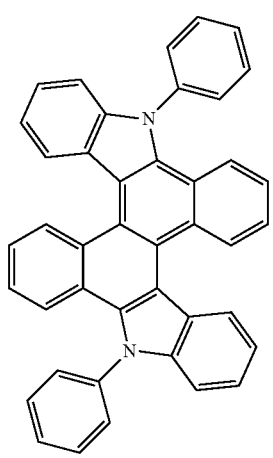

181
-continued
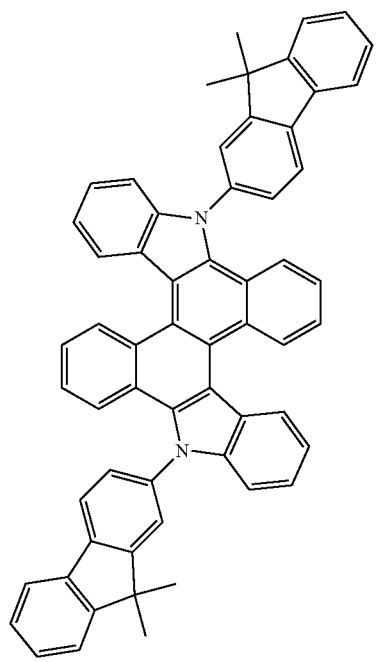
182
-continued
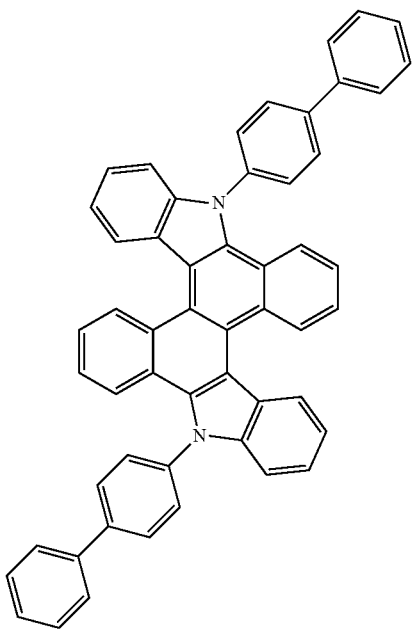
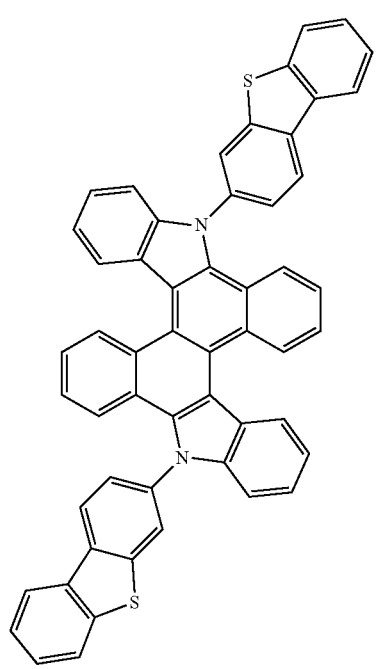
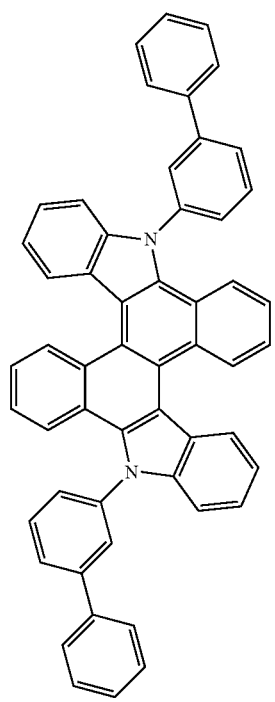

183
-continued
184
-continued
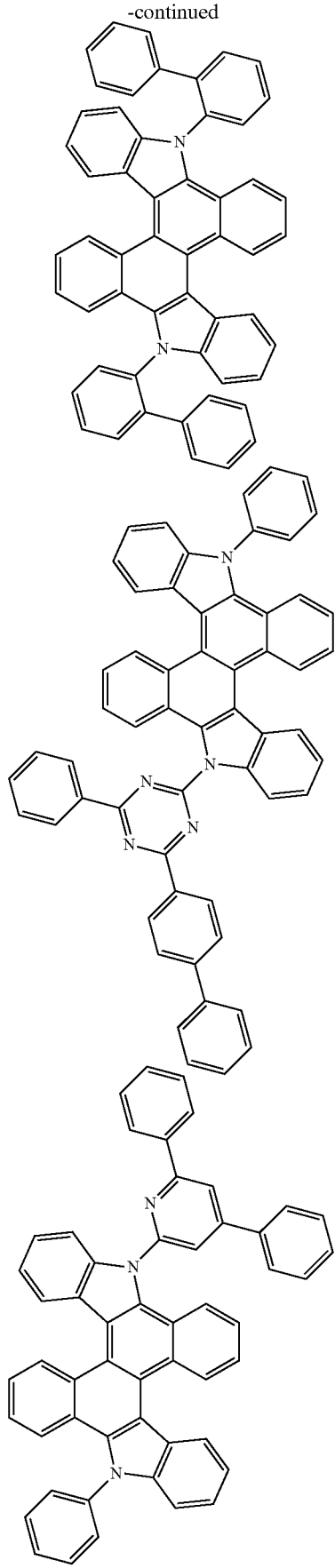
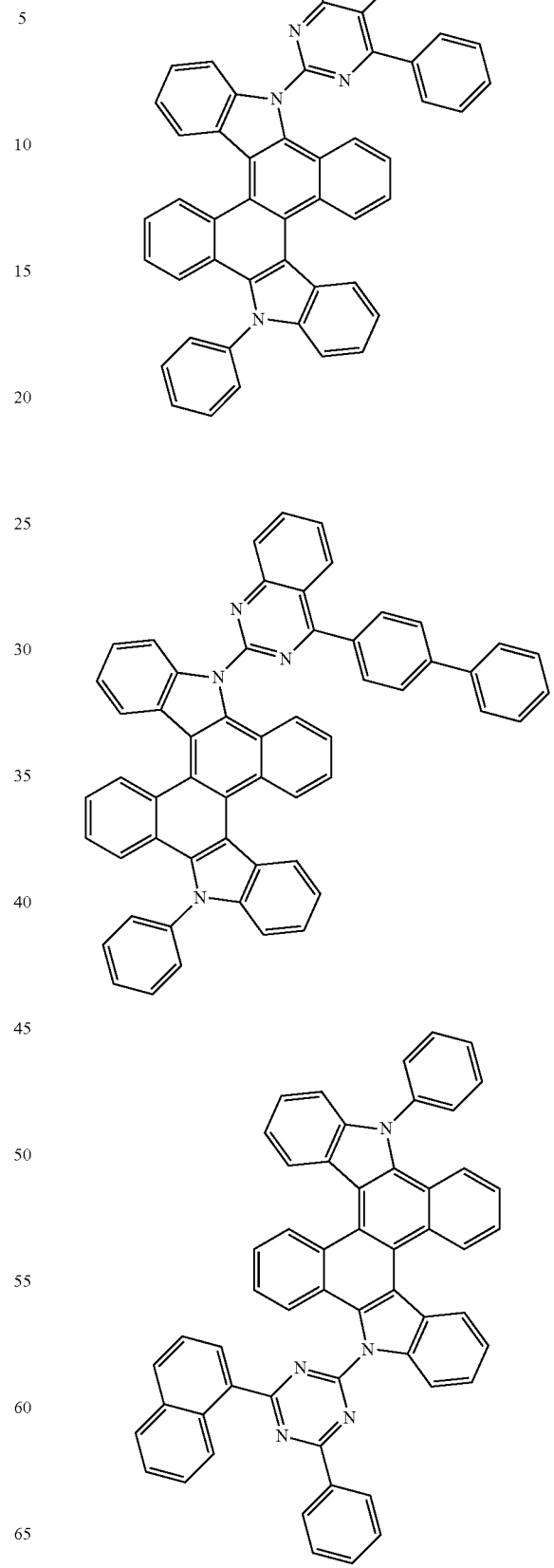

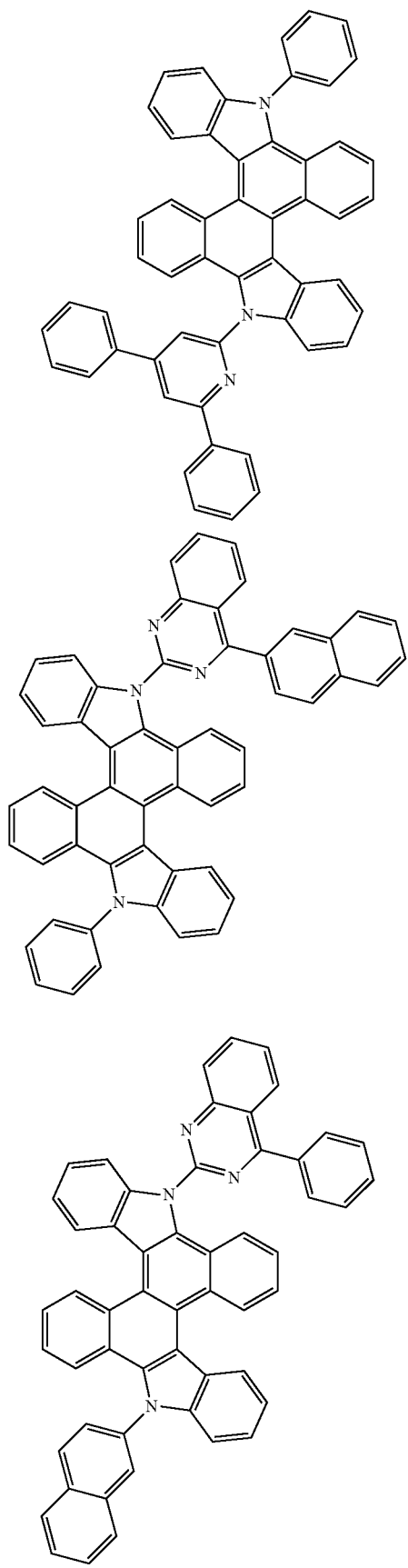
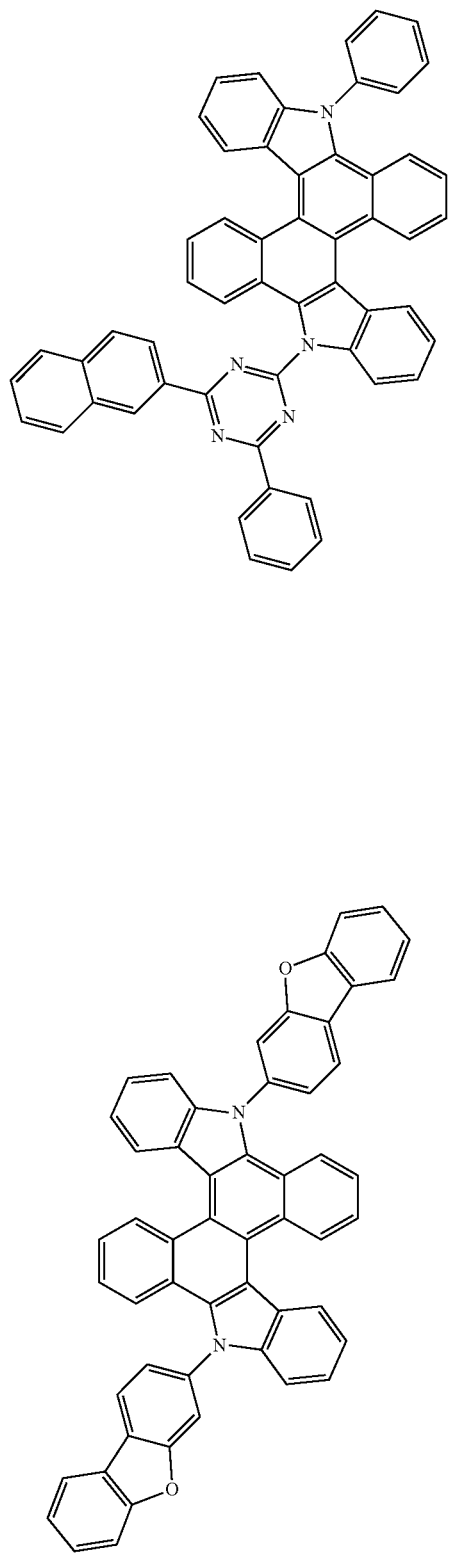

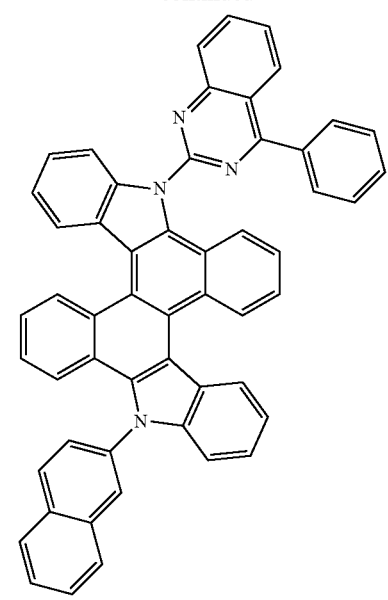
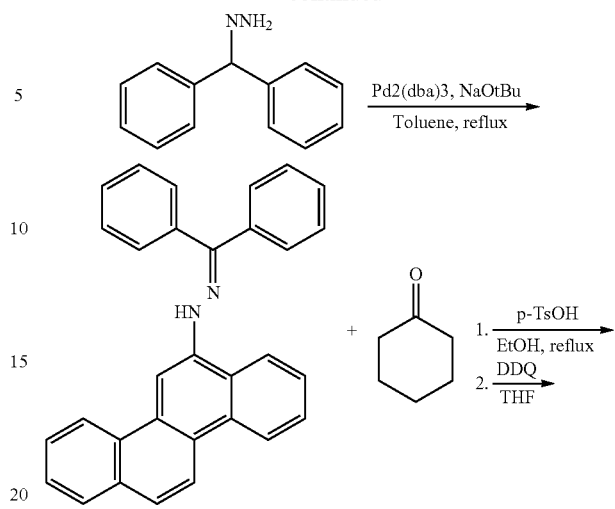
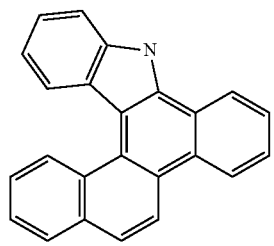
[Reaction Formula 2]
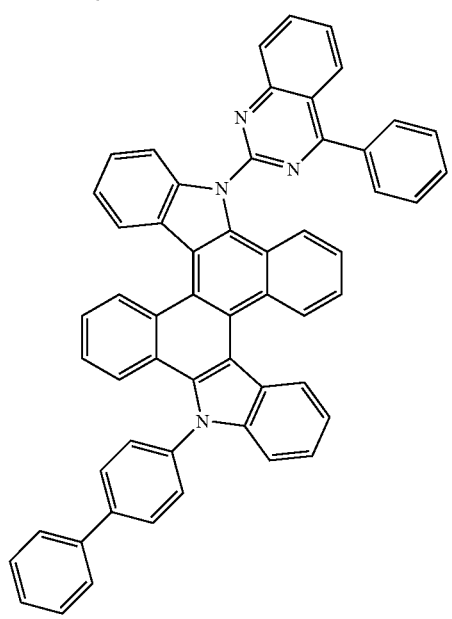
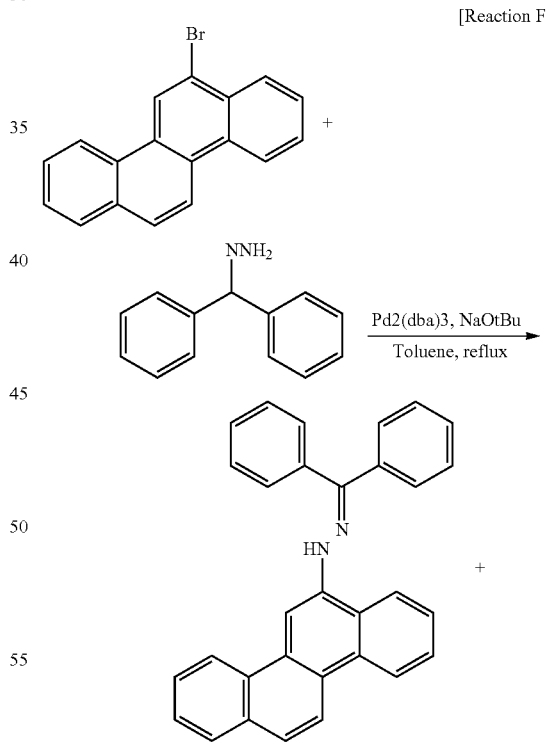
The compound according to an exemplary embodiment of the present application may be prepared by a preparation method to be described below.
For example, in the compound of Chemical Formula 1, a core structure may be prepared as in the following Reaction Formulae 1 to 5.
[Reaction Formula 1]
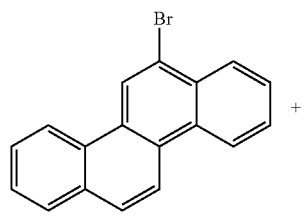
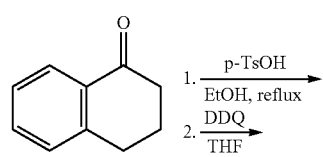

189
-continued
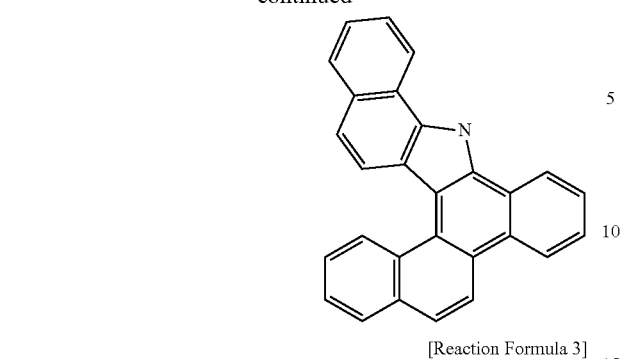
[Reaction Formula 3]
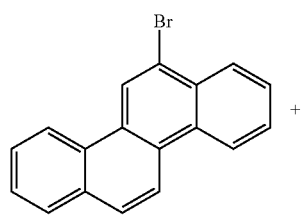
+
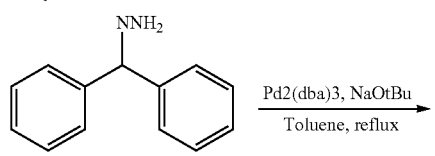
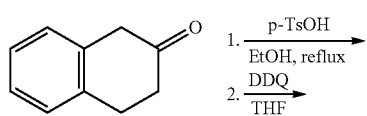
+
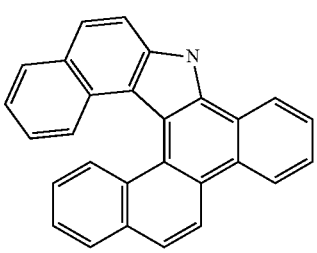
[Reaction Formula 4]
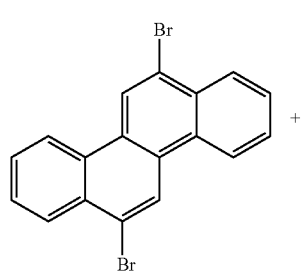
+
190
-continued
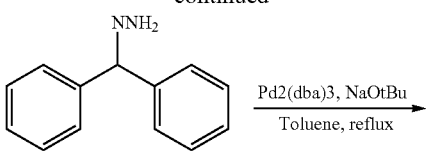
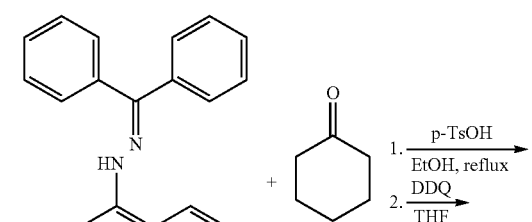
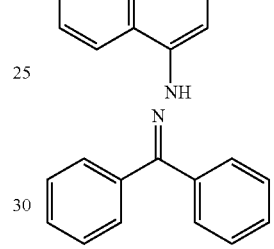
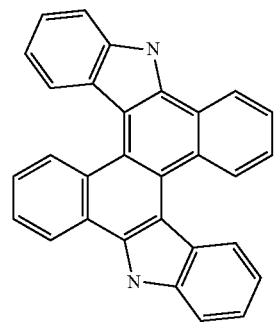
[Reaction Formula 5]
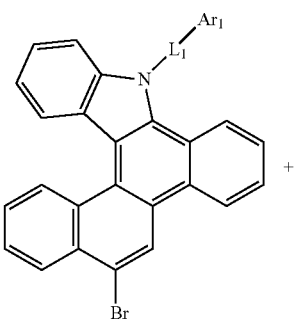
+

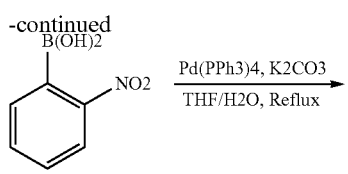

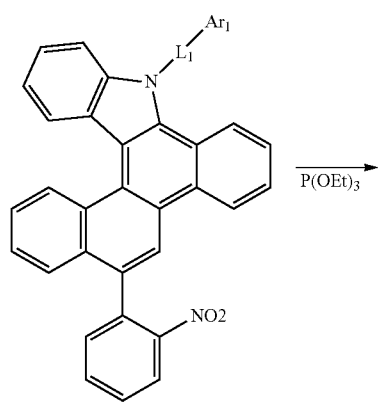

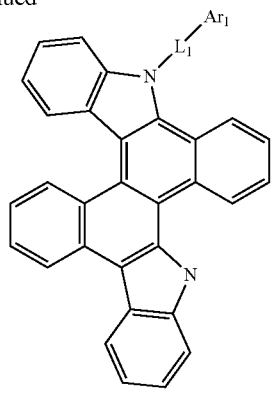

Reaction Formulae 1 to 5 only describe the examples of the method of synthesizing the core of Chemical Formula 1, and are not limited thereto, and the kind and position of substituent may be changed, if necessary.

The substituent may be bonded by a method known in the art, and the kind and position of the substituent or the number of substituents may be changed according to the technology known in the art. For example, the substituent may be linked as in the following Reaction Formulae 6 and 7, but is not limited thereto.

[Reaction Formula 6]

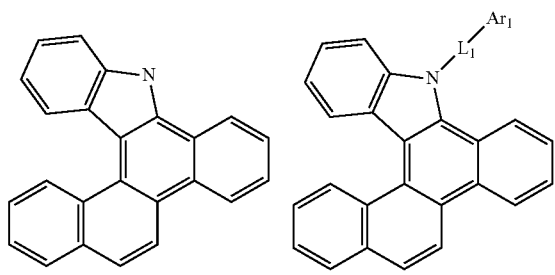

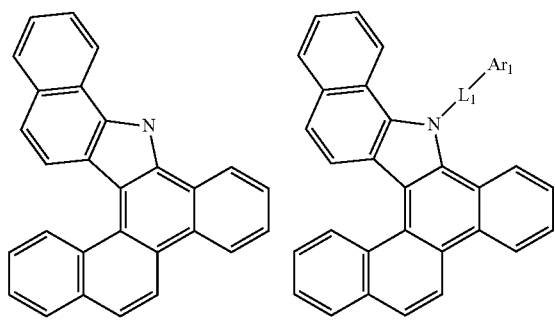

-continued
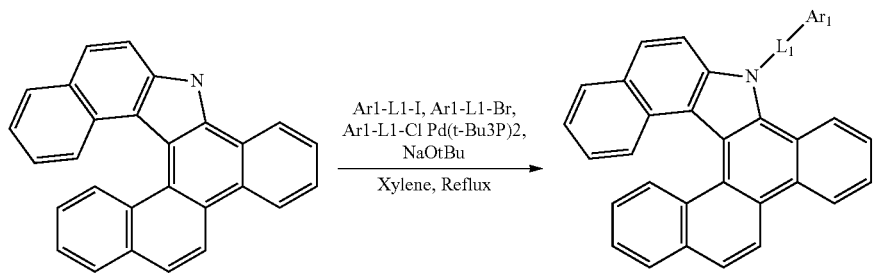
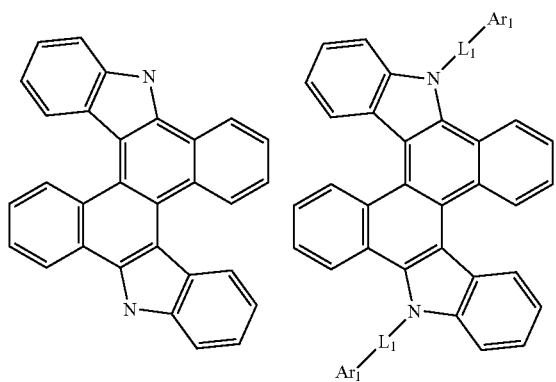
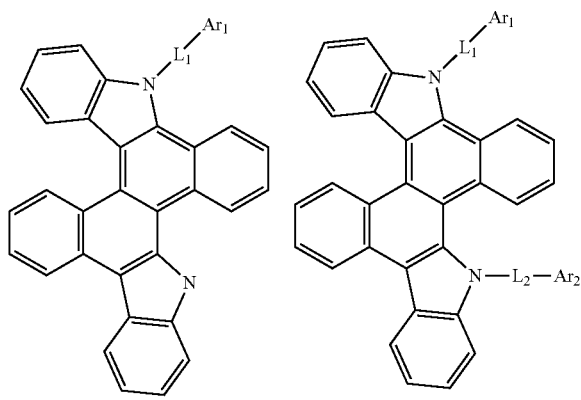
[Reaction Formula 7]
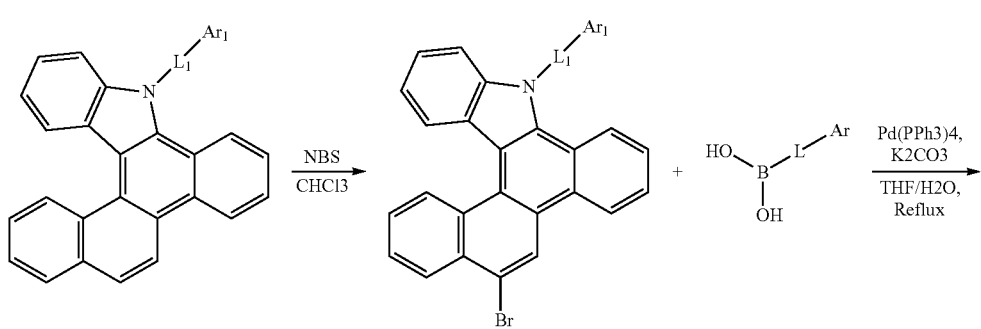

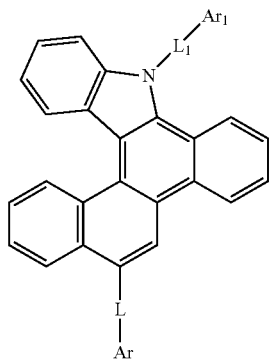

In Reaction Formulae 5 to 7, $L_1$, $L_2$, $Ar_1$, and $Ar_2$ are the same as those described above, and Ar is the same as the definition of $Ar_1$, and L is the same as the definition of $L_1$.

The specific preparation method will be described below.

Further, the present specification provides an organic electronic device including the above-described compound.

An exemplary embodiment of the present application provides an organic electronic device including: a first electrode; a second electrode provided to face the first electrode; and one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic electronic device of the present application may also be composed of a single-layered structure, but may be composed of a multi-layered structure in which two or more organic material layers are stacked. For example, as a representative example of the organic electronic device of the present invention, an organic light emitting device may have a structure including a hole injection layer, a hole transport layer, a light emitting layer, an electron transport layer, an electron injection layer, and the like as organic material layers. However, the structure of the organic electronic device is not limited thereto, and may include a fewer number of organic layers.

According to an exemplary embodiment of the present application, the organic electronic device may be selected from the group consisting of an organic light emitting device, an organic solar cell, an organic photoconductor (OPC), and an organic transistor.

Hereinafter, an organic light emitting device will be exemplified.

In an exemplary embodiment of the present application, the organic material layer includes a light emitting layer, and the light emitting layer includes the compound.

In an exemplary embodiment of the present application, the organic material layer includes a hole injection layer or a hole transport layer, and the hole injection layer or the hole transport layer includes the compound.

In another exemplary embodiment, the organic material layer includes a light emitting layer, and the light emitting layer includes the compound.

In an exemplary embodiment of the present application, the organic material layer includes an electron transport layer or an electron injection layer, and the electron transport layer or the electron injection layer includes the compound.

In an exemplary embodiment of the present application, the organic material layer includes an electron blocking layer or a hole blocking layer, and the electron blocking layer or the hole blocking layer includes the compound.

In an exemplary embodiment of the present application, the organic material layer includes an electron blocking layer, and the electron blocking layer includes the compound.

In an exemplary embodiment of the present application, the organic light emitting device further includes one or two or more layers selected from the group consisting of a hole injection layer, a hole transport layer, a light emitting layer, an electron transport layer, an electron injection layer, an electron blocking layer, and a hole blocking layer.

In an exemplary embodiment of the present application, the organic light emitting device includes: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the compound. In an exemplary embodiment of the present application, as the two or more organic material layers, two or more may be selected from the group consisting of an electron transport layer, an electron injection layer, a layer which transports and injects electrons simultaneously, and a hole blocking layer.

In an exemplary embodiment of the present application, the organic material layer includes two or more electron transport layers, and at least one of the two or more electron transport layers includes the compound. Specifically, in an exemplary embodiment of the present specification, the compound may also be included in one layer of the two or more electron transport layers, and may be included in each of the two or more electron transport layers.

In addition, in an exemplary embodiment of the present application, when the compound is included in each of the two or more electron transport layers, the other materials except for the compound may be the same as or different from each other.

In an exemplary embodiment of the present application, the organic material layer further includes a hole injection layer or a hole transport layer, which includes a compound including an arylamino group, a carbazolyl group, or a benzocarbazolyl group, in addition to the organic material layer including the compound.

In an exemplary embodiment of the present specification, the light emitting layer includes the compound of Chemical Formula 1 and further includes a light emitting dopant.

In another exemplary embodiment, the light emitting dopant includes a phosphorescent dopant.

In still another exemplary embodiment, the phosphorescent dopant includes an iridium-based phosphorescent dopant.

In yet another exemplary embodiment, the phosphorescent dopant material includes Ir(ppy)$_3$ or (piq)$_2$Ir(acac).

According to an exemplary embodiment of the present specification, the organic material layer includes a light emitting layer, and the light emitting layer includes a compound represented by the following Chemical Formula A-1.

[Chemical Formula A-1]

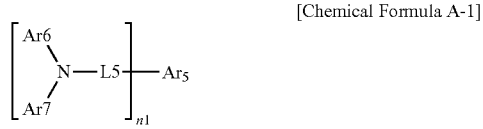

In Chemical Formula A-1, n1 is an integer of 1 or more,

Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L5 is a direct bond; a substituted or unsubstituted arylene group; or a substituted or unsubstituted heteroarylene group, Ar6 and Ar7 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula A-1 as a dopant of the light emitting layer.

According to an exemplary embodiment of the present specification, L5 is a direct bond.

According to an exemplary embodiment of the present specification, n1 is 2.

In an exemplary embodiment of the present specification, Ar5 is a divalent pyrene group which is unsubstituted or substituted with deuterium, a methyl group, an ethyl group, or a tert-butyl group.

According to an exemplary embodiment of the present specification, Ar6 and Ar7 are the same as or different from each other, and are each independently a substituted or unsubstituted aryl group having 6 to 30 carbon atoms.

According to an exemplary embodiment of the present specification, Ar6 and Ar7 are the same as or different from each other, and are each independently an aryl group which is unsubstituted or substituted with a germanium group substituted with an alkyl group.

According to an exemplary embodiment of the present specification, Ar6 and Ar7 are the same as or different from each other, and are each independently an aryl group which is unsubstituted or substituted with a trimethylgermanium group.

According to an exemplary embodiment of the present specification, Ar6 and Ar7 are the same as or different from each other, and are each independently a substituted or unsubstituted phenyl group.

According to an exemplary embodiment of the present specification, Ar6 and Ar7 are a phenyl group which is unsubstituted or substituted with a trimethylgermanium group.

According to an exemplary embodiment of the present specification, Chemical Formula A-1 is represented by the following compound.

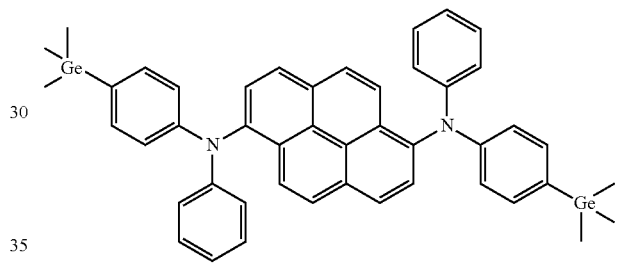

According to an exemplary embodiment of the present specification, the organic material layer includes a light emitting layer, and the light emitting layer includes a compound represented by the following Chemical Formula A-2.

[Chemical Formula A-2]

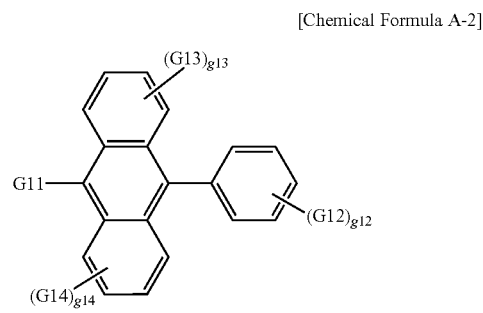

In Chemical Formula A-2,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

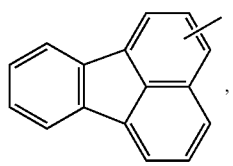

,

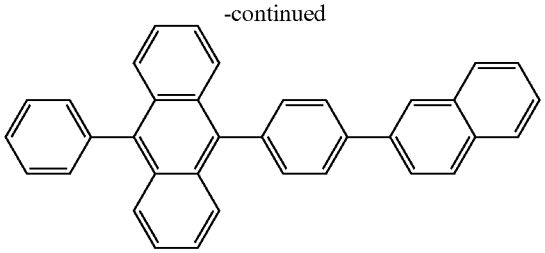

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula A-2 as a host of the light emitting layer.

According to an exemplary embodiment of the present specification, G11 is a phenyl group.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula A-2 is represented by any one of the following compounds.

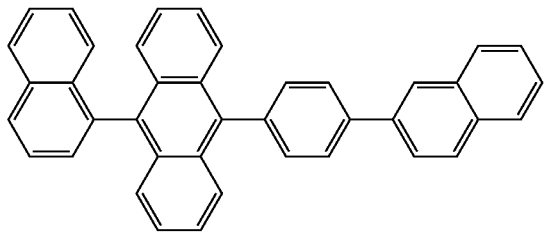

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse direction structure (inverted type) in which a negative electrode, one or more organic material layers, and a positive electrode are sequentially stacked on a substrate.

For example, the structure of the organic light emitting device according to an exemplary embodiment of the present specification is exemplified in FIGS. 1 and 2.

FIG. 1 exemplifies a structure of an organic electronic device in which a substrate 1, a positive electrode 2, a light emitting layer 3, and a negative electrode 4 are sequentially stacked. In the structure as described above, the compound may be included in the light emitting layer 3.

FIG. 2 exemplifies a structure of an organic electronic device in which a substrate 1, a positive electrode 2, a hole injection layer 5, a hole transport layer 6, a light emitting layer 3, an electron transport layer 7, and a negative electrode 4 are sequentially stacked. In the structure as described above, the compound may be included in one or more layers of the hole injection layer 5, the hole transport layer 6, the light emitting layer 3, and the electron transport layer 7.

In the structure as described above, the compound may be included in one or more of the hole injection layer, the hole transport layer, the light emitting layer, and the electron transport layer.

The organic light emitting device of the present application may be manufactured by the materials and methods known in the art, except that one or more layers of the organic material layers include the compound of the present application, that is, the compound.

When the organic light emitting device includes a plurality of organic material layers, the organic material layer may be formed of the same material or different materials.

The organic light emitting device of the present application may be manufactured by the materials and methods known in the art, except that one or more layers of the organic material layers include the compound, that is, the compound represented by Chemical Formula 1.

For example, the organic light emitting device of the present application may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be manufactured by sequentially stacking a negative electrode material, an organic material layer, and a positive electrode material on a substrate (International Publication No. 2003/012890). However, the manufacturing method is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene](PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, bathocuproine (BCP), an aluminum complex, and the like, but are not limited thereto.

The organic light emitting device according to the present specification may be a top emission type, a bottom emission type, or a dual emission type according to the material to be used.

In an exemplary embodiment of the present application, the compound may be included in an organic solar cell or an organic transistor in addition to the organic light emitting device.

The compound according to the present application may act by a principle similar to that applied to the organic light emitting device even in an organic electronic device such as an organic solar cell, an organic photoconductor, and an organic transistor.

MODE FOR INVENTION

Hereinafter, the present specification will be described in detail with reference to Examples in order to specifically explain the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

Synthesis Example 1

Preparation Example 1-1

[Compound 1]

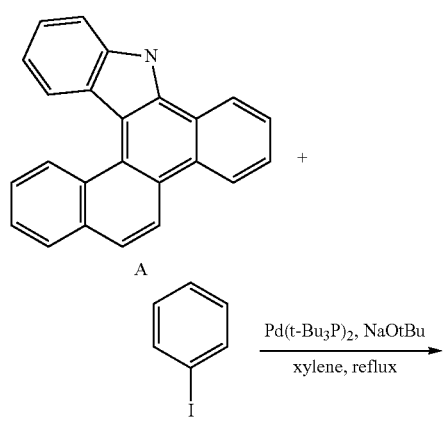

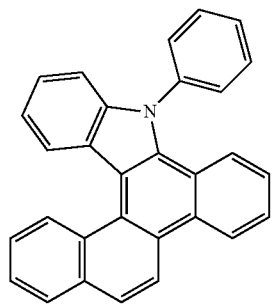

Under a nitrogen atmosphere, Chemical Formula A (10 g, 31.55 mmol) and iodobenzene (7.04 g, 34.70 mmol) were completely dissolved in 160 ml of xylene in a 500 ml-round bottom flask, and then sodium-tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 1 hour. The temperature was lowered to normal temperature, the mixture was filtered to remove the base, and then xylene was concentrated under reduced pressure, and the residue was columned at a ratio of tetrahydrofuran:hexane=1:20 to prepare Compound 1 (9.56 g, yield: 77%).

MS[M+H]$^+$=394

Preparation Example 1-2

[Compound 2]

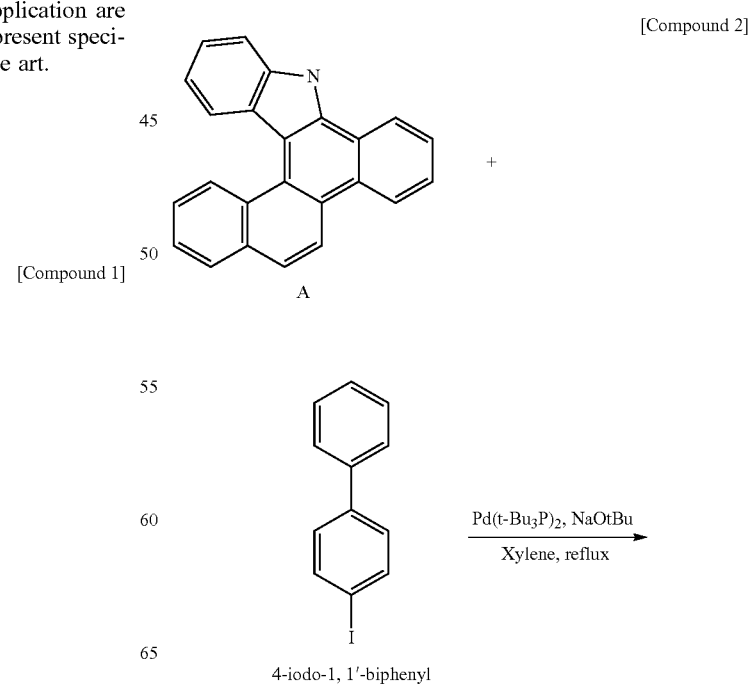

4-iodo-1,1'-biphenyl

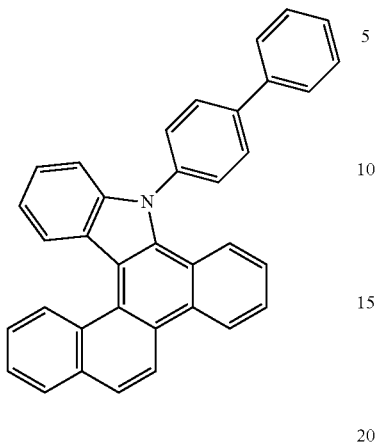

Under a nitrogen atmosphere, Chemical Formula A (10 g, 31.55 mmol) and 4-iodo-1,1'-biphenyl (9.72 g, 34.70 mmol) were completely dissolved in 180 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 2 hours. The temperature was lowered to normal temperature, the mixture was filtered to remove the base, and then xylene was concentrated under reduced pressure, and the residue was columned at a ratio of tetrahydrofuran:hexane=1:16 to prepare Compound 2 (12.45 g, yield: 84%).

MS[M+H]$^+$=470

Preparation Example 1-3

[Compound 3]

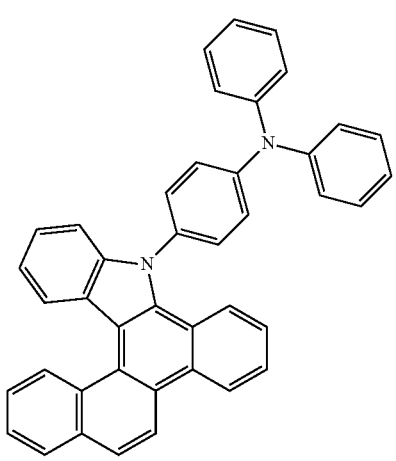

Under a nitrogen atmosphere, Chemical Formula A (10 g, 31.55 mmol) and 4-bromo-N,N-diphenylaniline (11.21 g, 34.70 mmol) were completely dissolved in 200 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 2 hours. The temperature was lowered to normal temperature, the mixture was filtered to remove the base, and then xylene was concentrated under reduced pressure, and the residue was columned at a ratio of tetrahydrofuran:hexane=1:15 to prepare Compound 3 (15.91 g, yield: 89%)

MS[M+H]$^+$=561

Preparation Example 1-4

[Compound 4]

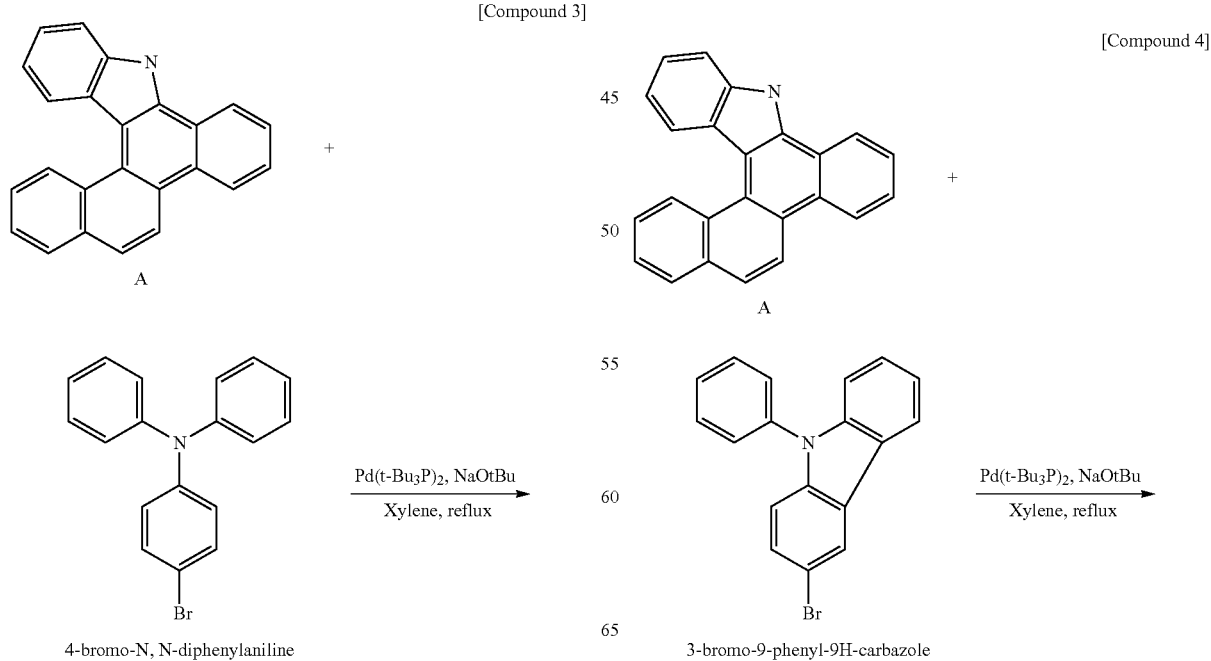

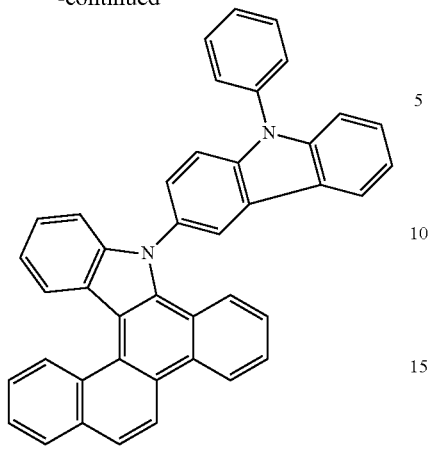

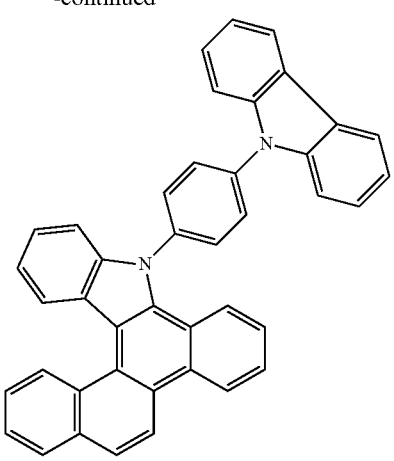

Under a nitrogen atmosphere, Chemical Formula A (10 g, 31.55 mmol) and 3-bromo-9-phenyl-9H-carbazole (11.20 g, 34.70 mmol) were completely dissolved in 230 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 4 hours. The temperature was lowered to normal temperature, the mixture was filtered to remove the base, and then xylene was concentrated under reduced pressure, and the residue was columned at a ratio of tetrahydrofuran:hexane=1:12 to prepare Compound 4 (14.39 g, yield: 82%).

MS[M+H]$^+$=559

Preparation Example 1-5

Under a nitrogen atmosphere, Chemical Formula A (10 g, 31.55 mmol) and 9-(4-bromophenyl)-9H-carbazole (11.20 g, 34.70 mmol) were completely dissolved in 220 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 5 hours. The temperature was lowered to normal temperature, the mixture was filtered to remove the base, and then xylene was concentrated under reduced pressure, and the residue was columned at a ratio of tetrahydrofuran:hexane=1:9 to prepare Compound 5 (12.85 g, yield: 73%).

MS[M+H]$^+$=559

Preparation Example 1-6

[Compound 5]

[Compound 6]

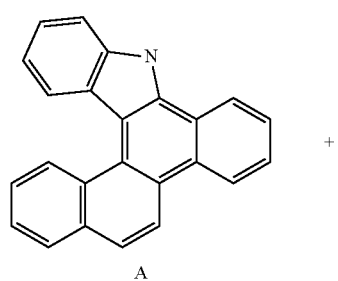

A

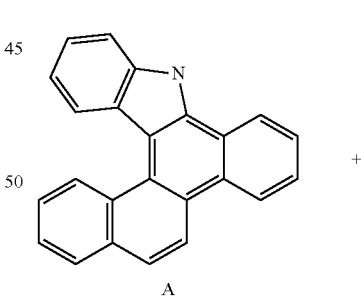

A

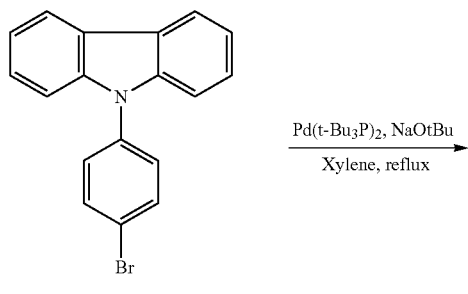

9-(4-bromophenyl)-9H-carbazole $\xrightarrow{\text{Pd(t-Bu}_3\text{P)}_2\text{, NaOtBu}}{\text{Xylene, reflux}}$

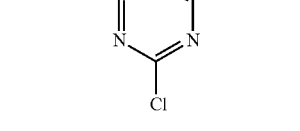

2-chloro-4,6-diphenyl-1,3,5-triazine $\xrightarrow{\text{Pd(t-Bu}_3\text{P)}_2\text{, NaOtBu}}{\text{Xylene, reflux}}$

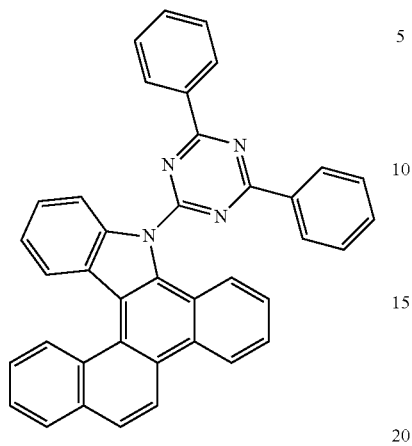

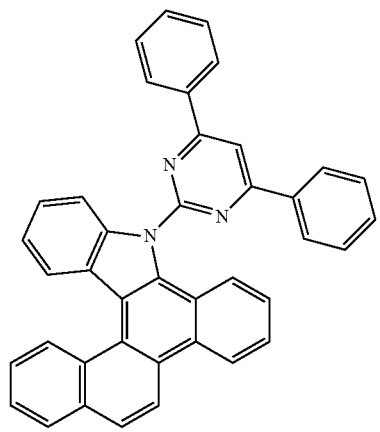

Under a nitrogen atmosphere, Chemical Formula A (10 g, 31.55 mmol) and 2-chloro-4,6-diphenyl-1,3,5-triazine (9.26 g, 34.70 mmol) were completely dissolved in 220 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 300 ml of ethyl acetate to prepare Compound 6 (12.45 g, yield: 84%).

MS[M+H]$^+$=549

Preparation Example 1-7

Under a nitrogen atmosphere, Chemical Formula A (10 g, 31.55 mmol) and 2-chloro-4,6-diphenylpyrimidine (9.26 g, 34.70 mmol) were completely dissolved in 220 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 320 ml of ethyl acetate to prepare Compound 7 (11.21 g, yield: 76%).

MS[M+H]$^+$=548

Preparation Example 1-8

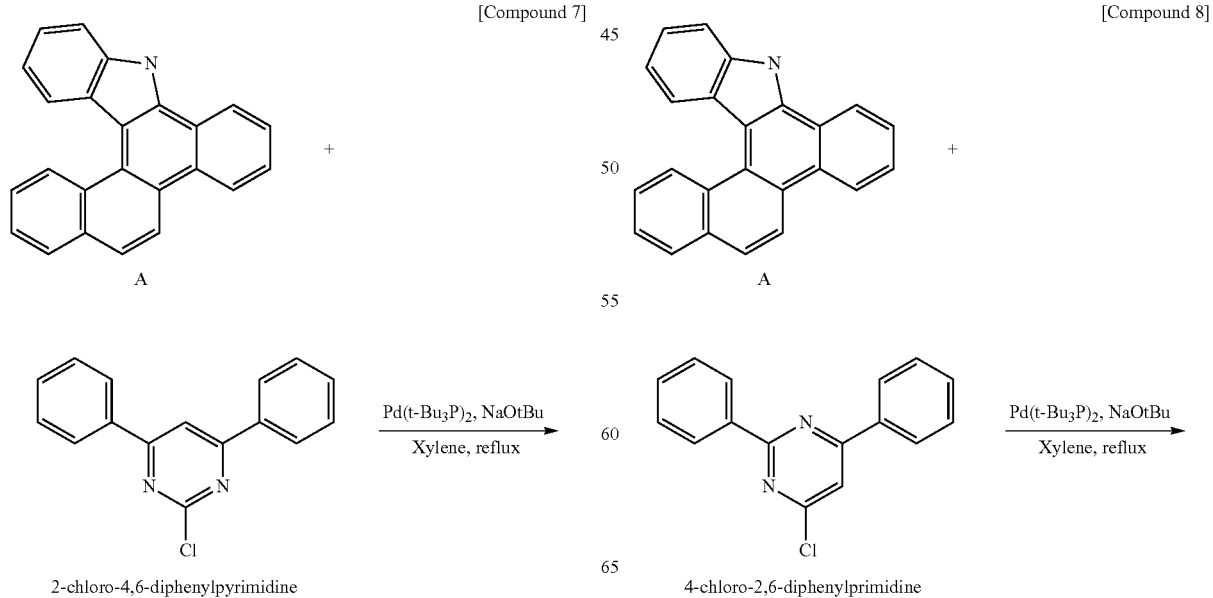

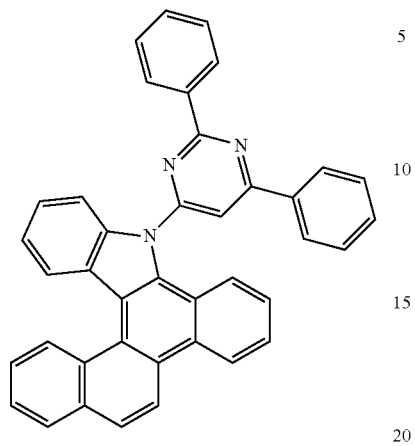

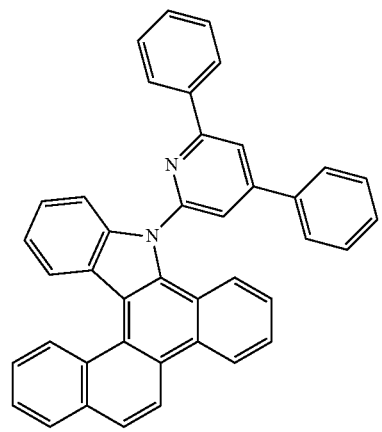

Under a nitrogen atmosphere, Chemical Formula A (10 g, 31.55 mmol) and 4-chloro-2,6-diphenylpyrimidine (9.26 g, 34.70 mmol) were completely dissolved in 230 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 350 ml of ethyl acetate to prepare Compound 8 (10.09 g, yield: 69%).

MS[M+H]$^+$=548

Under a nitrogen atmosphere, Chemical Formula A (10 g, 31.55 mmol) and 2-chloro-4,6-diphenylpyridine (9.26 g, 34.70 mmol) were completely dissolved in 230 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 350 ml of ethyl acetate to prepare Compound 9 (9.98 g, yield: 62%)

MS[M+H]$^+$=547

Preparation Example 1-9

Preparation Example 1-10

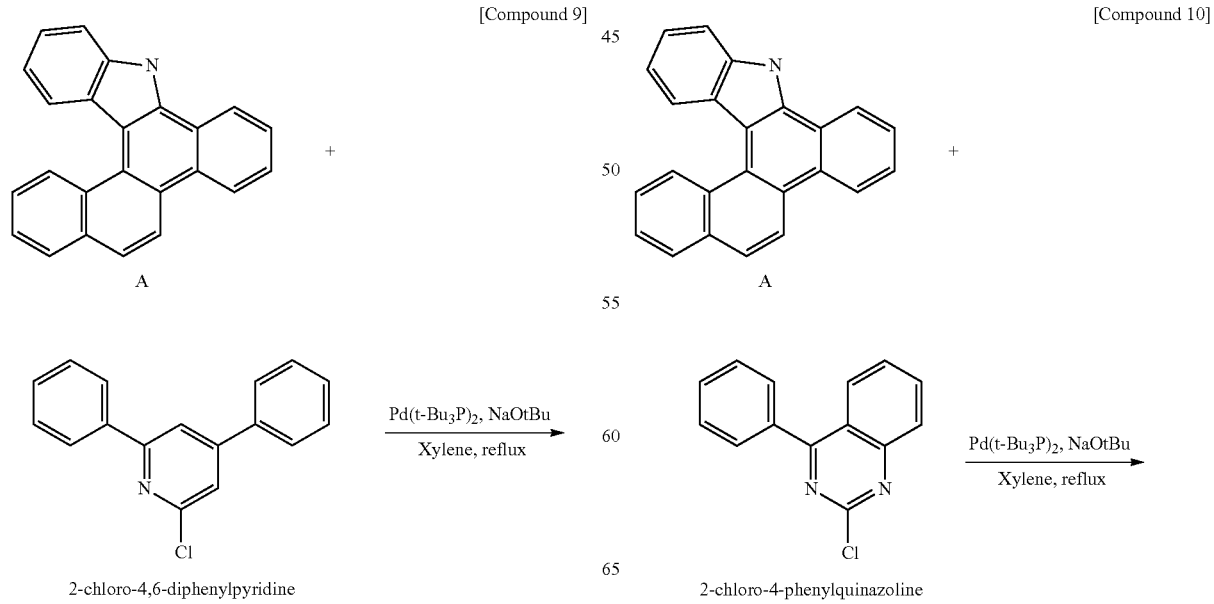

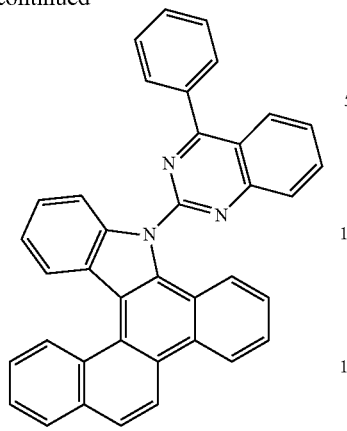

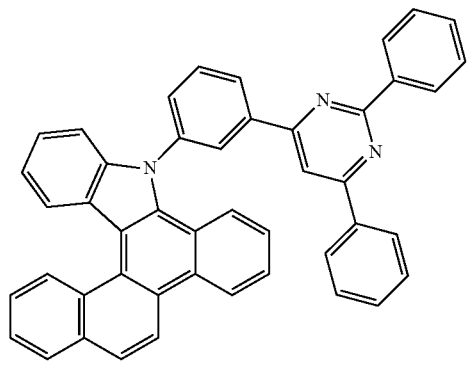

Under a nitrogen atmosphere, Chemical Formula A (10 g, 31.55 mmol) and 2-chloro-4-phenylquinazoline (8.33 g, 34.70 mmol) were completely dissolved in 290 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 6 hours. The temperature was lowered to normal temperature, the mixture was filtered to remove the base, and then xylene was concentrated under reduced pressure, and the residue was recrystallized with 310 ml of ethyl acetate to prepare Compound 10 (14.59 g, yield: 89%).

MS[M+H]$^+$=522

Under a nitrogen atmosphere, Chemical Formula A (10 g, 31.55 mmol) and 2-(3-bromophenyl)-4,6-diphenyl-1,3,5-triazine (13.43 g, 34.70 mmol) were completely dissolved in 220 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 6 hours. The temperature was lowered to normal temperature, the mixture was filtered to remove the base, and then xylene was concentrated under reduced pressure, and the residue was recrystallized with 330 ml of ethyl acetate to prepare Compound 11 (12.45 g, yield: 84%).

MS[M+H]$^+$=625

Preparation Example 1-11

Preparation Example 1-12

[Compound 11]

[Compound 12]

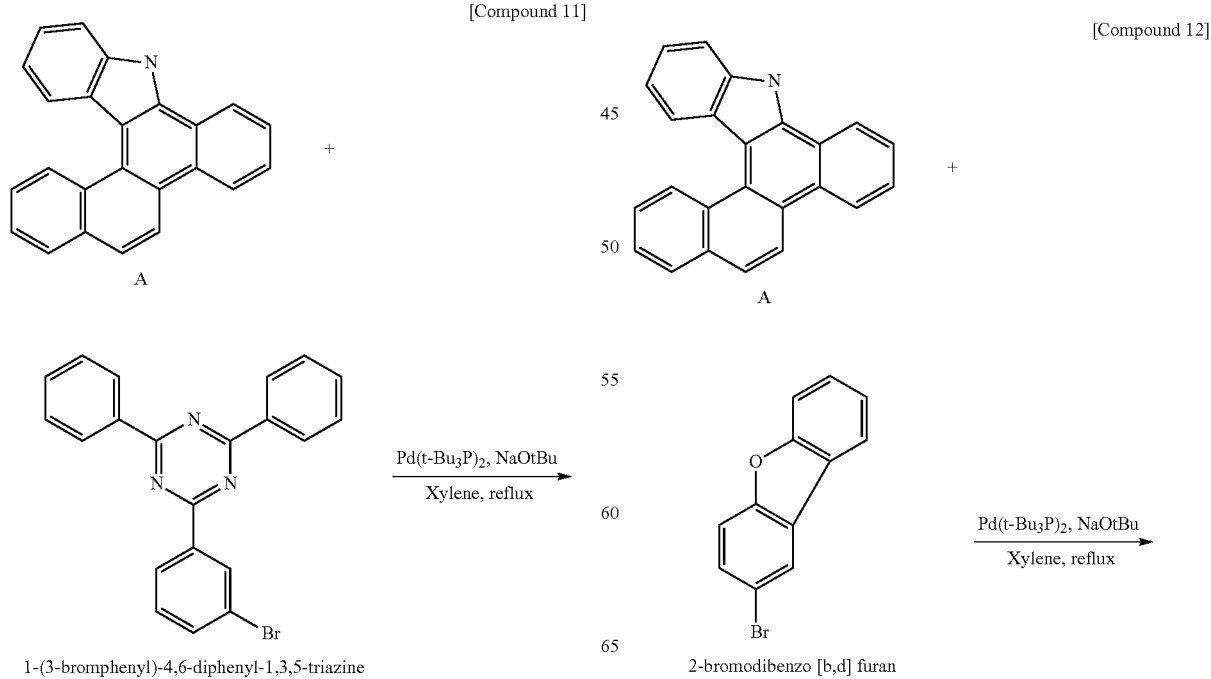

215

-continued

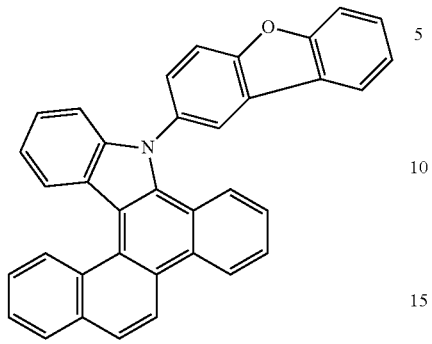

Under a nitrogen atmosphere, Chemical Formula A (10 g, 31.55 mmol) and 2-bromodibenzo[b,d]furan (8.54 g, 34.70 mmol) were completely dissolved in 190 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:13 to prepare Compound 12 (14.39 g, yield: 82%).

MS[M+H]$^+$=484

Preparation Example 1-13

216

-continued

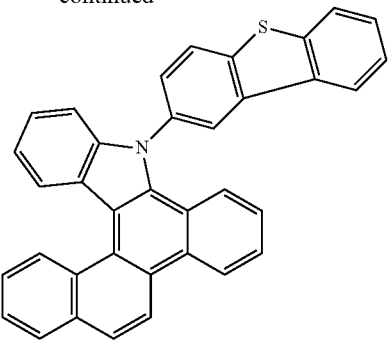

Under a nitrogen atmosphere, Chemical Formula A (10 g, 31.55 mmol) and 2-bromodibenzo[b,d]thiophene (9.09 g, 34.70 mmol) were completely dissolved in 190 ml of xylene in a 500 ml-round bottom flask, and then sodium tert-butoxide (3.94 g, 41.02 mmol) was added thereto, bis(tri-tert-butylphosphine) palladium(0) (0.16 g, 0.32 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:13 to prepare Compound 13 (12.97 g, yield: 74%).

MS[M+H]$^+$=500

Preparation Example 1-14

[Compound 13]

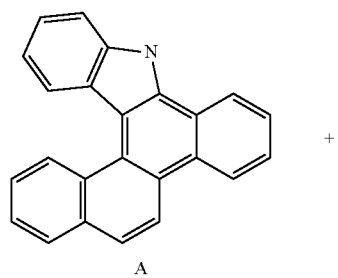

A

+

[Compound 14]

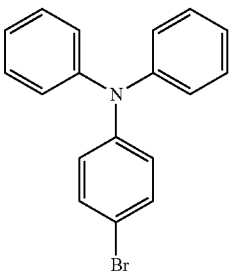

B

+

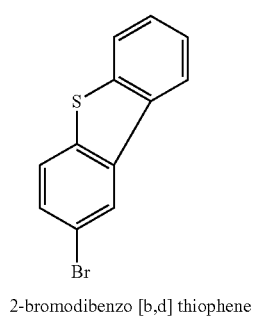

2-bromodibenzo [b,d] thiophene

Pd(t-Bu$_3$P)$_2$, NaOtBu
Xylene, reflux
⟶

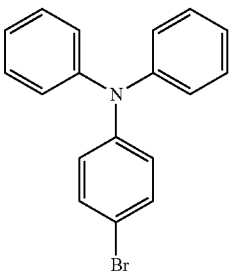

4-bromo-N,N-diphenylaniline

Pd(t-Bu$_3$P)$_2$, NaOtBu
Xylene, reflux
⟶

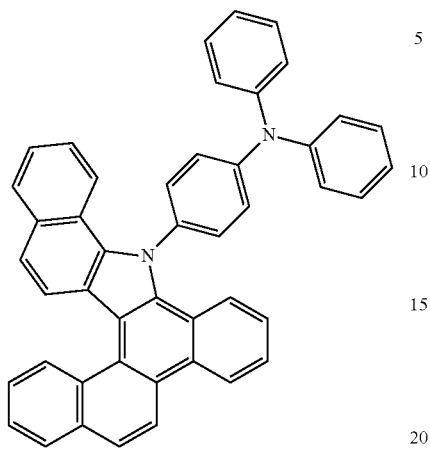

Under a nitrogen atmosphere, Chemical Formula B (10 g, 27.25 mmol) and 4-bromo-N,N-diphenylaniline (9.59 g, 29.97 mmol) were completely dissolved in 180 ml of xylene in a 500 ml-round bottom flask, and then sodium tert-butoxide (3.40 g, 35.43 mmol) was added thereto, bis(tri-tert-butylphosphine) palladium(0) (0.14 g, 0.27 mmol) was put thereinto, and then the resulting mixture was heated and stirred for 3 hours. The temperature was lowered to normal temperature, the mixture was filtered to remove the base, and then xylene was concentrated under reduced pressure, and the residue was columned at a ratio of tetrahydrofuran:hexane=1:13 to prepare Compound 14 (12.97 g, yield: 74%).

MS[M+H]$^+$=611

Preparation Example 1-15

Under a nitrogen atmosphere, Chemical Formula C (10 g, 27.25 mmol) and 2-chloro-4,6-diphenyl-1,3,5-triazine (8.01 g, 29.97 mmol) were completely dissolved in 220 ml of xylene in a 500 ml-round bottom flask, and then sodium tert-butoxide (3.40 g, 35.43 mmol) was added thereto, bis(tri-tert-butylphosphine) palladium(0) (0.14 g, 0.27 mmol) was put thereinto, and then the resulting mixture was heated and stirred for 6 hours. The temperature was lowered to normal temperature, the mixture was filtered to remove the base, and then xylene was concentrated under reduced pressure, and the residue was recrystallized with 250 ml of ethyl acetate to prepare Compound 15 (11.74 g, yield: 68%).

MS[M+H]$^+$=599

Preparation Example 1-16

[Compound 15]

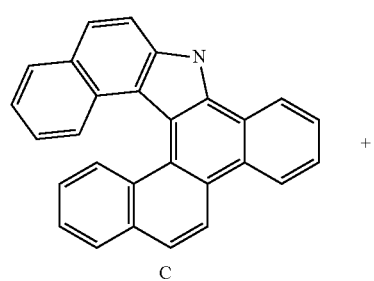

C

+

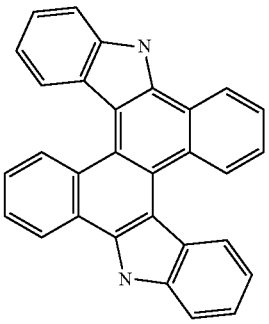

2-chloro-4,6-diphenyl-1,3,5-triazine

Pd(t-Bu$_3$P)$_2$, NaOtBu
───────────────→
Xylene, reflux

[Compound 16]

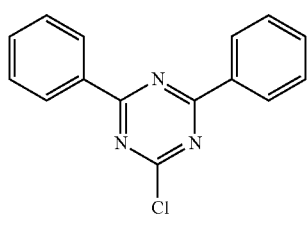

D

+

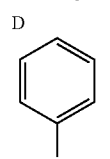

Iodobenzene

Pd(t-Bu$_3$P)$_2$, NaOtBu
───────────────→
Xylene, reflux

-continued

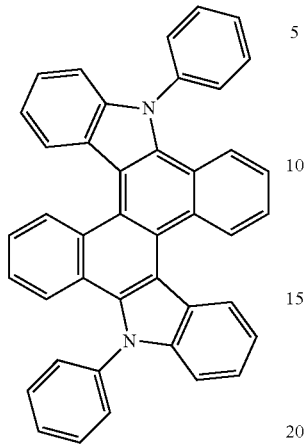

Under a nitrogen atmosphere, Chemical Formula D (10 g, 24.69 mmol) and iodobenzene (5.52 g, 27.16 mmol) were completely dissolved in 180 ml of xylene in a 500 ml-round bottom flask, and then sodium-tert-butoxide (3.08 g, 32.69 mmol) was added thereto, bis(tri-tert-butylphosphine) palladium(0) (0.13 g, 0.25 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 220 ml of ethyl acetate to prepare Compound 16 (12.97 g, yield: 74%).

MS[M+H]$^+$=559

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

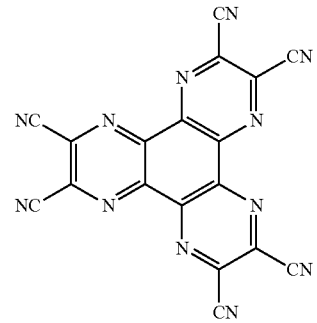

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

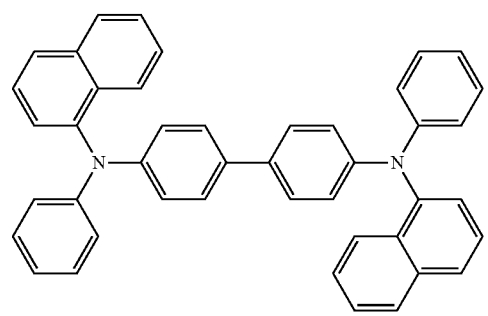

[NPB]

Subsequently, the following Compound 1 was vacuum deposited to have a film thickness of 100 Å on the hole transport layer, thereby forming an electron blocking layer.

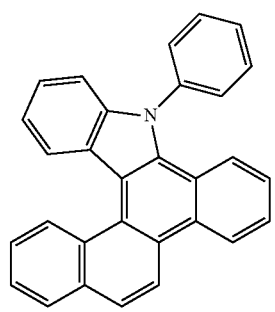

[Compound 1]

Subsequently, the following BH and BD were vacuum deposited at a weight ratio of 25:1 to have a film thickness of 300 Å on the electron blocking layer, thereby forming a light emitting layer.

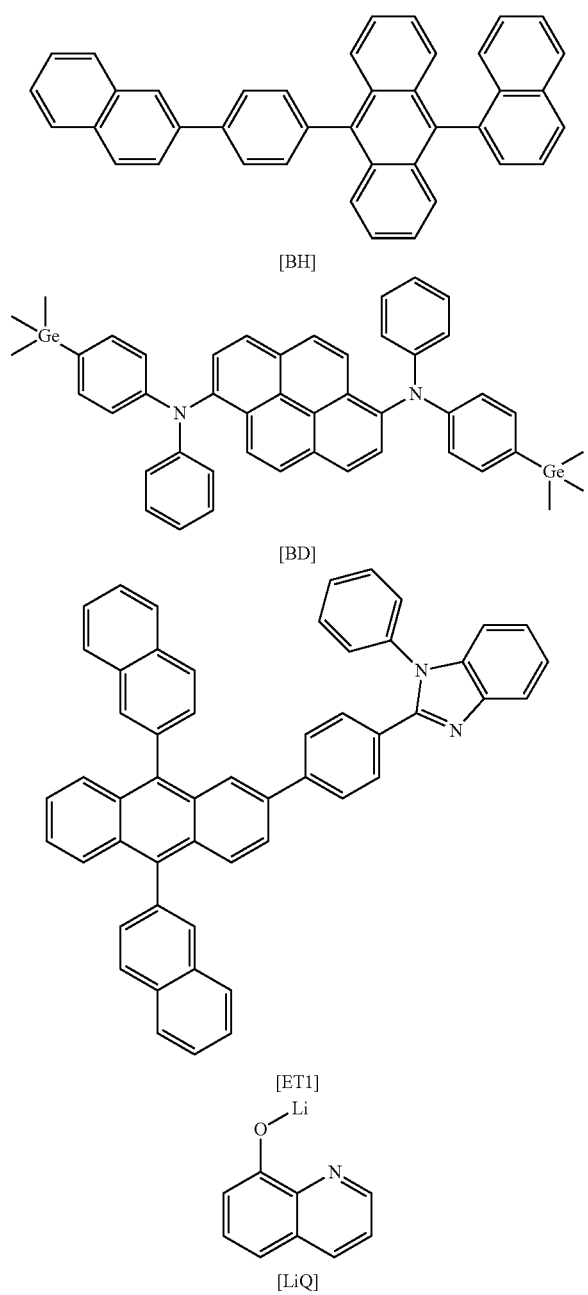

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 2 was used instead of Compound 1 in Experimental Example 1-1.

Experimental Example 1-3

An organic light emitting device was manufactured in the same manner as in Experimental Example 1-1, except that Compound 3 was used instead of Compound 1 in Experimental Example 1-1.

Experimental Example 1-4

An organic light emitting device was manufactured in the same manner as in Experimental Example 1-1, except that Compound 4 was used instead of Compound 1 in Experimental Example 1-1.

Experimental Example 1-5

An organic light emitting device was manufactured in the same manner as in Experimental Example 1-1, except that Compound 5 was used instead of Compound 1 in Experimental Example 1-1.

Experimental Example 1-6

An organic light emitting device was manufactured in the same manner as in Experimental Example 1-1, except that Compound 12 was used instead of Compound 1 in Experimental Example 1-1.

Experimental Example 1-7

An organic light emitting device was manufactured in the same manner as in Experimental Example 1-1, except that Compound 13 was used instead of Compound 1 in Experimental Example 1-1.

Experimental Example 1-8

An organic light emitting device was manufactured in the same manner as in Experimental Example 1-1, except that Compound 14 was used instead of Compound 1 in Experimental Example 1-1.

Experimental Example 1-9

An organic light emitting device was manufactured in the same manner as in Experimental Example 1-1, except that Compound 16 was used instead of Compound 1 in Experimental Example 1-1.

Comparative Example 1-1

An organic light emitting device was manufactured in the same manner as in Experimental Example 1-1, except that a compound of the following EB1 was used instead of Compound 1 in Experimental Example 1-1.

[EB1]

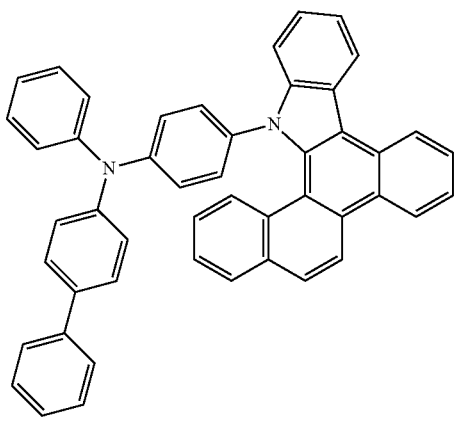

Comparative Example 1-2

An organic light emitting device was manufactured in the same manner as in Experimental Example 1-1, except that a compound of the following EB2 was used instead of Compound 1 in Experimental Example 1-1.

[EB2]

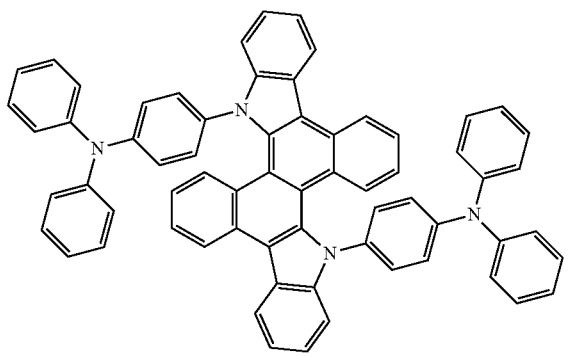

Comparative Example 1-3

An organic light emitting device was manufactured in the same manner as in Experimental Example 1-1, except that a compound of the following EB3 was used instead of Compound 1 in Experimental Example 1-1.

[EB3]

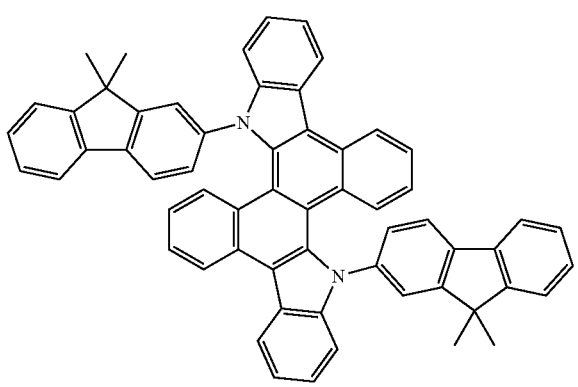

When current was applied to the organic light emitting devices manufactured in Experimental Examples 1-1 to 1-9 and Comparative Examples 1-1 to 1-3, the results of Table 1 were obtained.

TABLE 1

| | Compound (Electron blocking layer) | Voltage (V@10 mA/ cm$^2$) | Efficiency (cd/A@10 mA/ cm$^2$) | Color coordinate (x, y) |
|---|---|---|---|---|
| Experimental Example 1-1 | Compound 1 | 3.65 | 6.43 | (0.138, 0.127) |
| Experimental Example 1-2 | Compound 2 | 3.61 | 6.42 | (0.139, 0.127) |
| Experimental Example 1-3 | Compound 3 | 3.69 | 6.39 | (0.138, 0.126) |
| Experimental Example 1-4 | Compound 4 | 3.69 | 6.38 | (0.138, 0.127) |
| Experimental Example 1-5 | Compound 5 | 3.64 | 6.38 | (0.137, 0.125) |
| Experimental Example 1-6 | Compound 12 | 3.85 | 6.13 | (0.136, 0.125) |
| Experimental Example 1-7 | Compound 13 | 3.81 | 6.12 | (0.136, 0.127) |
| Experimental Example 1-8 | Compound 14 | 3.89 | 6.08 | (0.136, 0.125) |
| Experimental Example 1-9 | Compound 16 | 3.87 | 6.07 | (0.137, 0.125) |
| Comparative Example 1-1 | EB1 | 4.53 | 5.31 | (0.136, 0.127) |
| Comparative Example 1-2 | EB2 | 4.83 | 5.11 | (0.136, 0.127) |
| Comparative Example 1-3 | EB3 | 4.93 | 5.03 | (0.136, 0.127) |

As seen in Table 1, the organic light emitting device manufactured by using the compound of the present invention as an electron blocking layer exhibits excellent characteristics in terms of the efficiency, and driving voltage and/or stability of the organic light emitting device.

The organic light emitting device shows lower voltage and higher efficiency characteristics than the organic light emitting devices manufactured by using, as an electron blocking layer, the compounds of Comparative Examples 1-1 to 1-3 in which a carbazole ring is formed in a direction different from the core of the present invention.

As in the result of Table 1, it could be confirmed that the compound according to the present invention had excellent electron blocking capability, and thus could be applied to an organic light emitting device.

Experimental Example 2-1

An experiment was performed in the same manner as in Experimental Example 1-1, except that the compound TCTA was used as the electron blocking layer, and Compound 1 was used instead of NPB as the hole transport layer.

[TCTA]

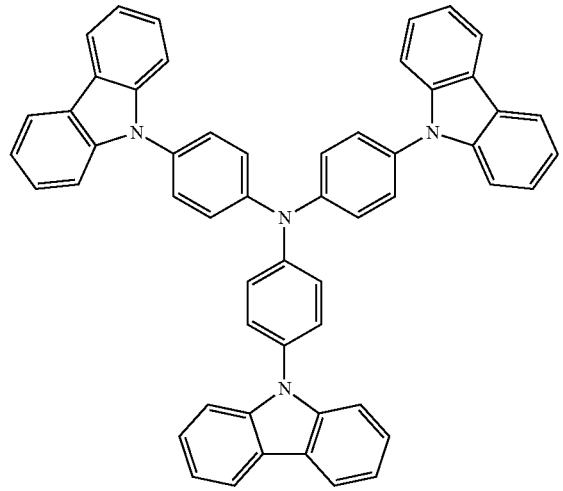

Experimental Example 2-2

An experiment was performed in the same manner as in Experimental Example 2-1, except that as the hole transport layer, Compound 2 was used instead of Compound 1.

Experimental Example 2-3

An experiment was performed in the same manner as in Experimental Example 2-1, except that as the hole transport layer, Compound 3 was used instead of Compound 1.

Experimental Example 2-4

An experiment was performed in the same manner as in Experimental Example 2-1, except that as the hole transport layer, Compound 4 was used instead of Compound 1.

Experimental Example 2-5

An experiment was performed in the same manner as in Experimental Example 2-1, except that as the hole transport layer, Compound 5 was used instead of Compound 1.

Experimental Example 2-6

An experiment was performed in the same manner as in Experimental Example 2-1, except that as the hole transport layer, Compound 12 was used instead of Compound 1.

Experimental Example 2-7

An experiment was performed in the same manner as in Experimental Example 2-1, except that as the hole transport layer, Compound 13 was used instead of Compound 1.

Experimental Example 2-8

An experiment was performed in the same manner as in Experimental Example 2-1, except that as the hole transport layer, Compound 14 was used instead of Compound 1.

Experimental Example 2-9

An experiment was performed in the same manner as in Experimental Example 2-1, except that as the hole transport layer, Compound 16 was used instead of Compound 1.

Comparative Example 2-1

An organic light emitting device was manufactured in the same manner as in Experimental Example 2-1, except that a compound of the following HT1 was used instead of Compound 1 in Experimental Example 2-1.

[HT1]

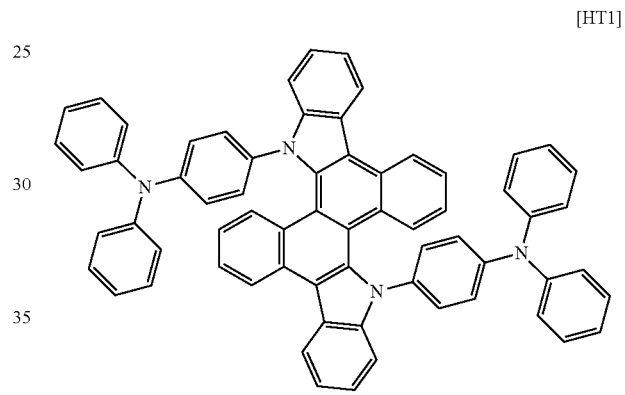

Comparative Example 2-2

An organic light emitting device was manufactured in the same manner as in Experimental Example 2-1, except that a compound of the following HT2 was used instead of Compound 1 in Experimental Example 2-1.

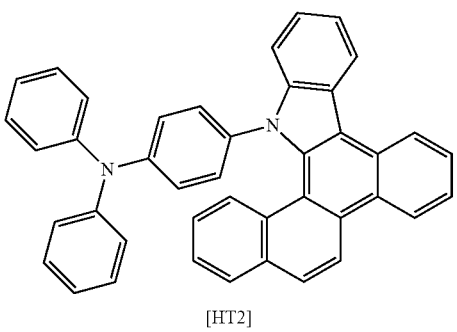

[HT2]

When current was applied to the organic light emitting devices manufactured in Experimental Examples 2-1 to 2-9 and Comparative Examples 2-1 and 2-2, the results of Table 2 were obtained.

TABLE 2

| Compound (Hole transport layer) | | Voltage (V@10 mA/ cm²) | Efficiency (cd/A@10 mA/ cm²) | Color coordinate (x, y) |
|---|---|---|---|---|
| Experimental Example 2-1 | Compound 1 | 3.45 | 5.25 | (0.137, 0.125) |
| Experimental Example 2-2 | Compound 2 | 3.54 | 5.31 | (0.136, 0.125) |
| Experimental Example 2-3 | Compound 3 | 3.51 | 5.28 | (0.136, 0.127) |
| Experimental Example 2-4 | Compound 4 | 3.41 | 5.30 | (0.136, 0.125) |
| Experimental Example 2-5 | Compound 5 | 3.42 | 5.21 | (0.136, 0.127) |
| Experimental Example 2-6 | Compound 12 | 3.54 | 5.02 | (0.136, 0.125) |
| Experimental Example 2-7 | Compound 13 | 3.64 | 5.01 | (0.136, 0.127) |
| Experimental Example 2-8 | Compound 14 | 3.61 | 5.15 | (0.136, 0.125) |
| Experimental Example 2-9 | Compound 16 | 3.3 | 5.00 | (0.137, 0.125) |
| Comparative Example 2-1 | HT1 | 4.01 | 4.63 | (0.136, 0.127) |
| Comparative Example 2-2 | HT2 | 4.25 | 4.42 | (0.136, 0.127) |

As seen in Table 2, the organic light emitting device manufactured by using the compound of the present invention as a hole transport layer exhibits better Characteristics, in terms of the efficiency, and driving voltage and/or stability of the organic light emitting device, than the organic light emitting devices manufactured by using, as an electron blocking layer, the compounds of Comparative Examples 2-1 and 2-2, in which a carbazole ring is formed in a direction different from the core of the present invention.

As in the result of Table 1, it could be confirmed that the compound according to the present invention had excellent hole transport capability, and thus could be applied to an organic light emitting device.

As in the results of Tables 1 and 2, it could be confirmed that the compound according to the present invention had excellent electron blocking capability and hole transport capability, and thus could be applied to an organic light emitting device.

Experimental Example 3

The compounds synthesized in the Synthesis Examples were subjected to high purity sublimation purification by a typically known method, and then green organic light emitting devices were manufactured by the following method.

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

An organic EL device was manufactured by configuring the light emitting device in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the thus prepared ITO transparent electrode by using CBP as a host. The structures of m-MTDATA, TCTA, Ir(ppy)$_3$, CBP, and BCP are as follows.

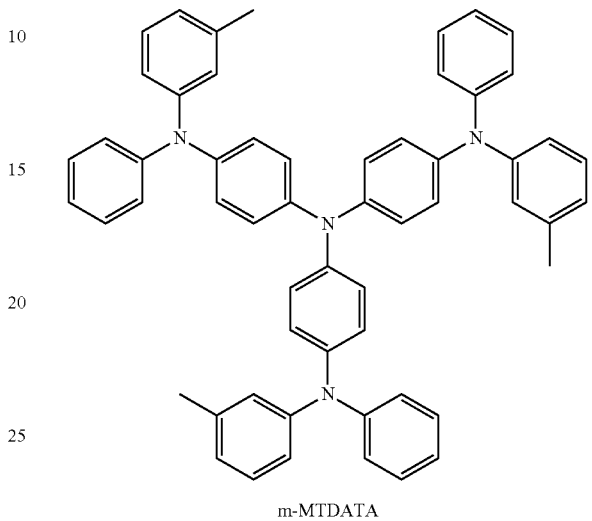

m-MTDATA

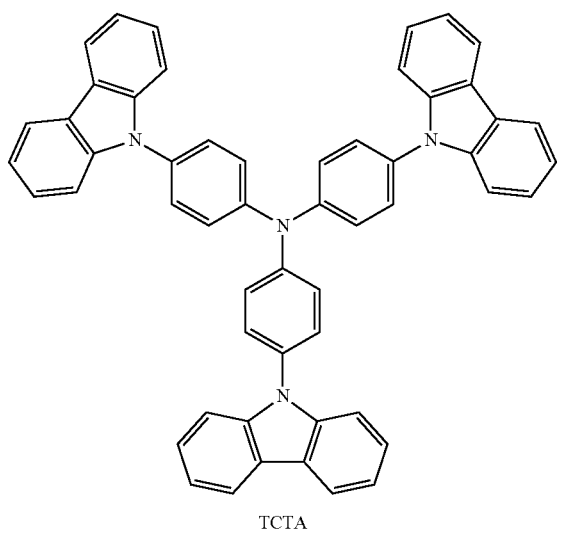

TCTA

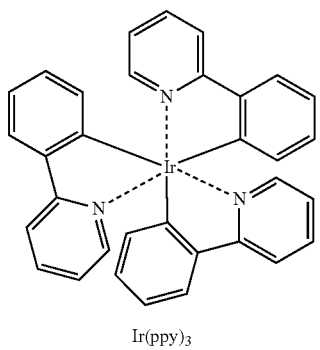

Ir(ppy)$_3$

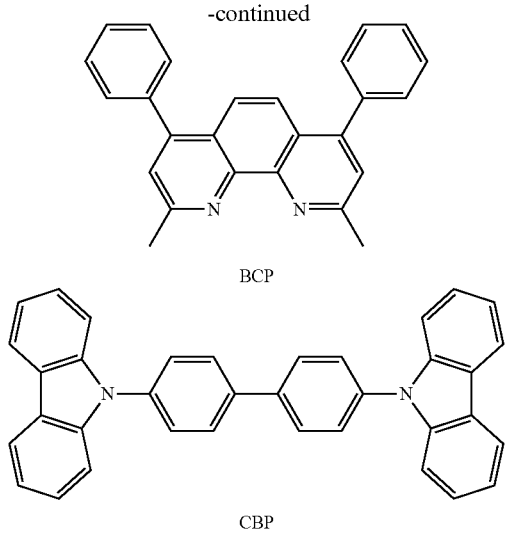

BCP

CBP

Experimental Example 3-1

An organic light emitting device was manufactured in the same manner as in Experimental Example 3, except that Compound 6 was used instead of CBP in Experimental Example 3.

Experimental Example 3-2

An organic light emitting device was manufactured in the same manner as in Experimental Example 3, except that Compound 7 was used instead of CBP in Experimental Example 3.

Experimental Example 3-3

An organic light emitting device was manufactured in the same manner as in Experimental Example 3, except that Compound 8 was used instead of CBP in Experimental Example 3.

Experimental Example 3-4

An organic light emitting device was manufactured in the same manner as in Experimental Example 3, except that Compound 9 was used instead of CBP in Experimental Example 3.

Experimental Example 3-5

An organic light emitting device was manufactured in the same manner as in Experimental Example 3, except that Compound 10 was used instead of CBP in Experimental Example 3.

Experimental Example 3-6

An organic light emitting device was manufactured in the same manner as in Experimental Example 3, except that Compound 11 was used instead of CBP in Experimental Example 3.

When current was applied to the organic light emitting devices manufactured in Experimental Example 3 and Experimental Examples 3-1 to 3-6, the results of Table 3 were obtained.

TABLE 3

| Compound (Host) | Voltage (V@10 mA/ $cm^2$) | Efficiency (cd/A@10 mA/ $cm^2$) | EL peak (nm) |
|---|---|---|---|
| Experimental Example 3 (Comparative Example 3-1) CBP | 7.62 | 36.12 | 516 |
| Experimental Example 3-1 Compound 6 | 6.60 | 44.93 | 517 |
| Experimental Example 3-2 Compound 7 | 6.56 | 45.24 | 516 |
| Experimental Example 3-3 Compound 8 | 6.61 | 44.72 | 517 |
| Experimental Example 3-4 Compound 9 | 6.59 | 44.65 | 518 |
| Experimental Example 3-5 Compound 10 | 6.68 | 44.31 | 517 |
| Experimental Example 3-6 Compound 11 | 6.53 | 44.63 | 517 |

As a result of the experiments, it could be confirmed that the green organic light emitting devices of Experimental Examples 3-1 to 3-6 in which the compound according to the present invention was used as a host material of the light emitting layer exhibited better performances, in terms of current efficiency and driving voltage, than the green organic light emitting device of Experimental Example 3 (Comparative Example 3-1) in which CBP in the related art was used. It can be seen that the compounds having triazine, pyrimidine, pyridine, and quinazoline as the substituent are suitable for a green organic light emitting device.

Experimental Example 4-1

The compounds synthesized in the Synthesis Examples were subjected to high purity sublimation purification by a typically known method, and then red organic light emitting devices were manufactured by the following method.

An ITO glass was patterned and then washed, such that the light emitting area of the ITO glass became 2 mm×2 mm. The substrate was mounted on a vacuum chamber, and then the base pressure was allowed to be $1\times10^{-6}$ torr, and then for the organic material, DNTPD (700 Å), α-NPB (300 Å), and Compound 6 prepared by the present invention were used as hosts (90 wt %) on the ITO, the following $(piq)_2Ir(acac)$ (10 wt %) was co-deposited (300 Å) as a dopant, films were formed in the order of $Alq_3$ (350 Å), LiF (5 Å), and Al (1,000 Å), and measurements were made at 0.4 mA.

The structures of DNTPD, α-NPB, $(piq)_2Ir(acac)$, and $Alq_3$ are as follows.

Experimental Example 4-2

An organic light emitting device was manufactured in the same manner as in Experimental Example 4-1, except that Compound 7 was used instead of Compound 6 in Experimental Example 4-1.

Experimental Example 4-3

An organic light emitting device was manufactured in the same manner as in Experimental Example 4-1, except that Compound 8 was used instead of Compound 6 in Experimental Example 4-1.

Experimental Example 4-4

An organic light emitting device was manufactured in the same manner as in Experimental Example 4-1, except that Compound 9 was used instead of Compound 6 in Experimental Example 4-1.

Experimental Example 4-5

An organic light emitting device was manufactured in the same manner as in Experimental Example 4-1, except that Compound 10 was used instead of Compound 6 in Experimental Example 4-1.

Experimental Example 4-6

An organic light emitting device was manufactured in the same manner as in Experimental Example 4-1, except that Compound 11 was used instead of Compound 6 in Experimental Example 4-1.

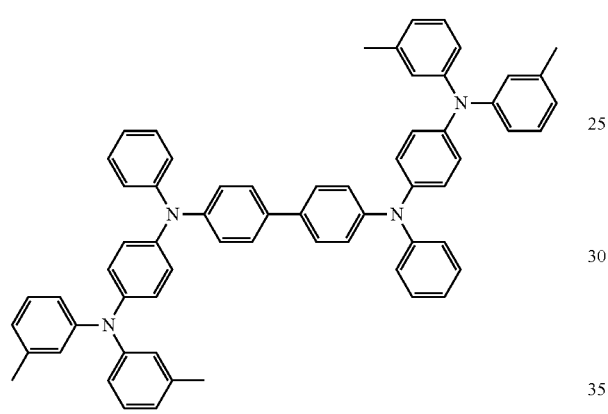

[DNTPD]

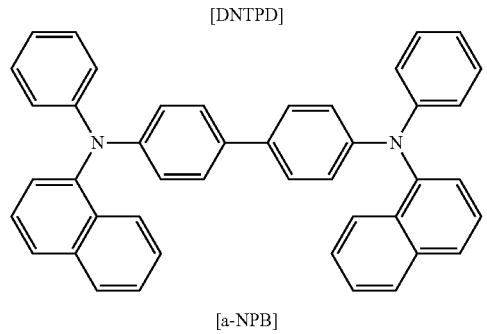

[a-NPB]

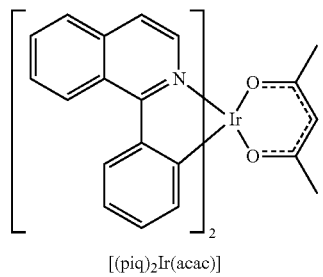

[(piq)$_2$Ir(acac)]

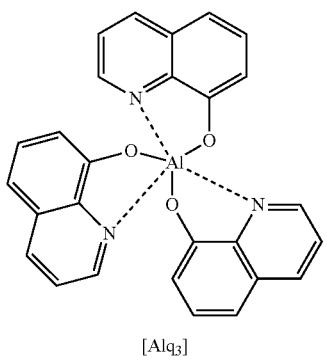

[Alq$_3$]

Comparative Example 4-1

An organic light emitting device for Comparative Example 4-1 was manufactured equally, except that CBP frequently used as a general phosphorescent host material was used instead of the organic light emitting compound prepared by the present invention as a host of the light emitting layer in the device structures of the Examples.

For the organic light emitting devices manufactured according to the following Examples 4-1 to 4-6 and Comparative Example 4-1, the voltages, current densities, luminances, color coordinates, and lifetimes were measured, and the results are shown in the following [Table 4]. T95 means the time taken for the luminance to be reduced to 95% of the initial luminance (5,000 nit).

TABLE 4

| Classification | Host | Dopant | Voltage (V) | Luminance (cd/m$^2$) | CIEx | CIEy | T95 (hr) |
|---|---|---|---|---|---|---|---|
| Experimental Example 4-1 | Compound 6 | [(piq)$_2$Ir(acac)] | 4.4 | 1860 | 0.670 | 0.329 | 465 |
| Experimental Example 4-2 | Compound 7 | [(piq)$_2$Ir(acac)] | 4.2 | 1850 | 0.674 | 0.325 | 445 |
| Experimental Example 4-3 | Compound 8 | [(piq)$_2$Ir(acac)] | 4.1 | 1900 | 0.672 | 0.327 | 440 |
| Experimental Example 4-4 | Compound 9 | [(piq)$_2$Ir(acac)] | 4.3 | 1840 | 0.673 | 0.335 | 435 |
| Experimental Example 4-5 | Compound 10 | [(piq)$_2$Ir(acac)] | 4.4 | 1790 | 0.675 | 0.333 | 445 |

TABLE 4-continued

| Classification | Host | Dopant | Voltage (V) | Luminance (cd/m²) | CIEx | CIEy | T95 (hr) |
|---|---|---|---|---|---|---|---|
| Experimental Example 4-6 | Compound 11 | [(piq)₂Ir(acac)] | 4.2 | 1810 | 0.670 | 0.339 | 440 |
| Comparative Example 4-1 | CBP | [(piq)₂Ir(acac)] | 6.5 | 920 | 0.679 | 0.339 | 260 |

As a result of the experiments, it could be confirmed that the red organic light emitting devices of Experimental Examples 4-1 to 4-6 of Experimental Example 4 in which Compounds 6, 7, 8, 9, 10, and 11 prepared according to the present invention was used as a host material of the light emitting layer exhibited better performances, in terms of current efficiency, driving voltage, and lifetime, than the red organic light emitting device of Comparative Example 4-1 in which CBP in the related art was used. It can be seen that the compounds having triazine and quinazoline as the substituent are suitable for a red organic light emitting device.

Although the preferred exemplary embodiments (an electron blocking layer, a hole transport layer, a green light emitting layer, and a red light emitting layer) of the present invention have been described above, the present invention is not limited thereto, and various modifications can be made and carried out within the scope of the claims and the detailed description of the invention, and also fall within the scope of the invention.

The invention claimed is:

1. A compound represented by the following Chemical Formula 1:

[Chemical Formula 1]

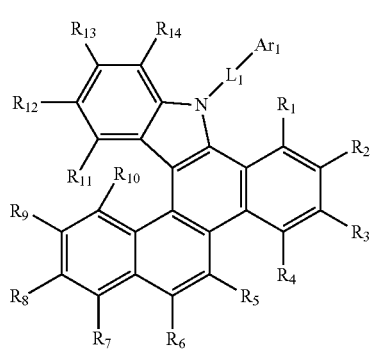

in Chemical Formula 1,
$L_1$ is a substituted or unsubstituted arylene group; or a substituted or unsubstituted divalent heterocyclic group,
$Ar_1$ is hydrogen; deuterium; a halogen group; a cyano group; a substituted or unsubstituted alkyl group; a substituted or unsubstituted aryl group; a substituted or unsubstituted heterocyclic group; a substituted or unsubstituted amine group; or a substituted or unsubstituted silyl group,
$R_1$ to $R_4$ and $R_7$ to $R_{10}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group,
$R_{11}$ to $R_{14}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring, and
$R_5$ and $R_6$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring, wherein when $R_5$ and $R_6$ combine to each other to form a ring, the ring is a 5-membered to 8-membered heterocyclic ring.

2. The compound of claim 1, wherein Chemical Formula 1 is represented by the following Chemical Formula 3 or 4:

[Chemical Formula 3]

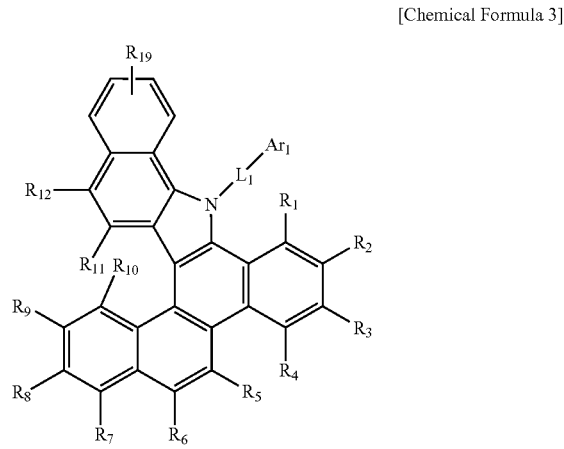

[Chemical Formula 4]

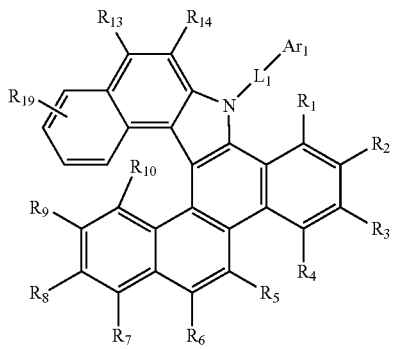

in Formulae 3 and 4, $L_1$, $Ar_1$, and $R_1$ to $R_{10}$ are the same as those defined in Chemical Formula 1, and $R_{19}$ is the same as the definition of $R_1$ of Chemical Formula 1.

3. The compound of claim 1, wherein $R_5$ and $R_6$ combine with each other to be represented by the following Chemical Formula 2:

[Chemical Formula 2]

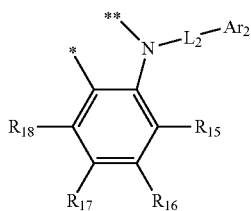

in Chemical Formula 2,

* and ** are a moiety bonded to a position of $R_5$ or $R_6$, $L_2$ is a substituted or unsubstituted arylene group; or a substituted or unsubstituted divalent heterocyclic group, $Ar_2$ is hydrogen; deuterium; a halogen group; a cyano group; a substituted or unsubstituted alkyl group; a substituted or unsubstituted aryl group; a substituted or unsubstituted heterocyclic group; or a substituted or unsubstituted silyl group, and $R_{15}$ to $R_{18}$ are the same as or different from each other, and are each independently hydrogen; deuterium; a halogen group; a hydroxy group; a nitro group; a cyano group; a substituted or unsubstituted alkyl group; a substituted or unsubstituted alkenyl group; a substituted or unsubstituted alkynyl group; a substituted or unsubstituted cycloalkyl group; a substituted or unsubstituted alkoxy group; a substituted or unsubstituted aryloxy group; a substituted or unsubstituted arylthioxy group; a substituted or unsubstituted amine group; a substituted or unsubstituted aryl group; or a substituted or unsubstituted heterocyclic group, or combine with an adjacent group to form a ring.

4. The compound of claim 3, wherein Chemical Formula 1 is represented by any one of the following Chemical Formulae 1-1, 1-2, 3-1, 3-2, 4-1, and 4-2:

[Chemical Formula 1-1]

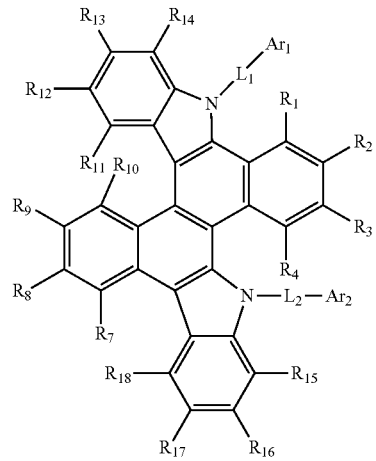

[Chemical Formula 1-2]

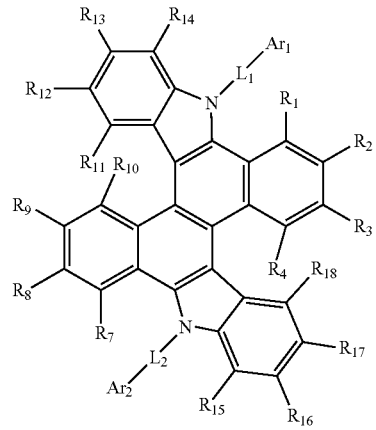

[Chemical Formula 3-1]

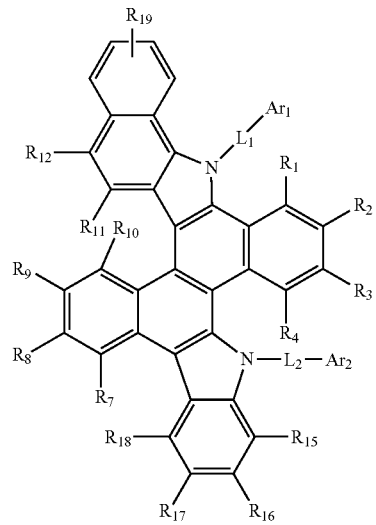

[Chemical Formula 3-2]

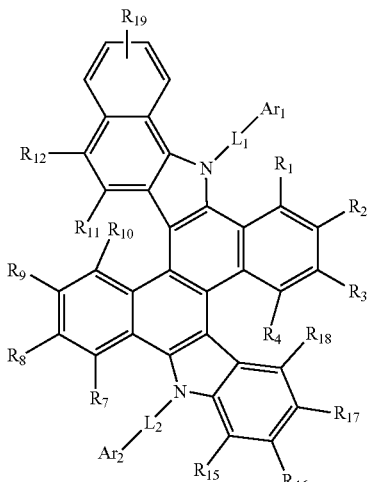

[Chemical Formula 4-1]

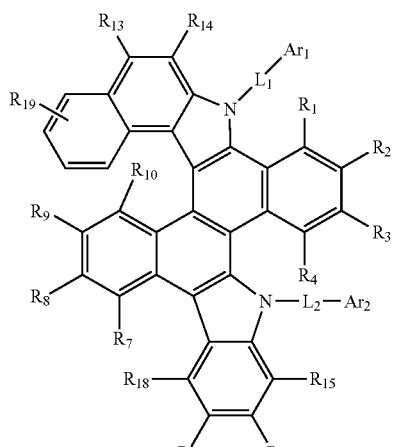

[Chemical Formula 4-2]

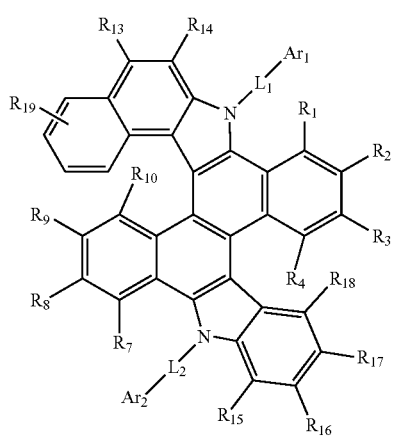

in Chemical Formulae 1-1, 1-2, 3-1, 3-2, 4-1, and 4-2, $L_1$, $L_2$, $Ar_1$, $Ar_2$, $R_1$ to $R_4$, and $R_7$ to $R_{18}$ are the same as those defined in Chemical Formulae 1 and 2, and $R_{19}$ is the same as the definition of $R_1$ of Chemical Formula 1.

5. The compound of claim 1, wherein $L_1$ is a substituted or unsubstituted phenylene group; a substituted or unsubstituted divalent biphenyl group; a substituted or unsubstituted naphthylene group; a substituted or unsubstituted pyridylene group; a substituted or unsubstituted pyrimidylene group; or a substituted or unsubstituted triazinylene group.

6. The compound of claim 1, wherein $R_6$ is $-L_3-Ar_3$,
   $L_3$ is a direct bond; a substituted or unsubstituted arylene group; or a substituted or unsubstituted divalent heterocyclic group, and
   $Ar_3$ is hydrogen; deuterium; a halogen group; a cyano group; a substituted or unsubstituted alkyl group; a substituted or unsubstituted aryl group; a substituted or unsubstituted amine group; a substituted or unsubstituted heterocyclic group; or a substituted or unsubstituted silyl group.

7. The compound of claim 1, wherein $R_{12}$ is $-L_4-Ar_4$,
   $L_4$ is a direct bond; a substituted or unsubstituted arylene group; or a substituted or unsubstituted divalent heterocyclic group, and
   $Ar_4$ is hydrogen; deuterium; a halogen group; a cyano group; a substituted or unsubstituted alkyl group; a substituted or unsubstituted aryl group; a substituted or unsubstituted heterocyclic group; or a substituted or unsubstituted silyl group.

8. The compound of claim 1, wherein $R_1$ to $R_4$ and $R_7$ to $R_{10}$ are the same as or different from each other, and are each independently hydrogen; deuterium; a halogen group; a $C_1$ to $C_{10}$ alkyl group; or a $C_6$ to $C_{20}$ aryl group.

9. The compound of claim 1, wherein the compound represented by Chemical Formula 1 is any one selected from the structural formulae of the following Group 1 to 3:

[Group 1]

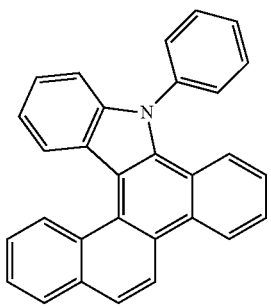

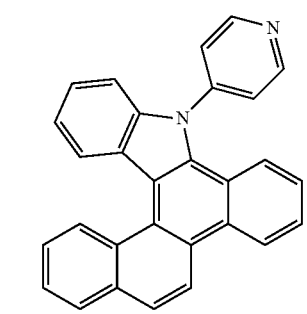

239
-continued
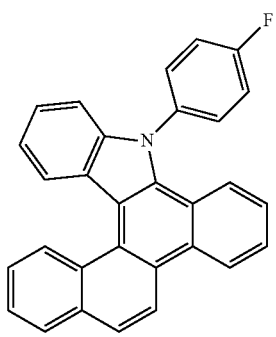
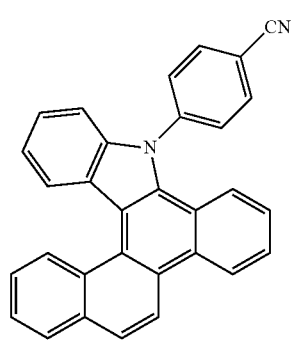
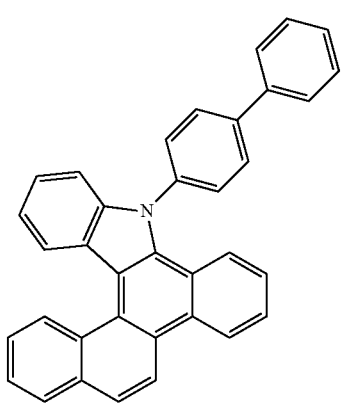
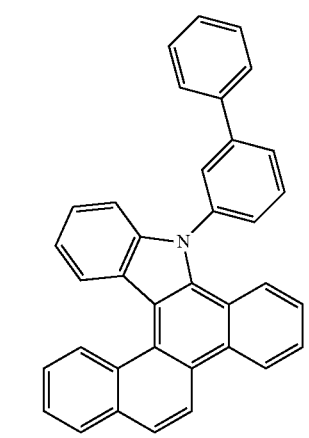
240
-continued
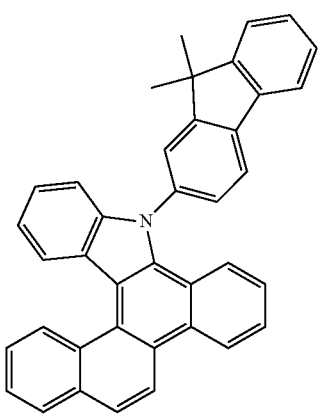
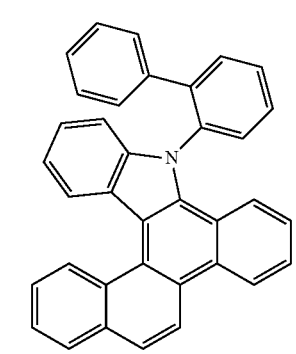
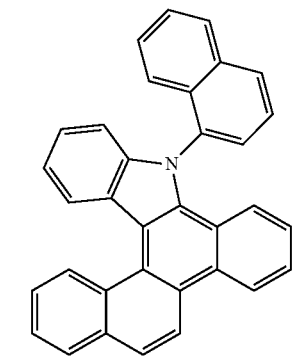
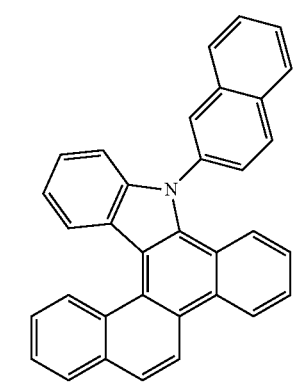

241
-continued
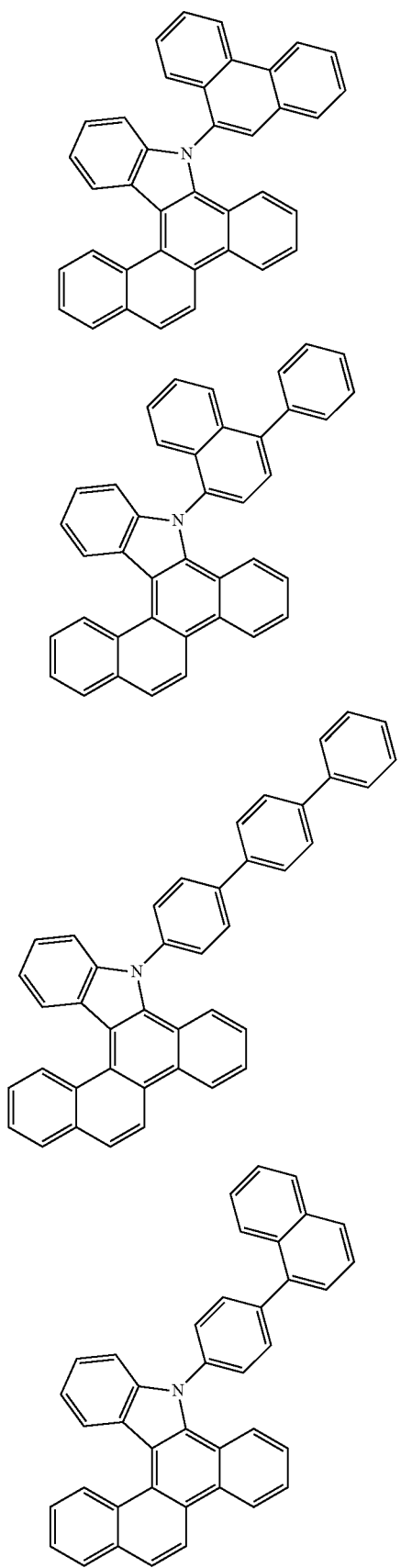
242
-continued
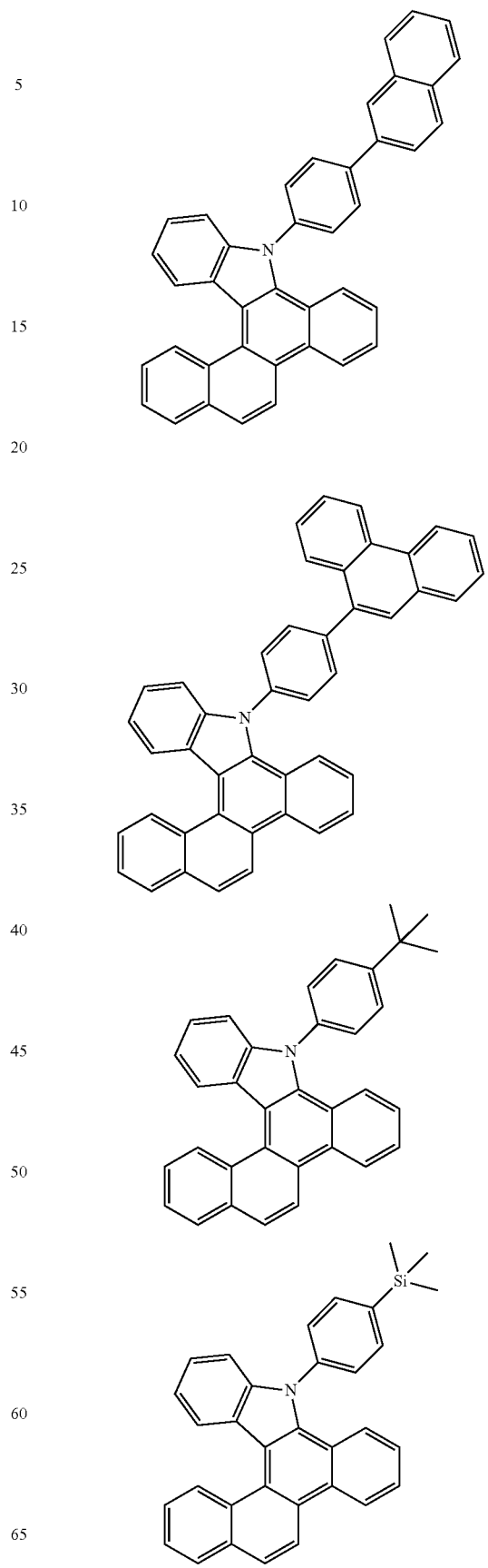

243
-continued
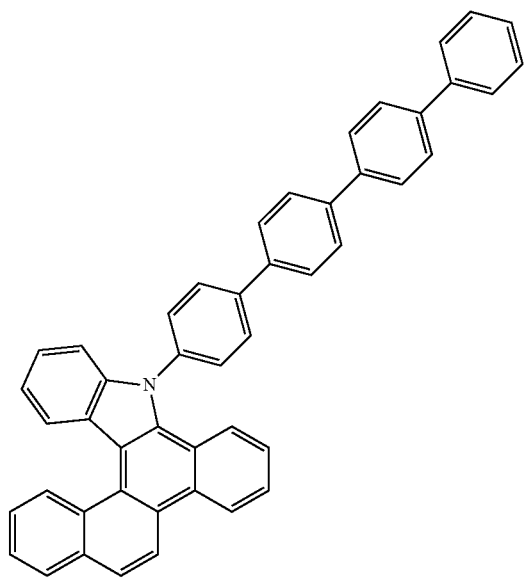
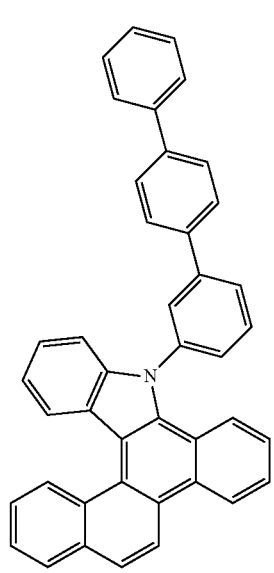
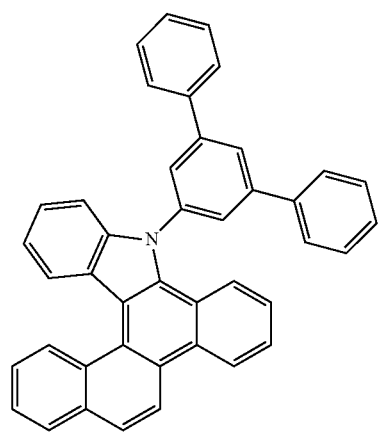
244
-continued
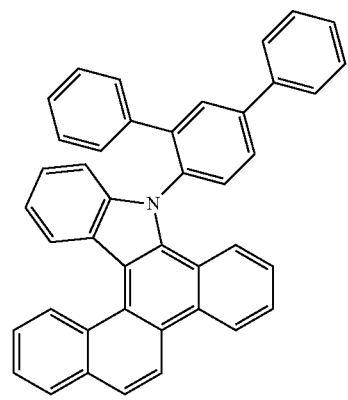
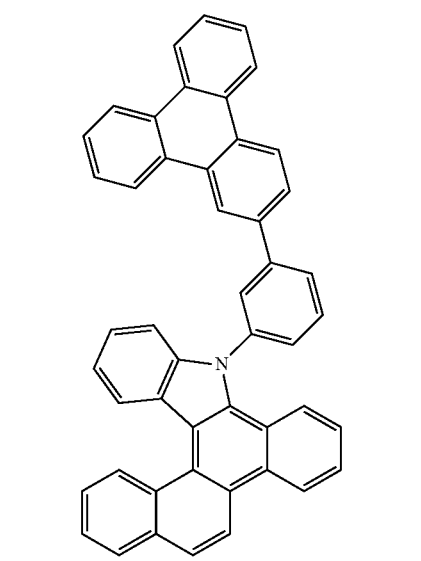
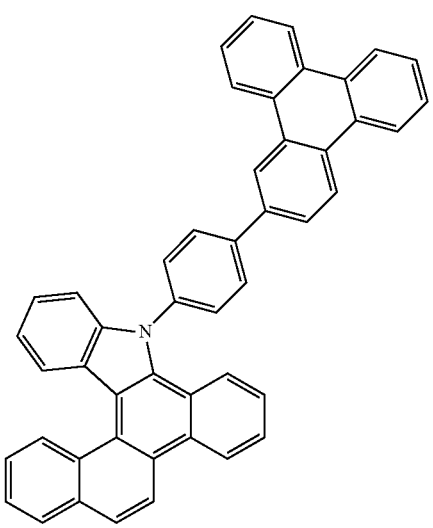

245
-continued
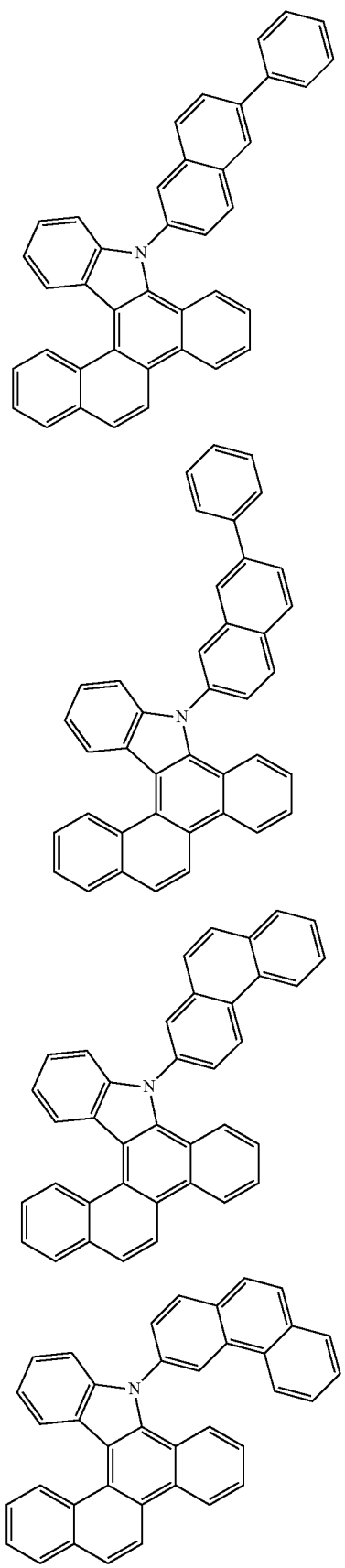
246
-continued
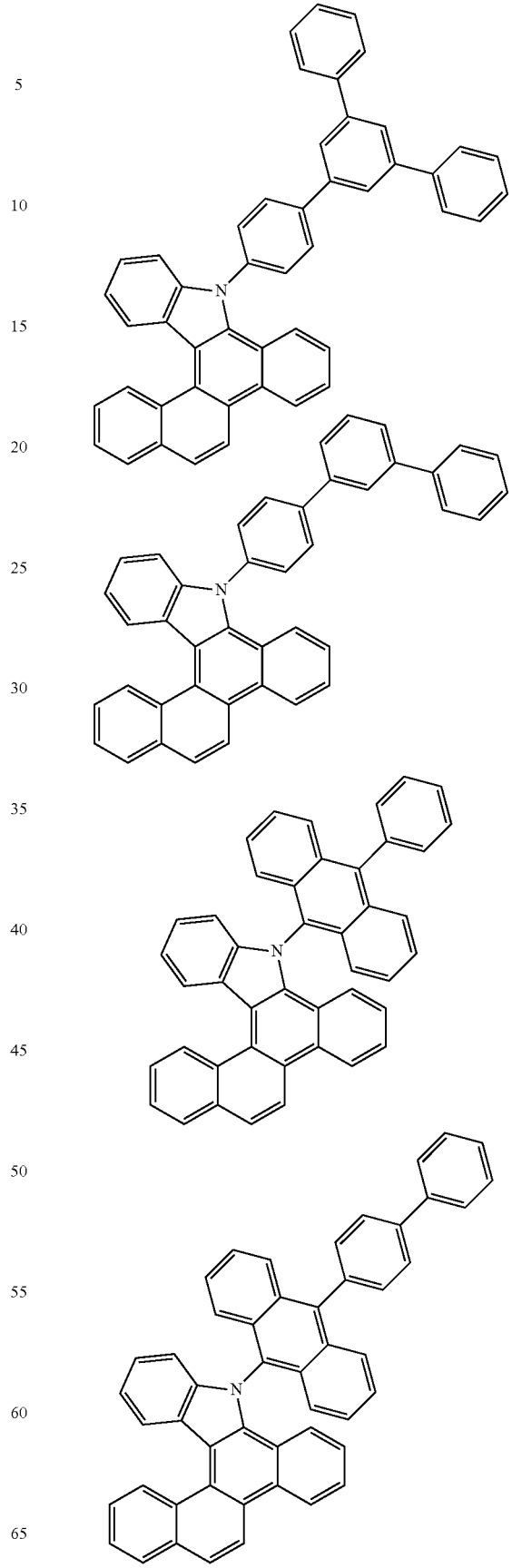

247
-continued
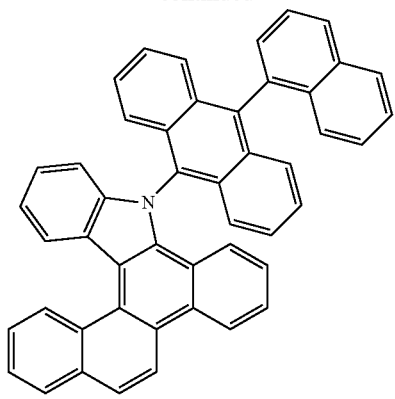
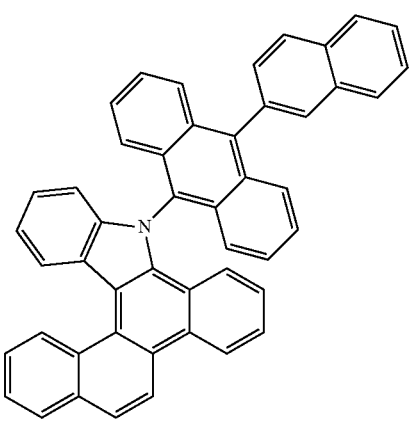
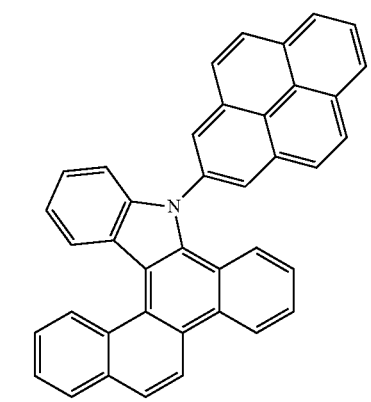
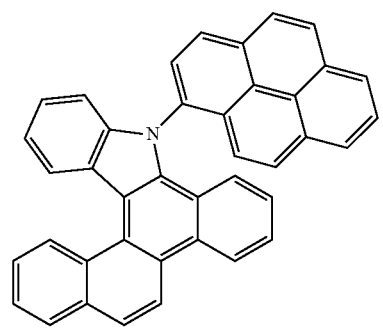
248
-continued
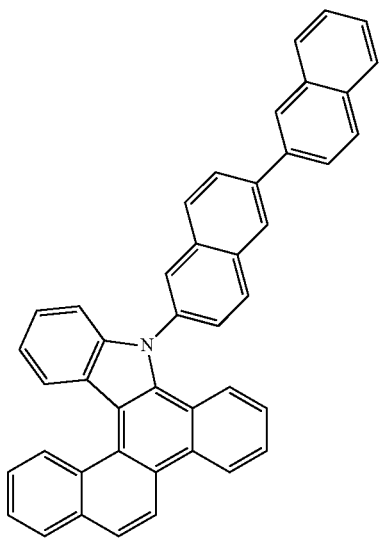
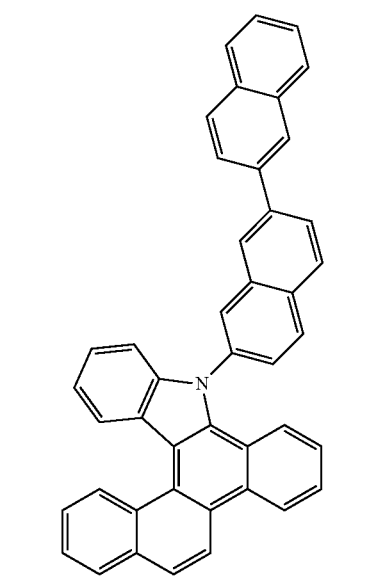
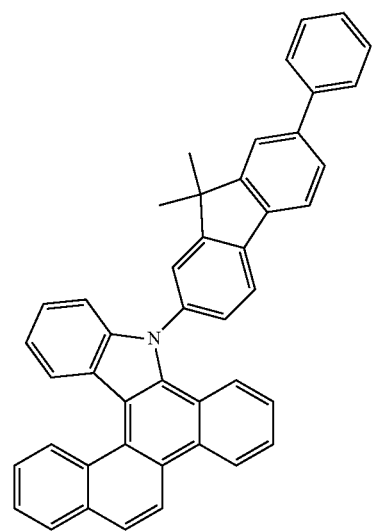

249
-continued
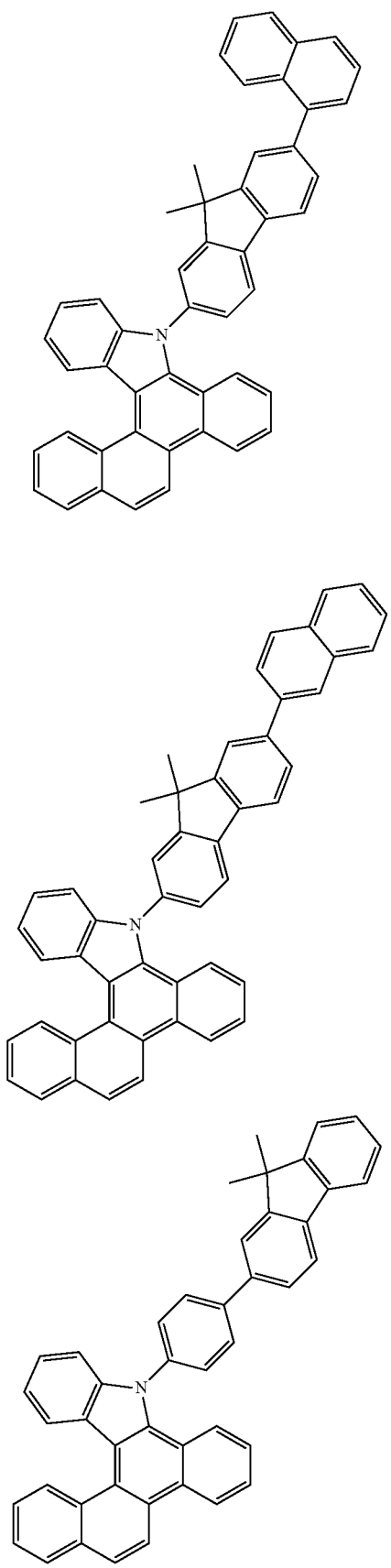
250
-continued
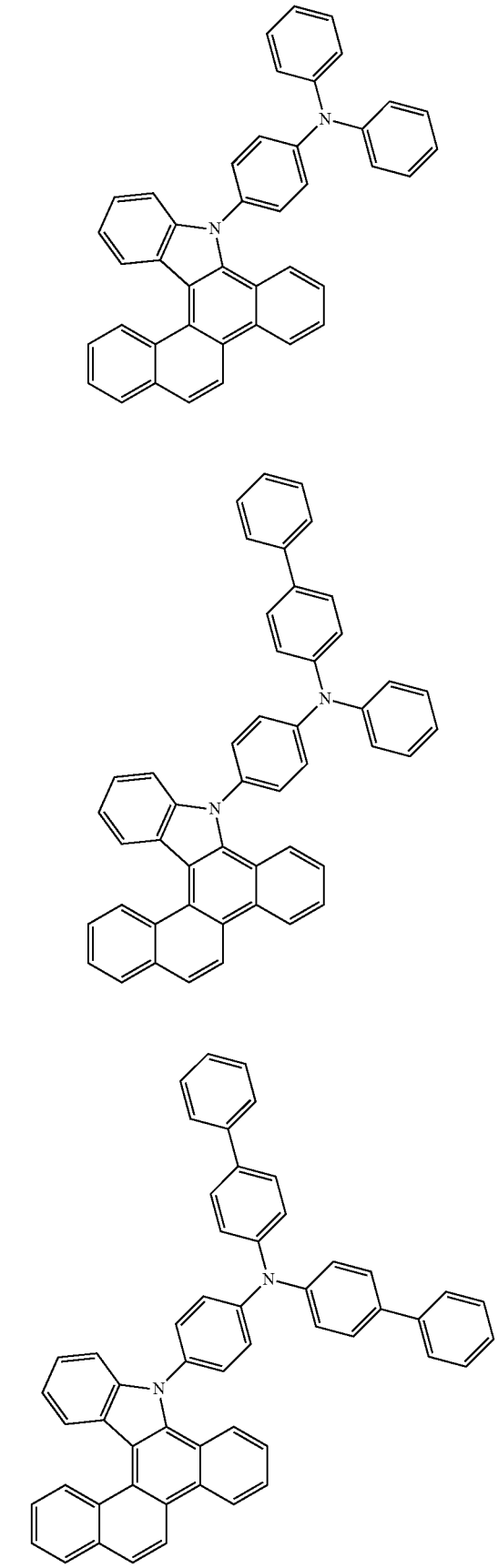 [SMILES: c1ccc(N(c2ccccc2)c2ccc(-n3c4ccccc4c4c5c6ccccc6ccc5c5ccccc5c43)cc2)cc1 ; c1ccc(-c2ccc(N(c3ccccc3)c3ccc(-n4c5ccccc5c5c6c7ccccc7ccc6c6ccccc6c54)cc3)cc2)cc1 ; c1ccc(-c2ccc(N(c3ccc(-c4ccccc4)cc3)c3ccc(-n4c5ccccc5c5c6c7ccccc7ccc6c6ccccc6c54)cc3)cc2)cc1]

251
-continued
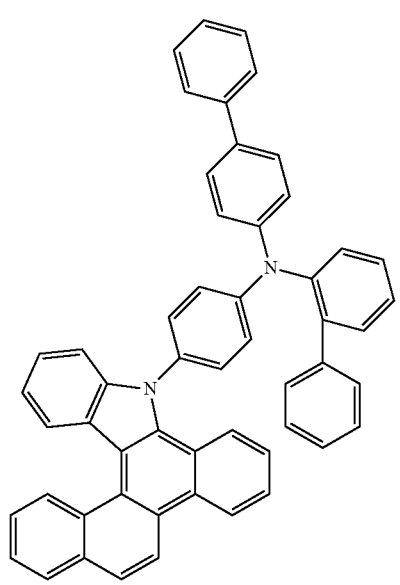
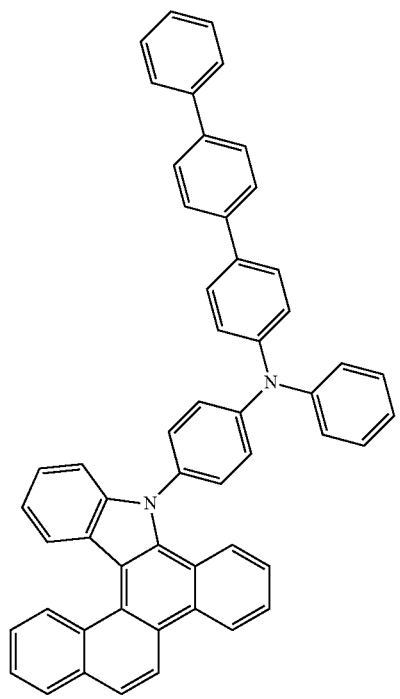
252
-continued
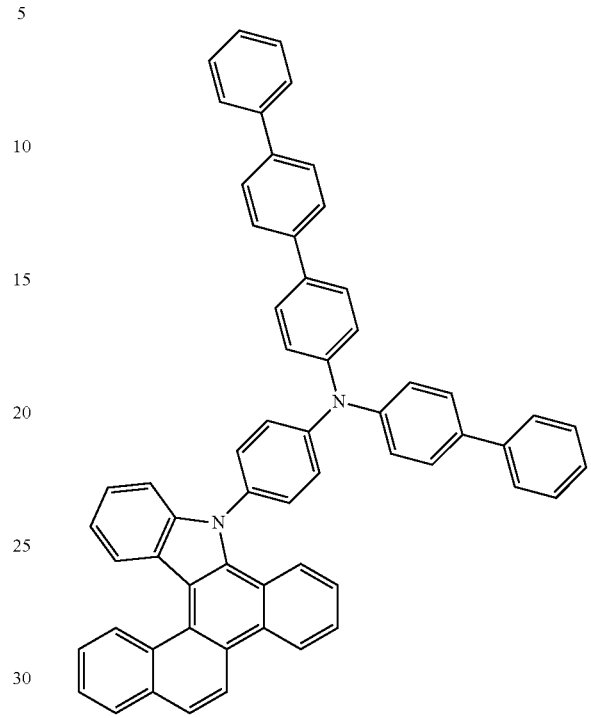
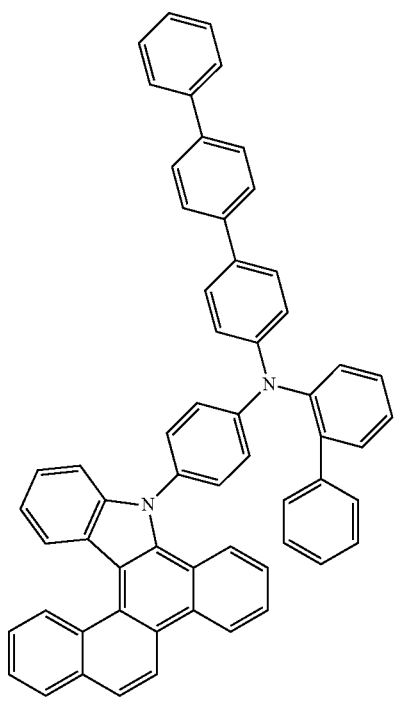

253
-continued
254
-continued
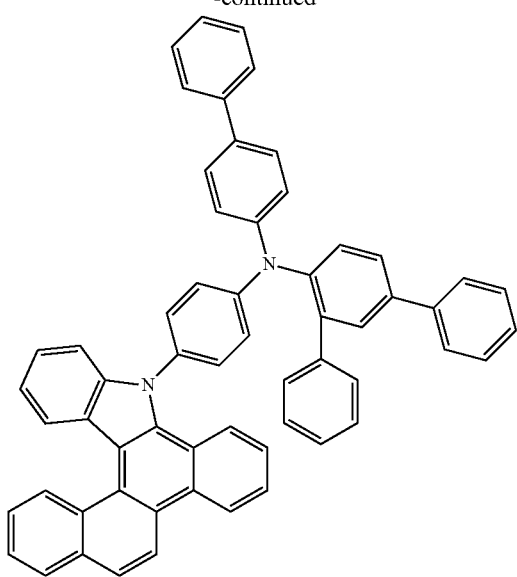
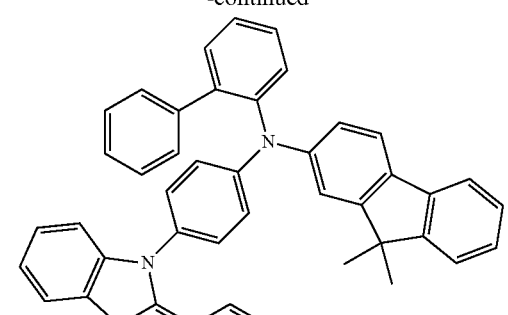
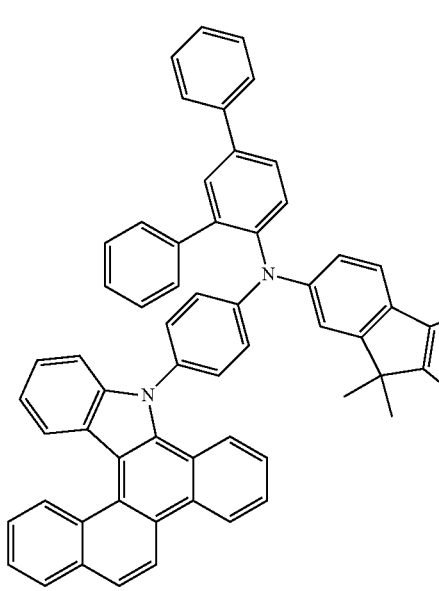
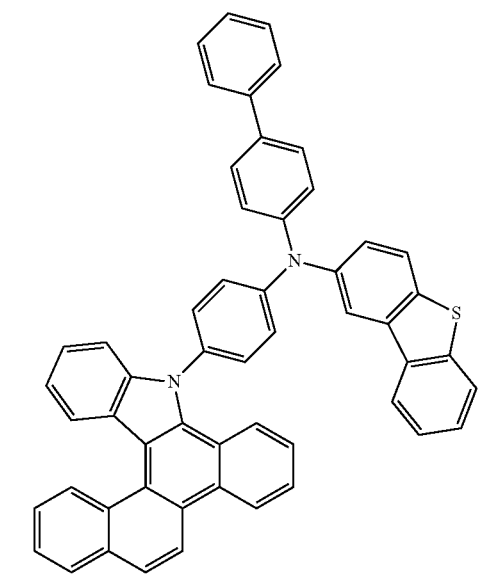

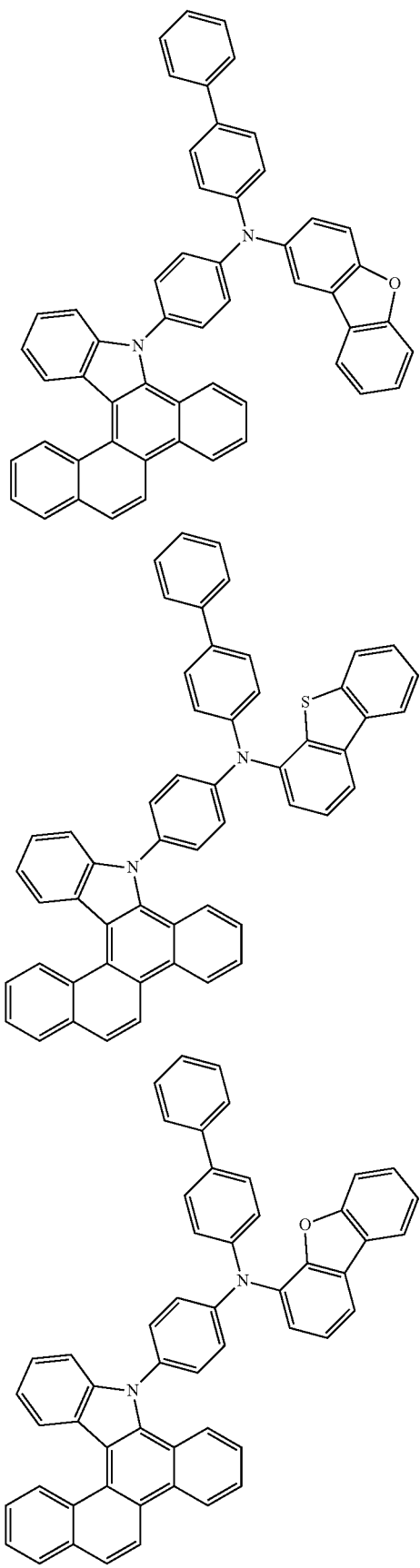
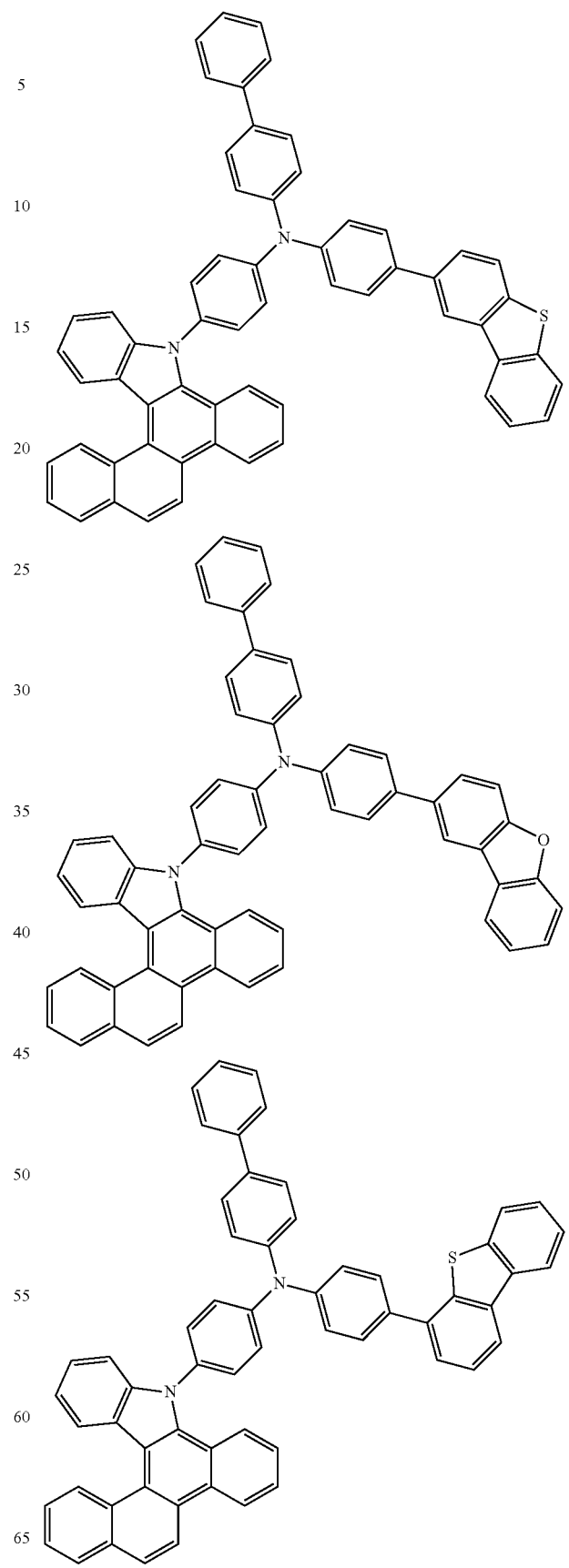

257
-continued
258
-continued
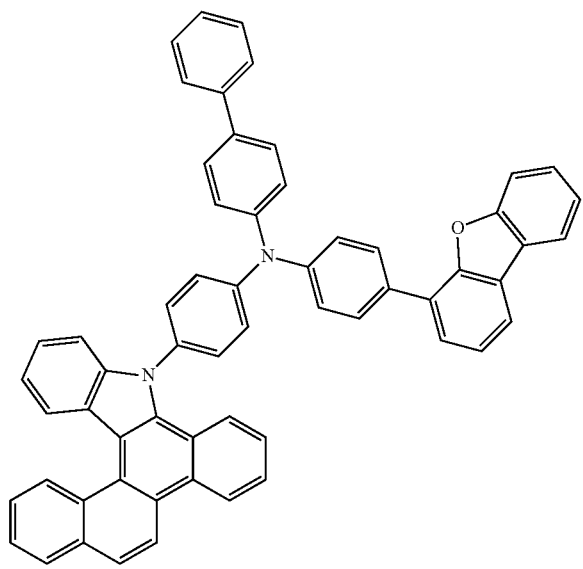
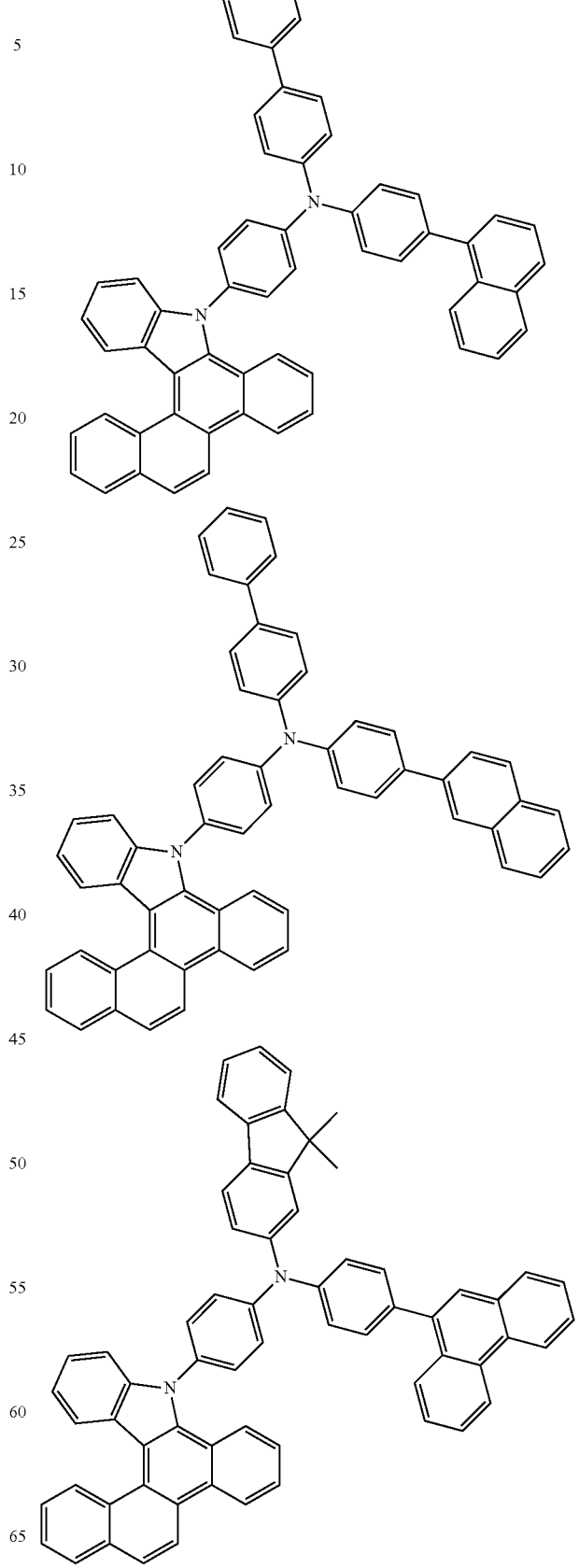

259
-continued
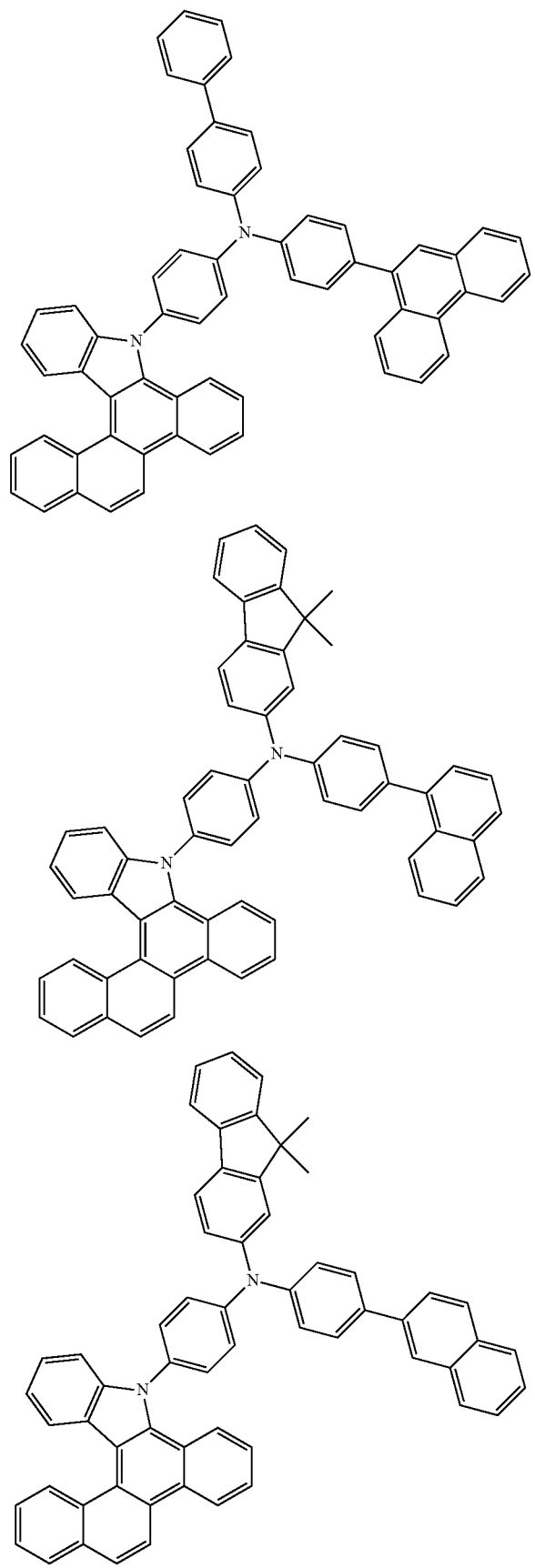
260
-continued
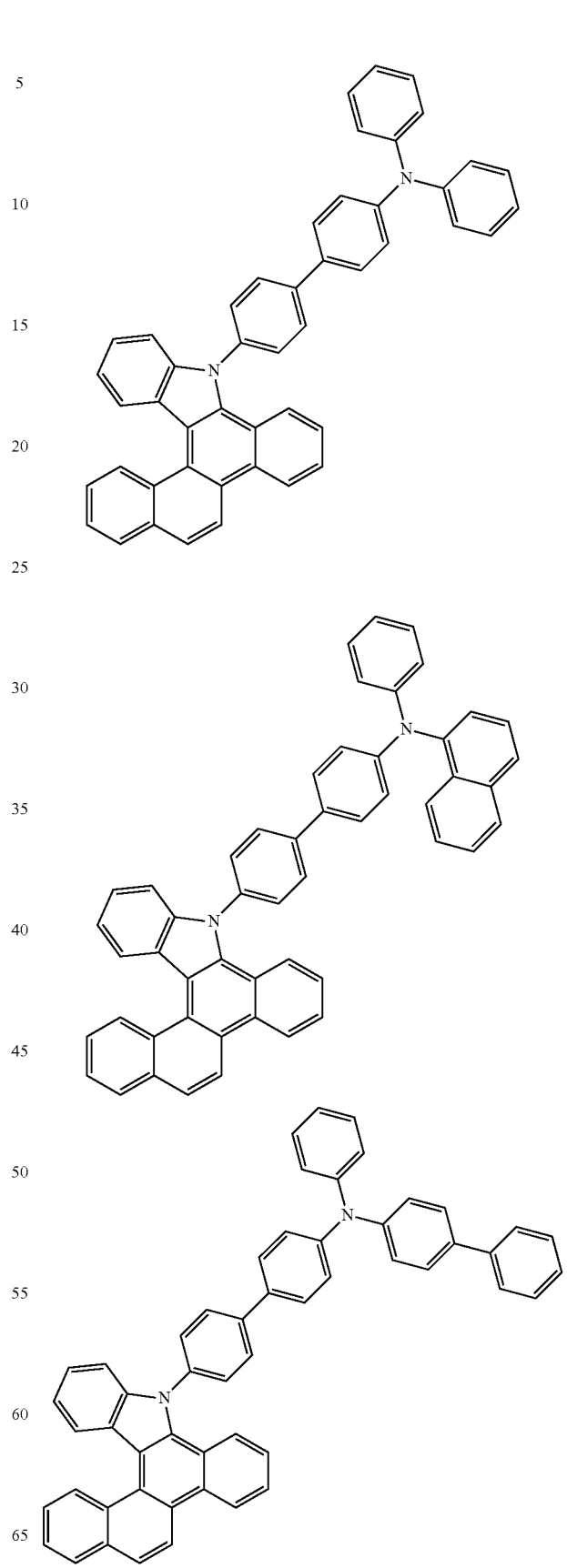

261
-continued
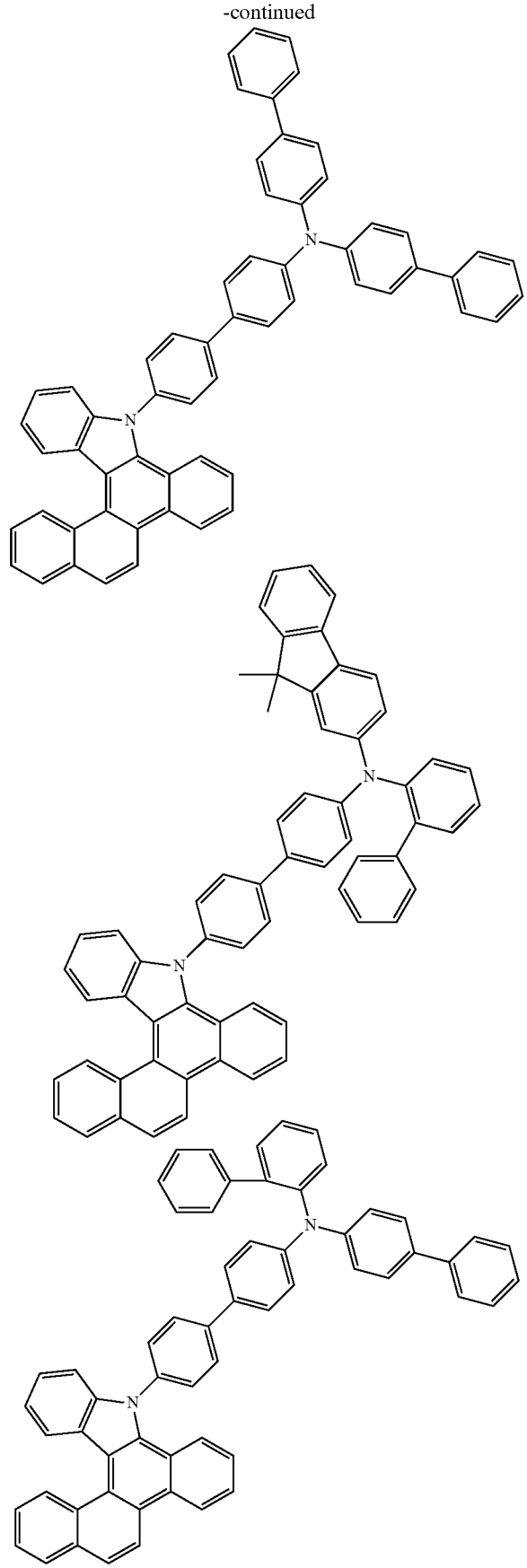
262
-continued
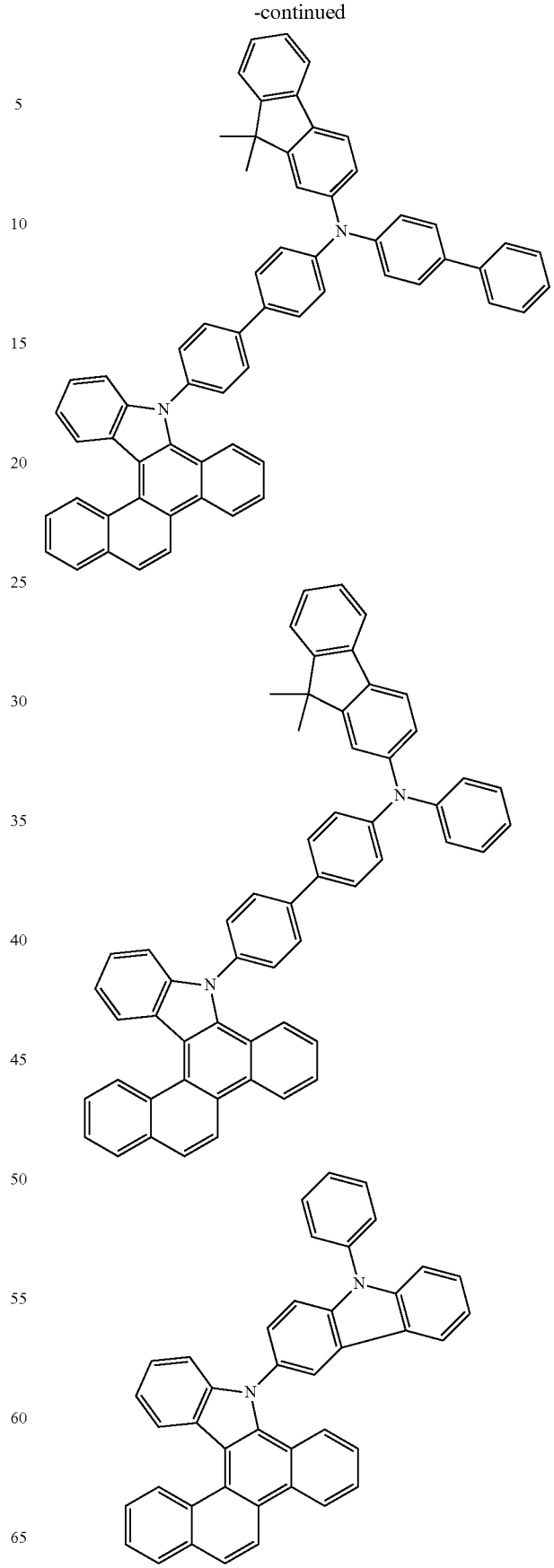

263
-continued
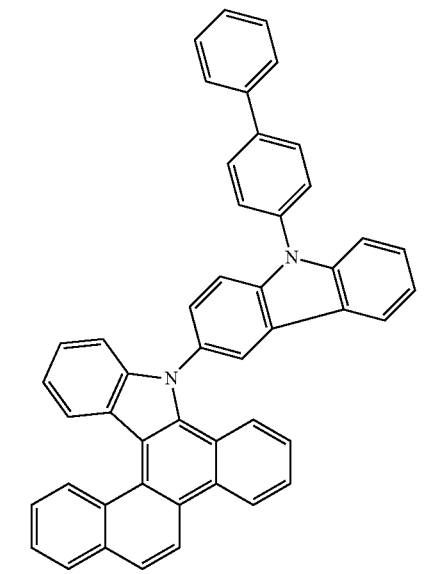
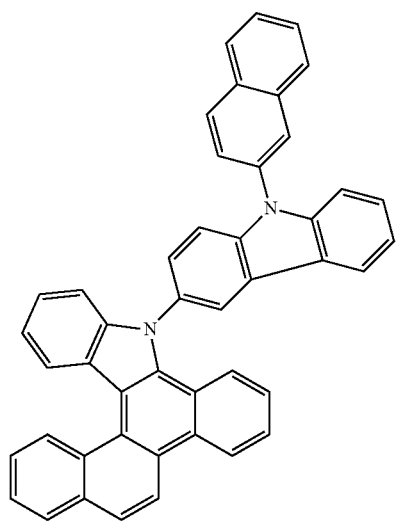
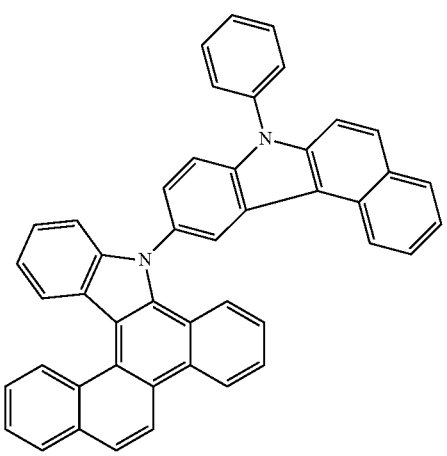
264
-continued
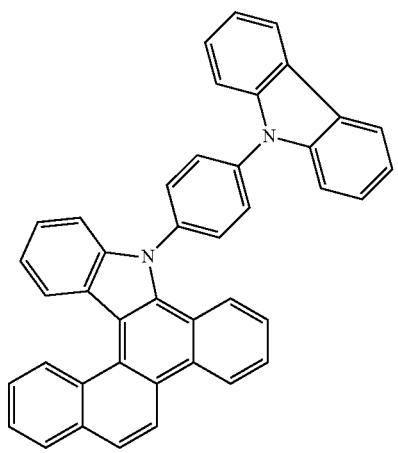
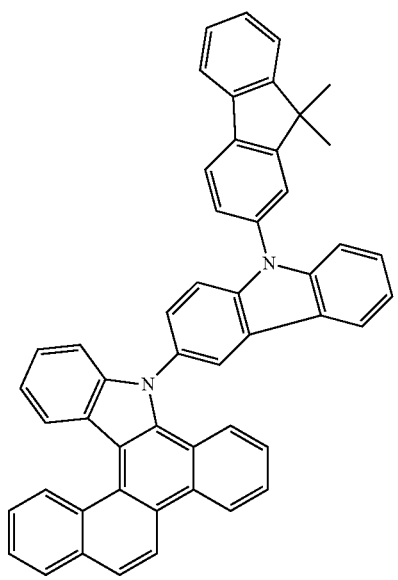
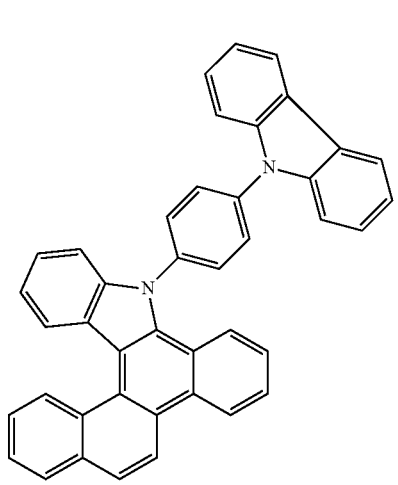

265
-continued
266
-continued
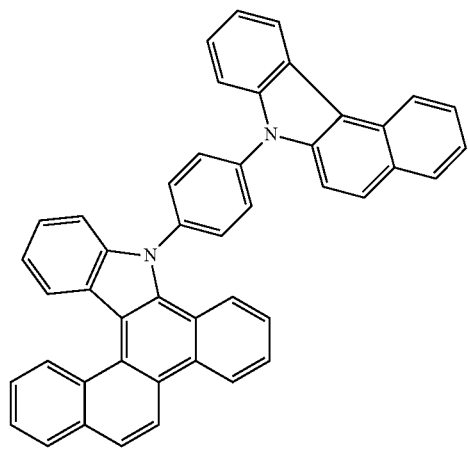
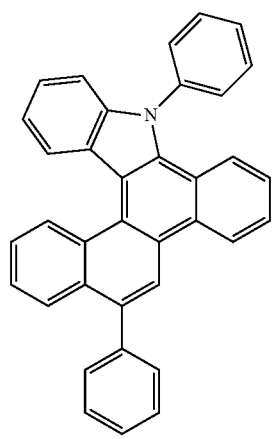
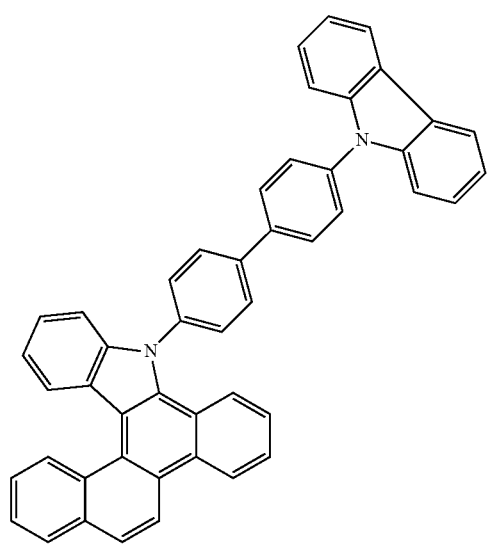
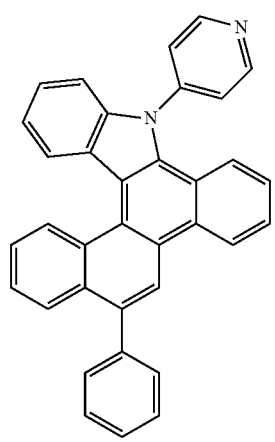
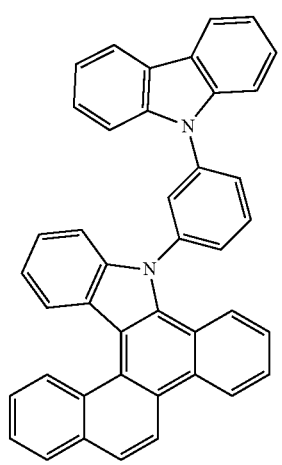
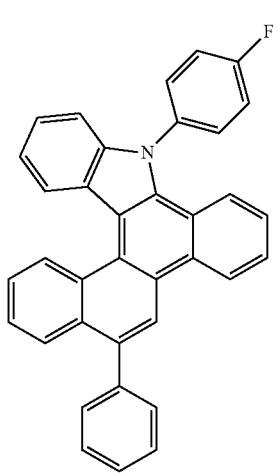

267
-continued
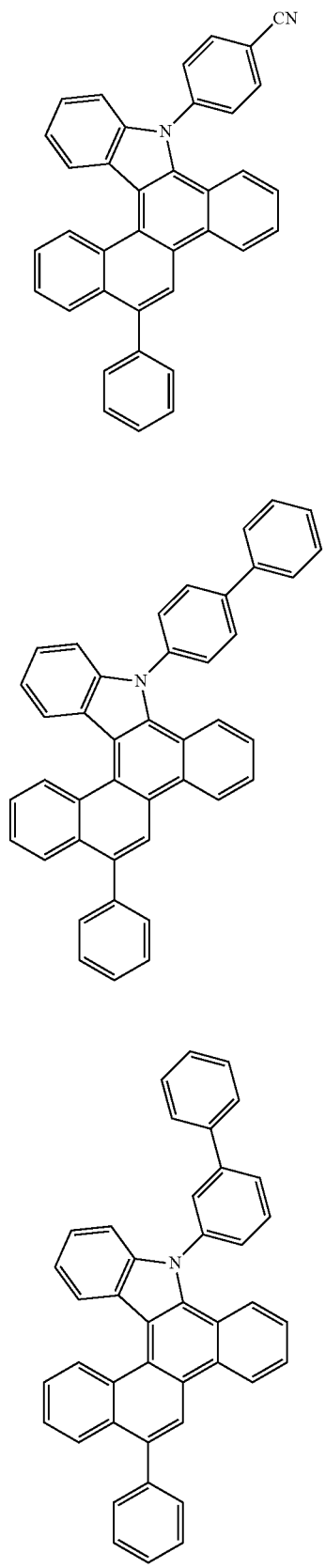
268
-continued
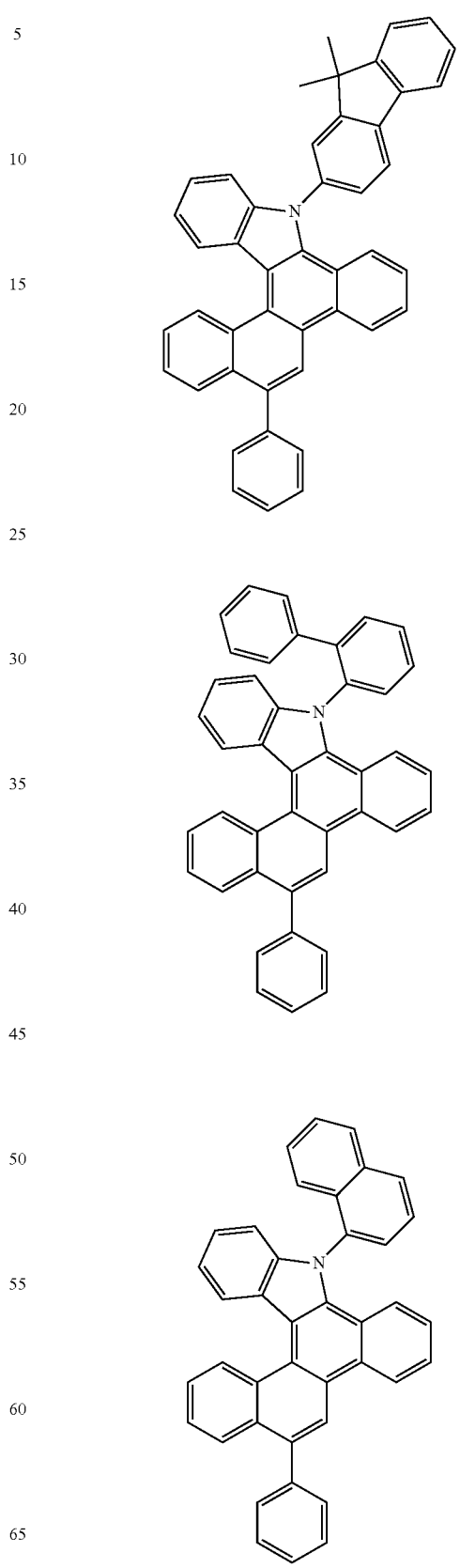

269
-continued
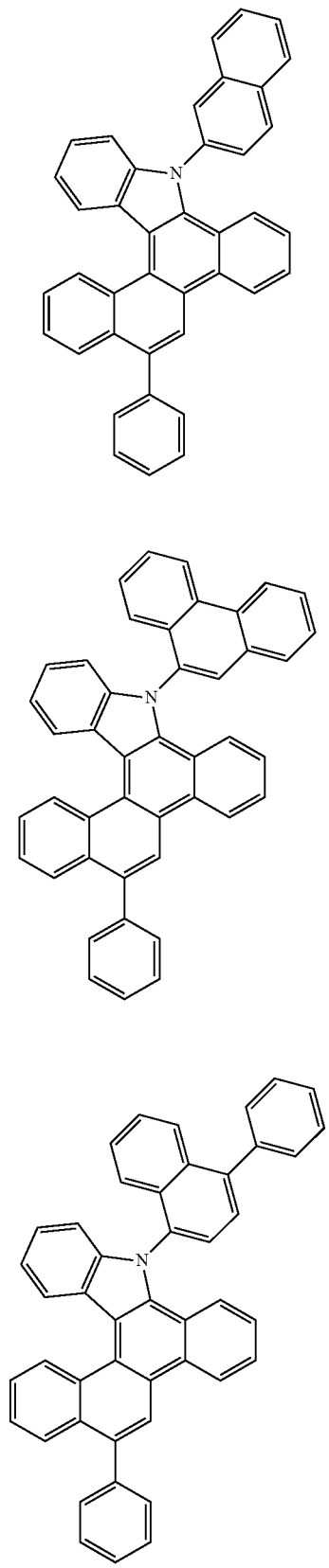
270
-continued
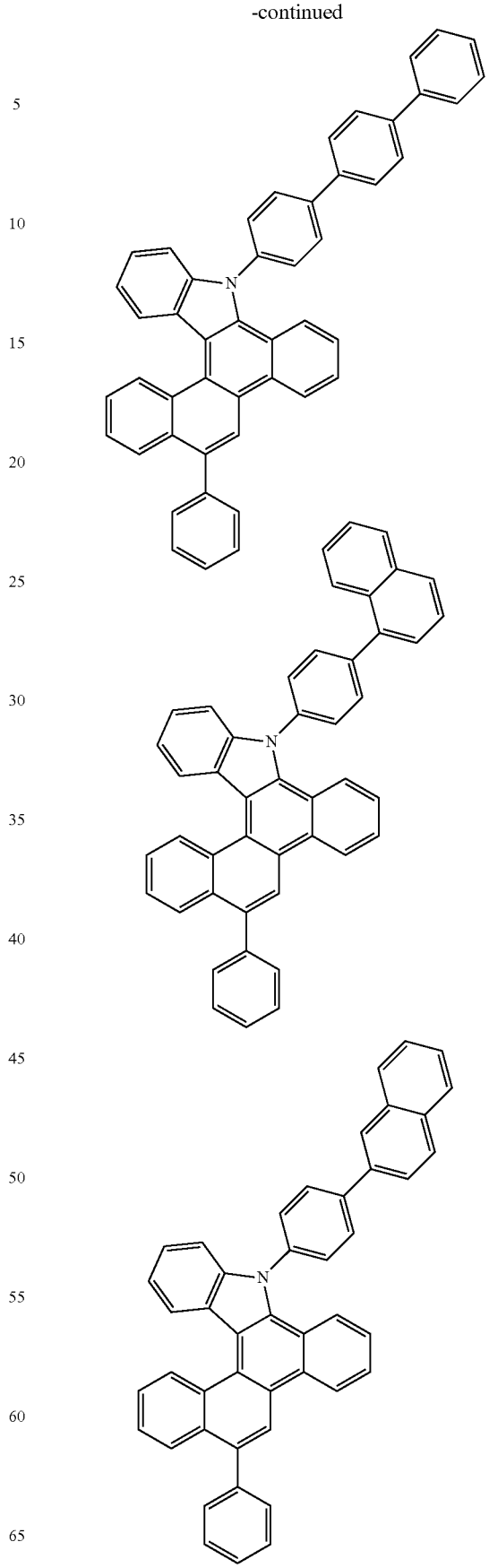

271
-continued
272
-continued
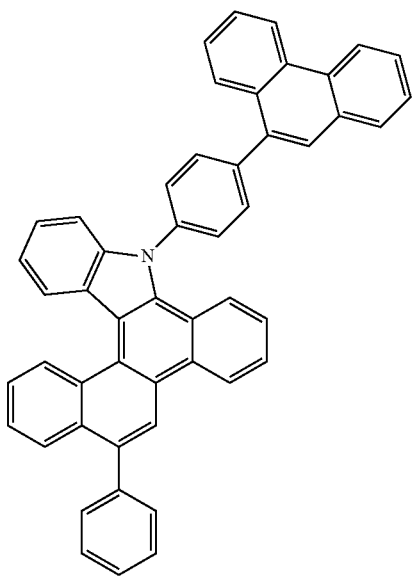
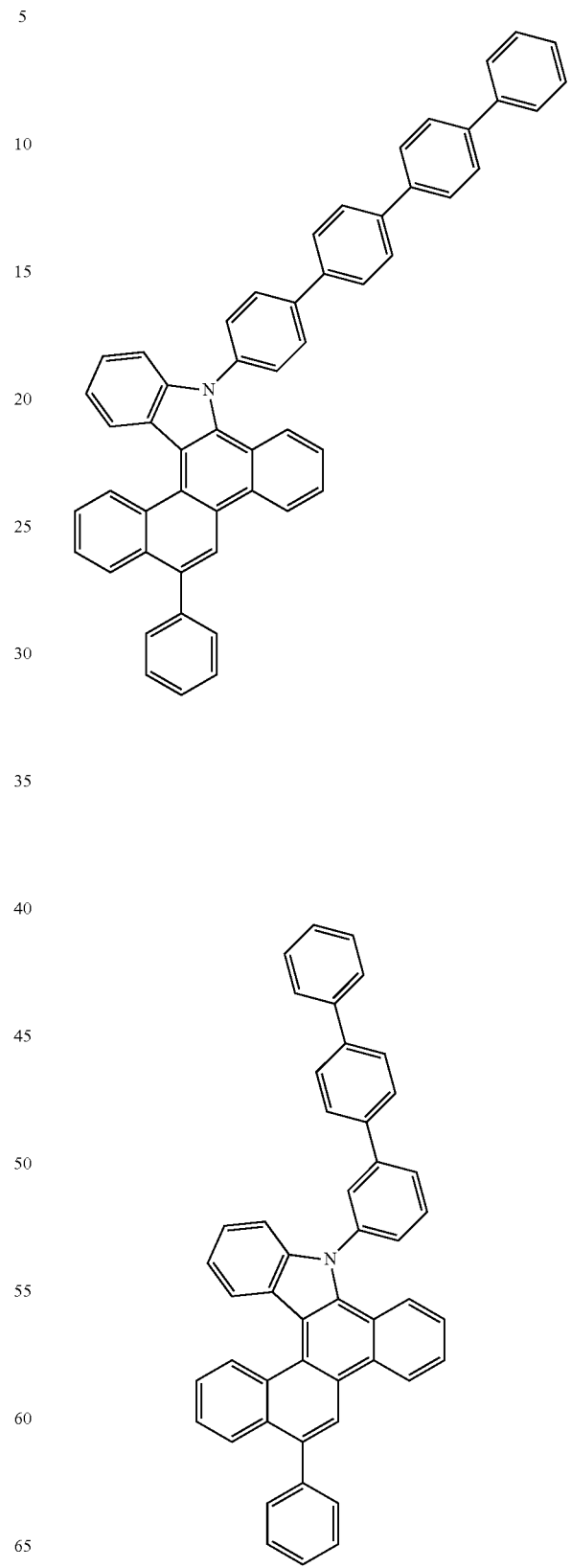

273
-continued
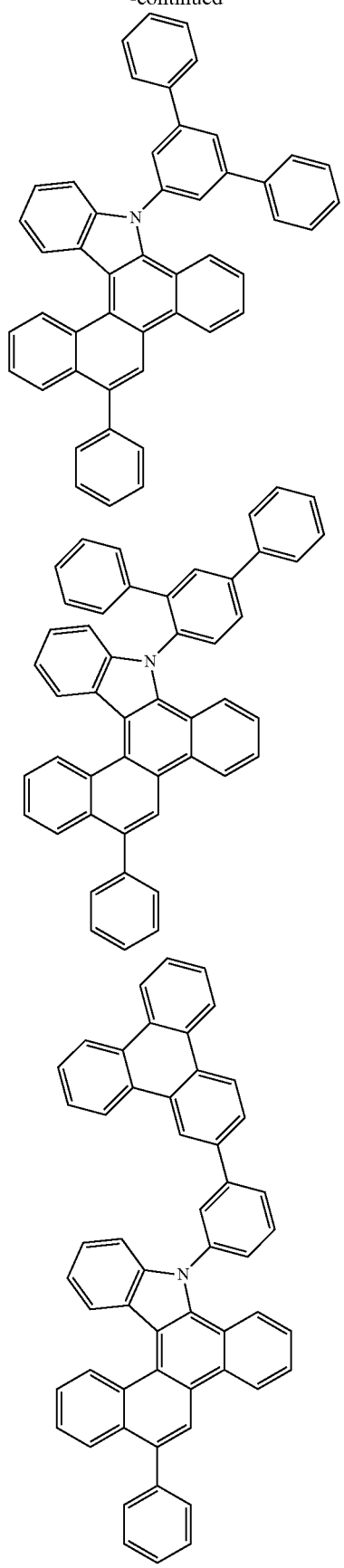
274
-continued
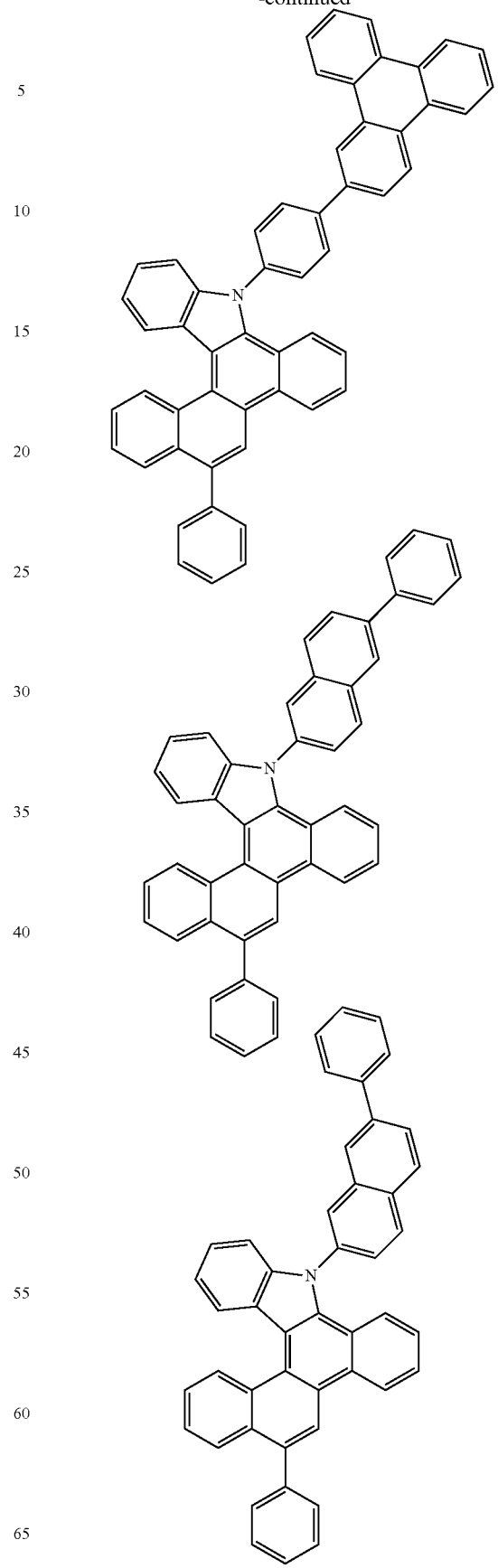

275
-continued
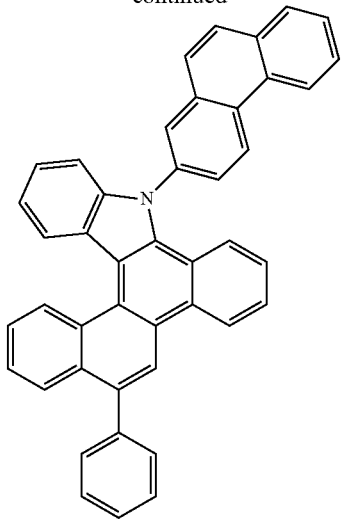
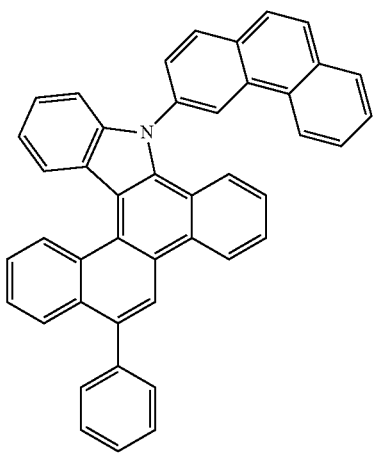
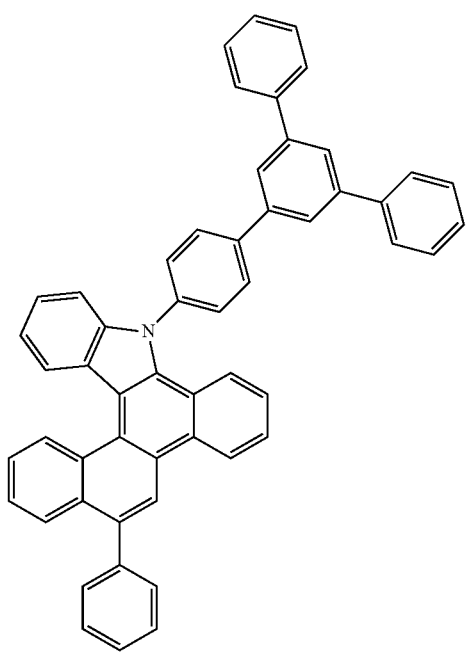
276
-continued
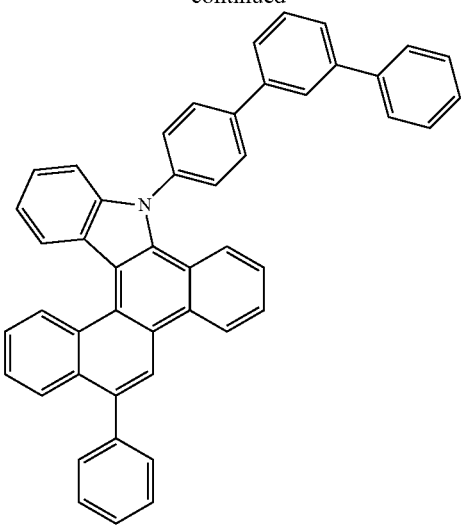
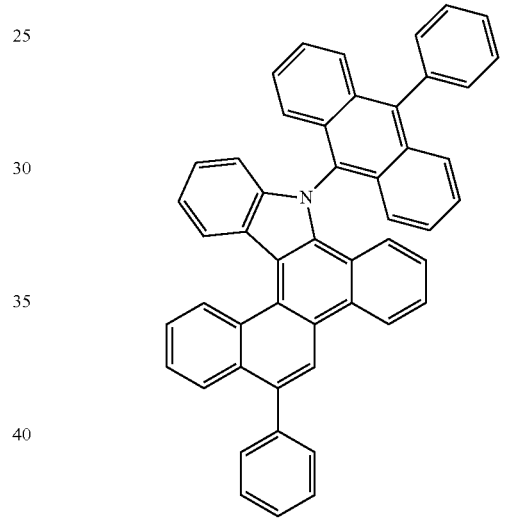
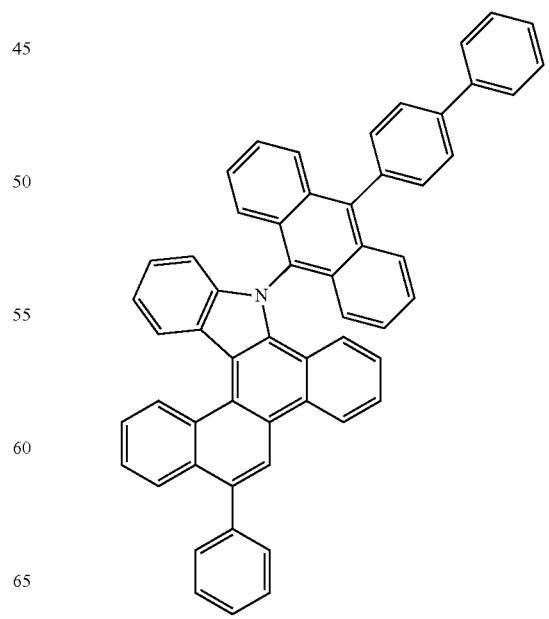

277
-continued
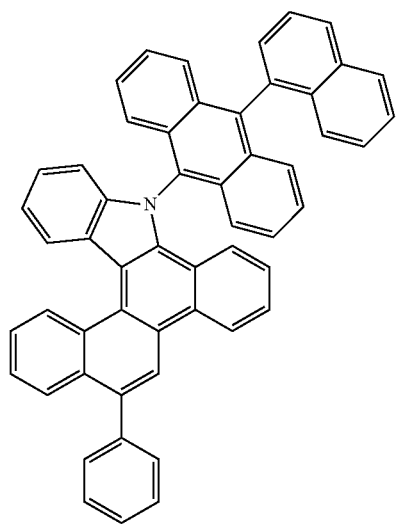
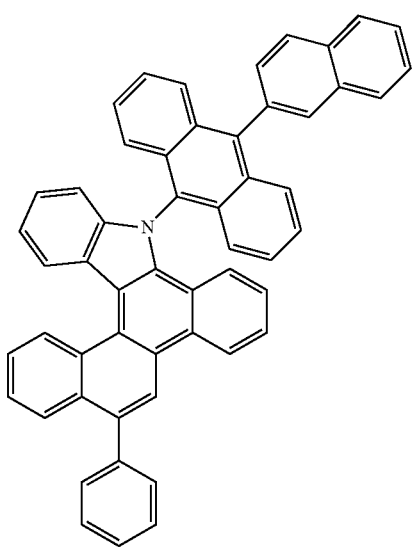
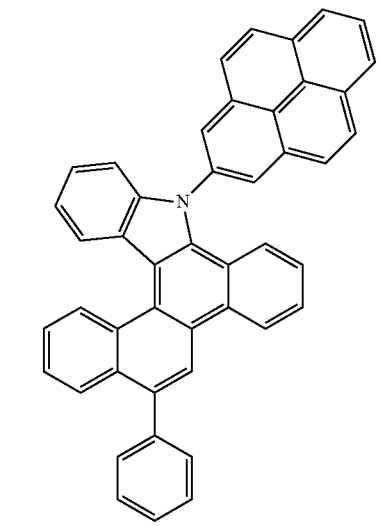
278
-continued
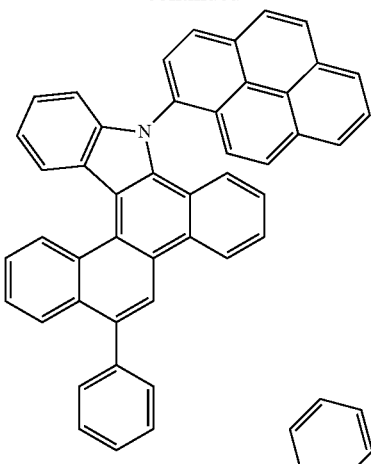
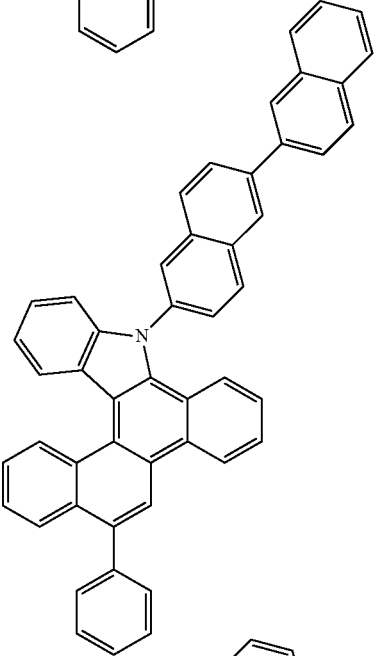
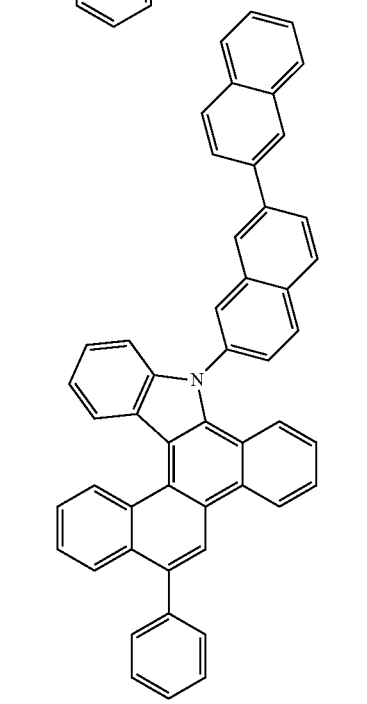

279
-continued
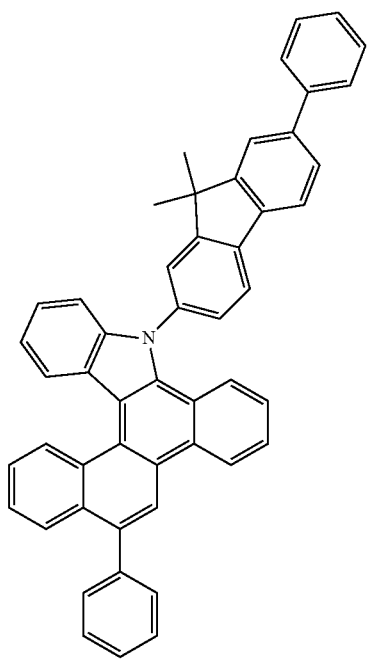
280
-continued
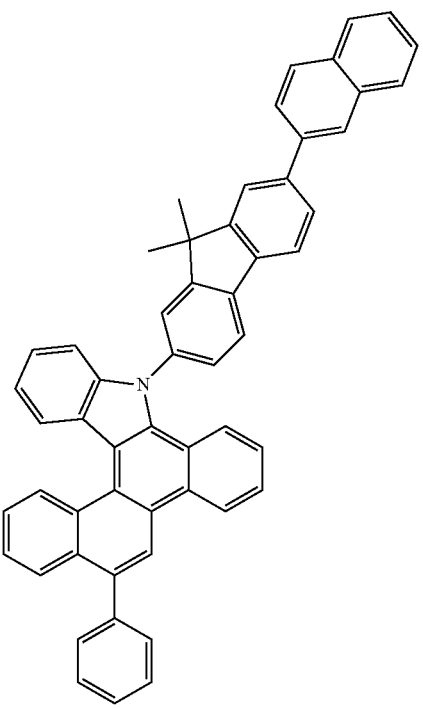
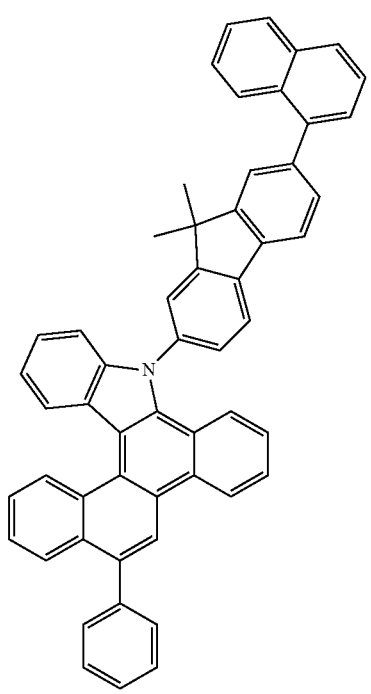
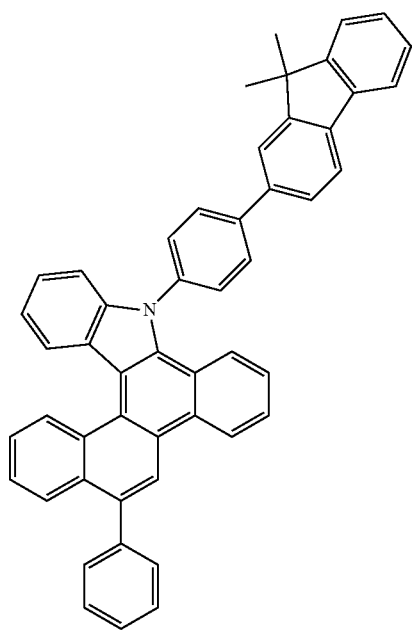

281
-continued
282
-continued
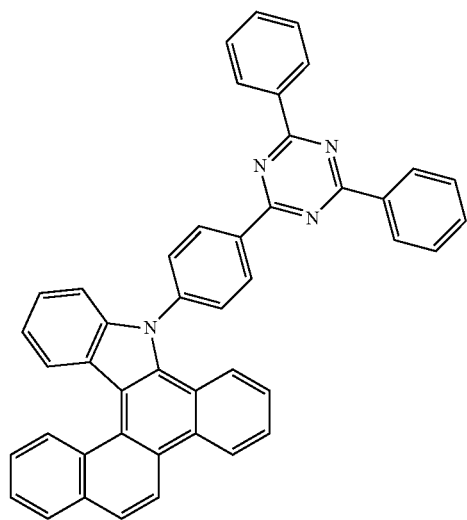
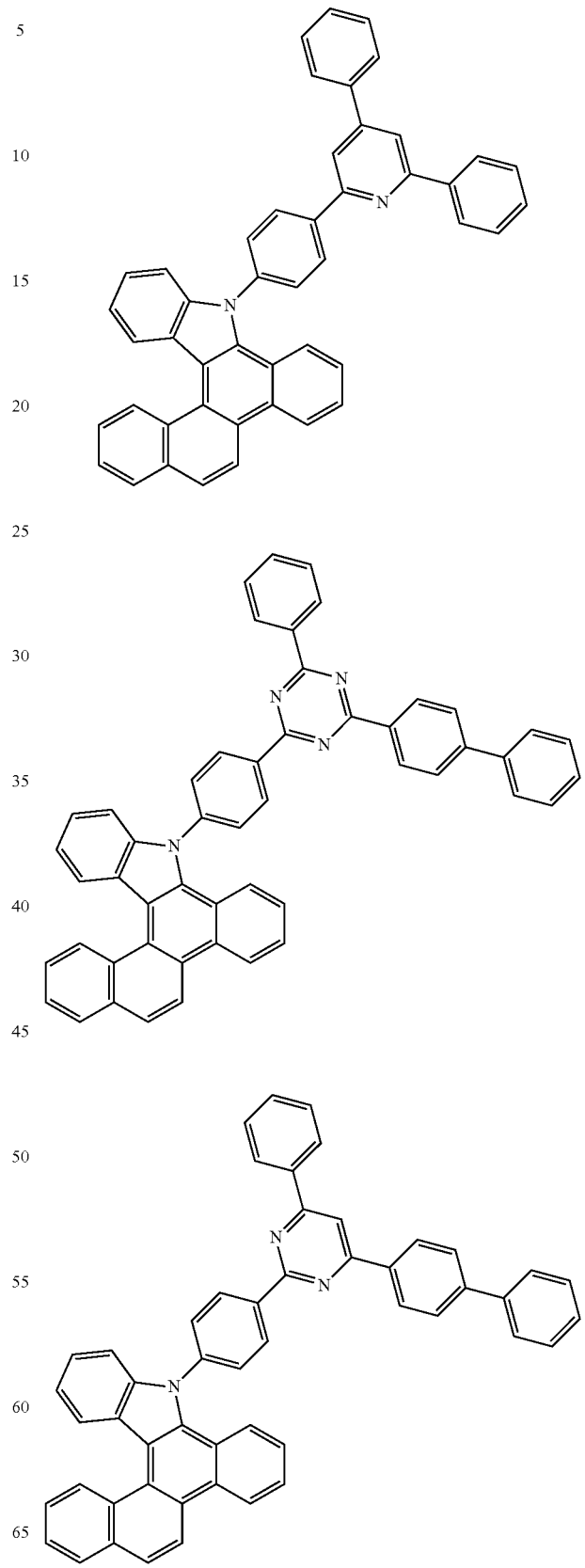

283
-continued
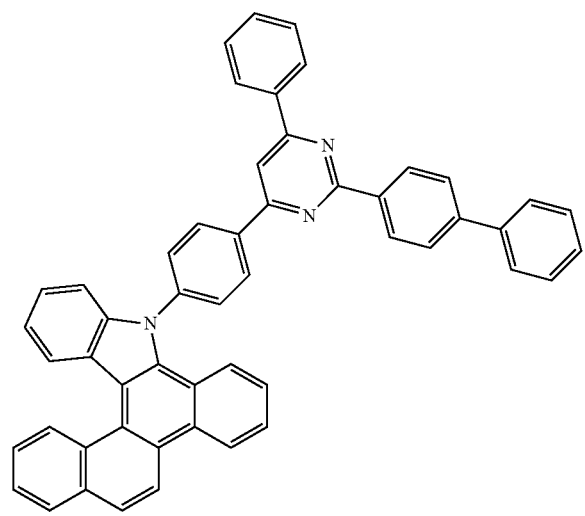
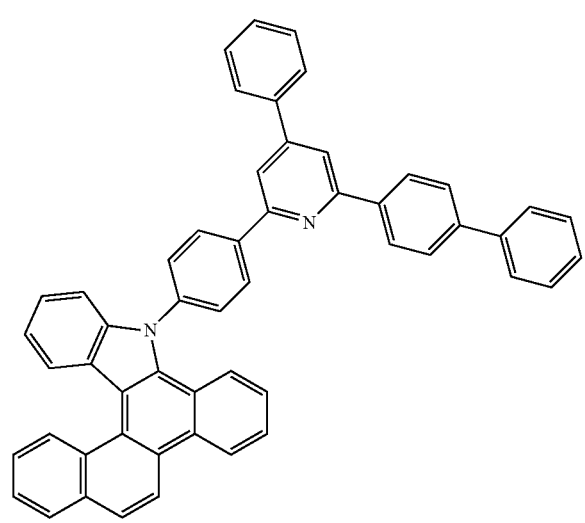
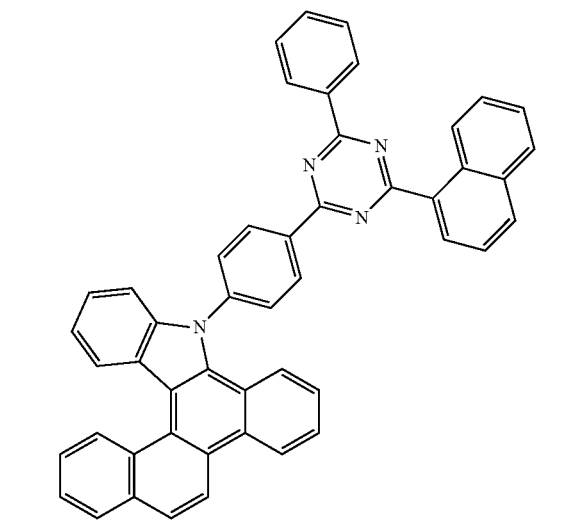
284
-continued
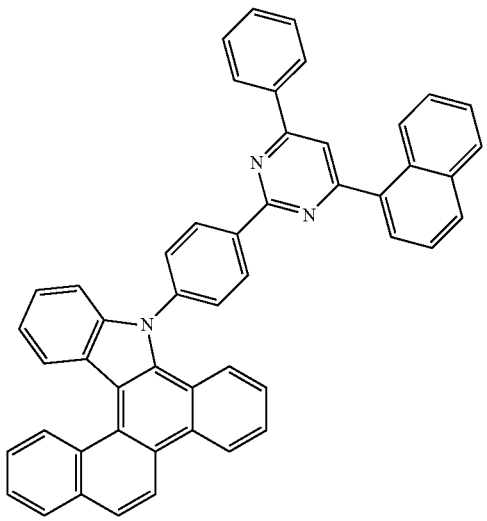
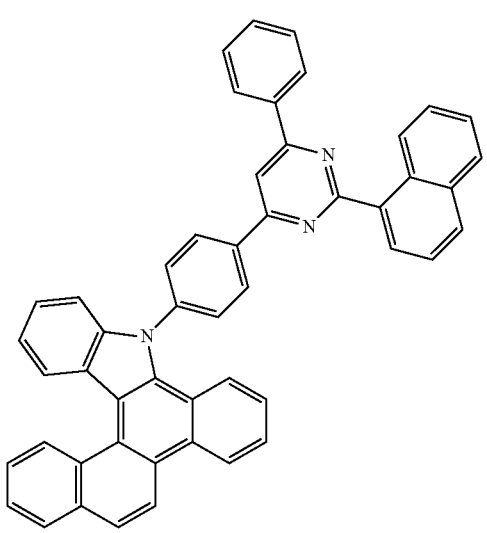
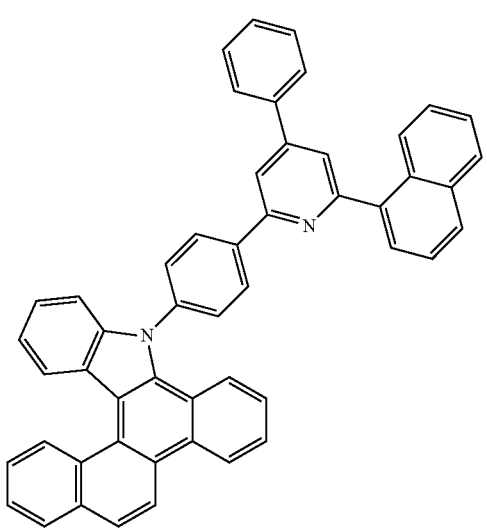

285
-continued
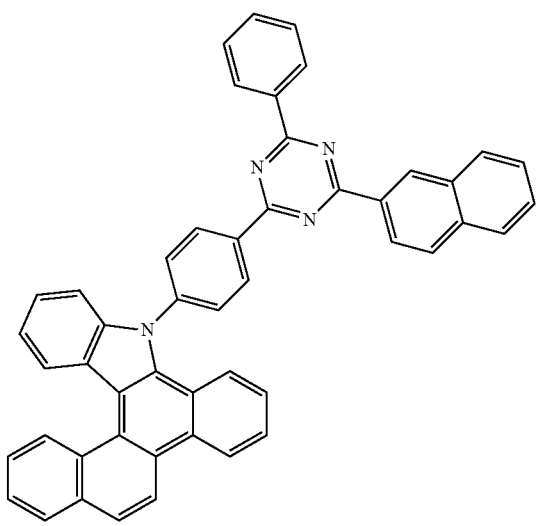
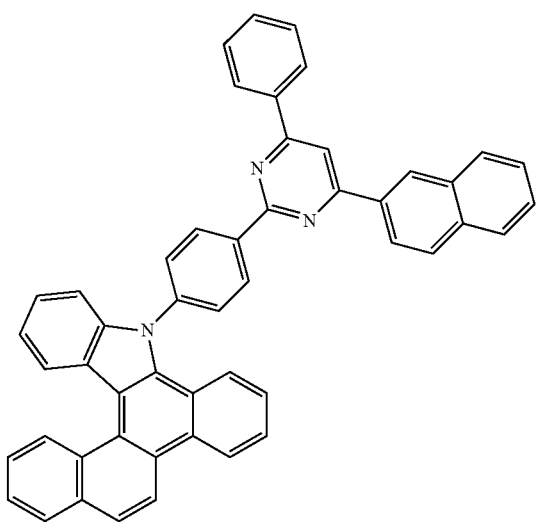
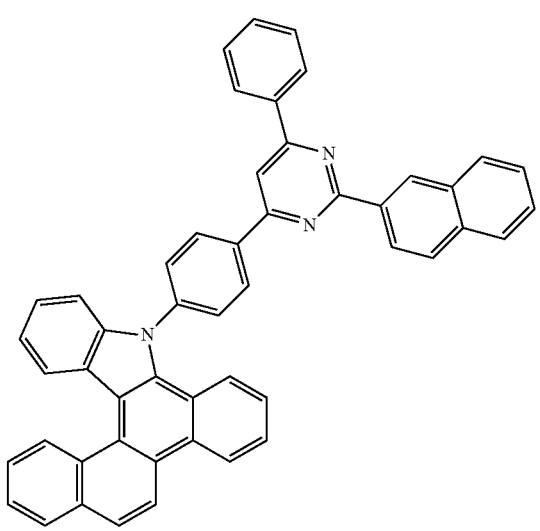
286
-continued
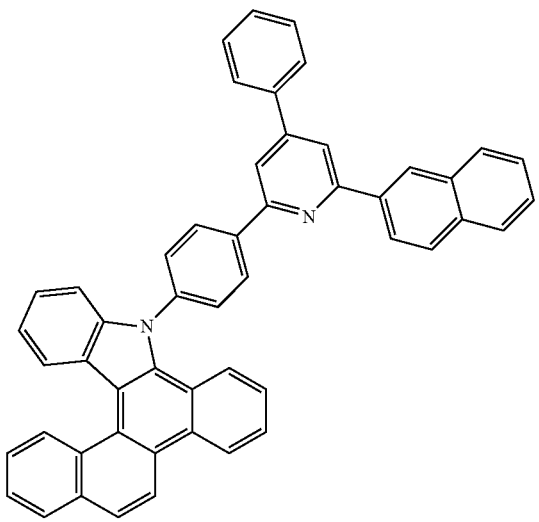
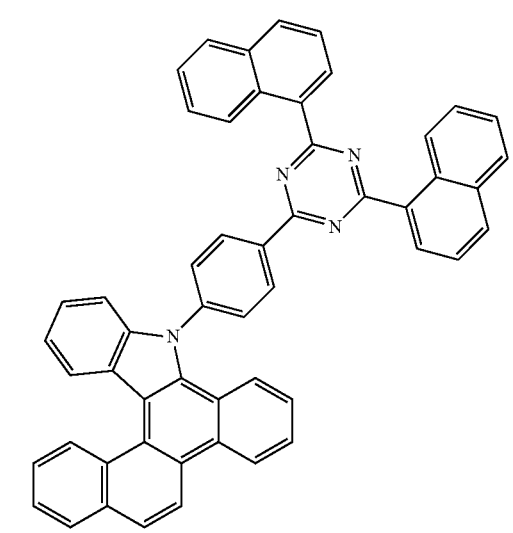
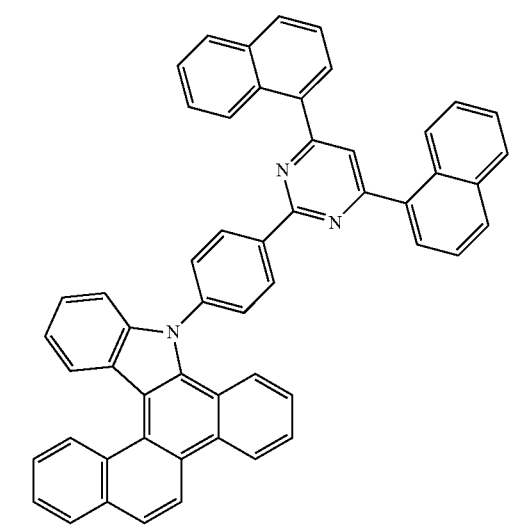

287
-continued
288
-continued
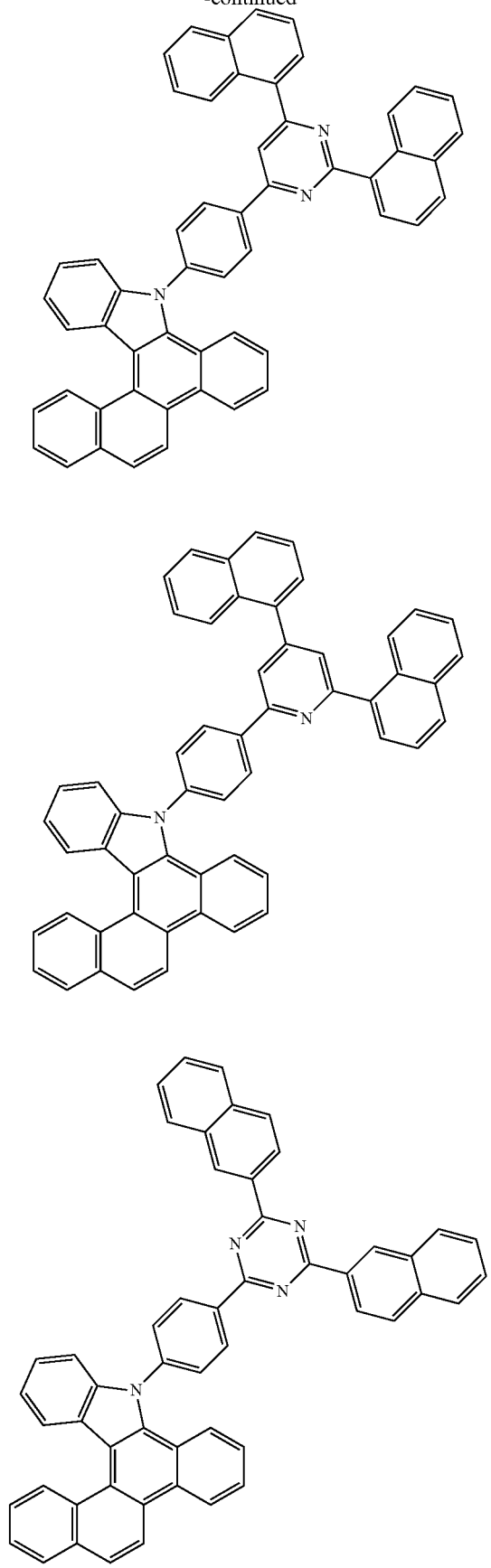
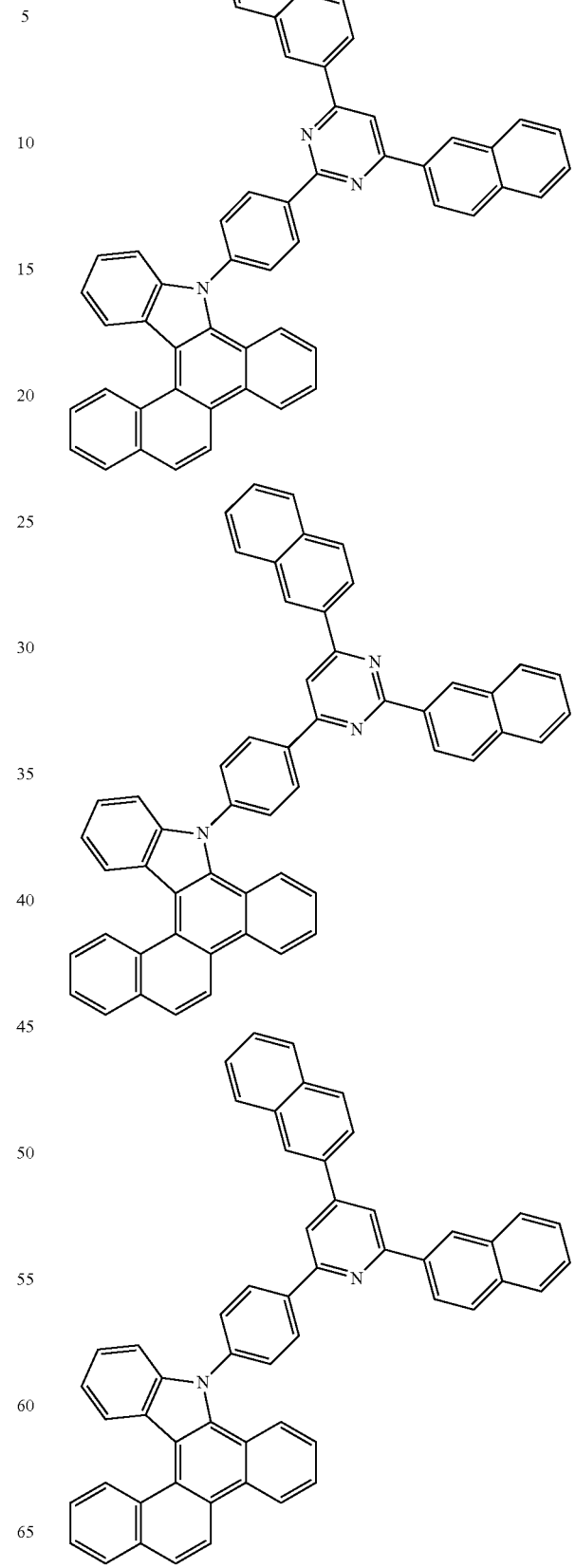

289
-continued
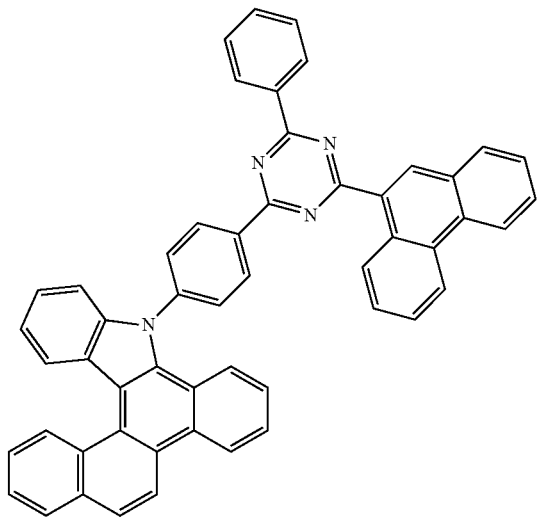
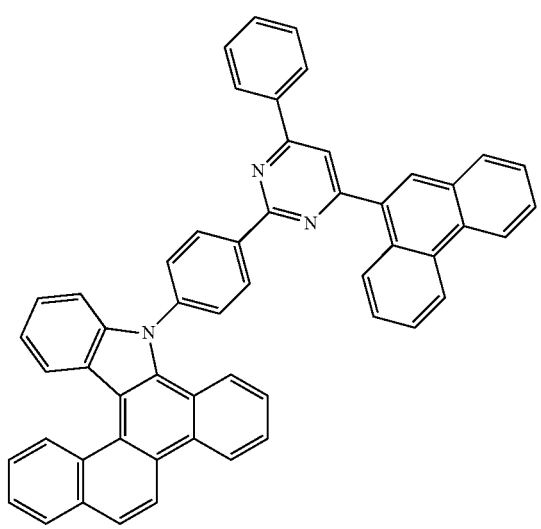
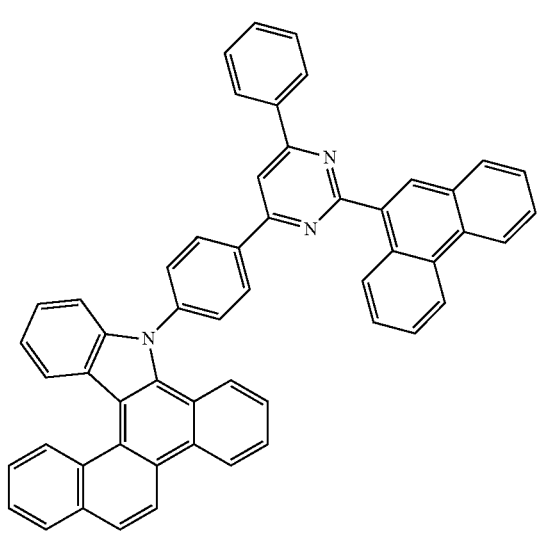
290
-continued
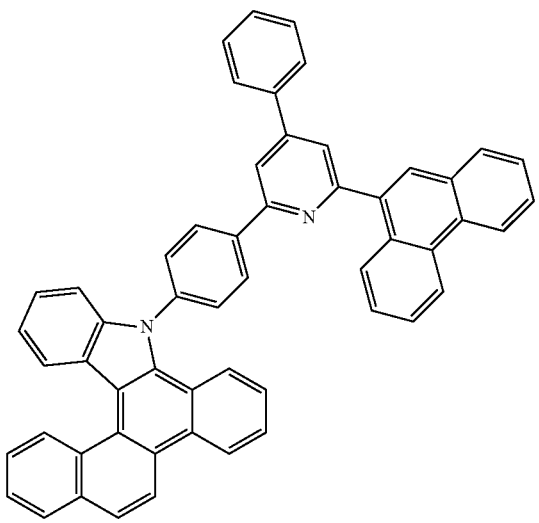
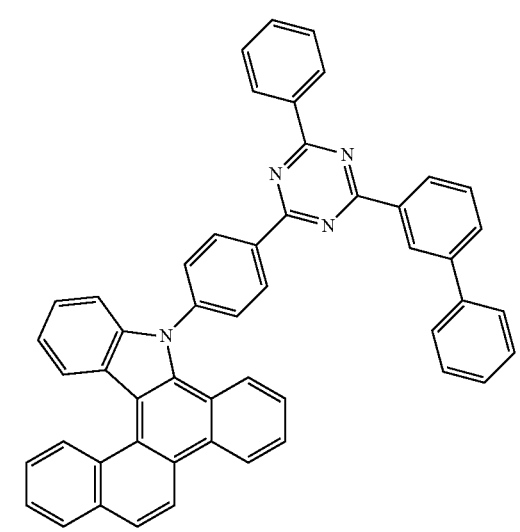
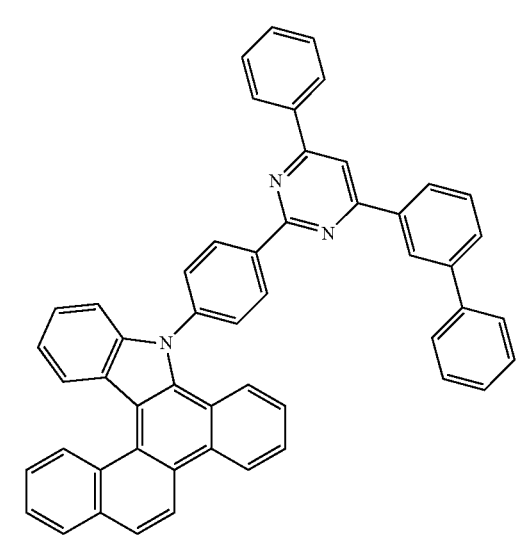

291
-continued
292
-continued
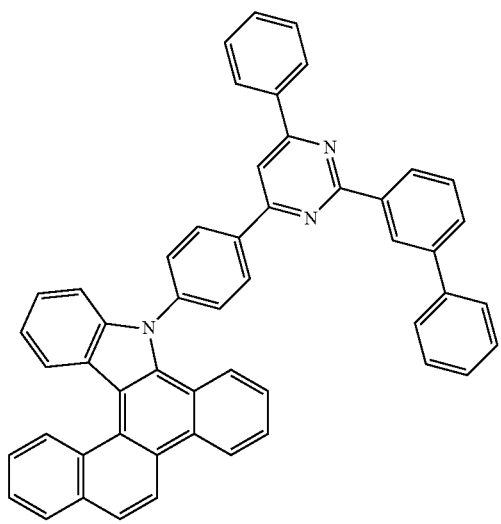
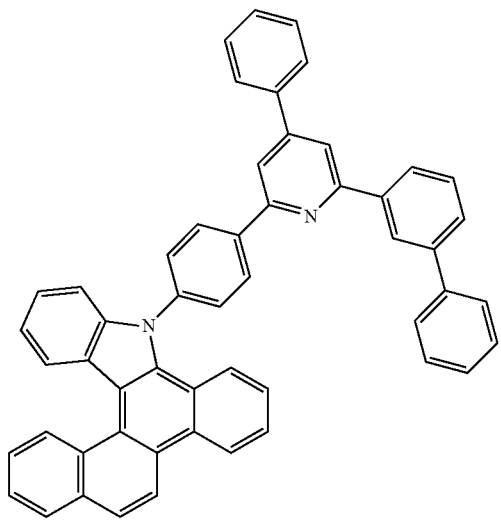
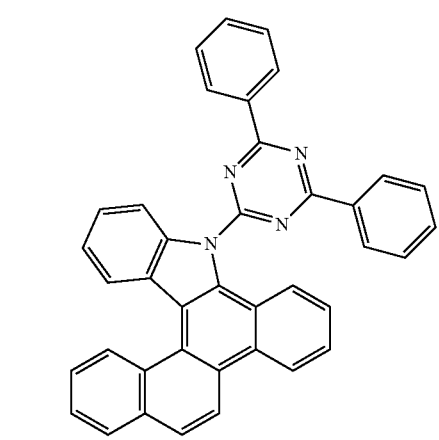
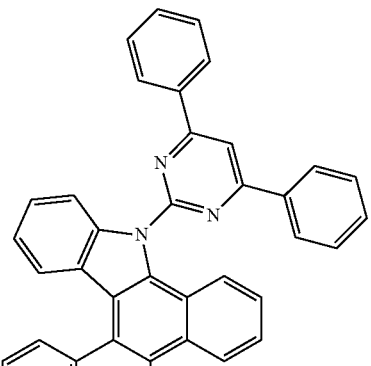
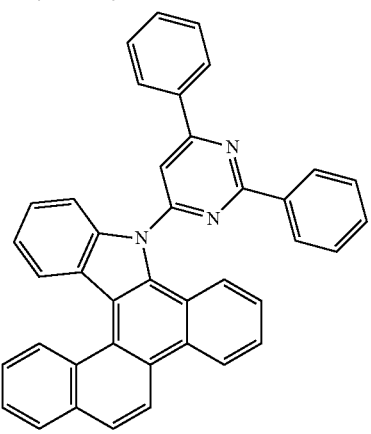
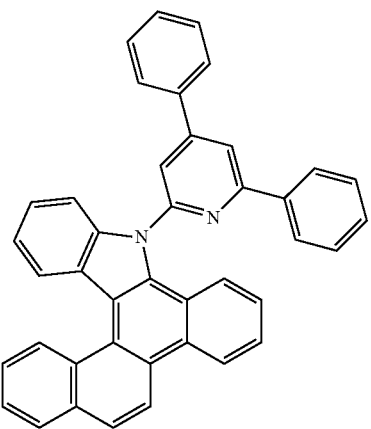
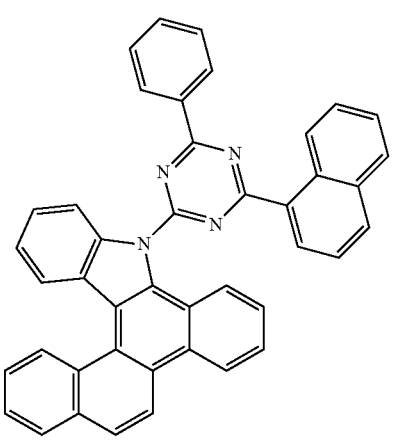

293
-continued
294
-continued
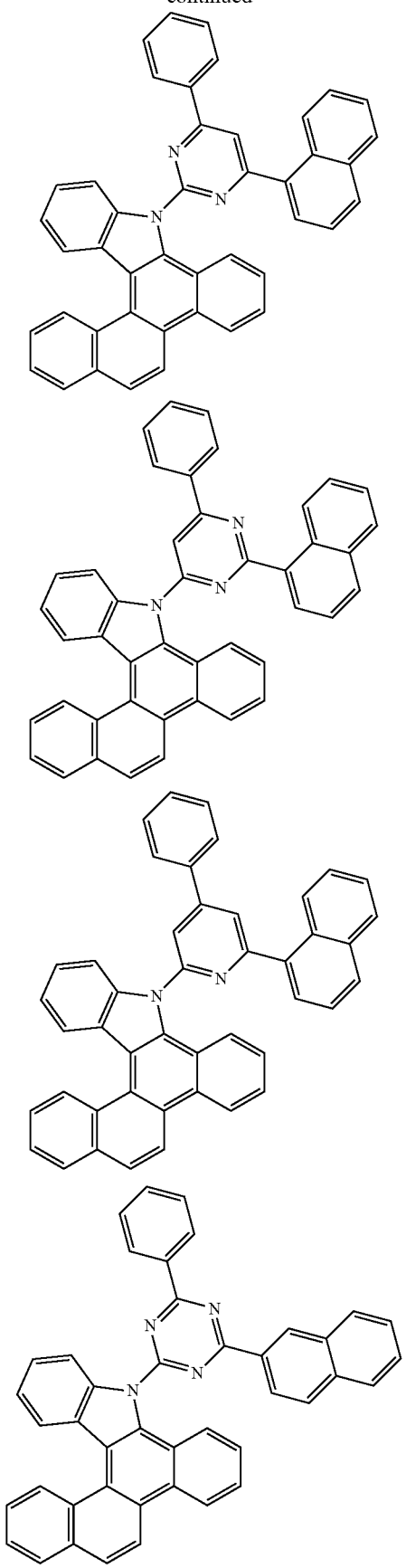
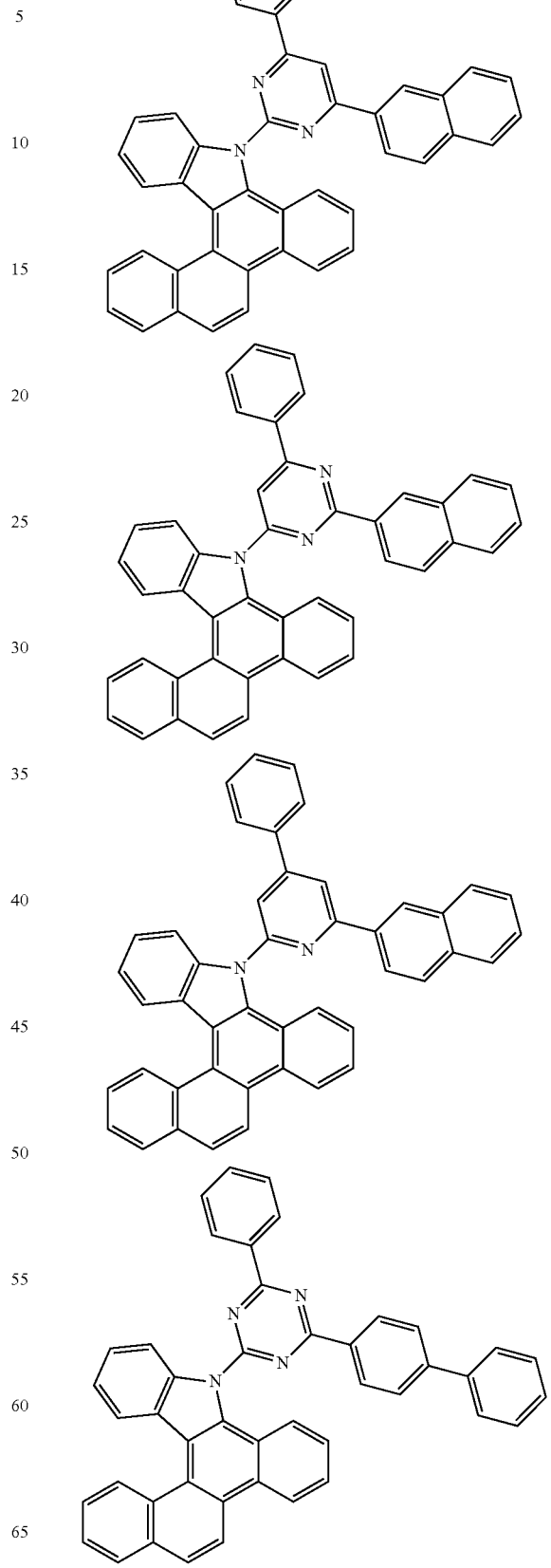

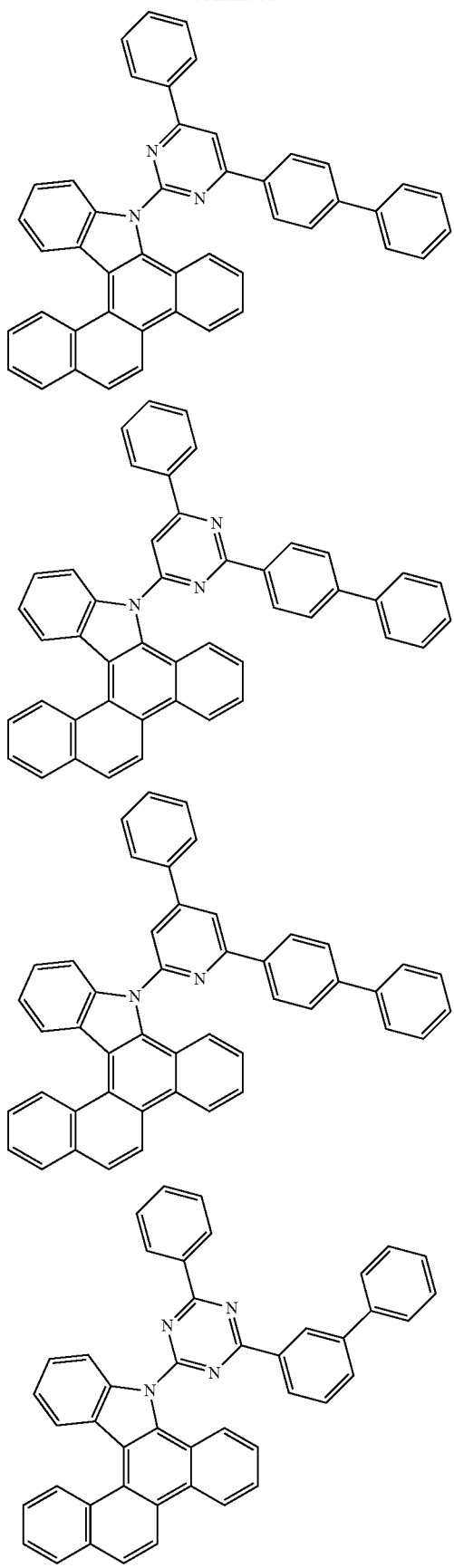
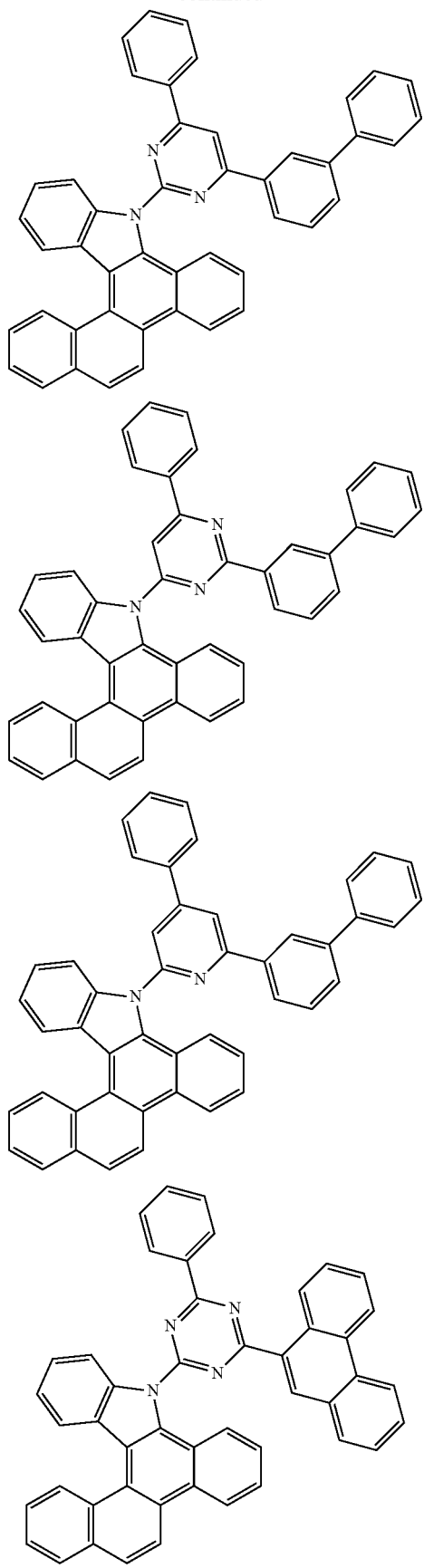

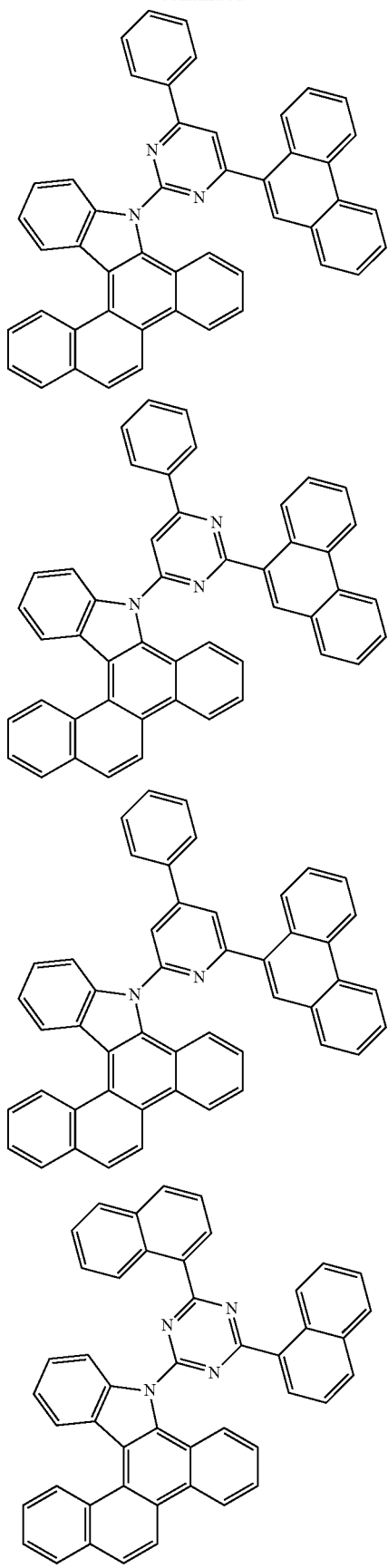
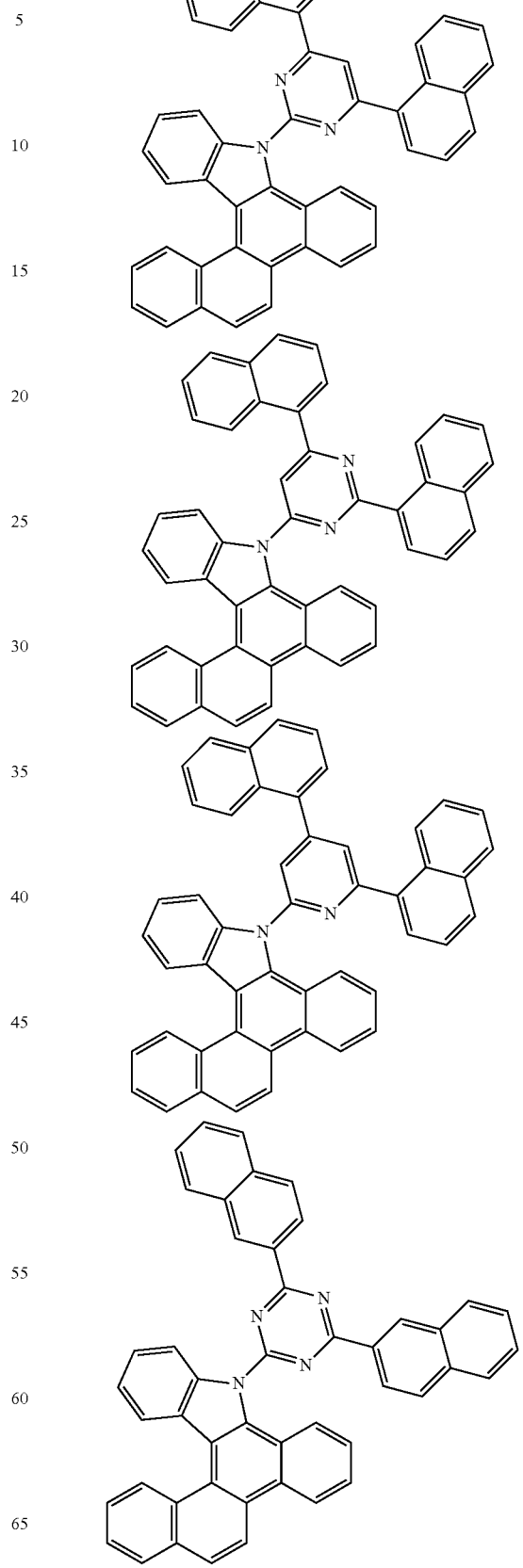

299
-continued
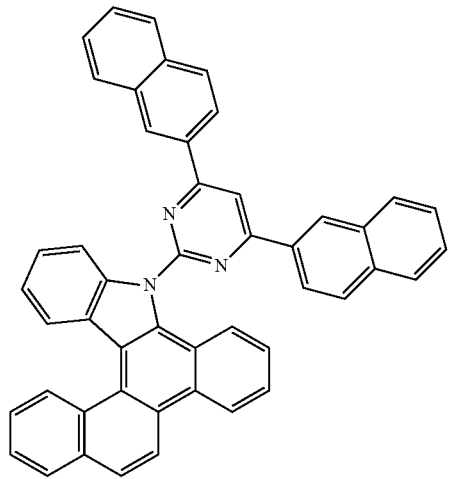
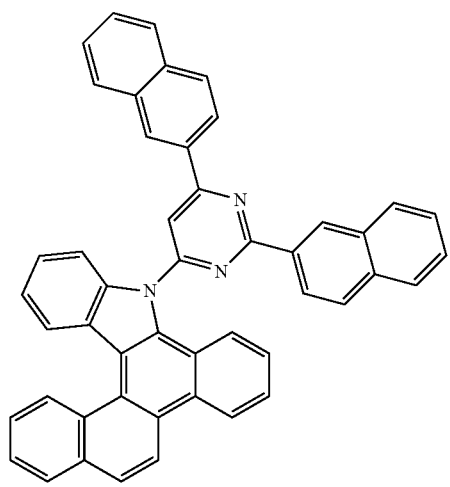
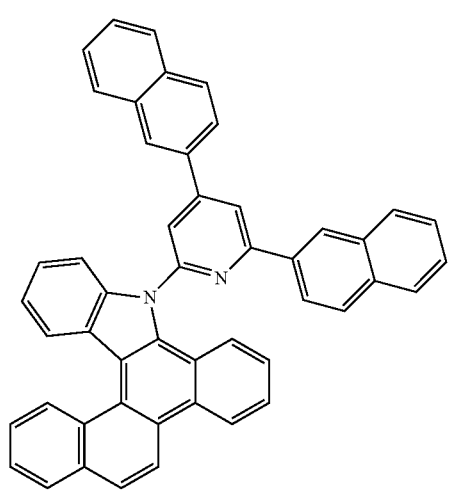
300
-continued
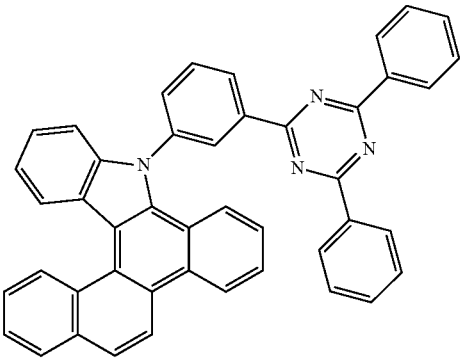
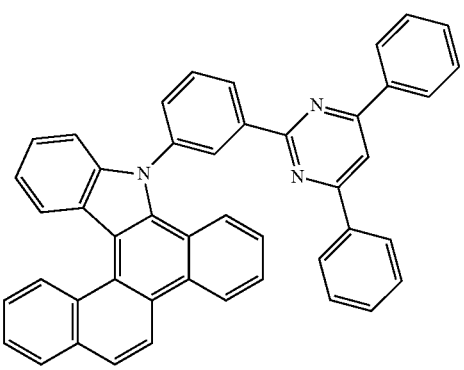
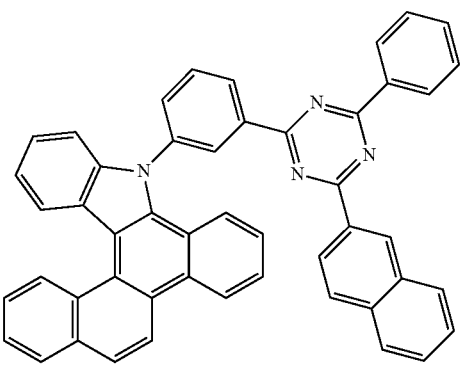
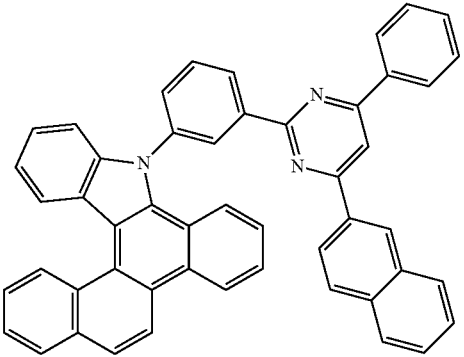

| 301 | 302 |
|---|---|
| 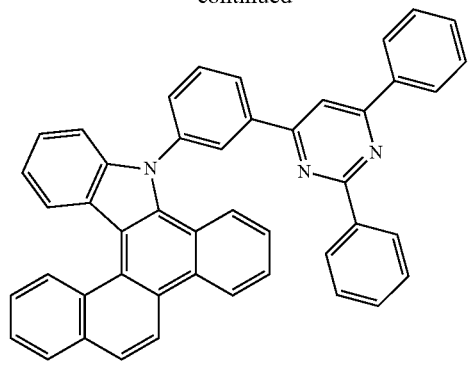 | 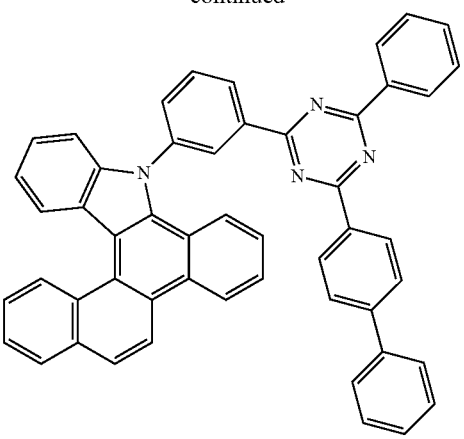 |
| 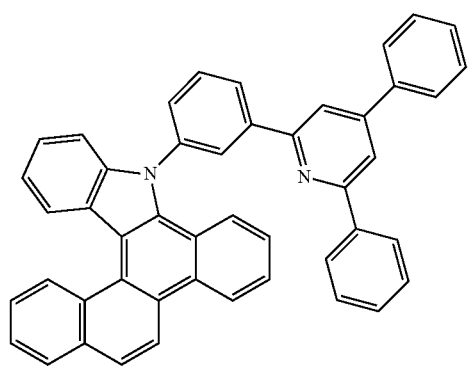 | 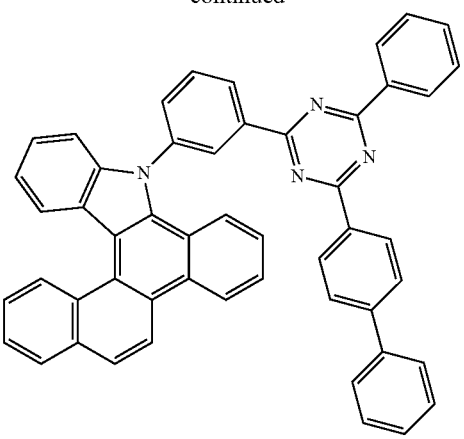 |
| 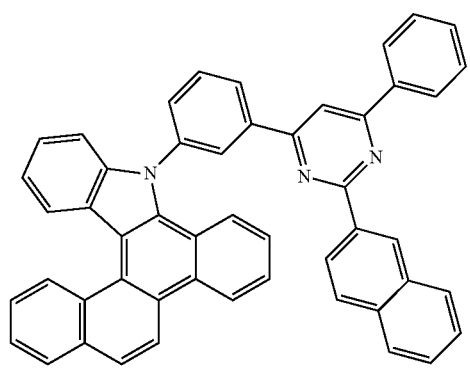 | 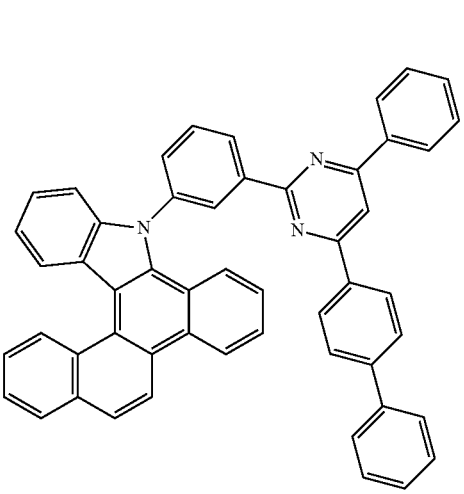 |
| 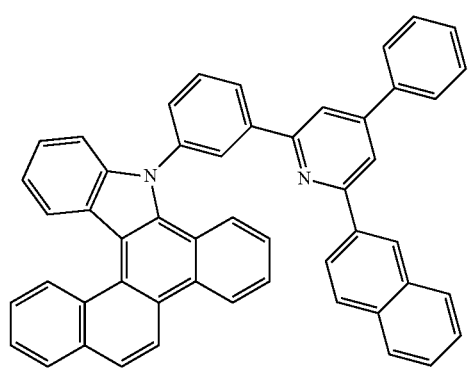 | 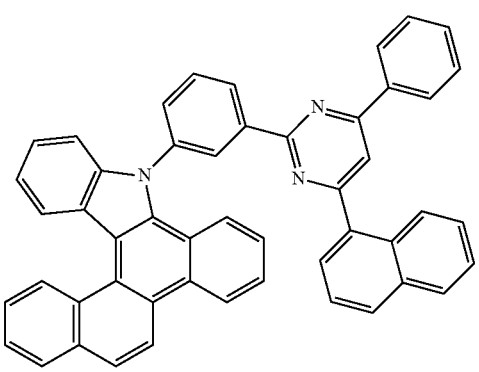 |

303
-continued
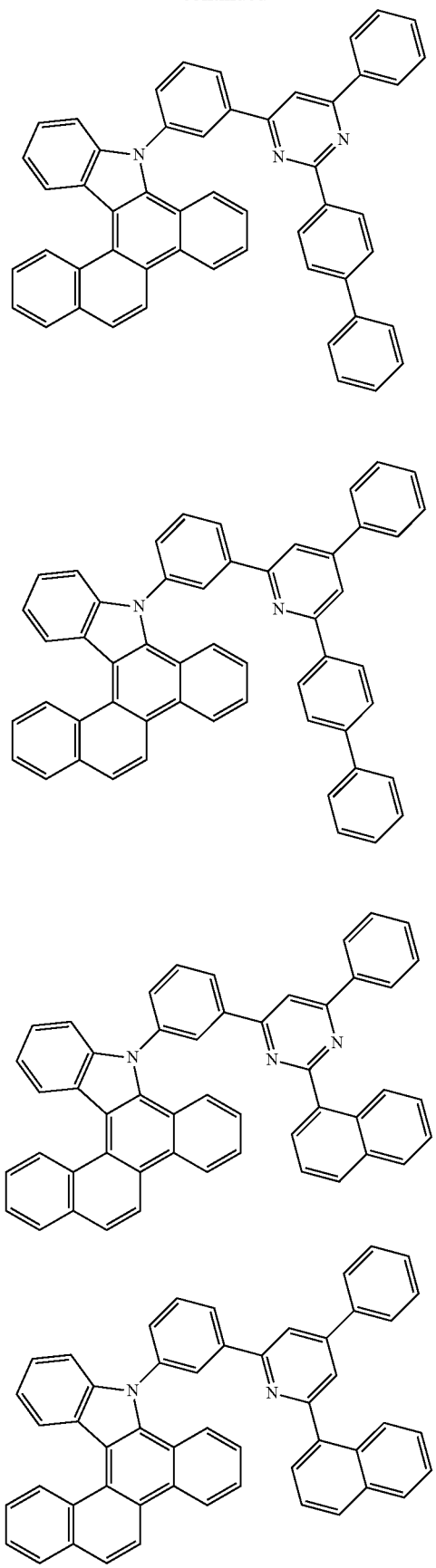
304
-continued
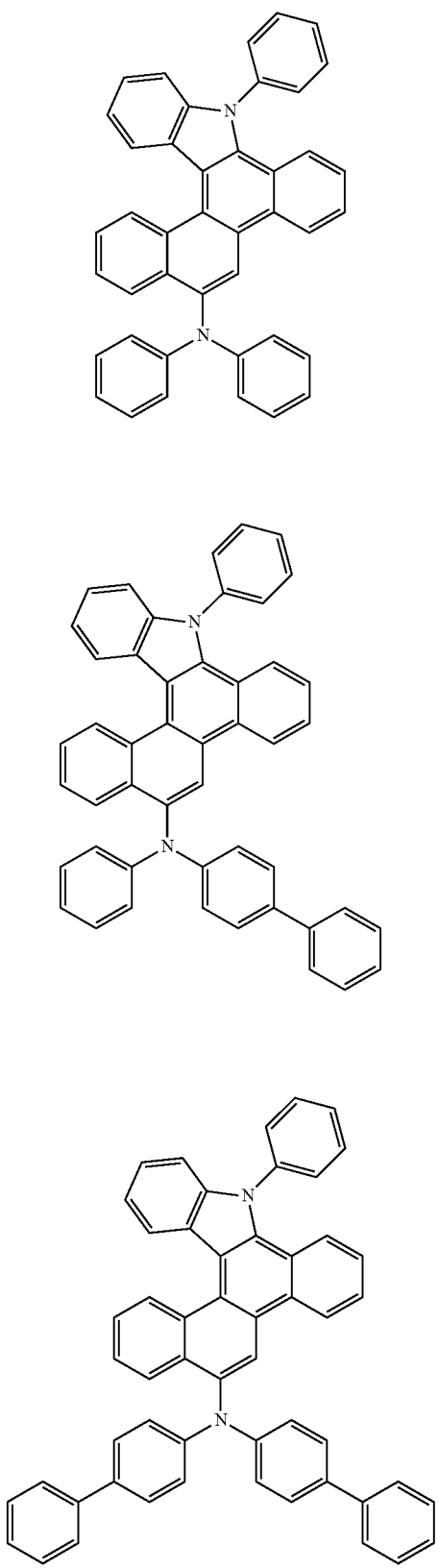

| 305 -continued | 306 -continued |
|---|---|
| 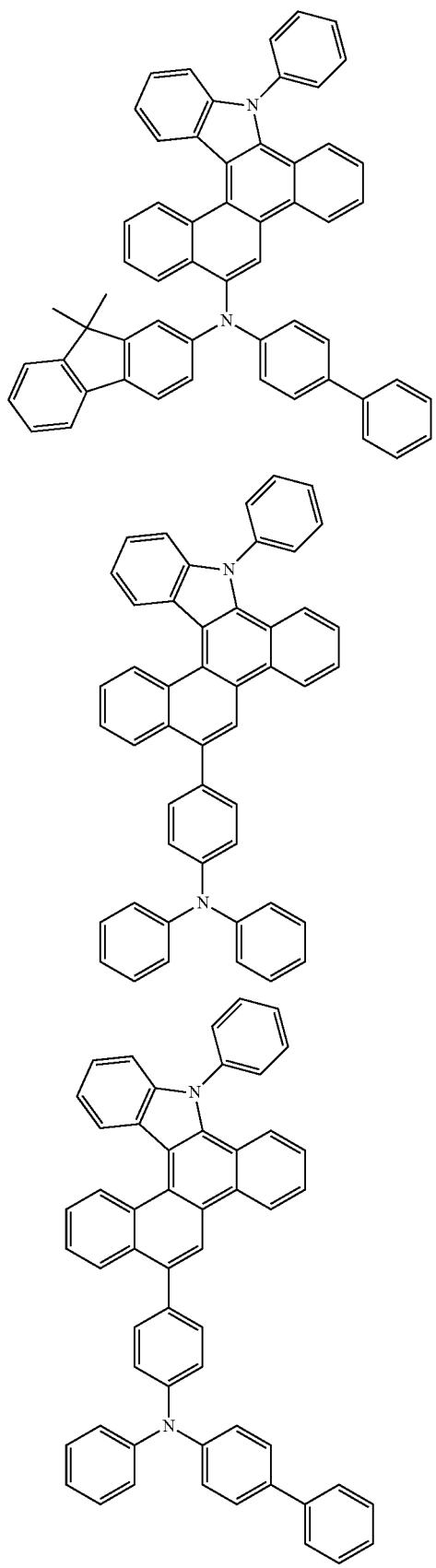 | 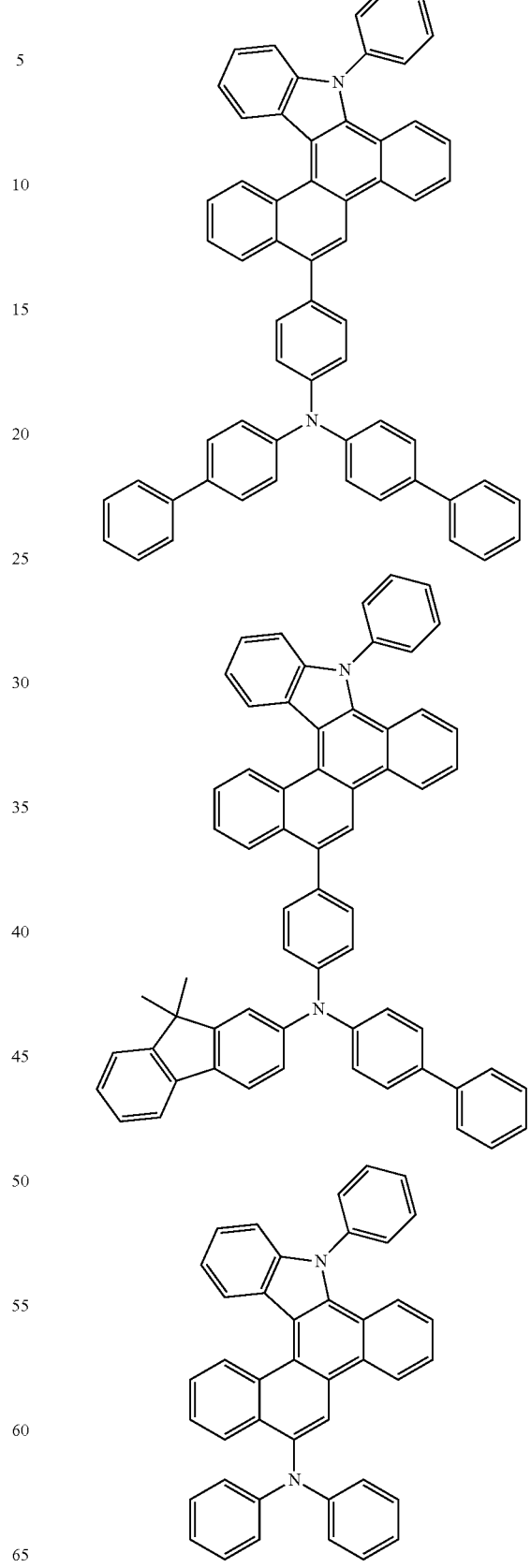 |

307
-continued
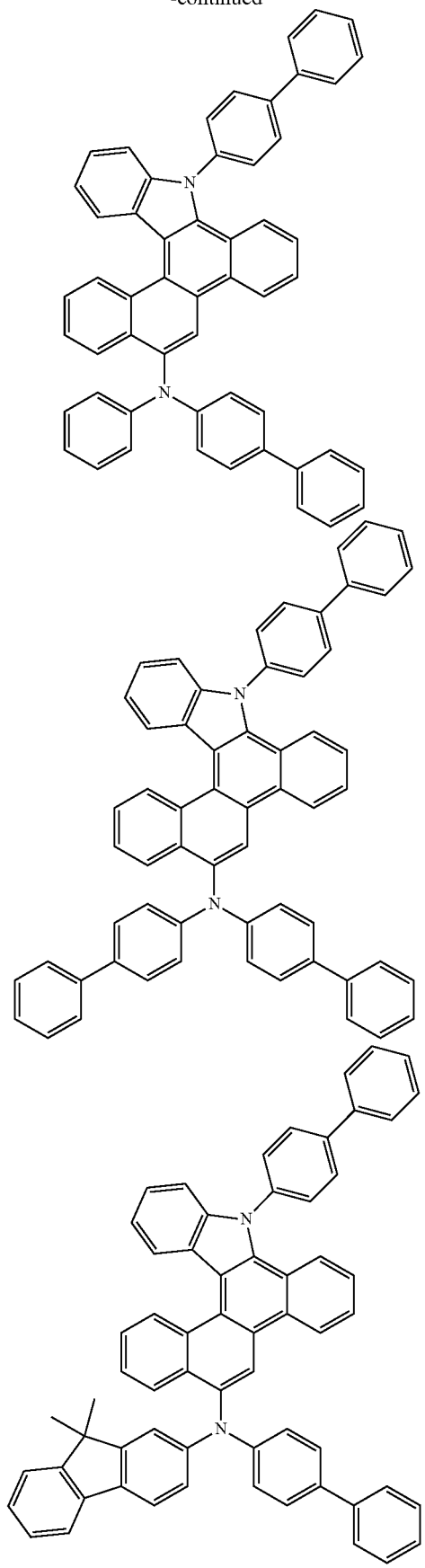
308
-continued
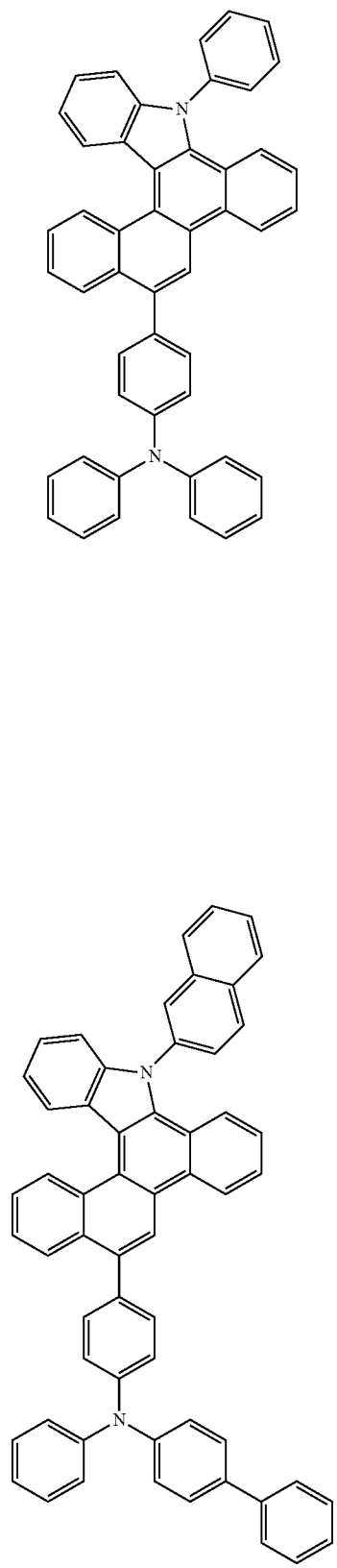

309
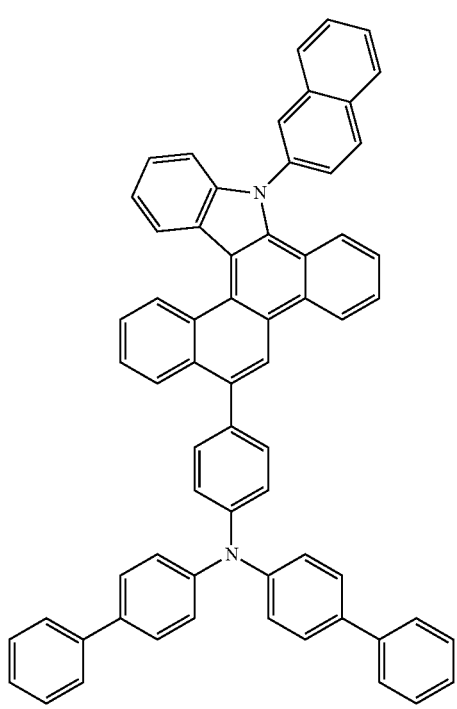
310
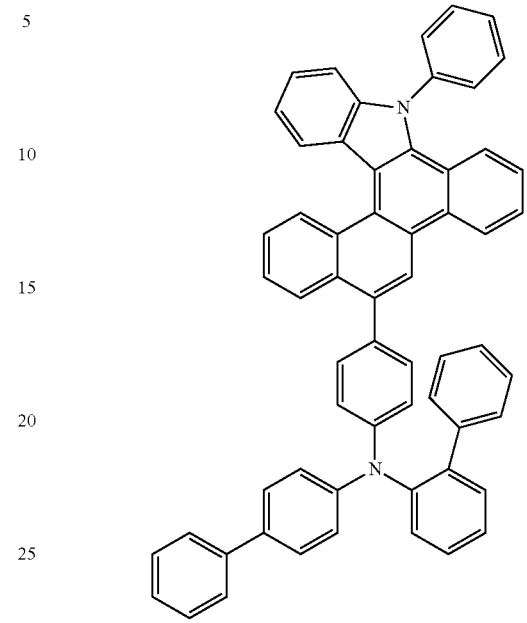
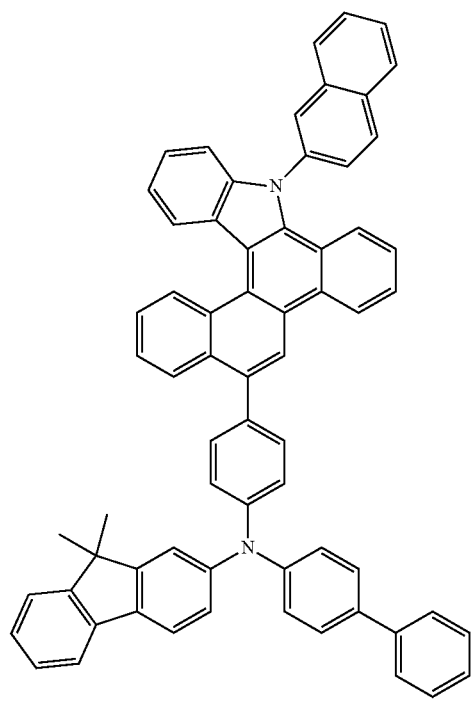
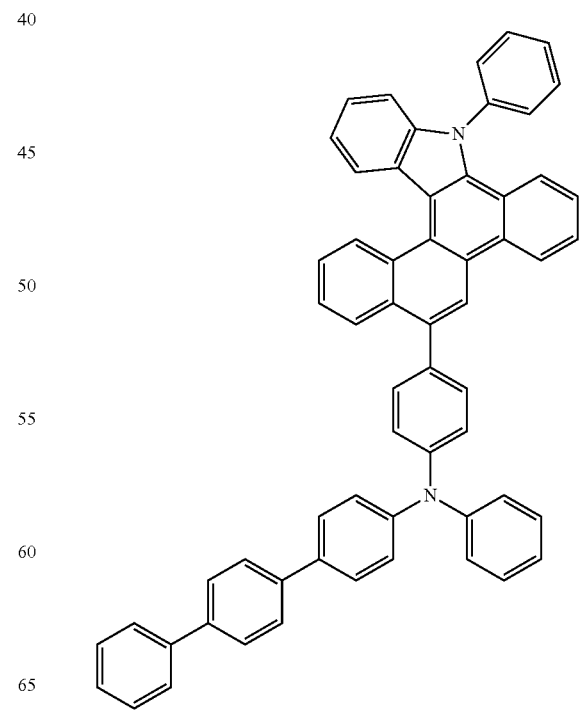

311
-continued
312
-continued
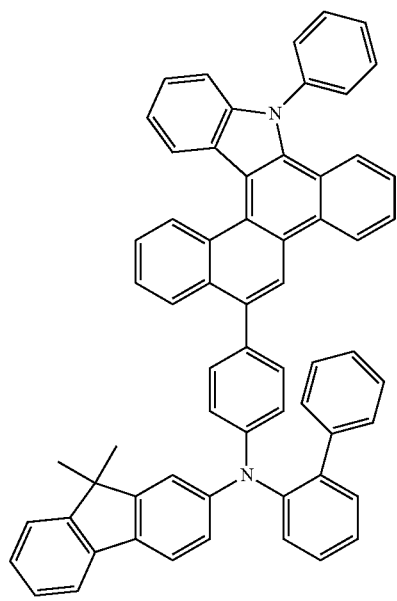
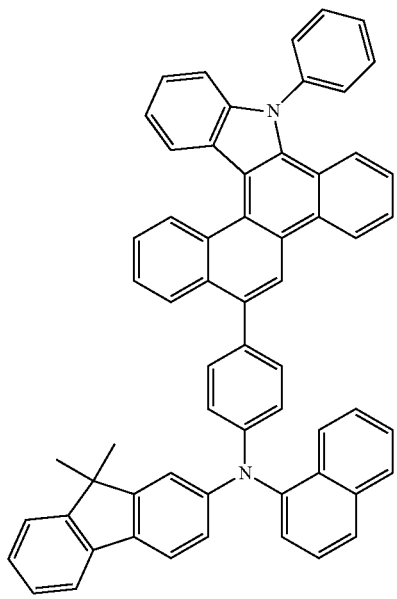
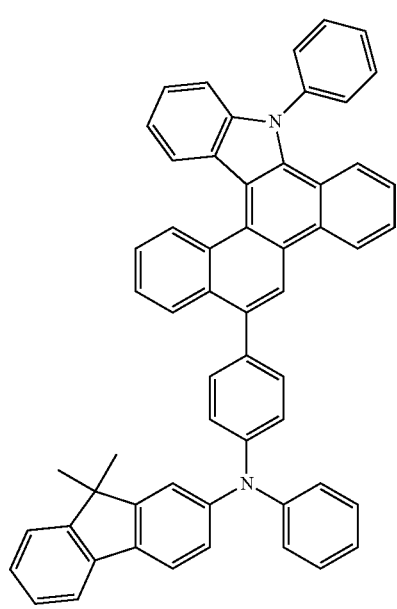
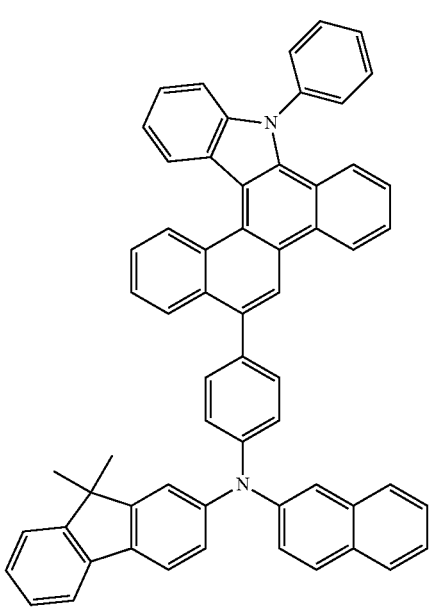

313
-continued
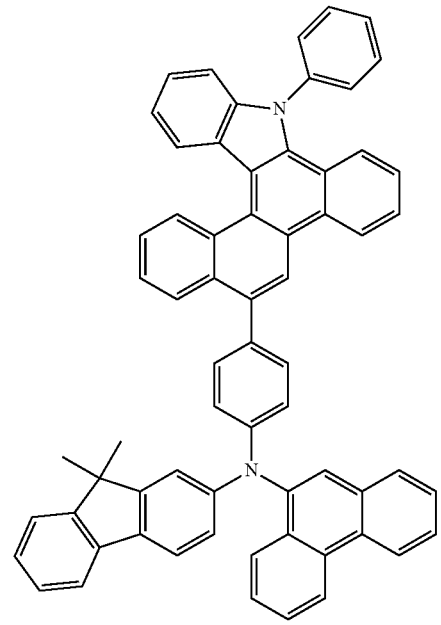
314
-continued
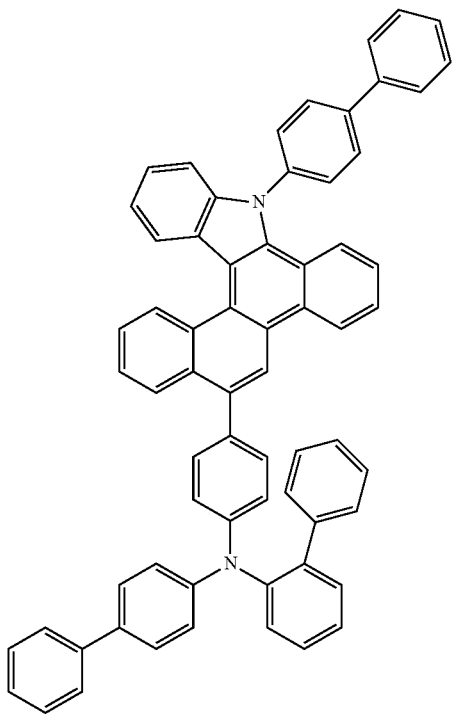
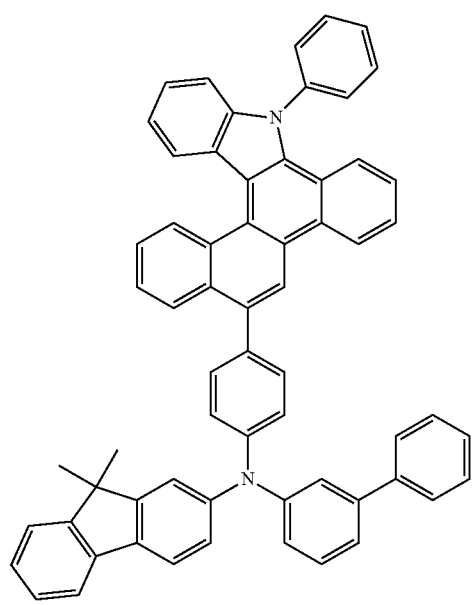
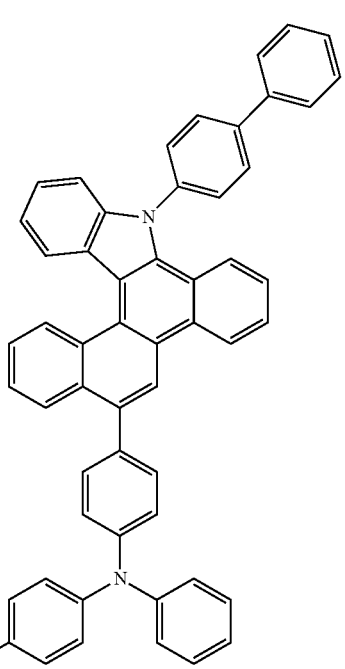

315
-continued
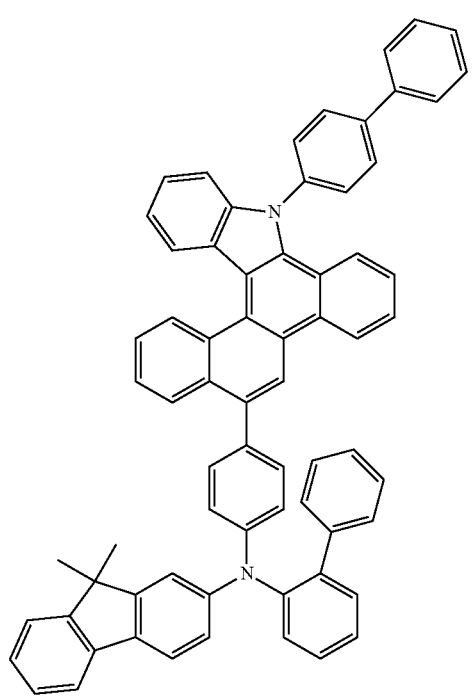
316
-continued
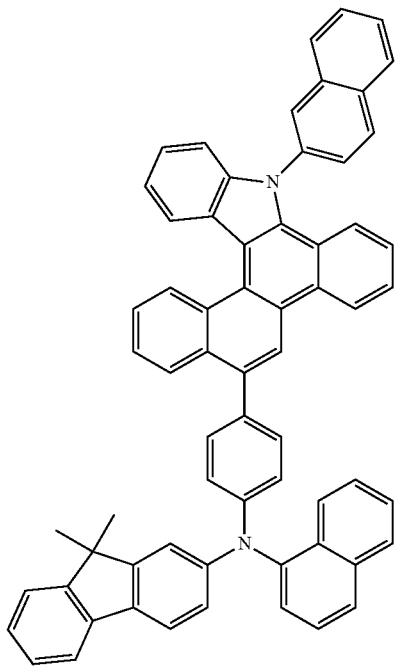
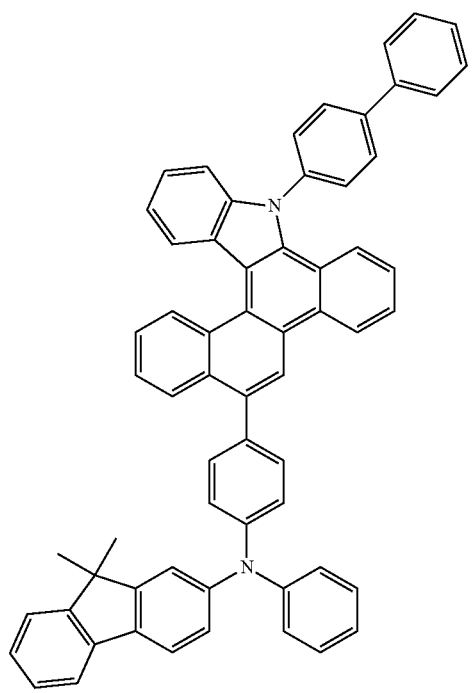
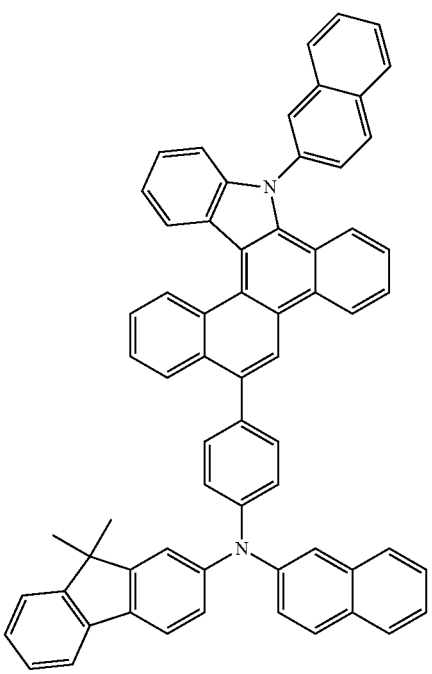

317
-continued
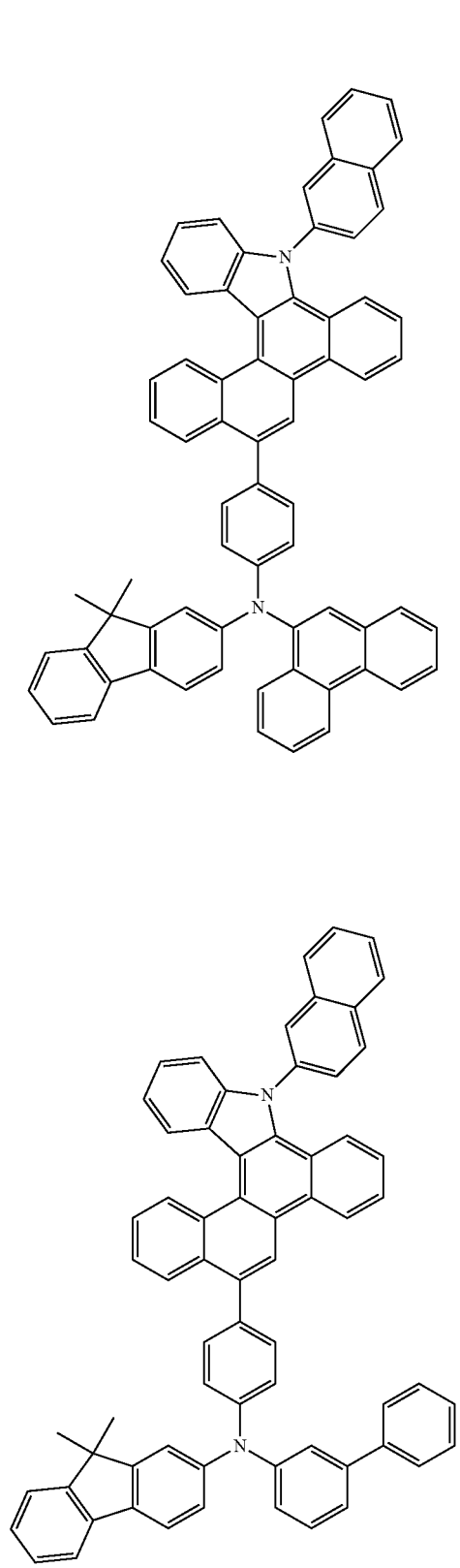
318
-continued
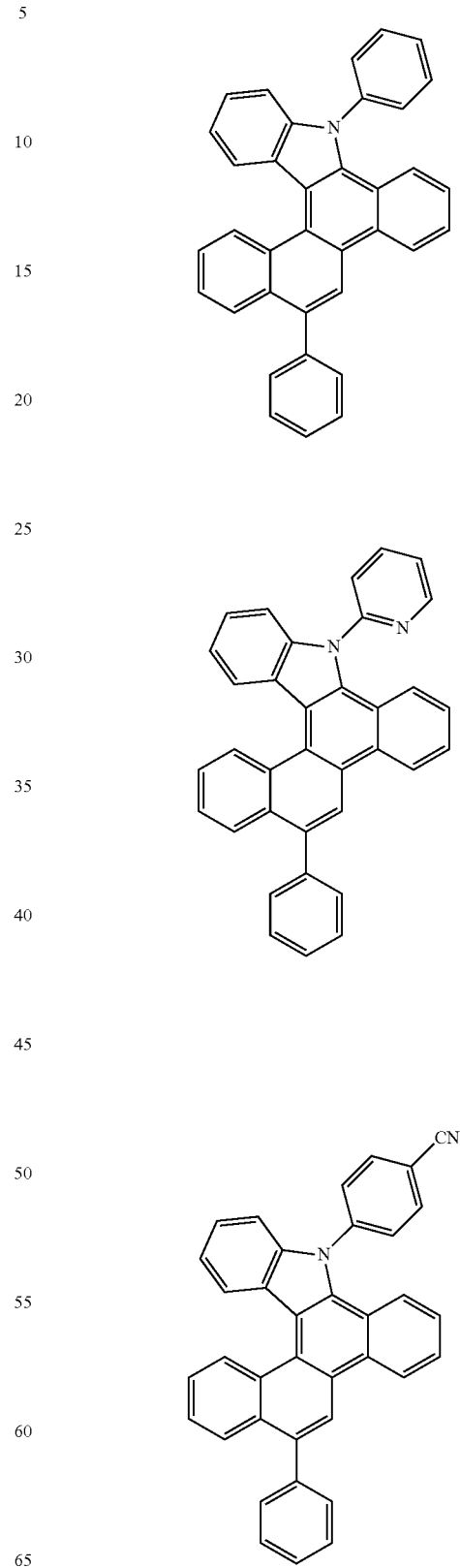

319
-continued
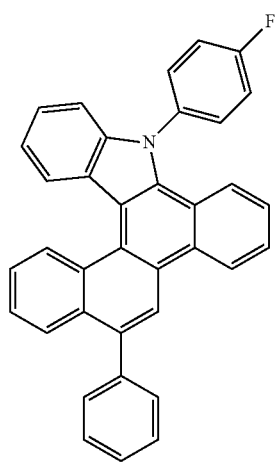
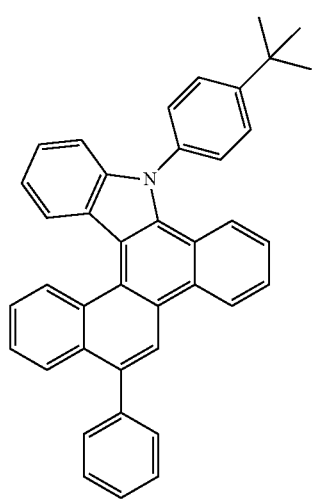
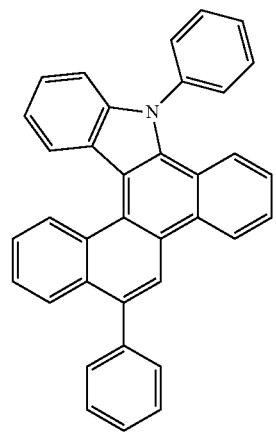
320
-continued
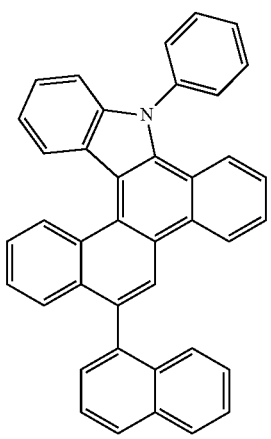
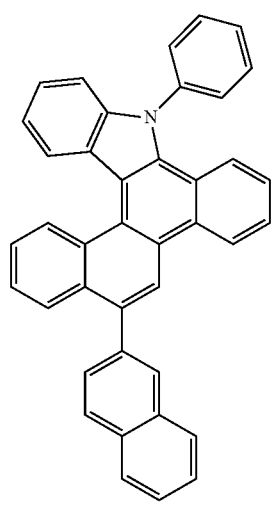
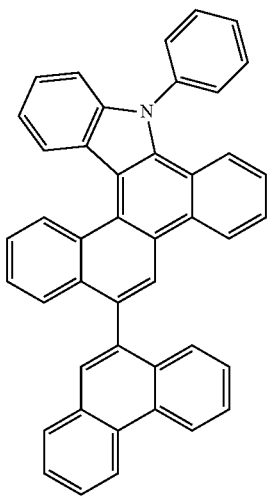

321
-continued
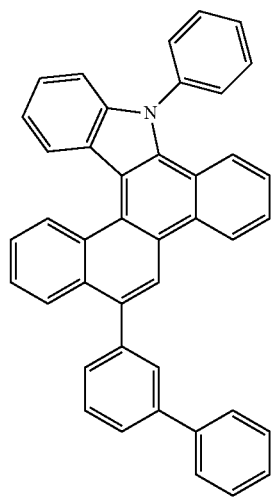
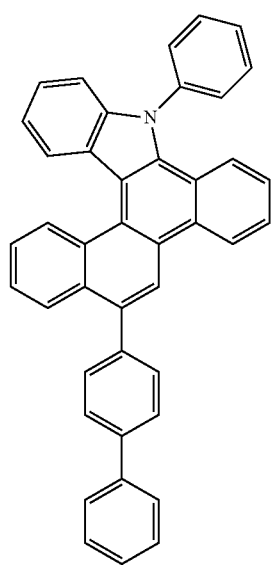
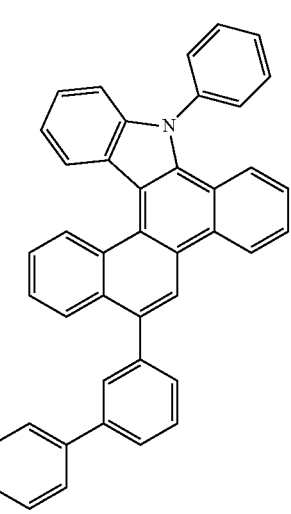
322
-continued
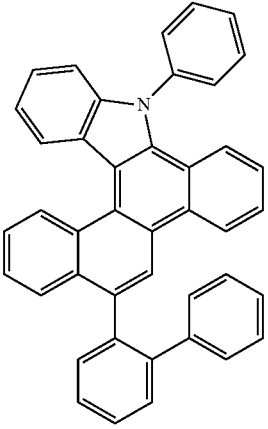
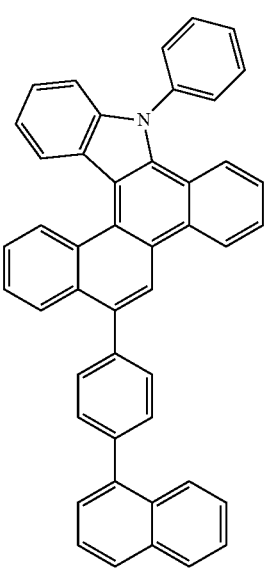
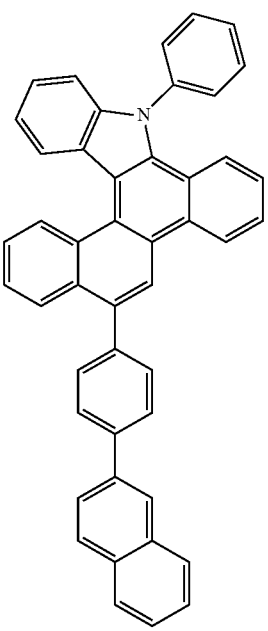

323
-continued
324
-continued
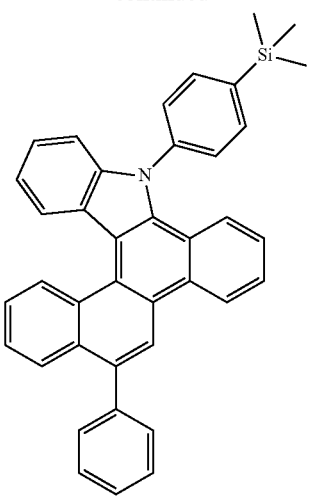
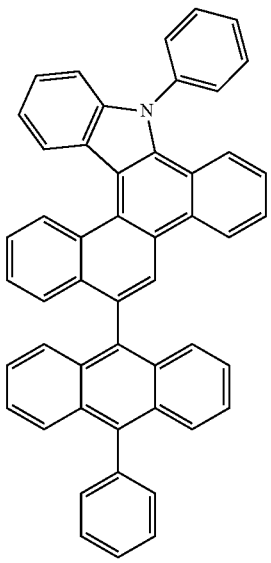
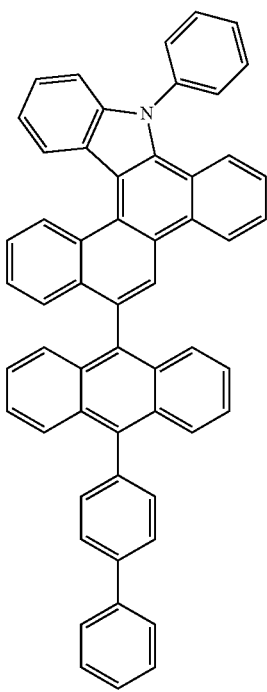

325
-continued
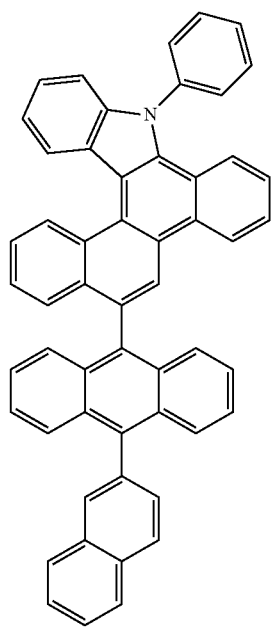
326
-continued
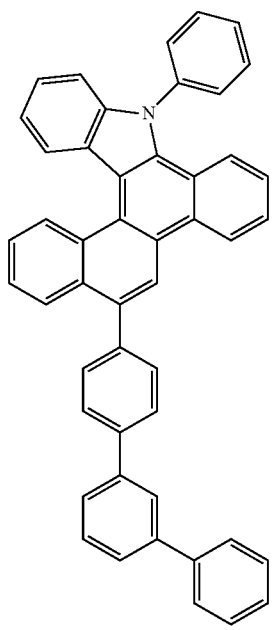
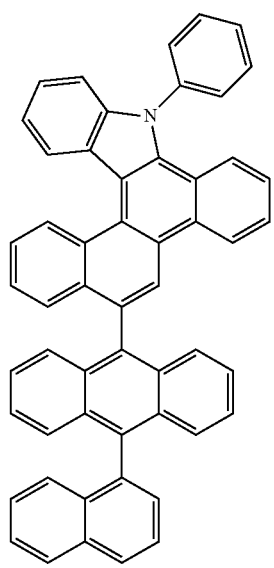

327
-continued
328
-continued
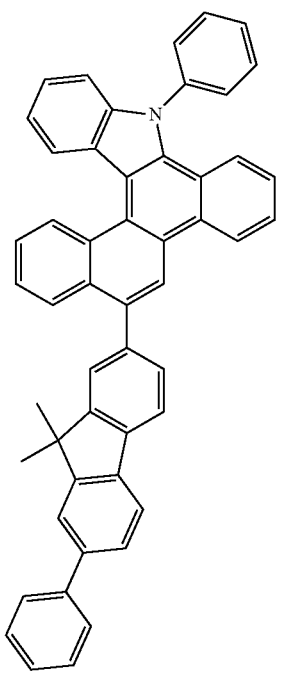
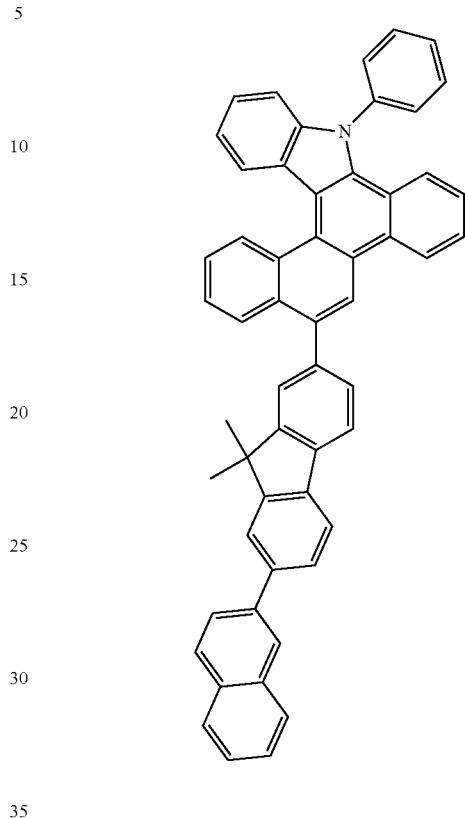
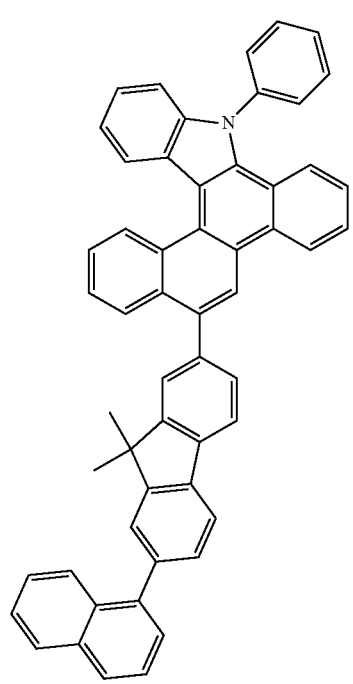

329
-continued
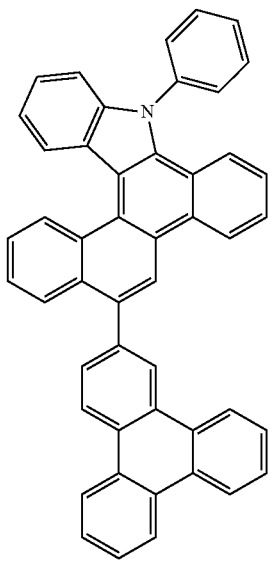
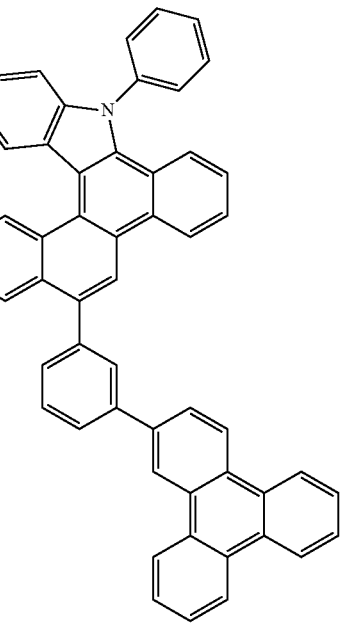
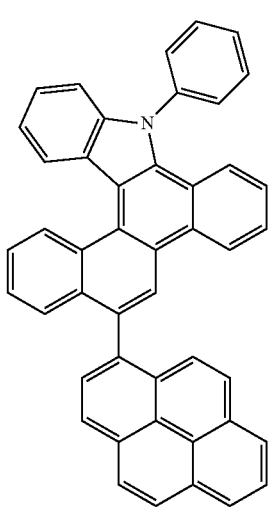
330
-continued
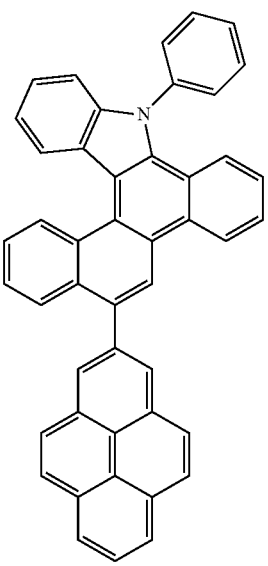
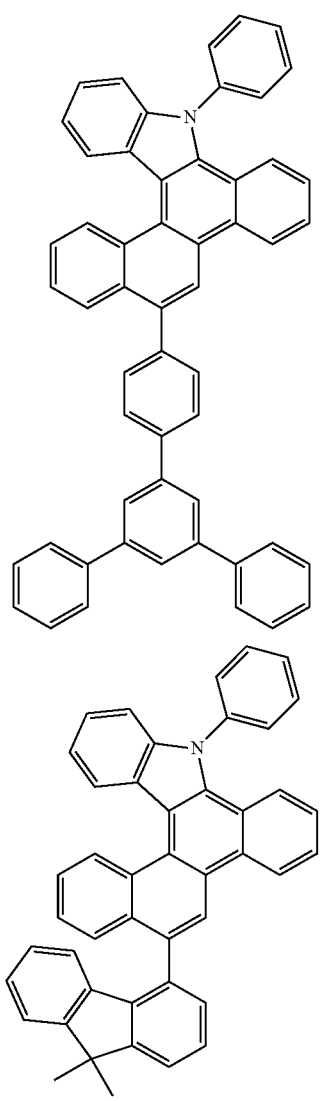

331
-continued
332
-continued
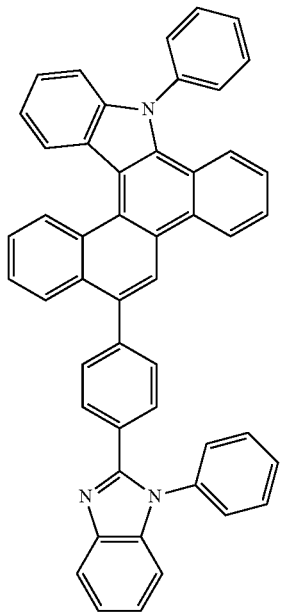
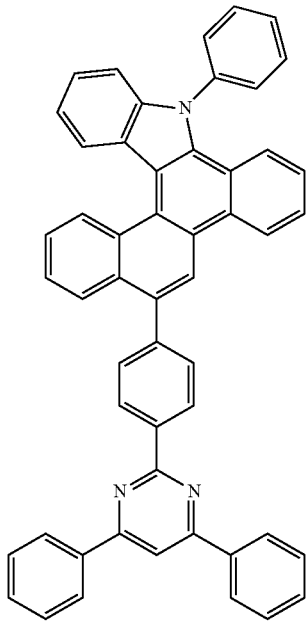
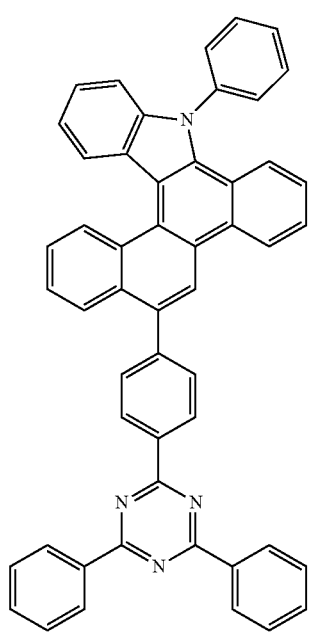

333
-continued
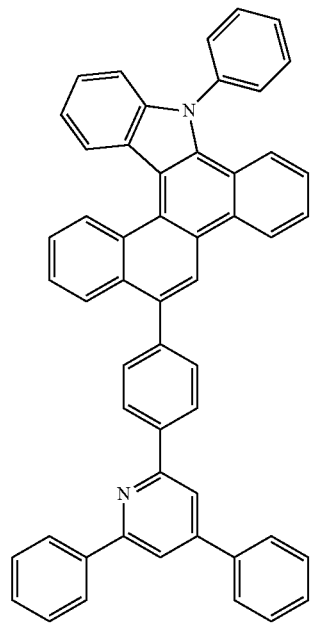
334
-continued
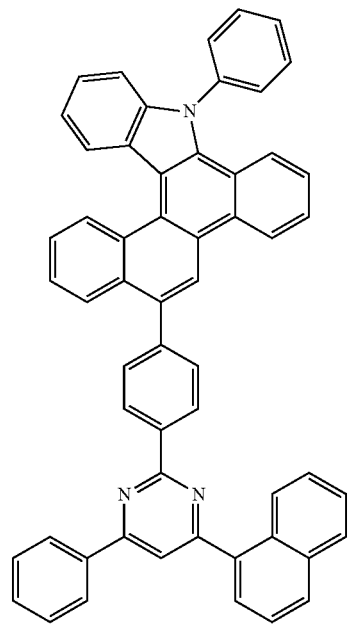
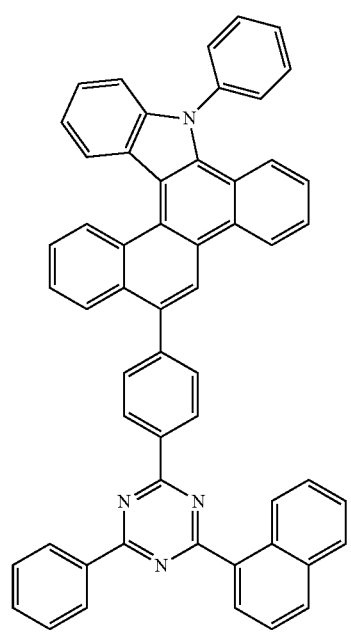
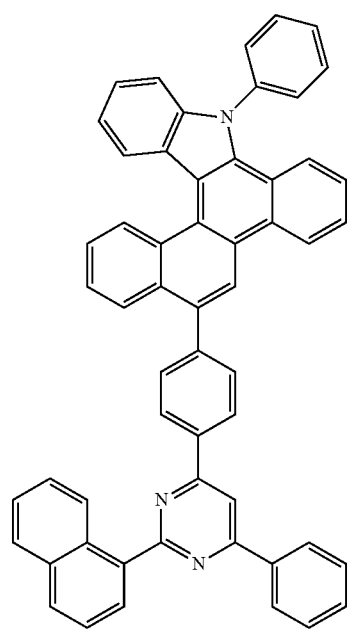

335
-continued
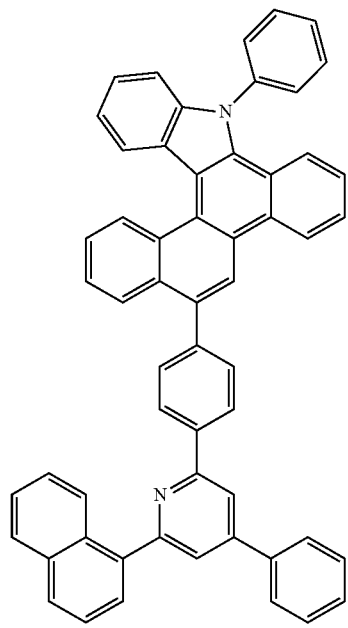
336
-continued
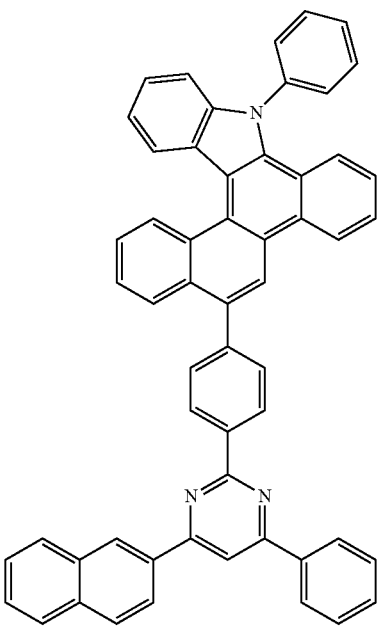
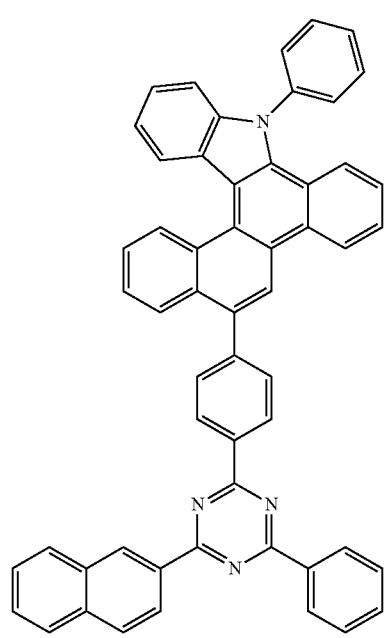
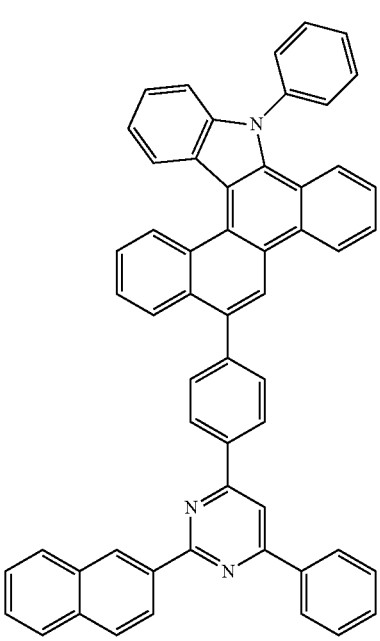

337
-continued
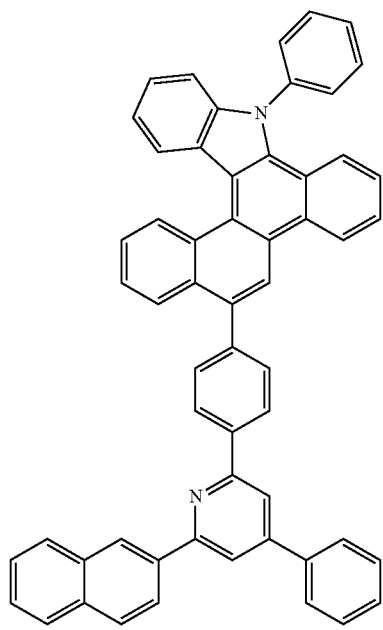
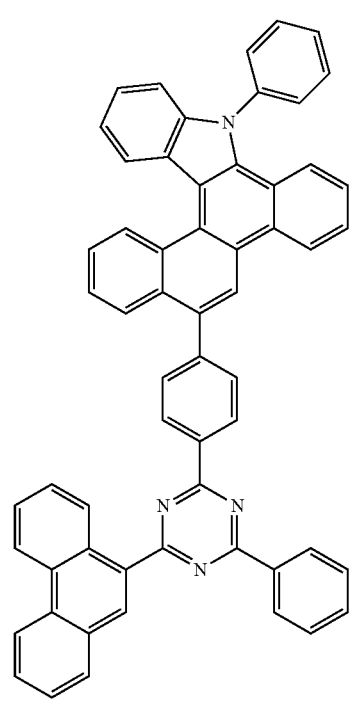
338
-continued
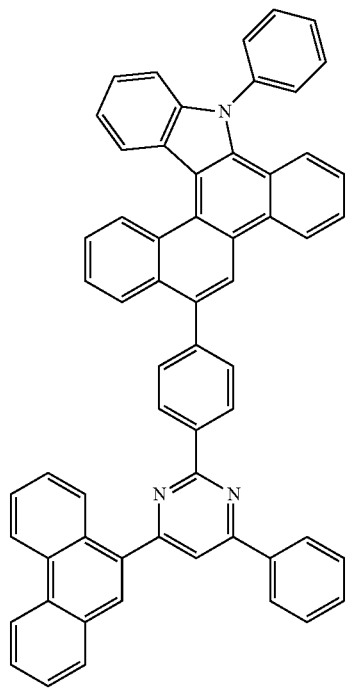
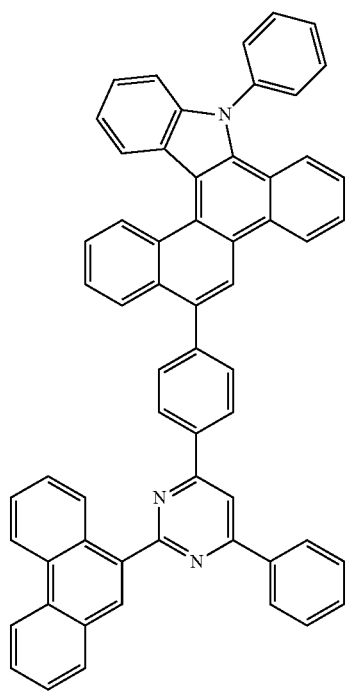

339
-continued
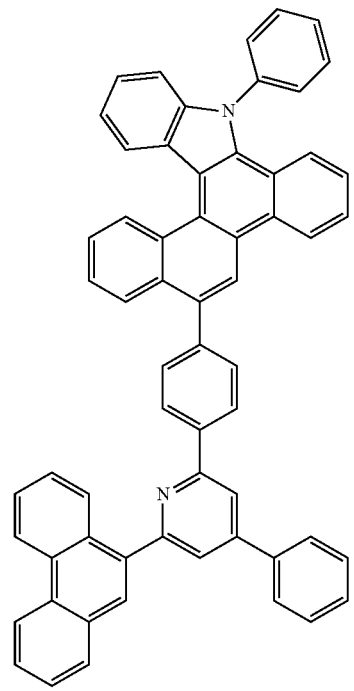
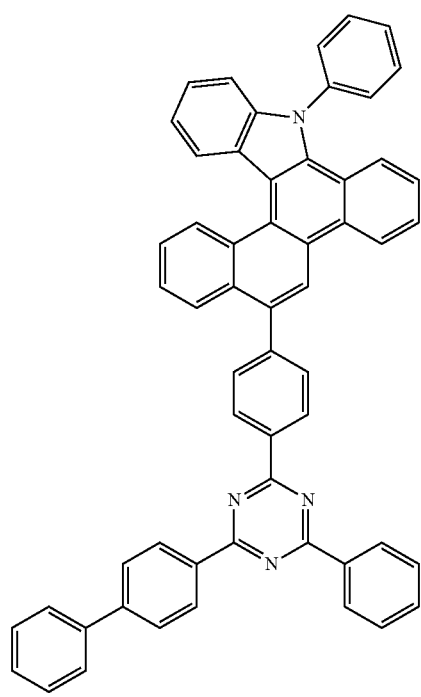
340
-continued
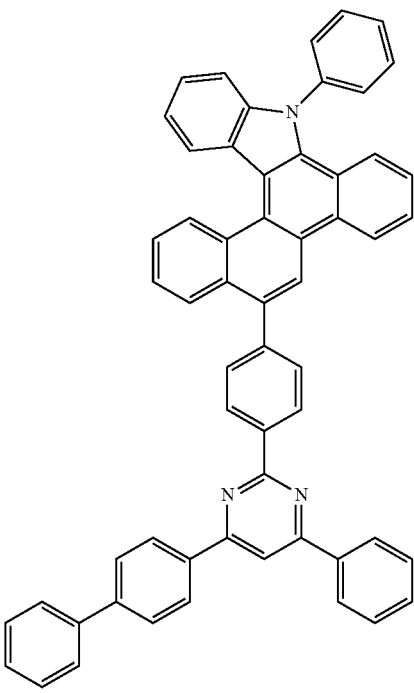
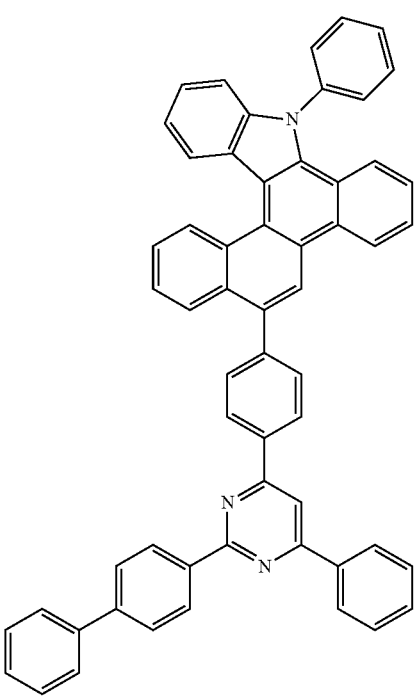

341
-continued
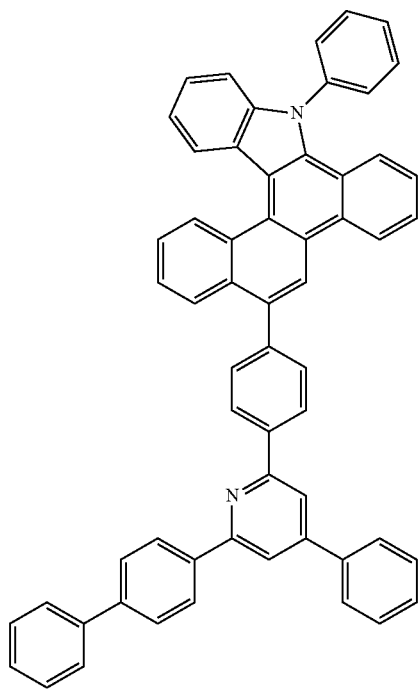
342
-continued
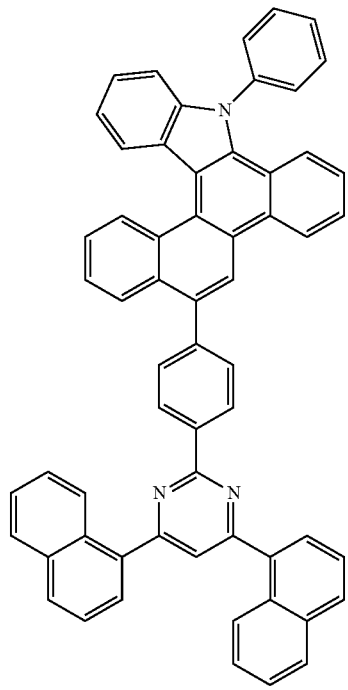
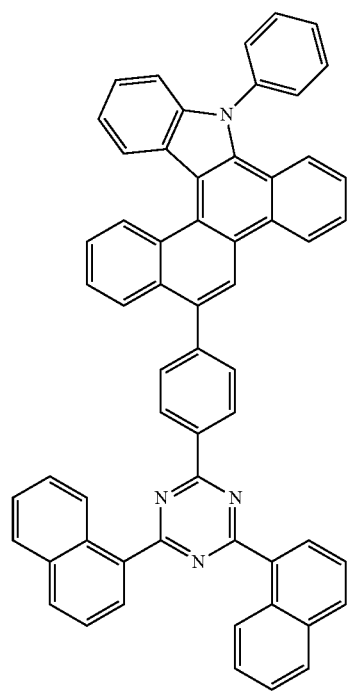
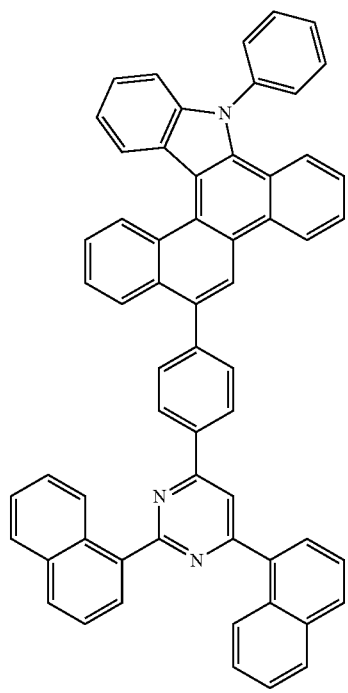

343
-continued
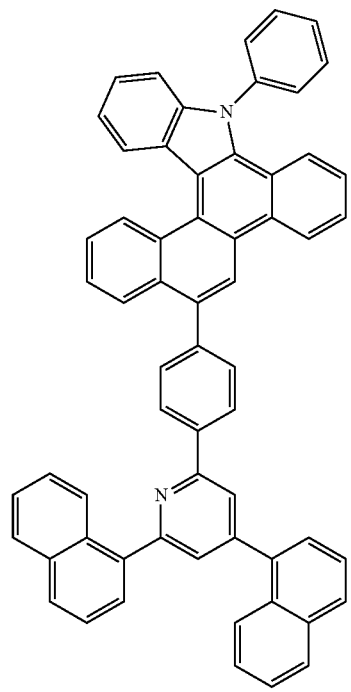
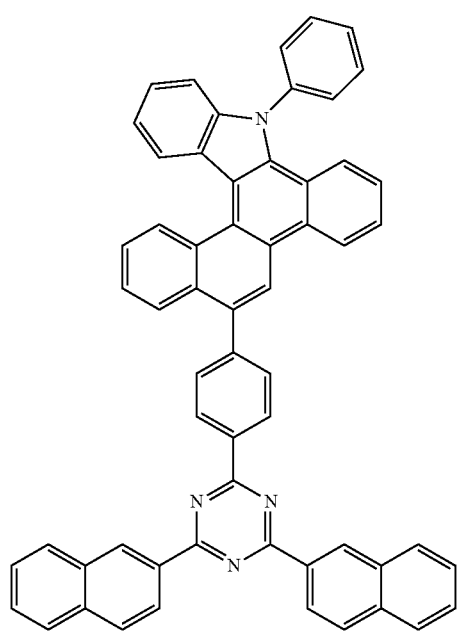
344
-continued
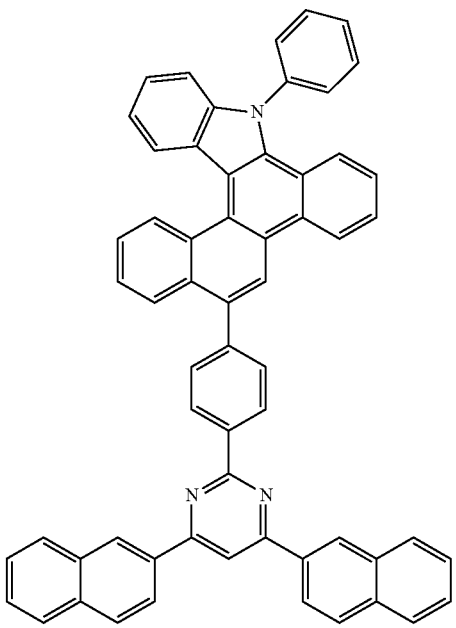
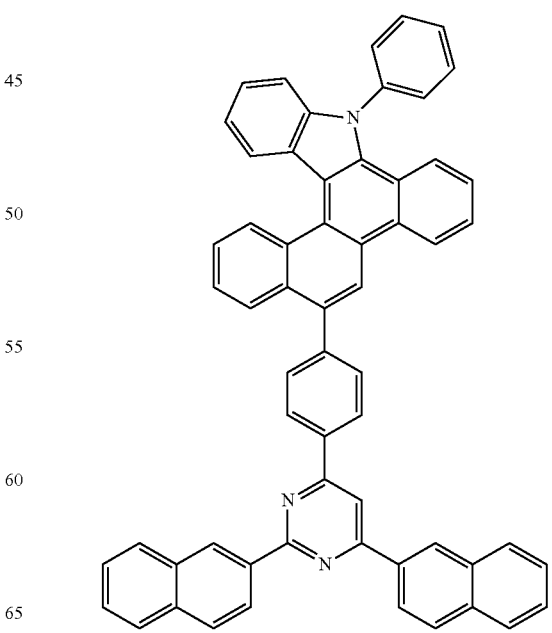

345
-continued
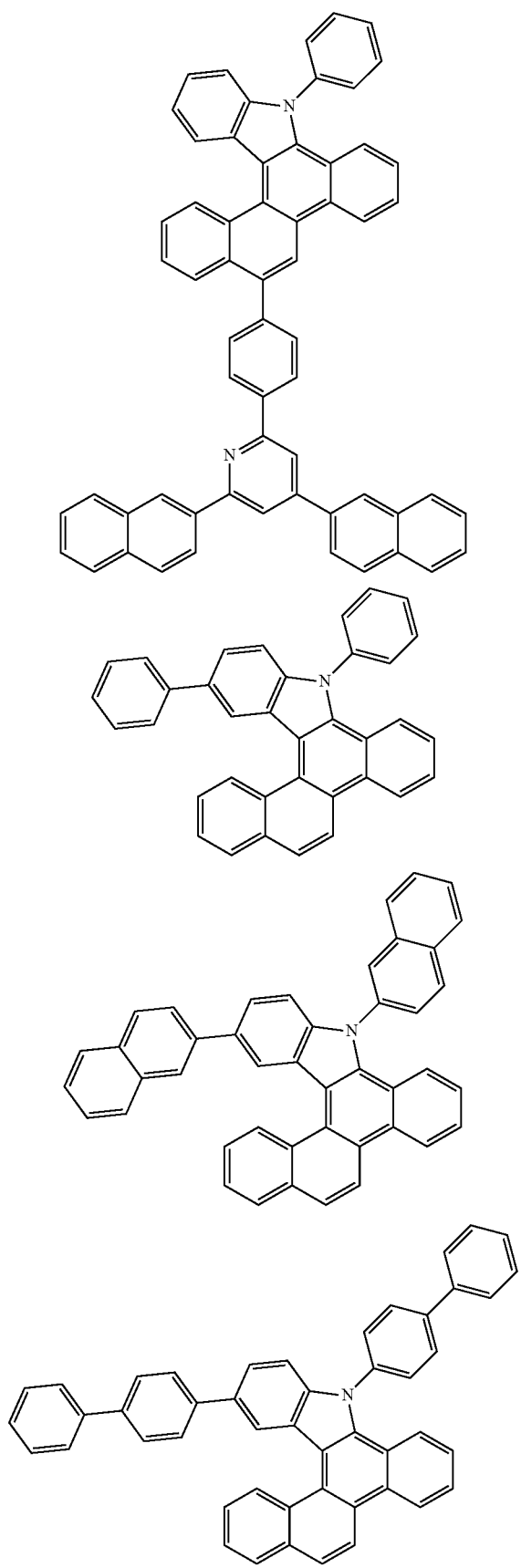
346
-continued
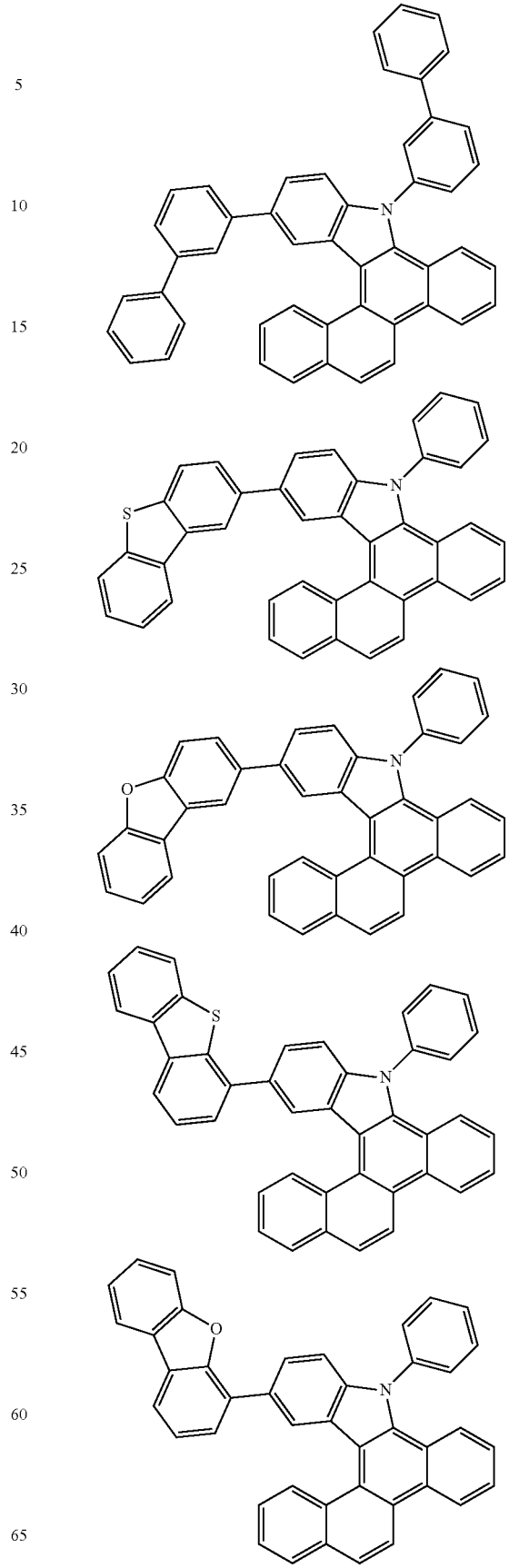

347
-continued
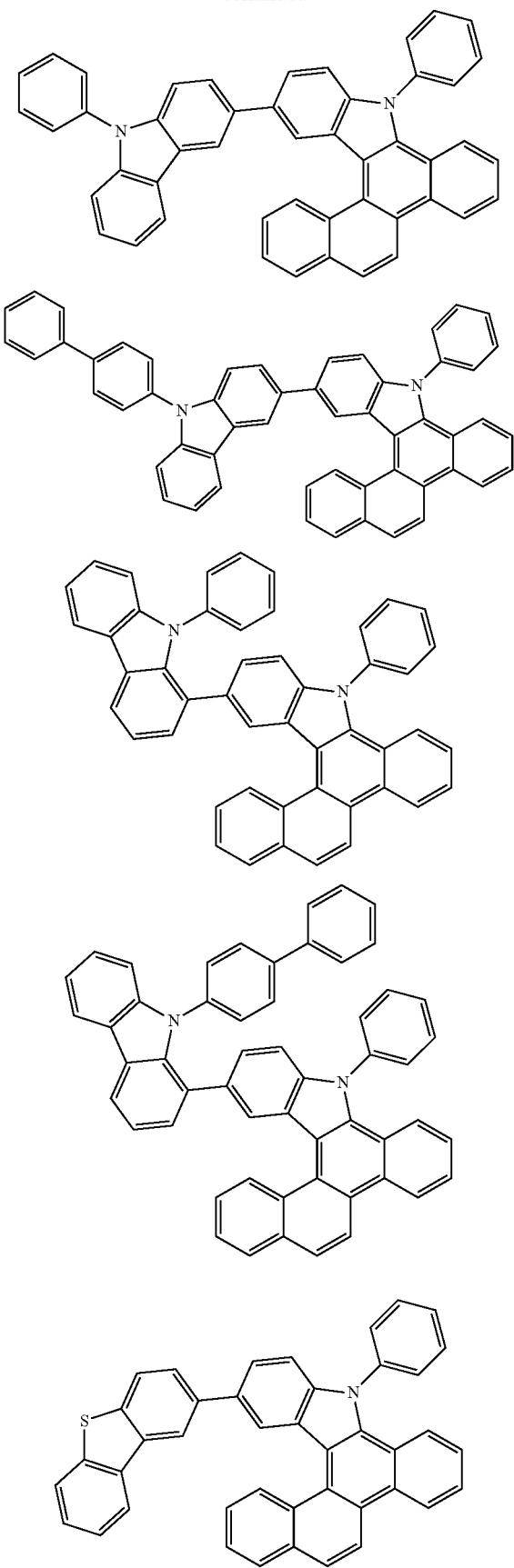
348
-continued
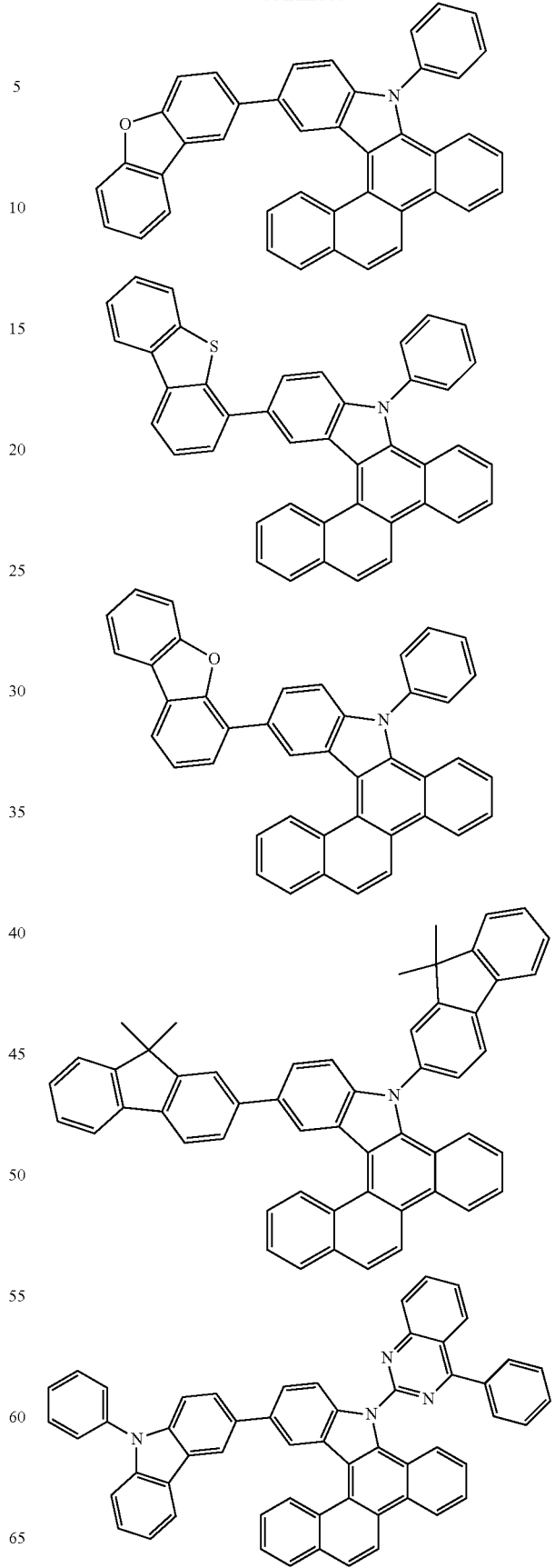

349
-continued
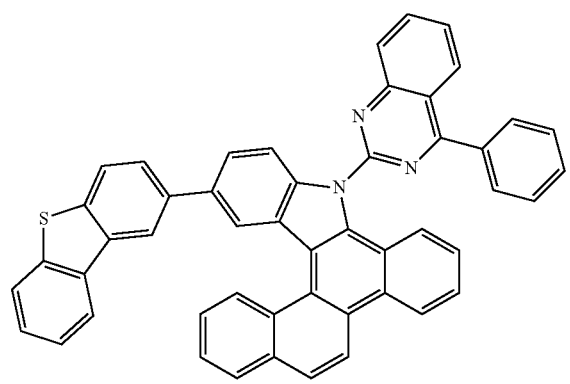
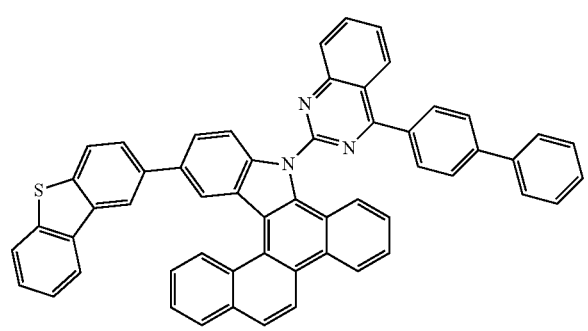
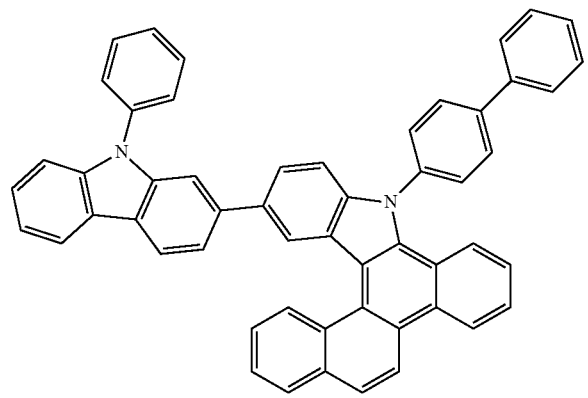
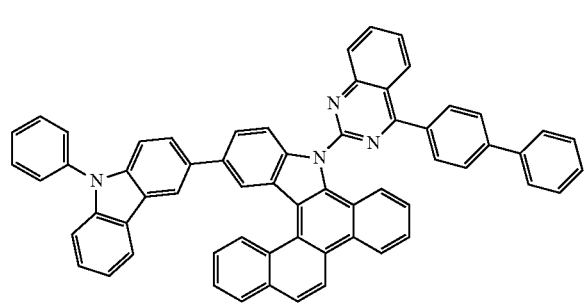
350
-continued
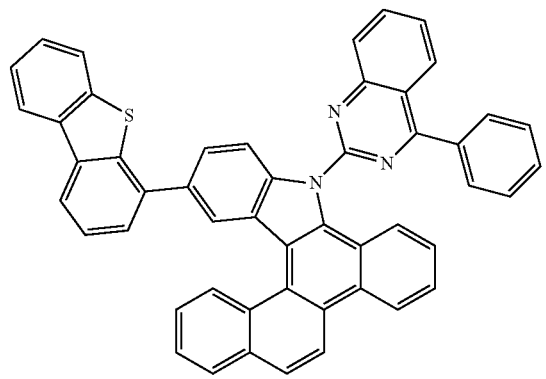
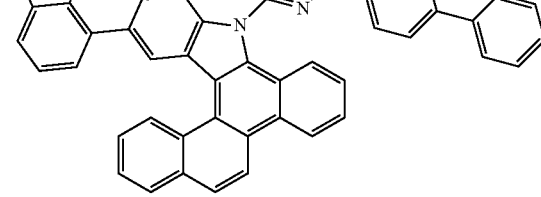
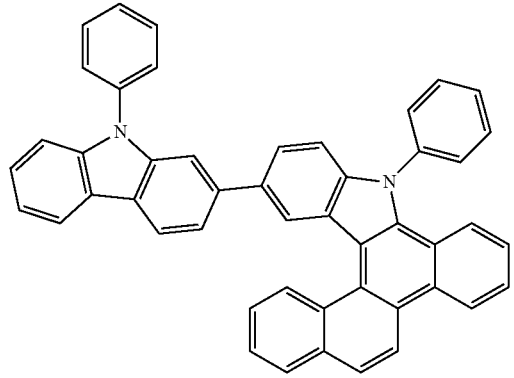
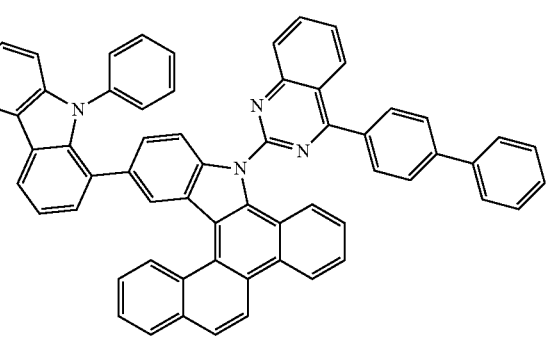

351
-continued
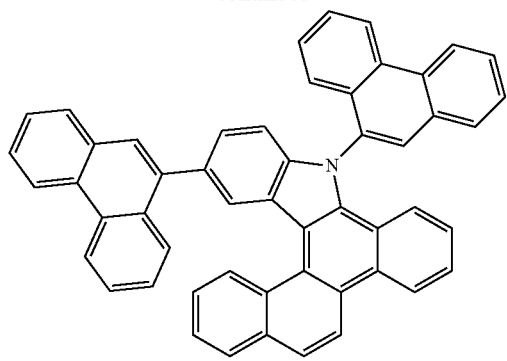
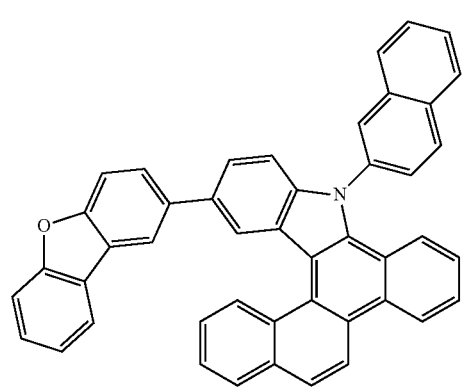
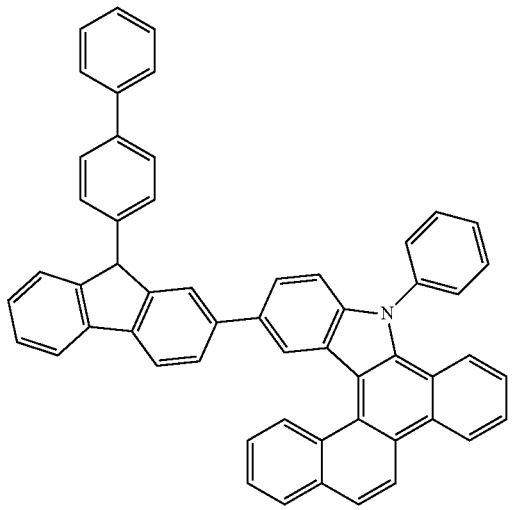
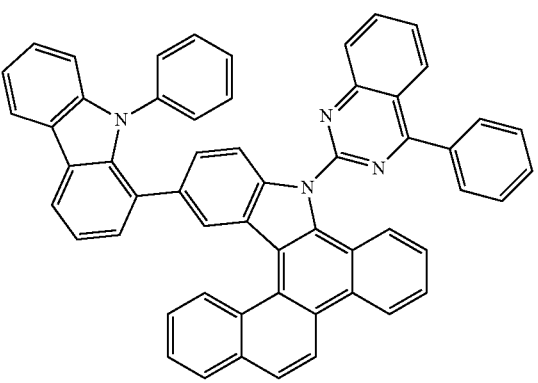
352
-continued
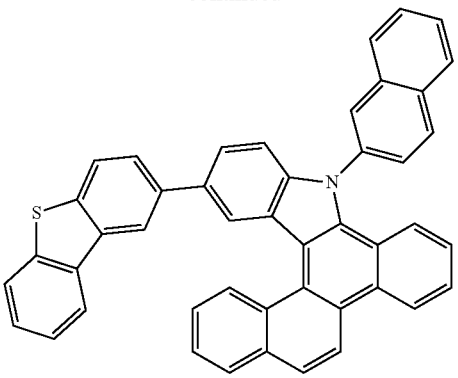
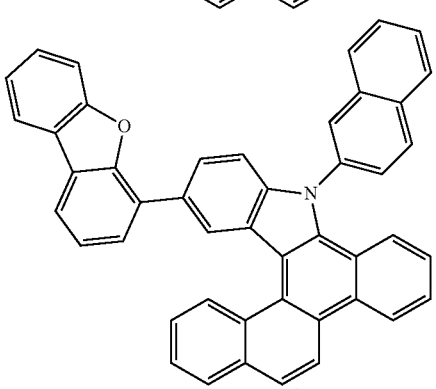
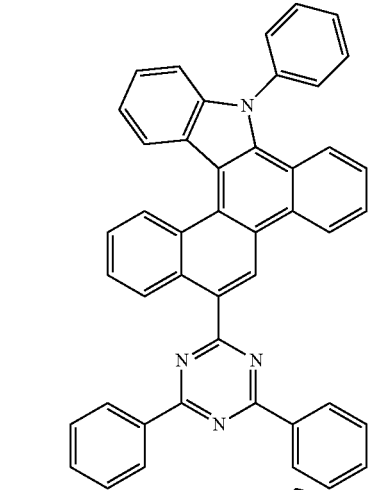
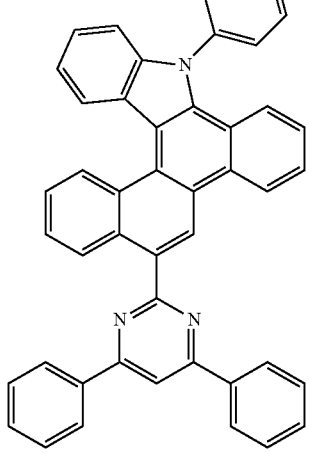

353
-continued
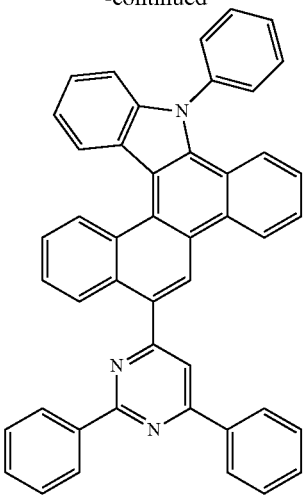
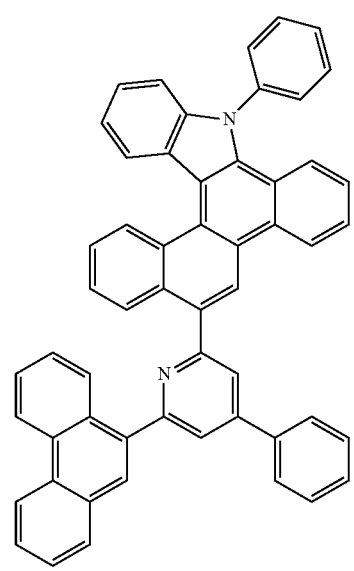
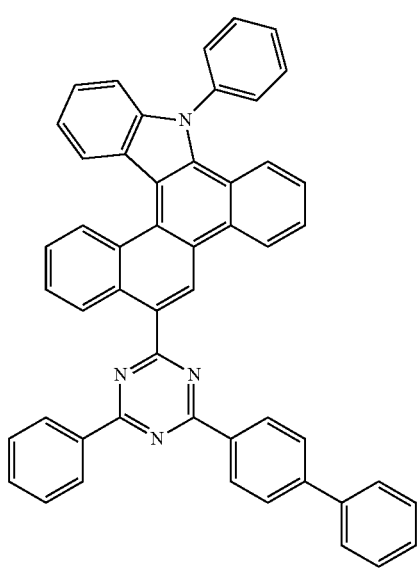
354
-continued
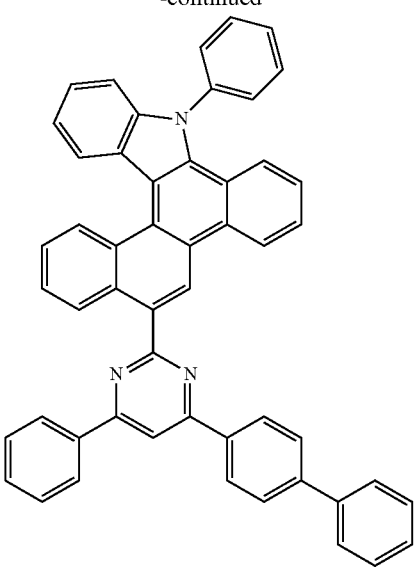
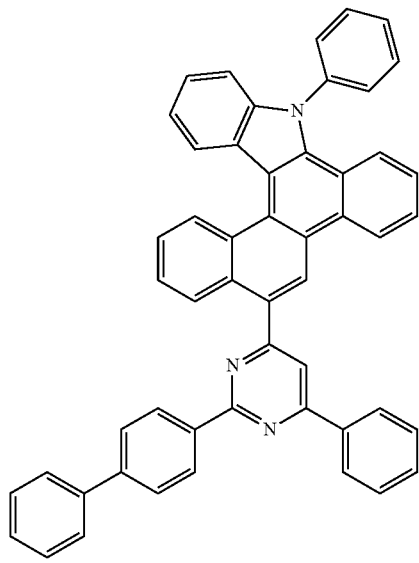
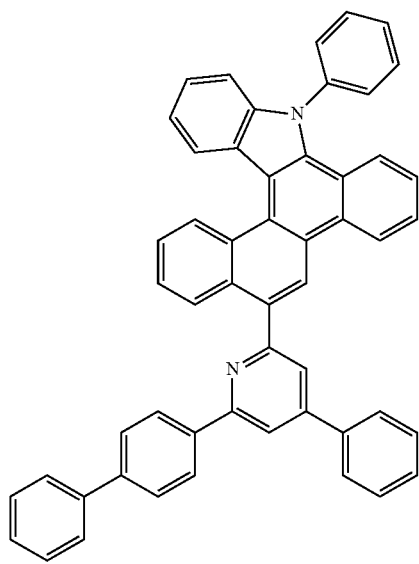

355
-continued
356
-continued
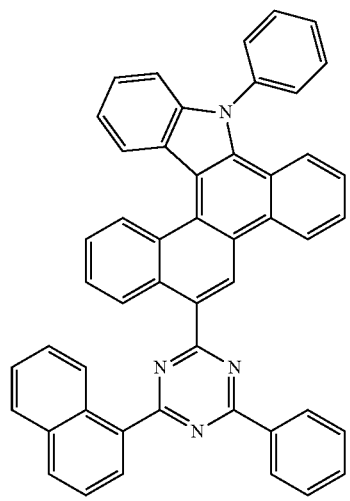
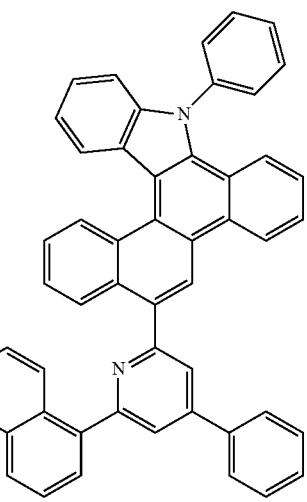
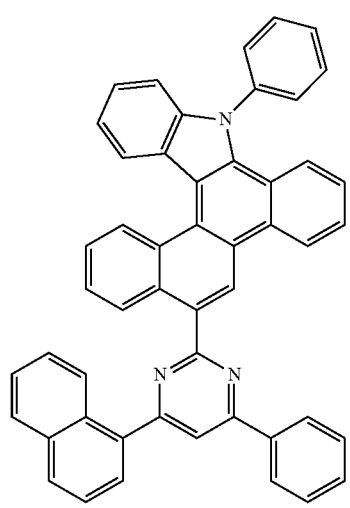
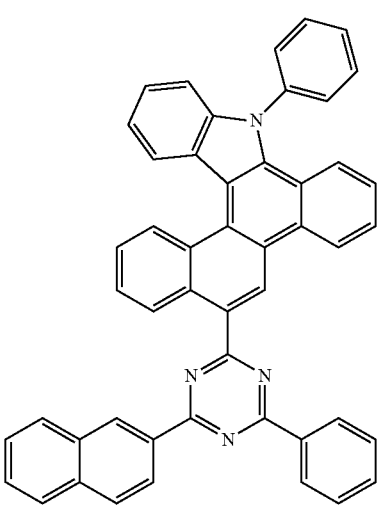
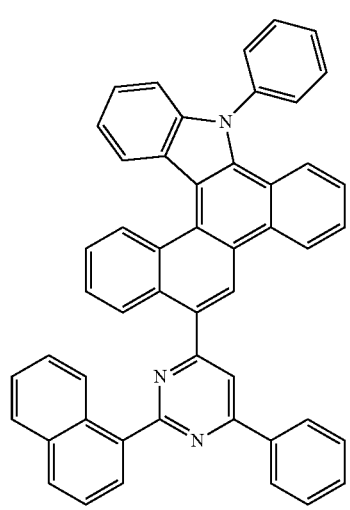
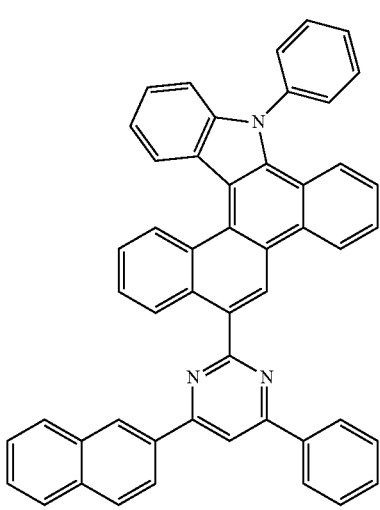

357
-continued
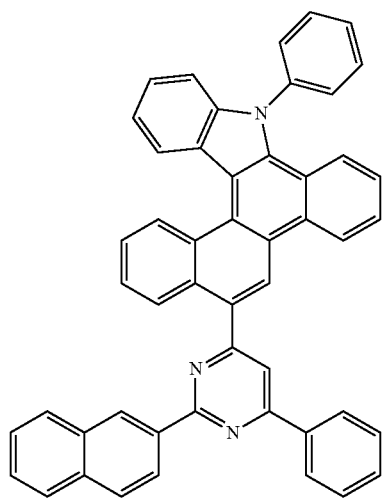
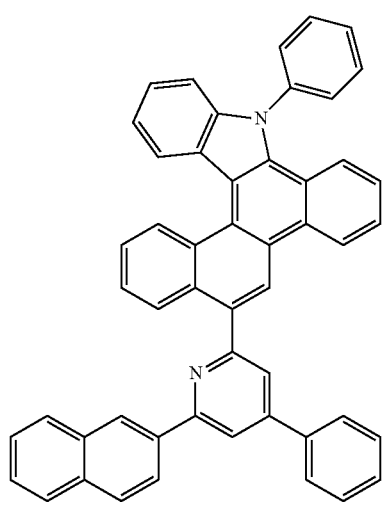
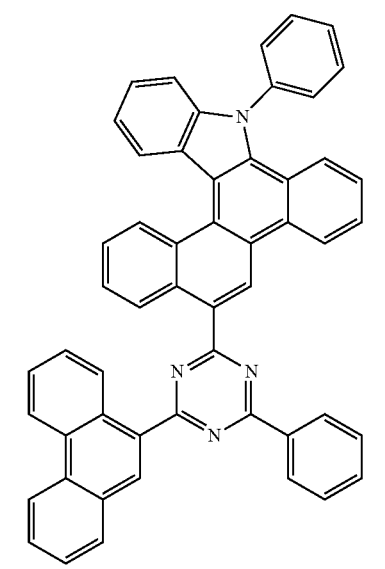
358
-continued
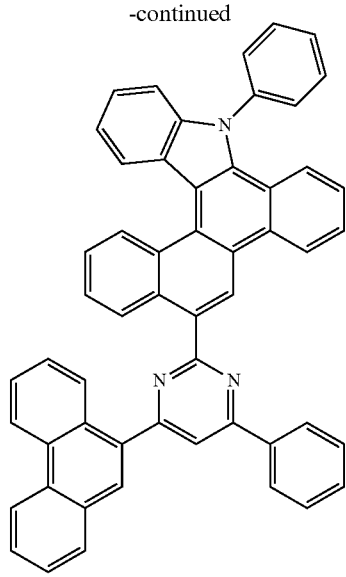
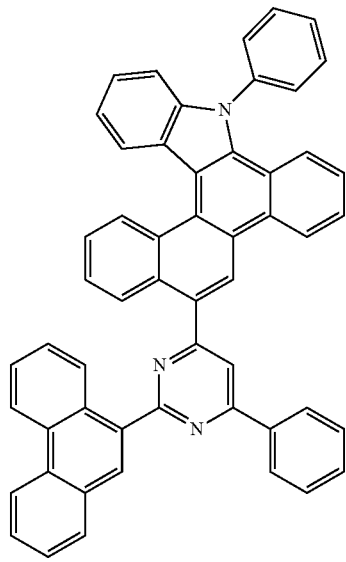
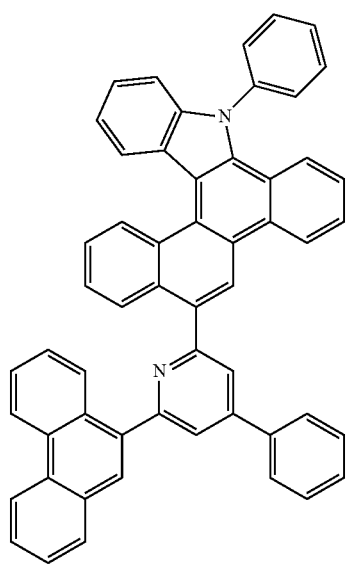

359
-continued
360
-continued
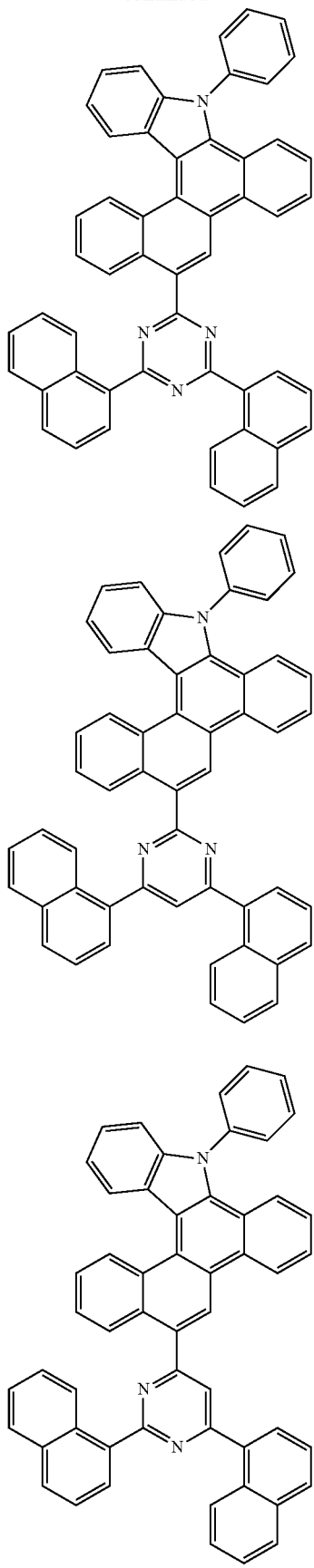
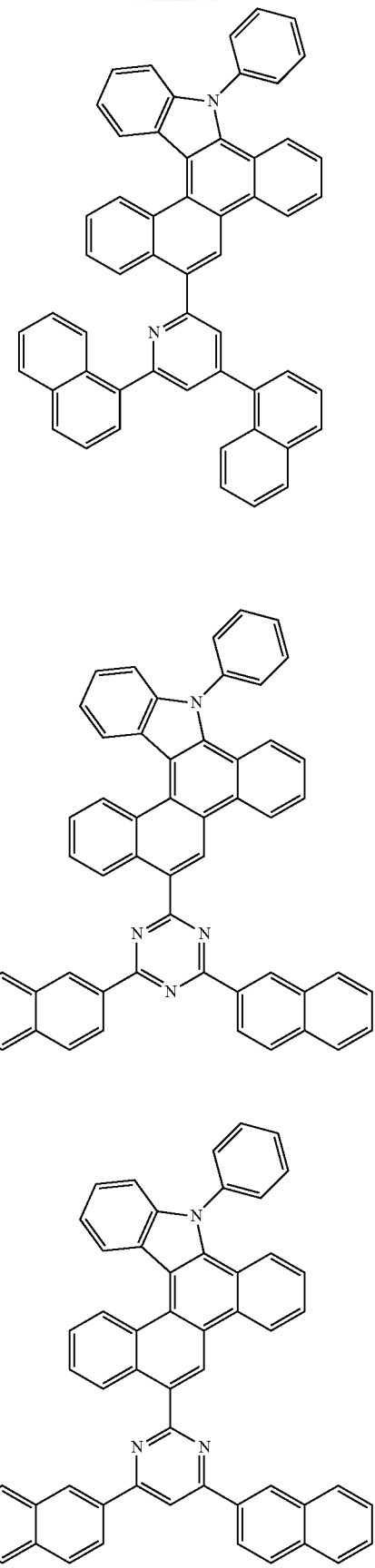

361
-continued
362
-continued
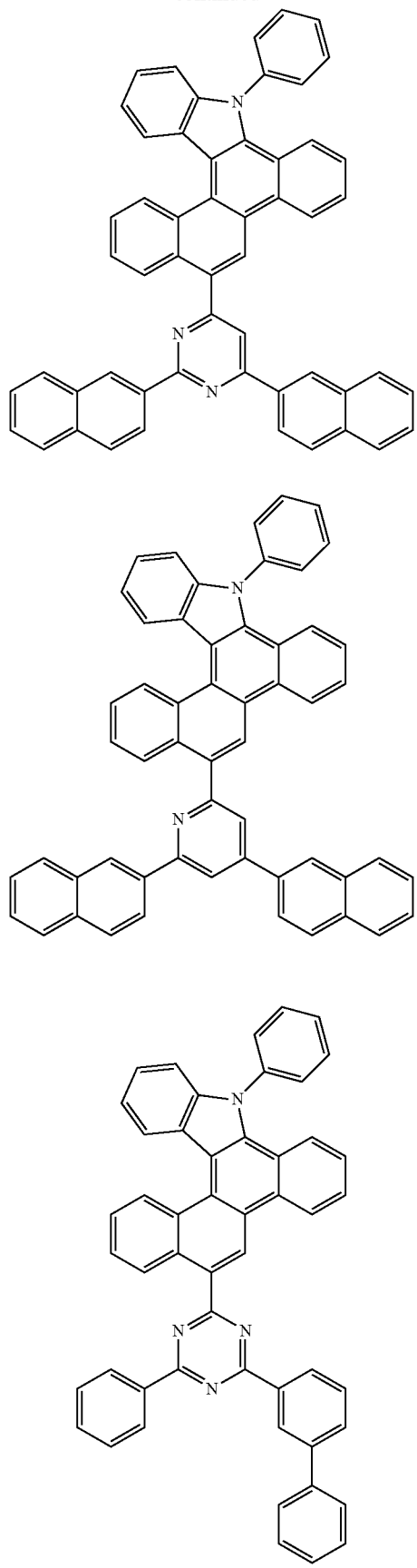

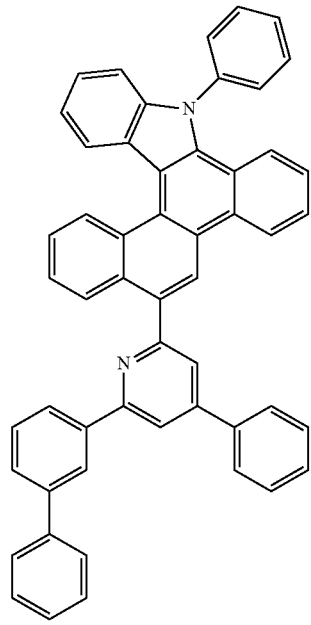
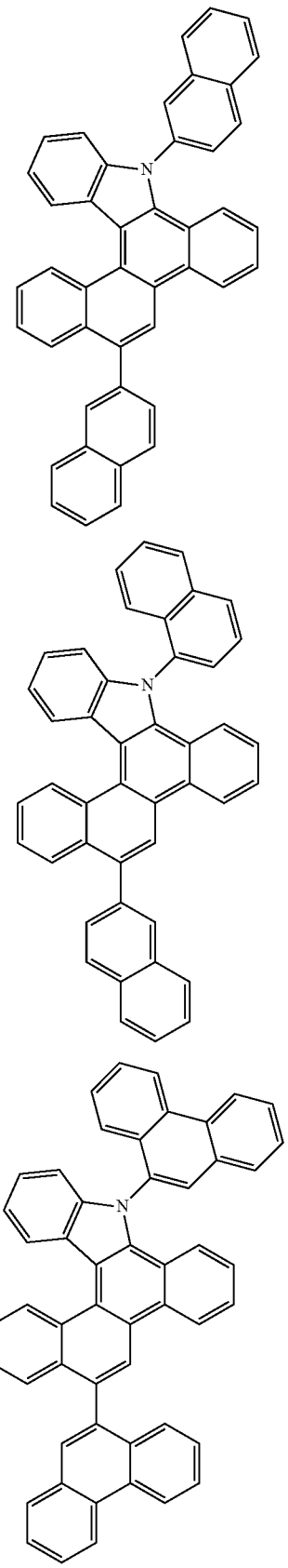

365
-continued
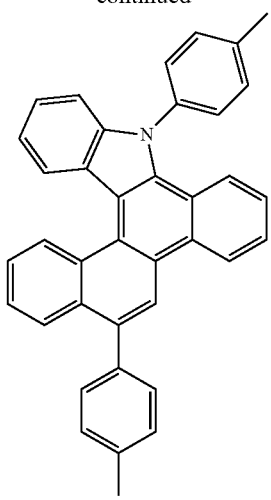
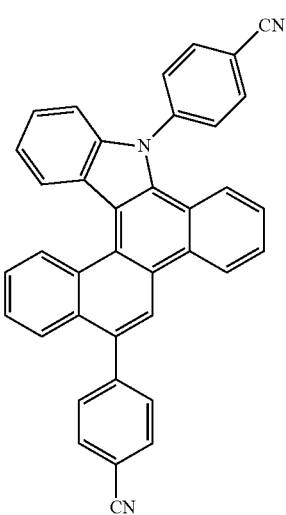
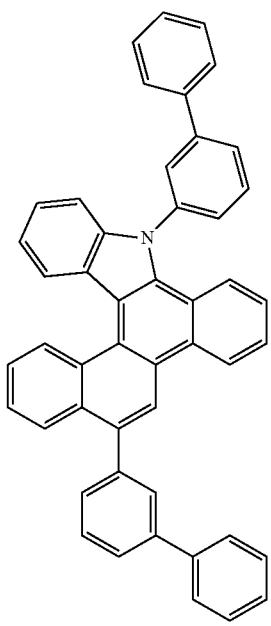
366
-continued
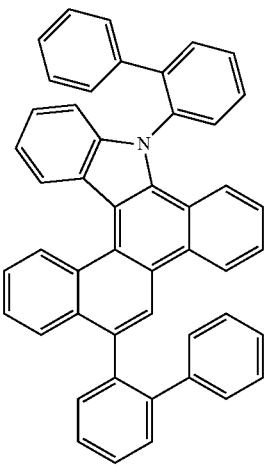
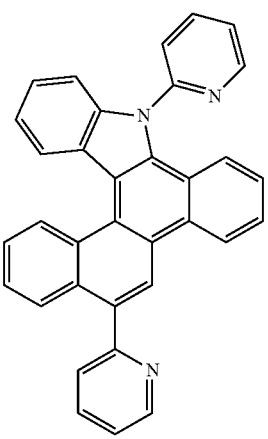
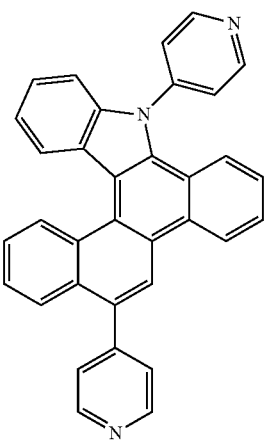

367
-continued
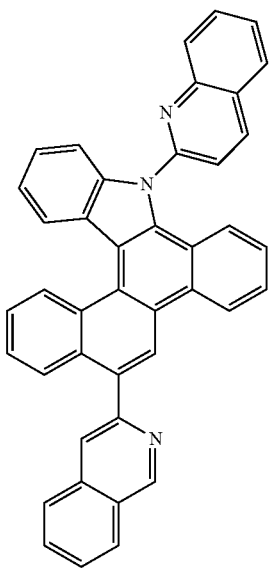
368
-continued
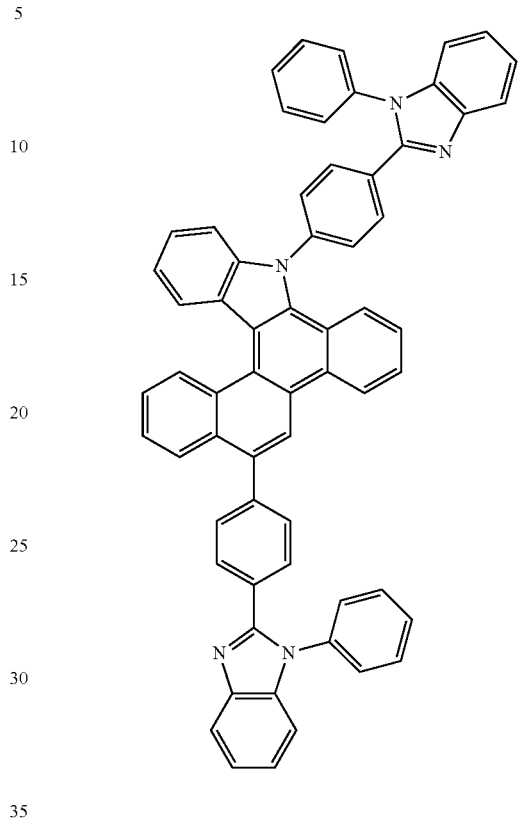
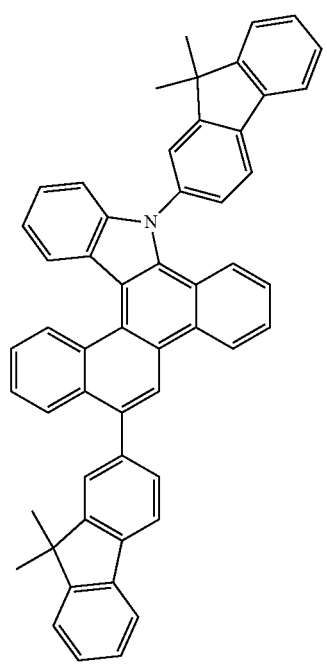
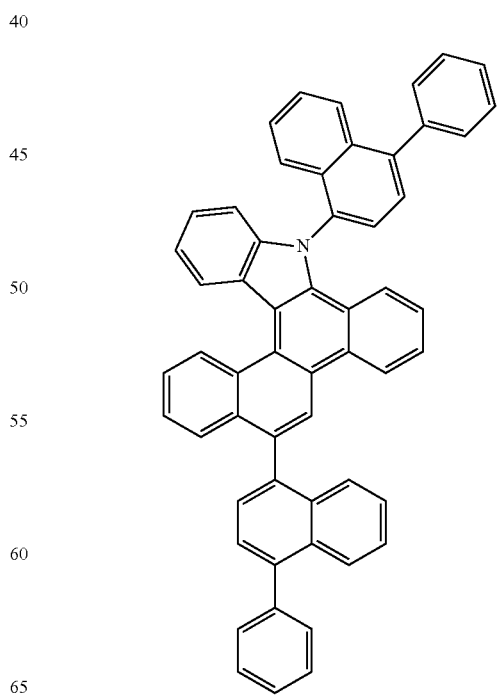

369
-continued
370
-continued
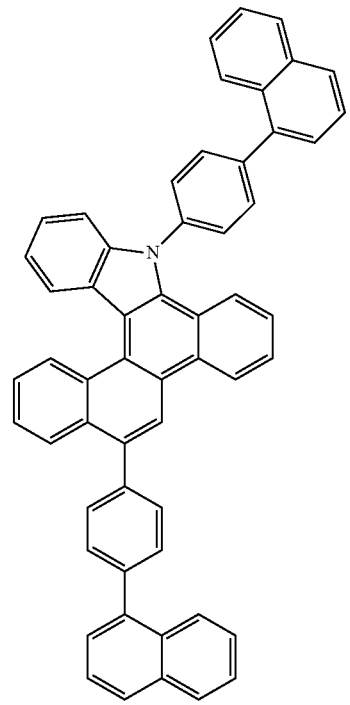
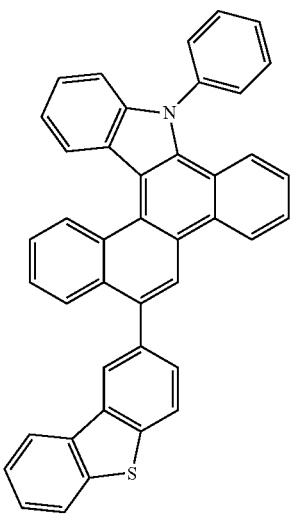
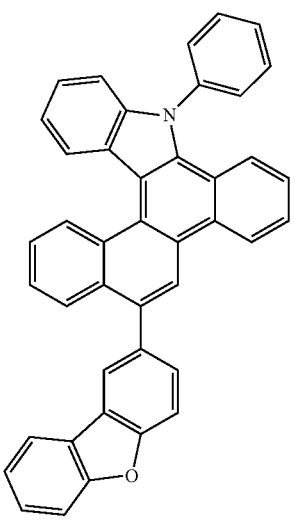
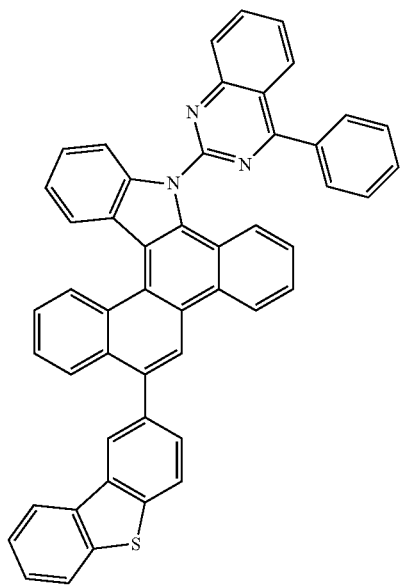

371
-continued
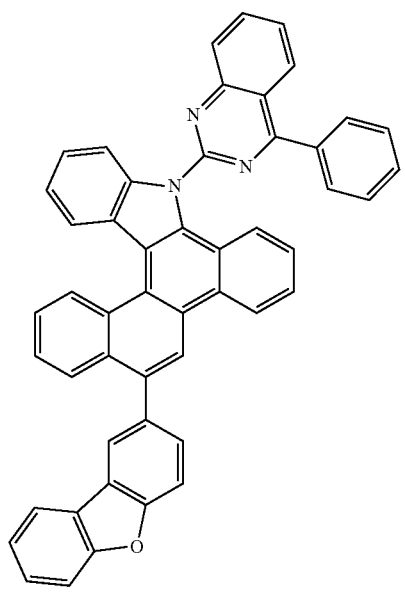
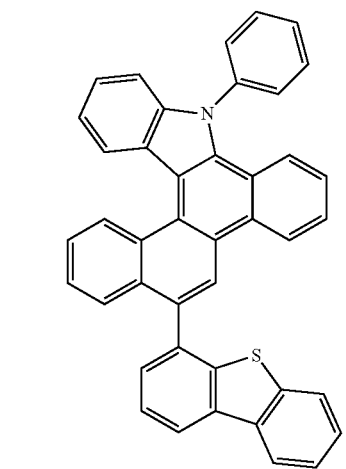
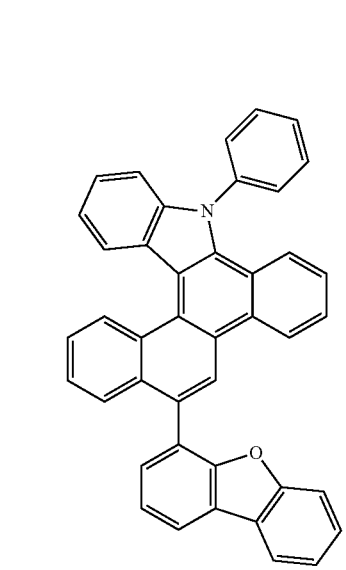
372
-continued
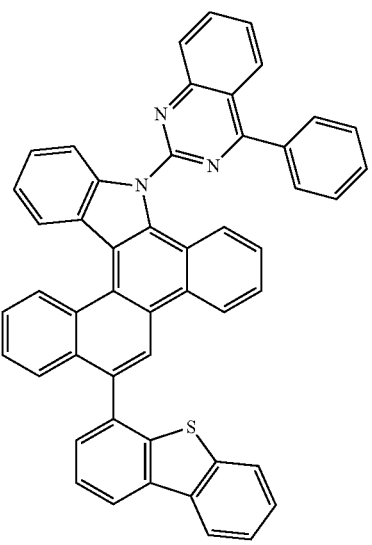
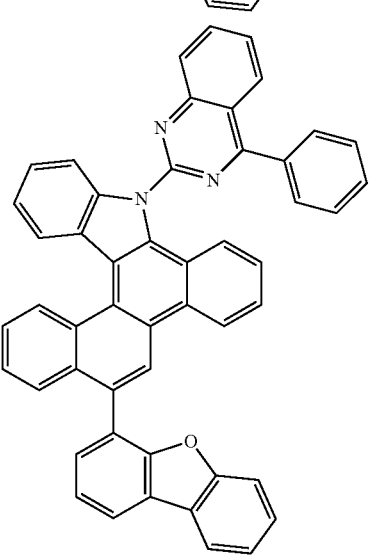
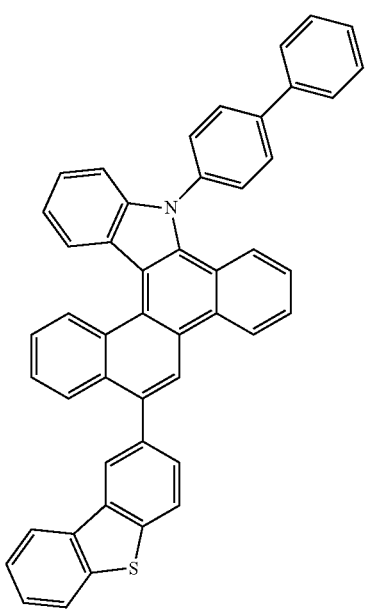

373
-continued
374
-continued
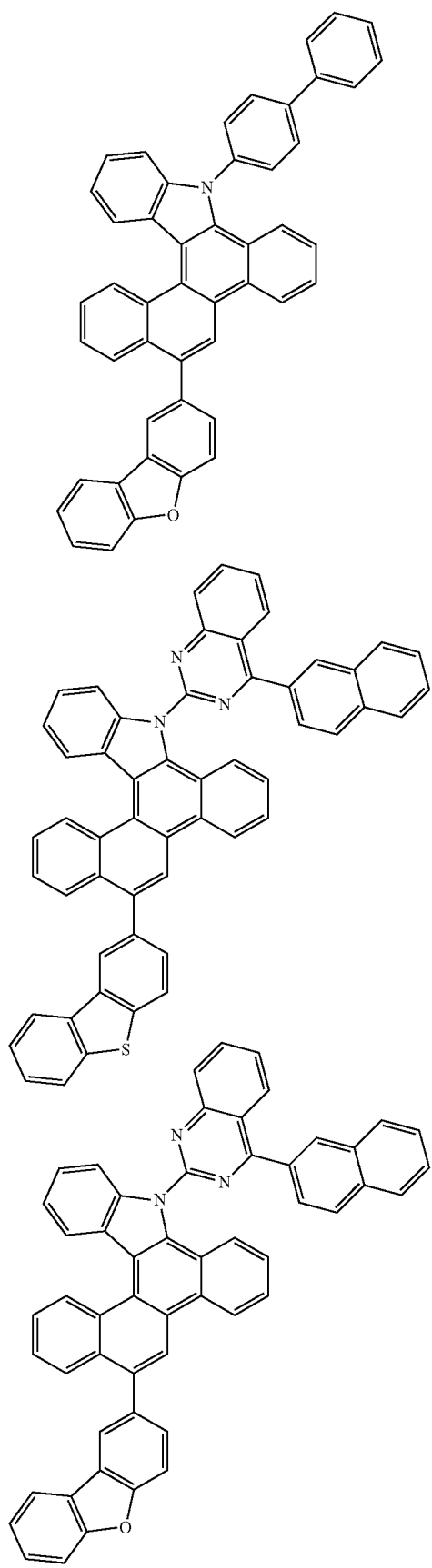
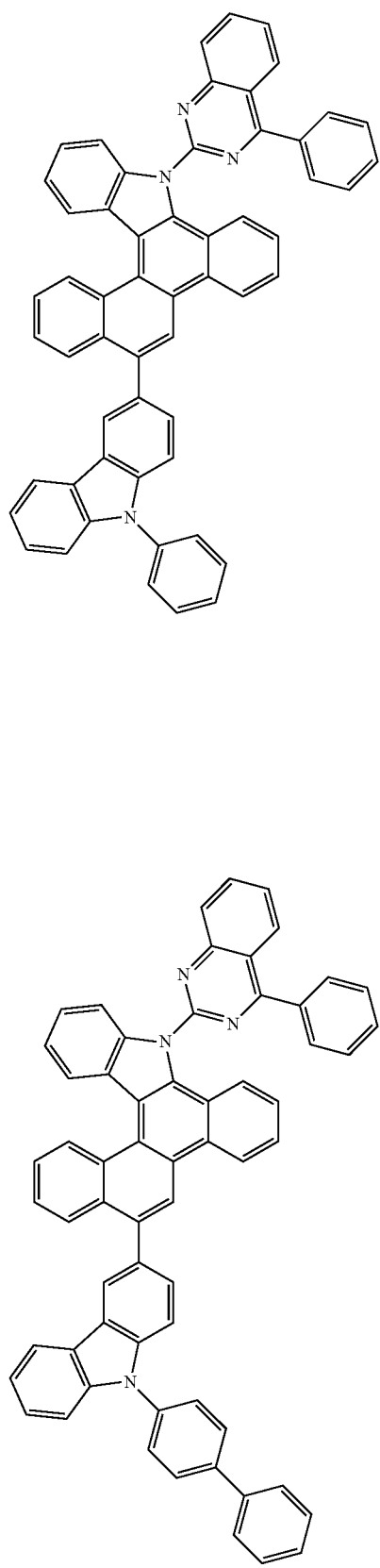

375
-continued
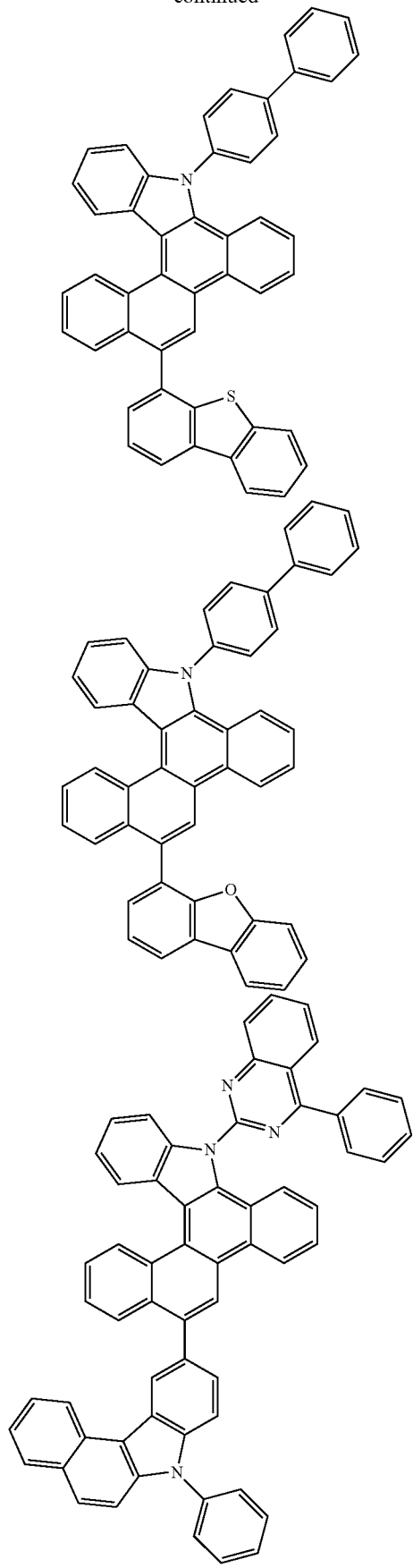
376
-continued
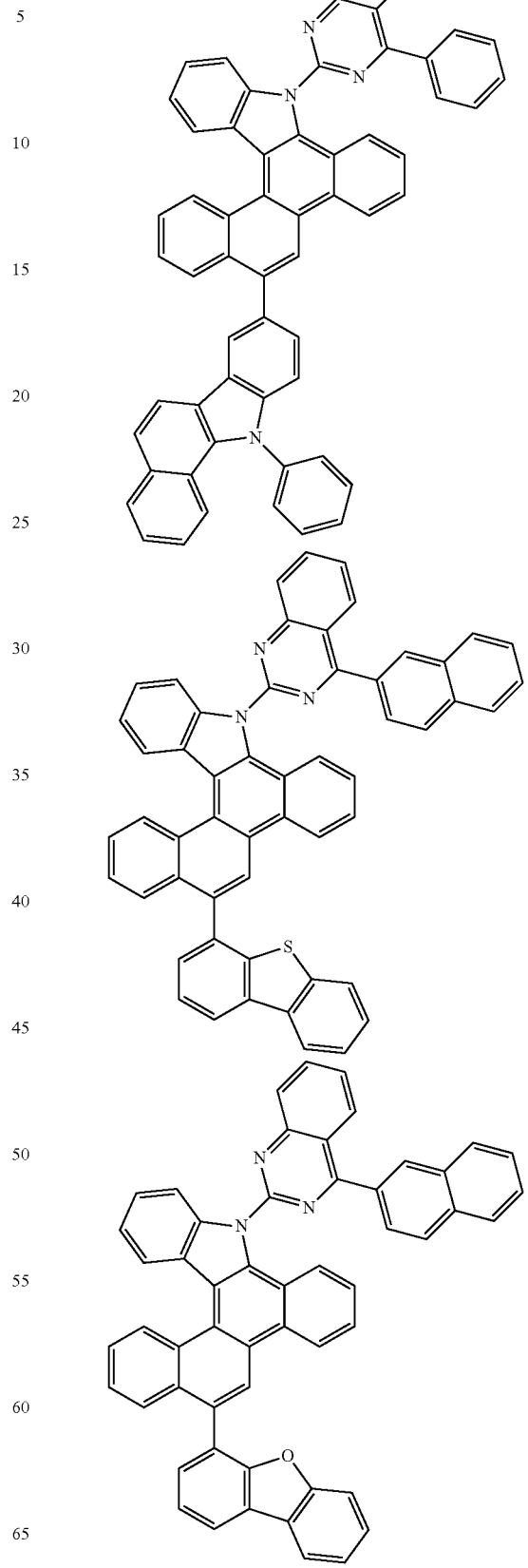

377
-continued
378
-continued
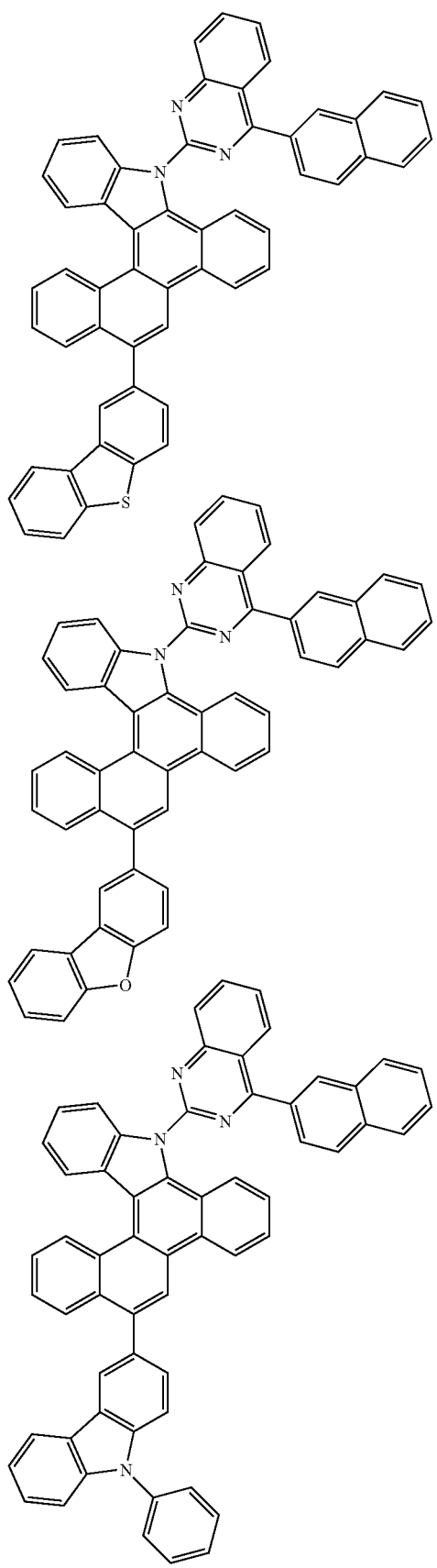
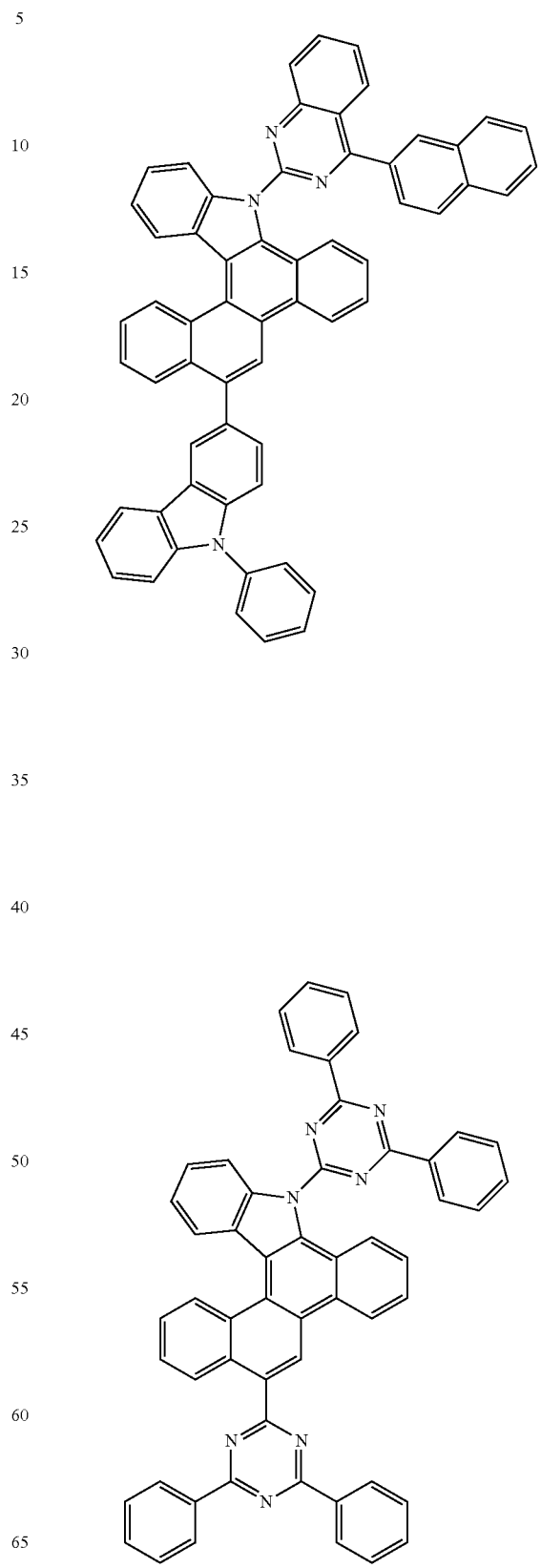

-continued
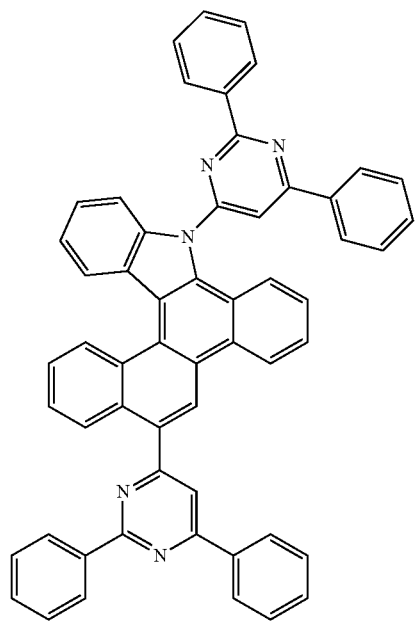
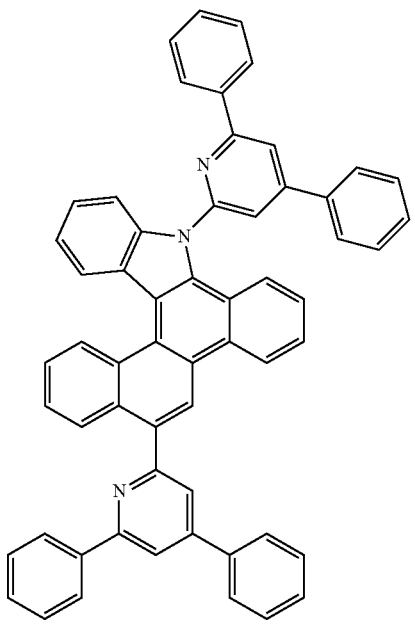
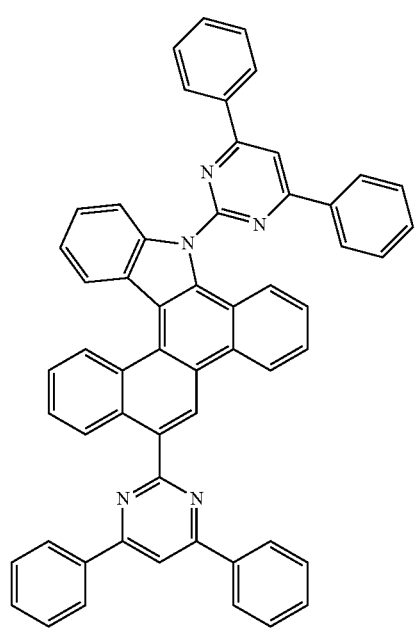
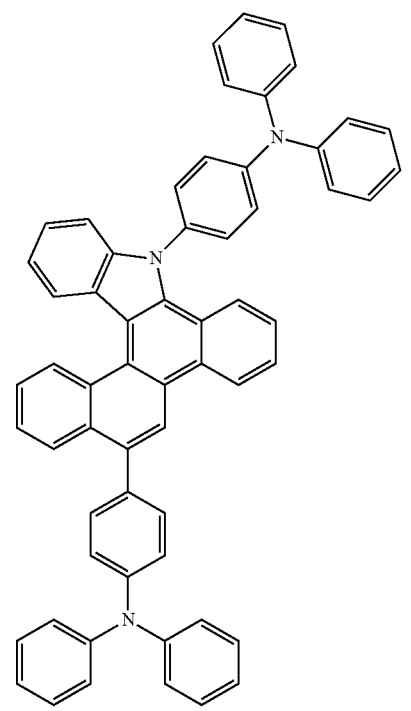

381
-continued
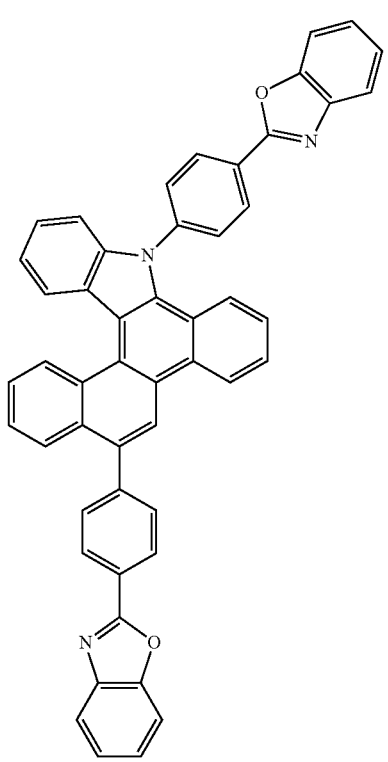
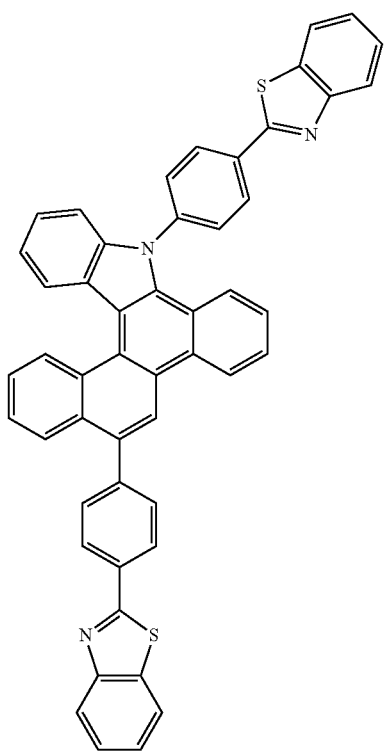
382
-continued
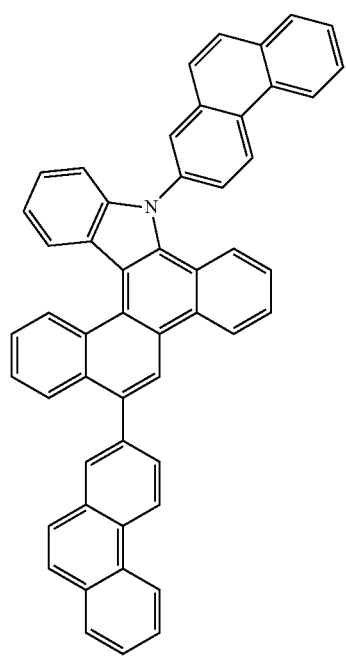
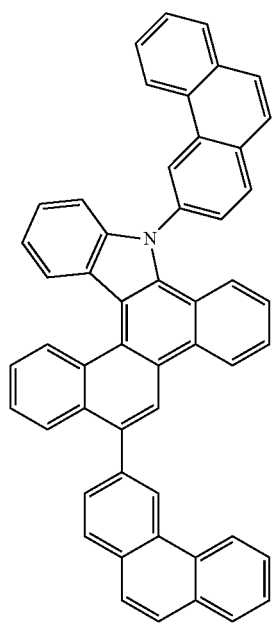

383
-continued
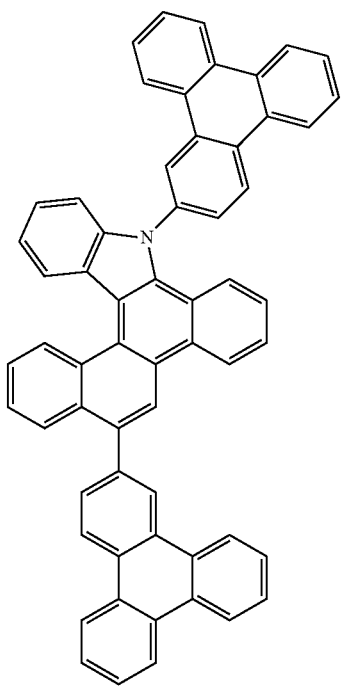
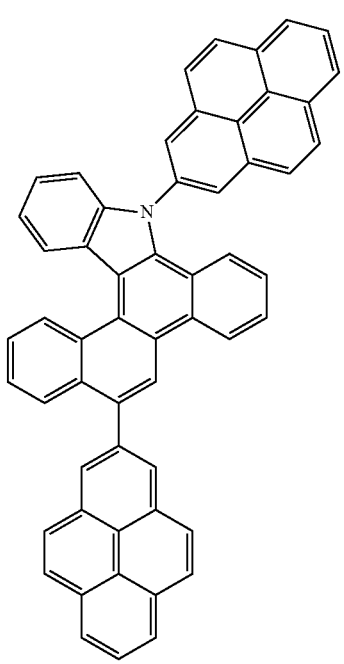
384
-continued
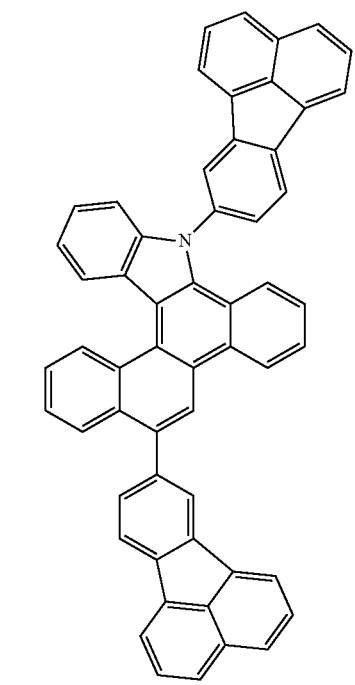
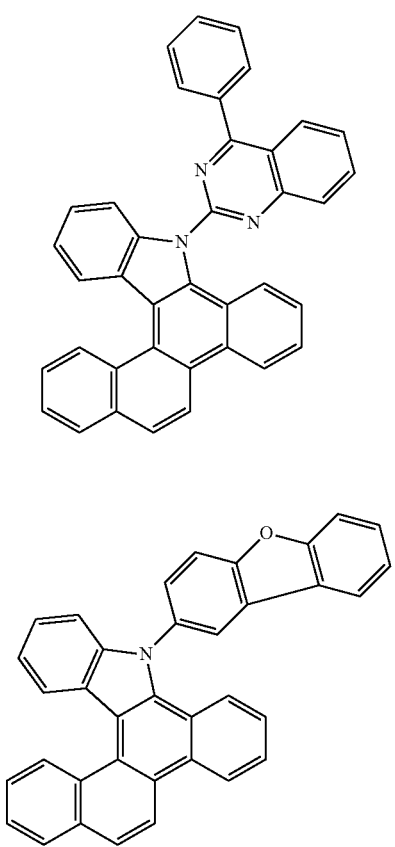

385
-continued
386
-continued
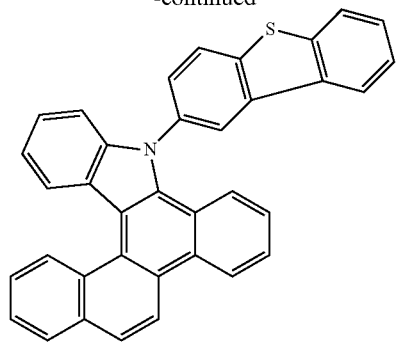
[Group 2]
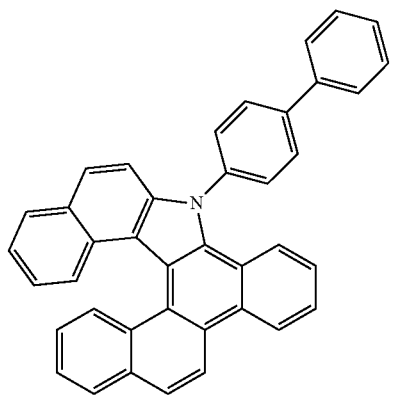
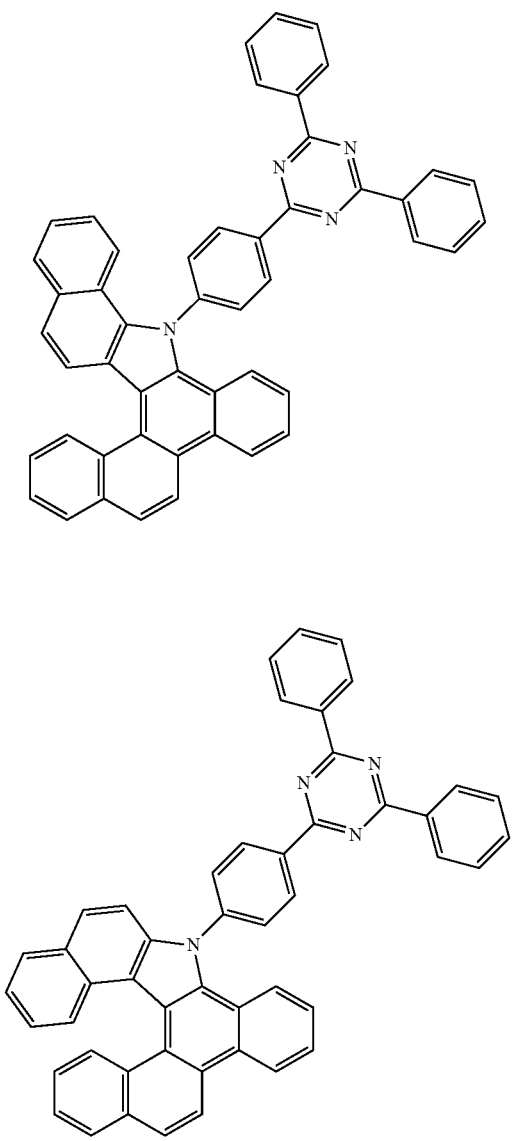

387
-continued
388
-continued
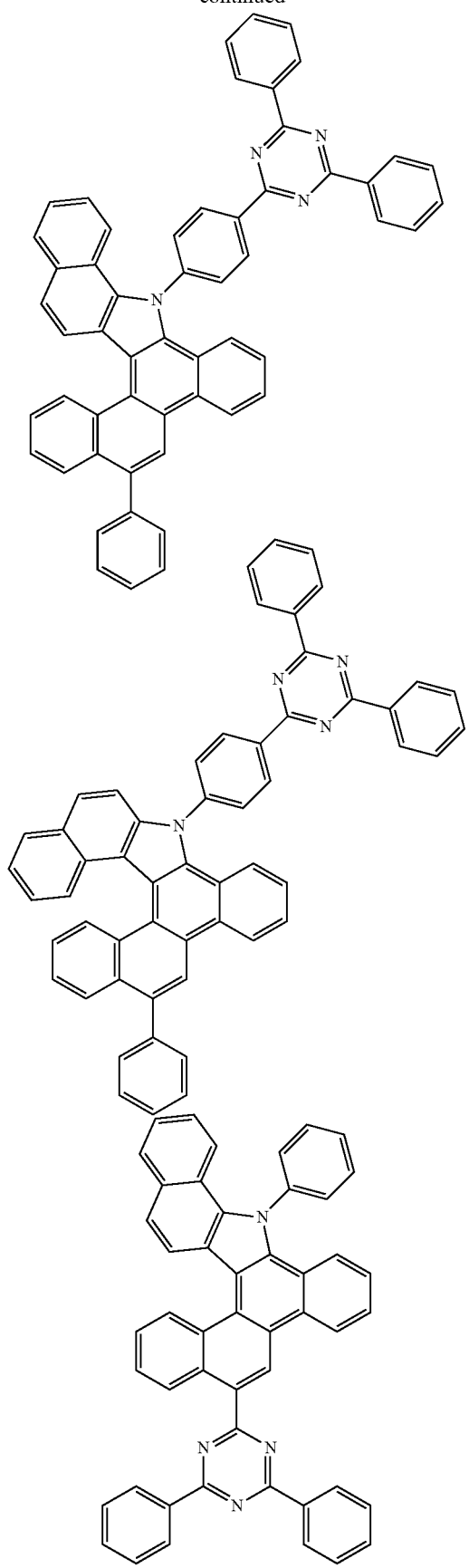
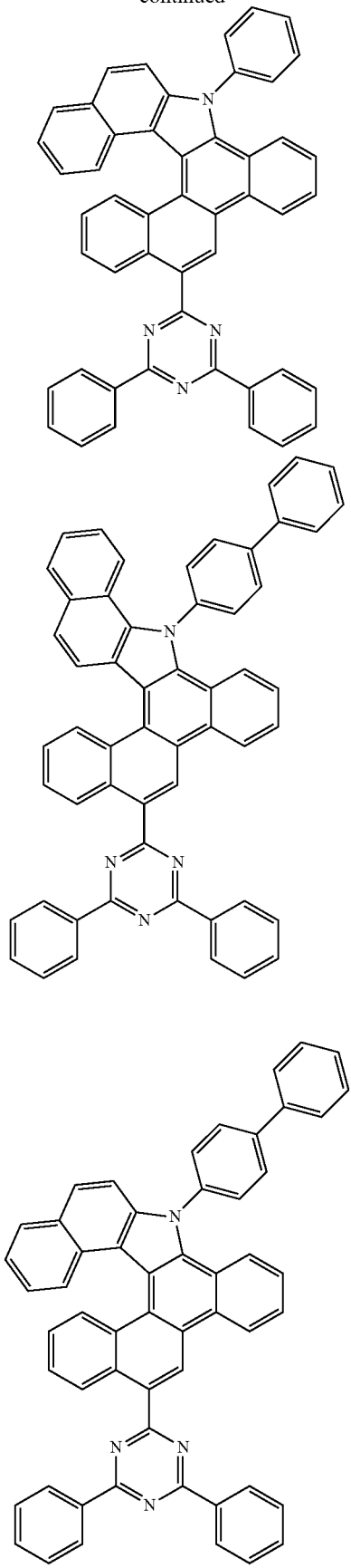

389
-continued
390
-continued
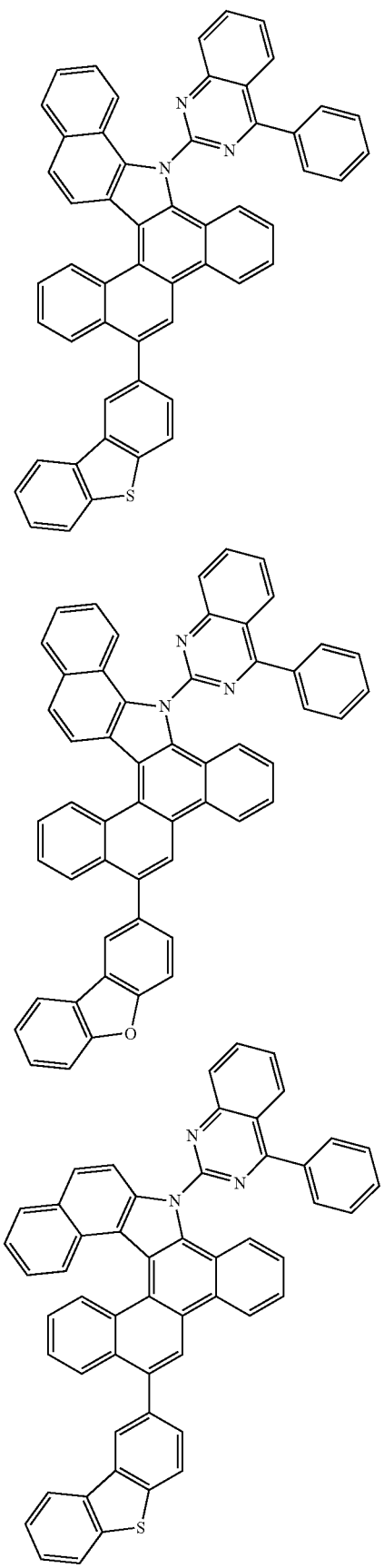
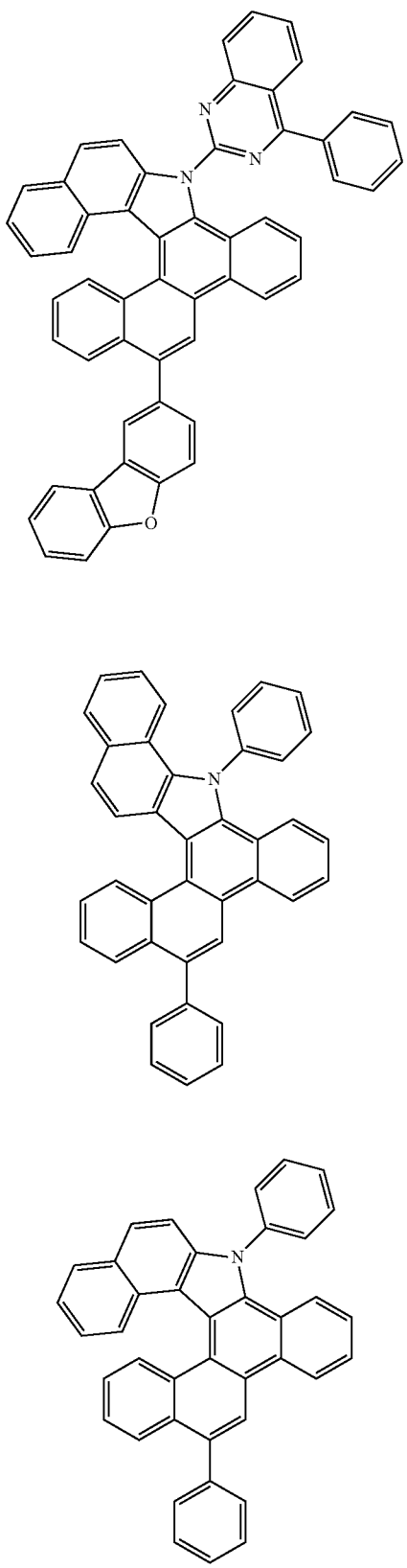

391
-continued
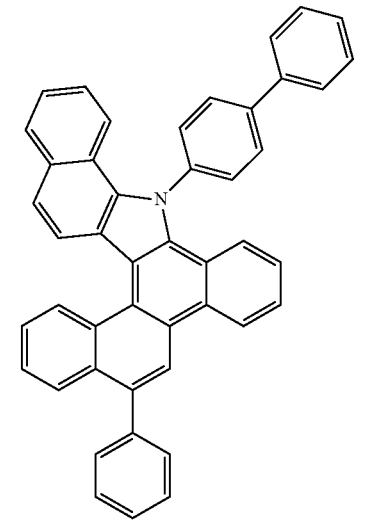
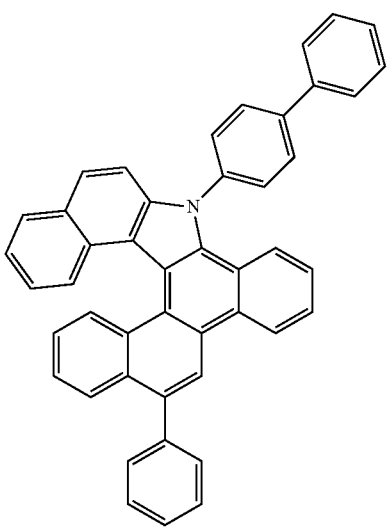
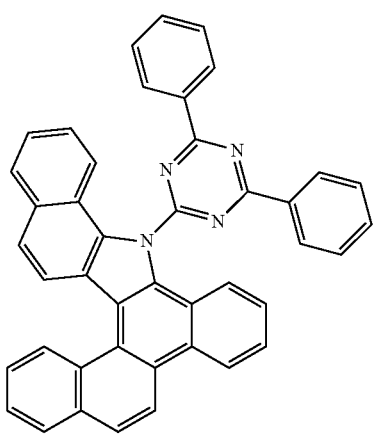
392
-continued
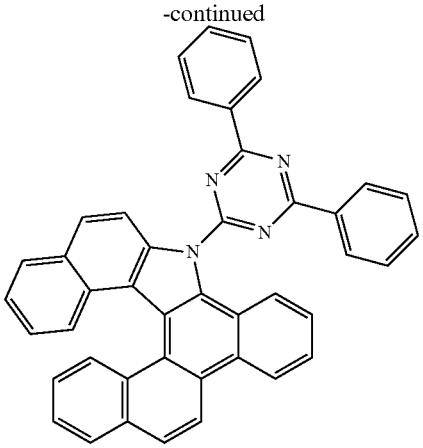
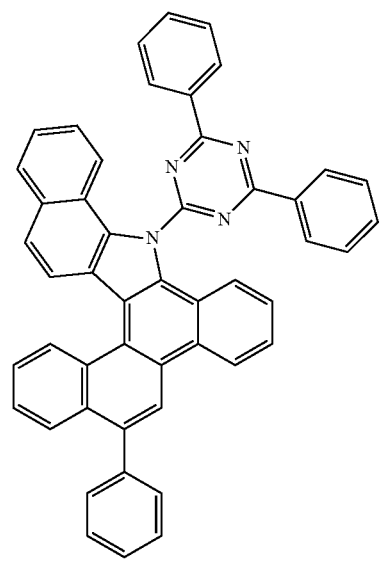
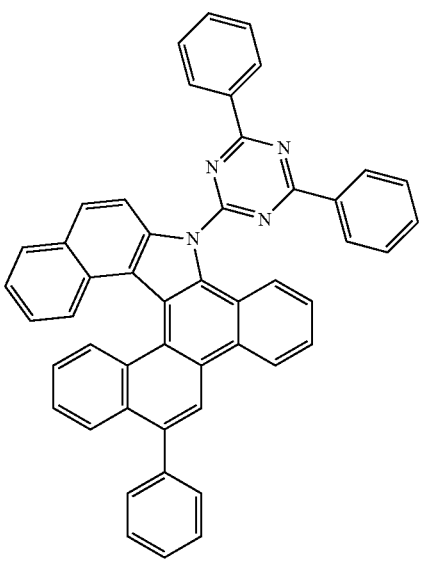

393
-continued
394
-continued
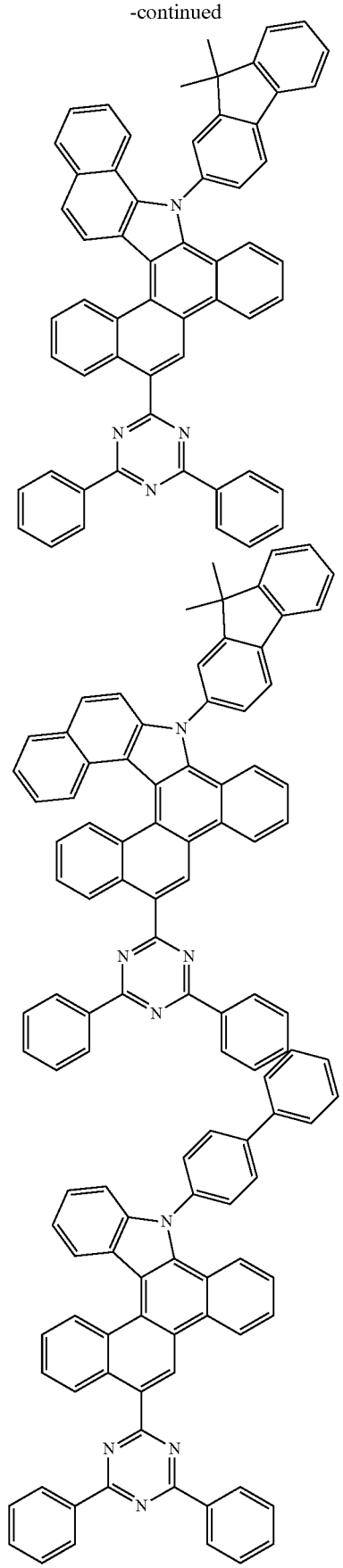
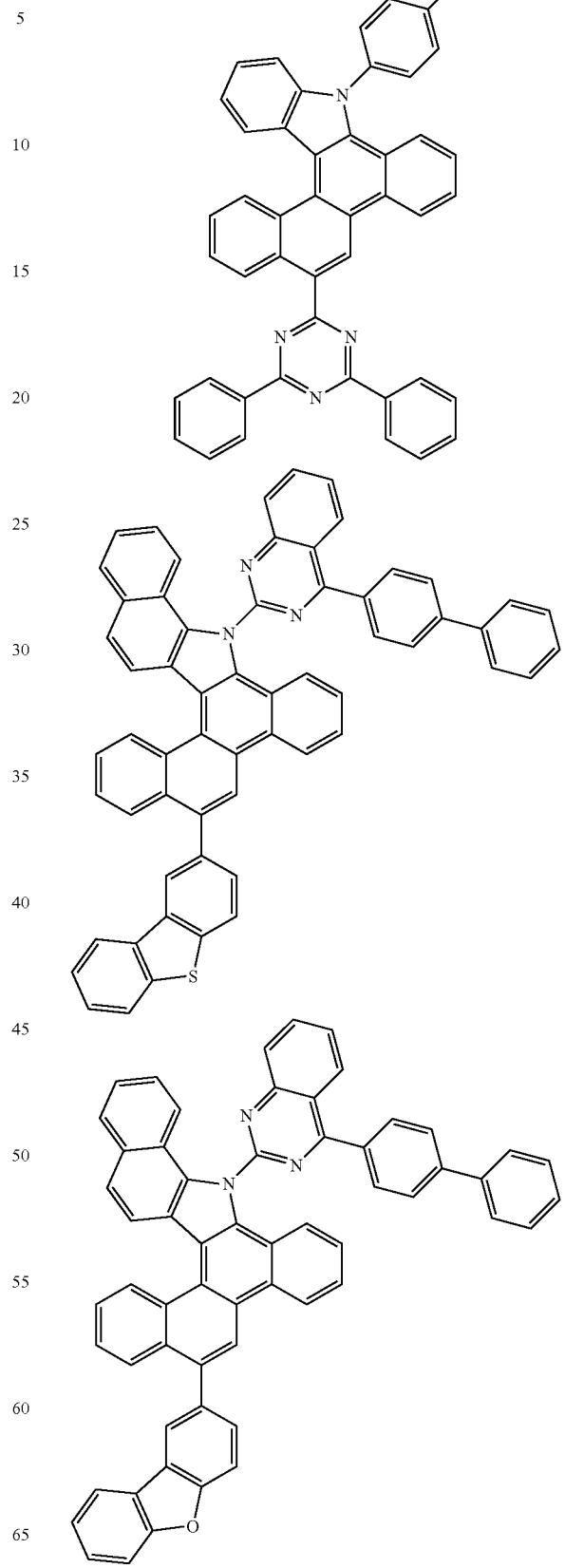

395
-continued
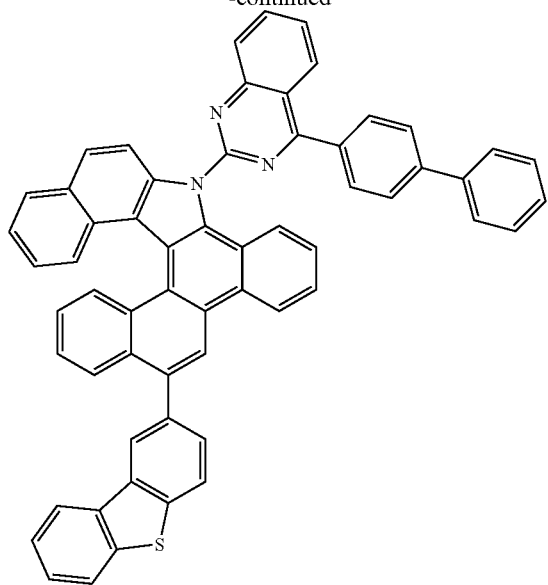
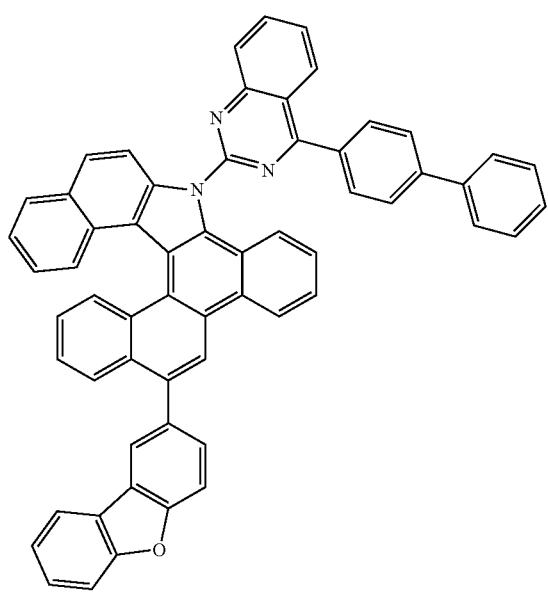
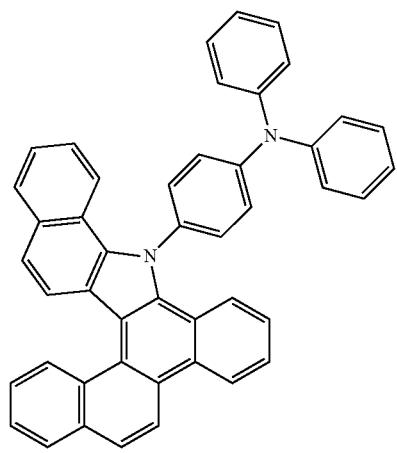
396
-continued
[Group 3]
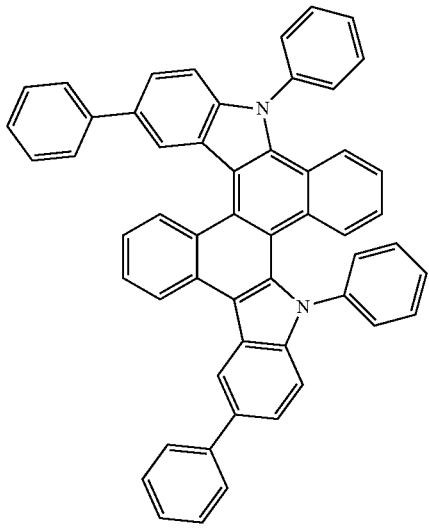
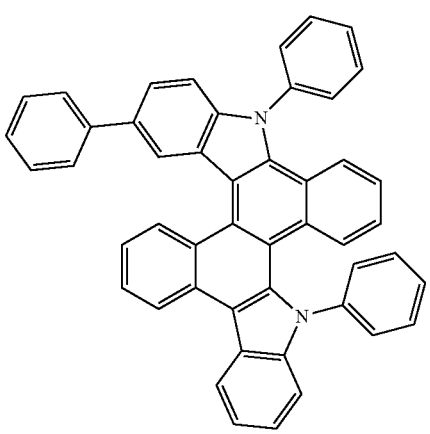

397
-continued
398
-continued
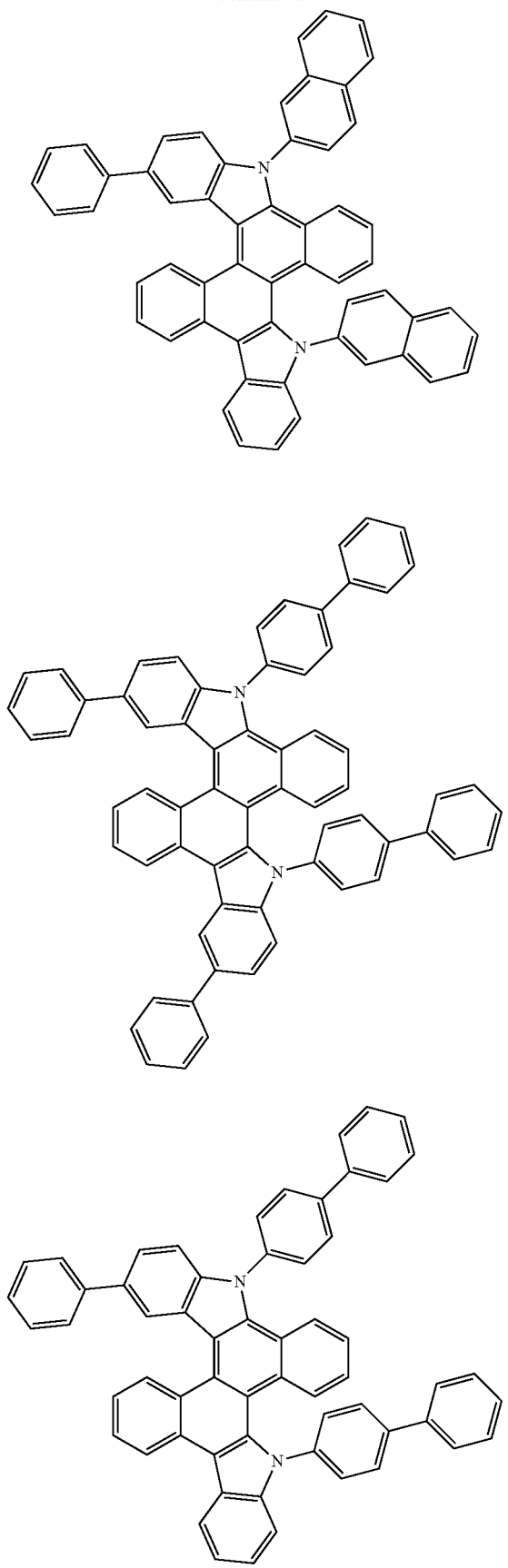
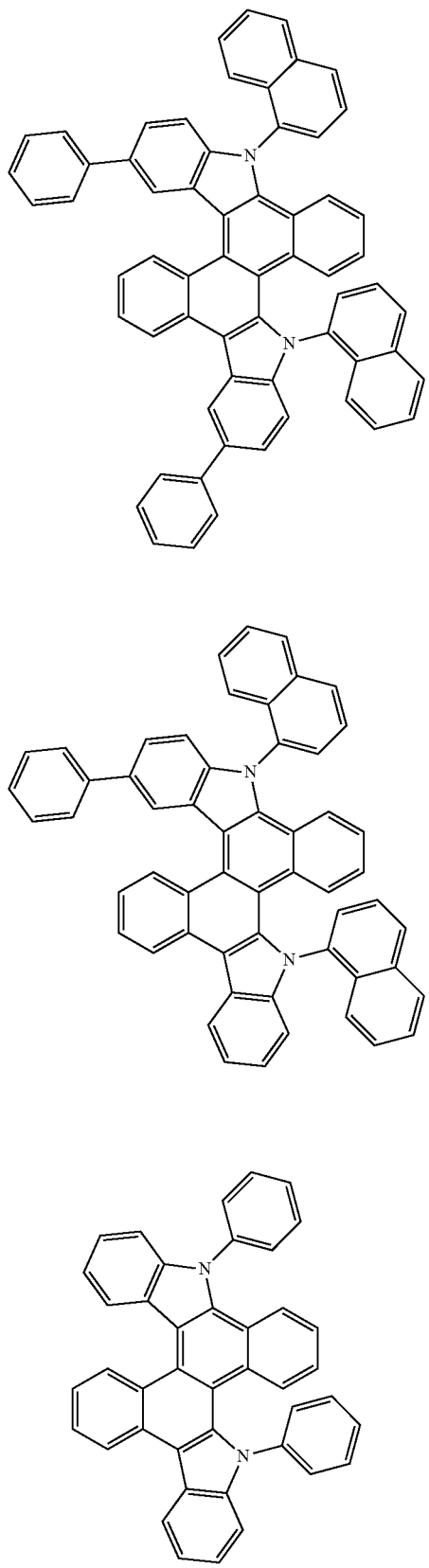

399
-continued
400
-continued
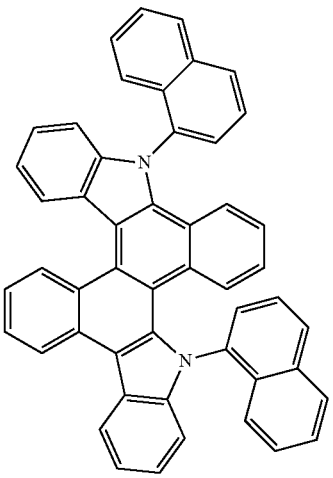
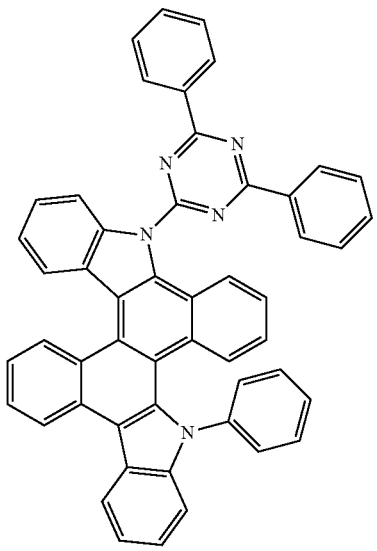
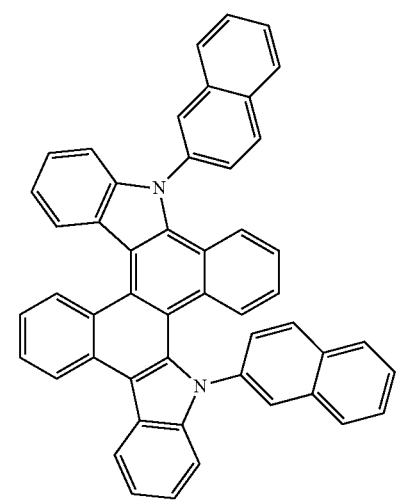
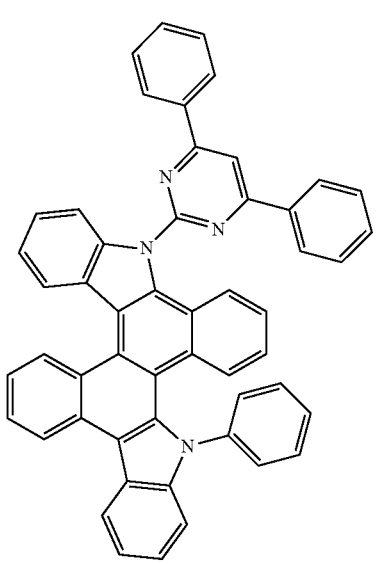
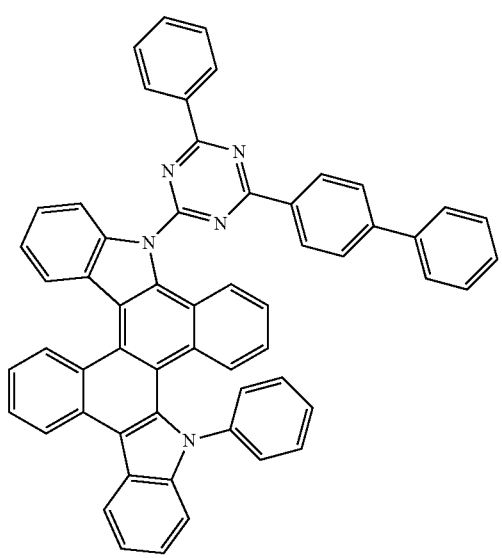
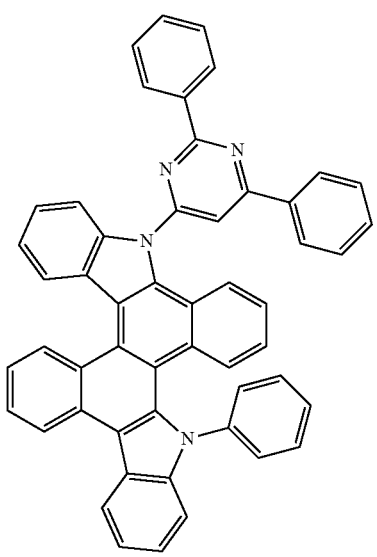

401
-continued
402
-continued
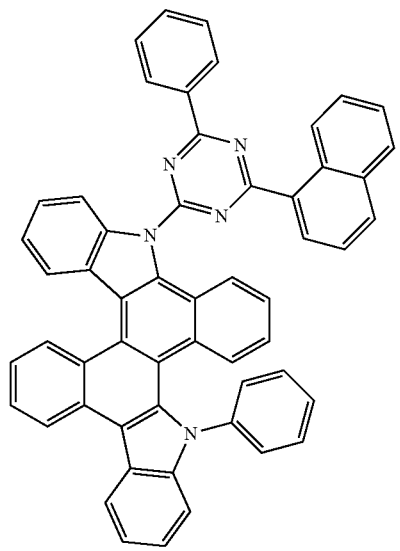
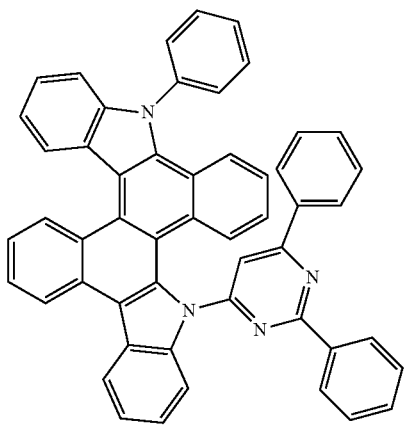
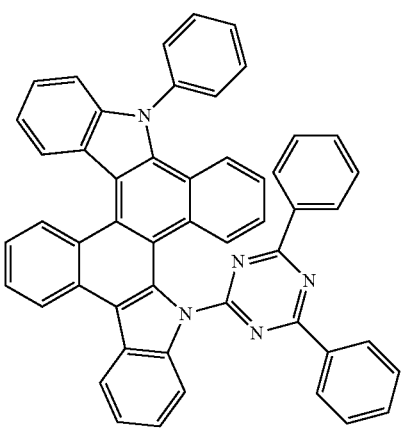
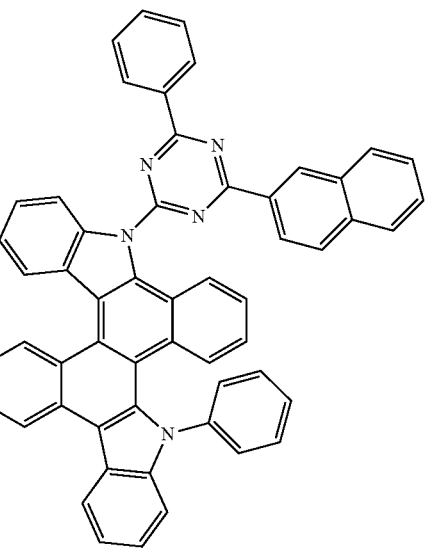
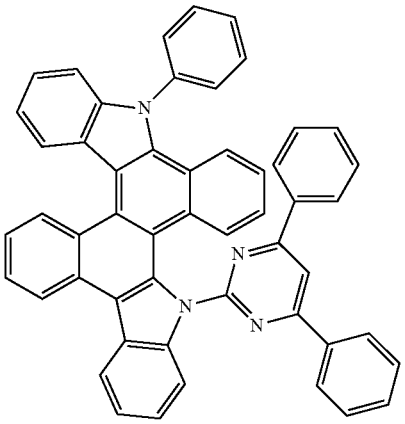
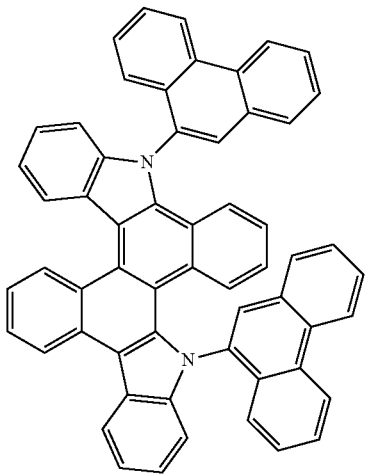

403
-continued
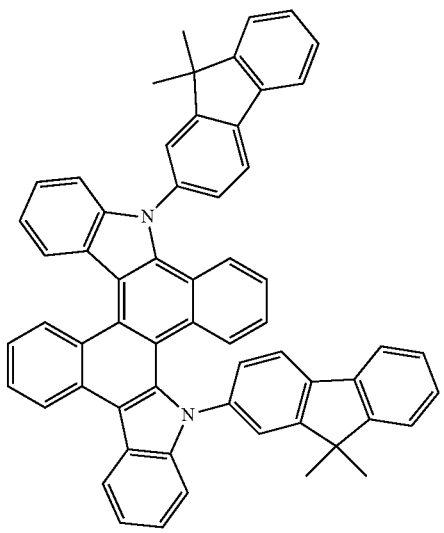
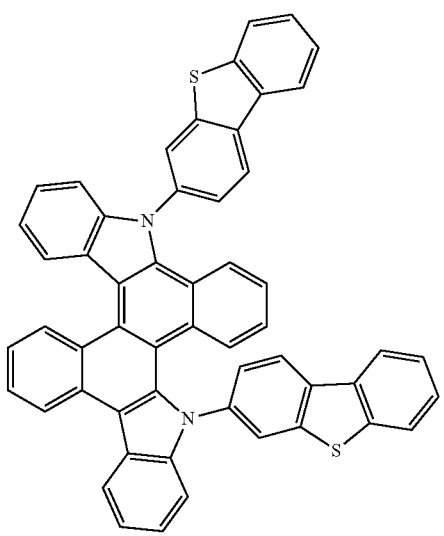
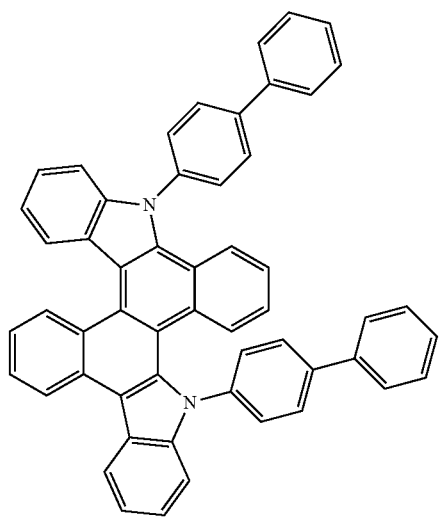
404
-continued
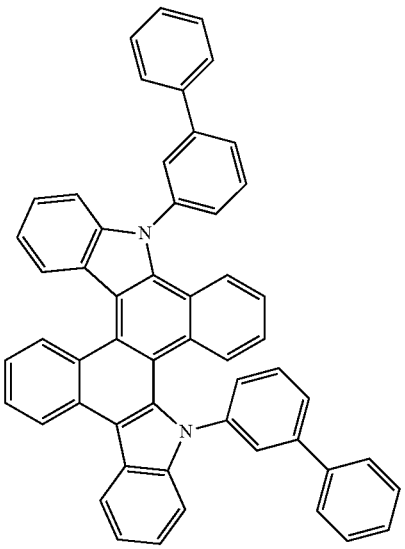
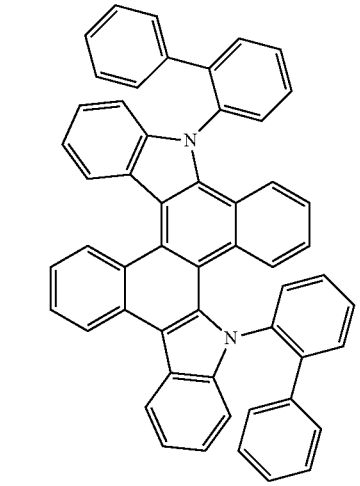
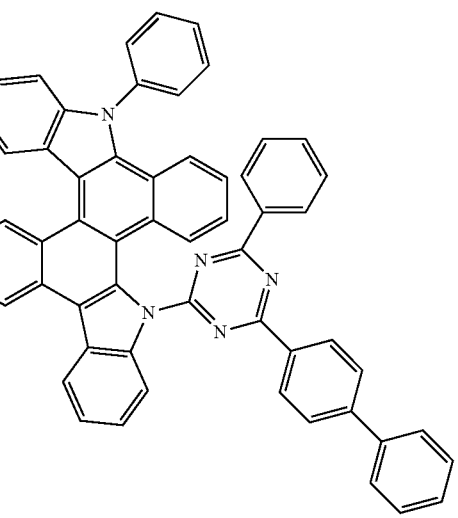

405
-continued
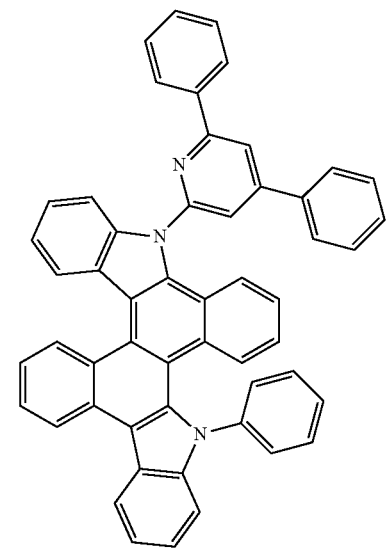
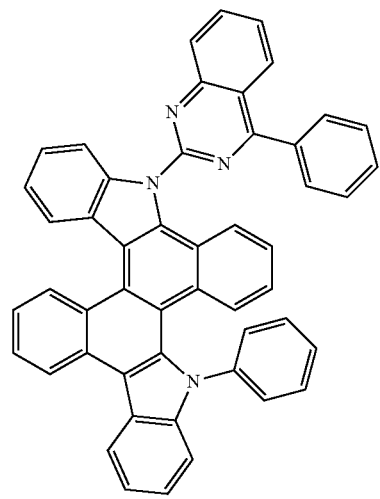
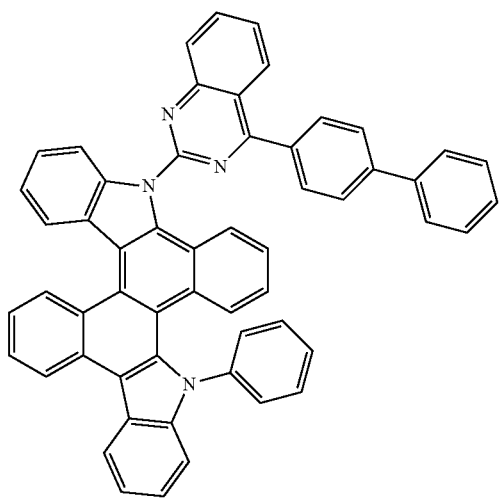
406
-continued
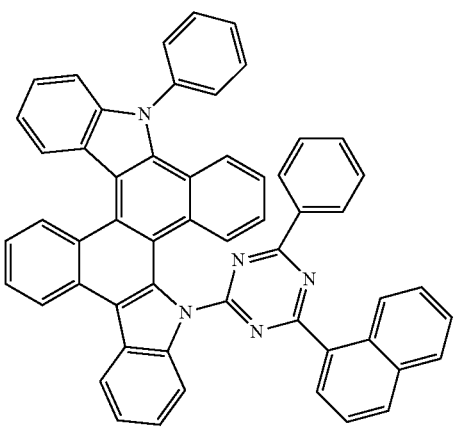
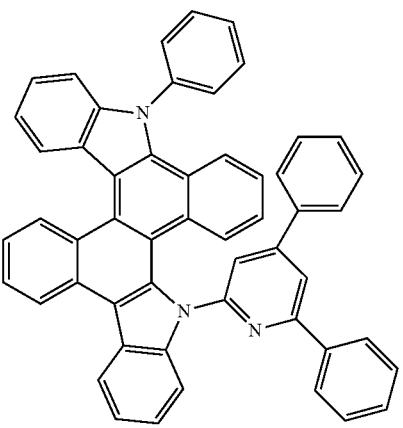
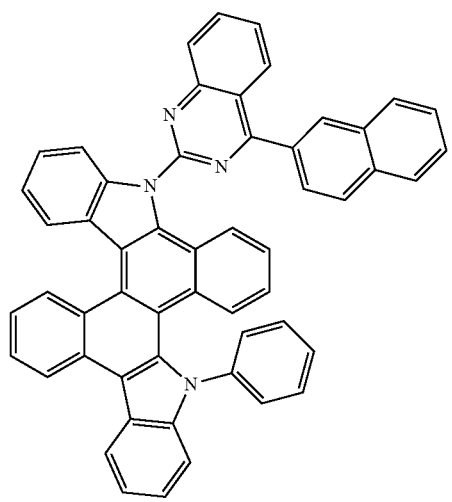

407
-continued
408
-continued
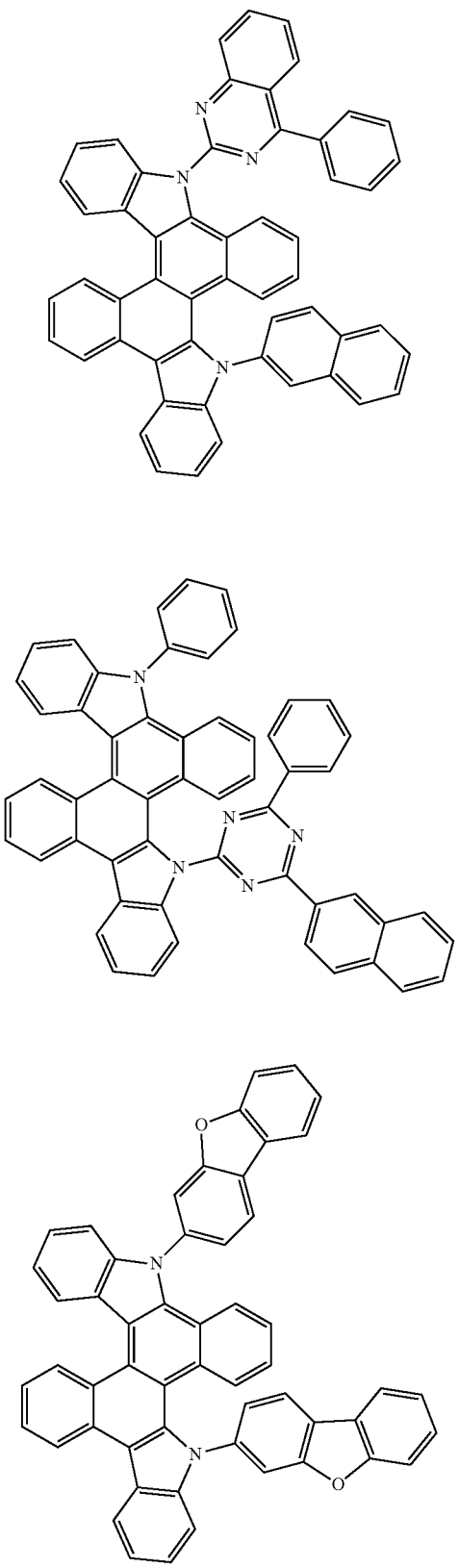
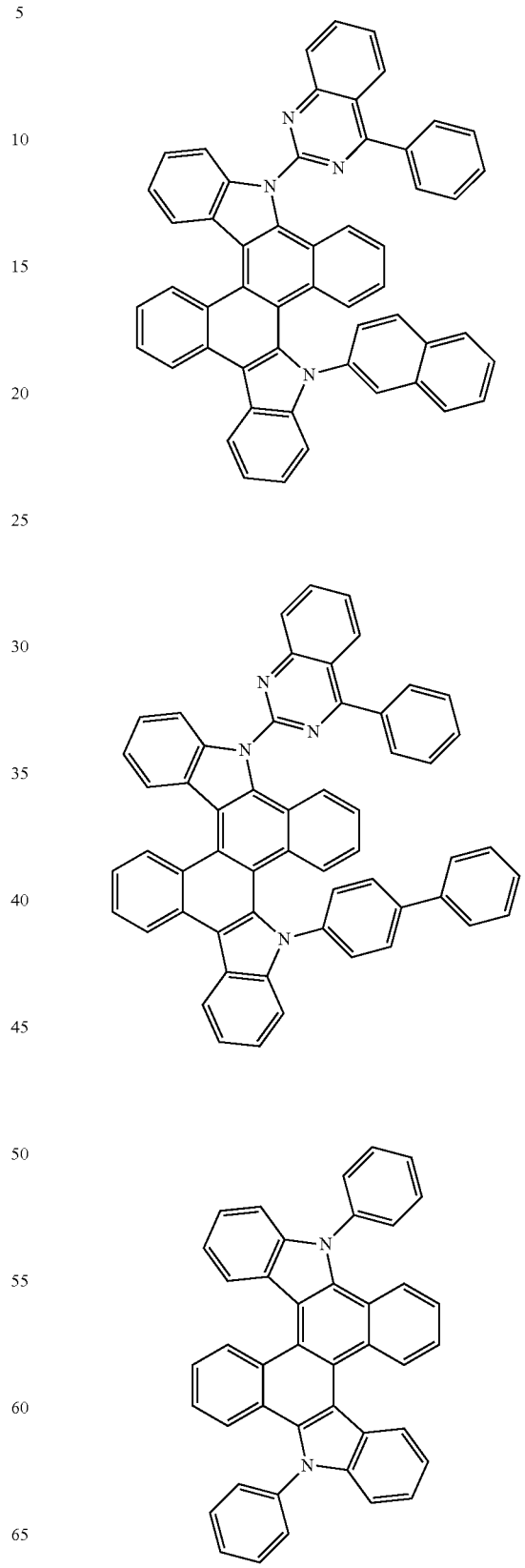

409
-continued
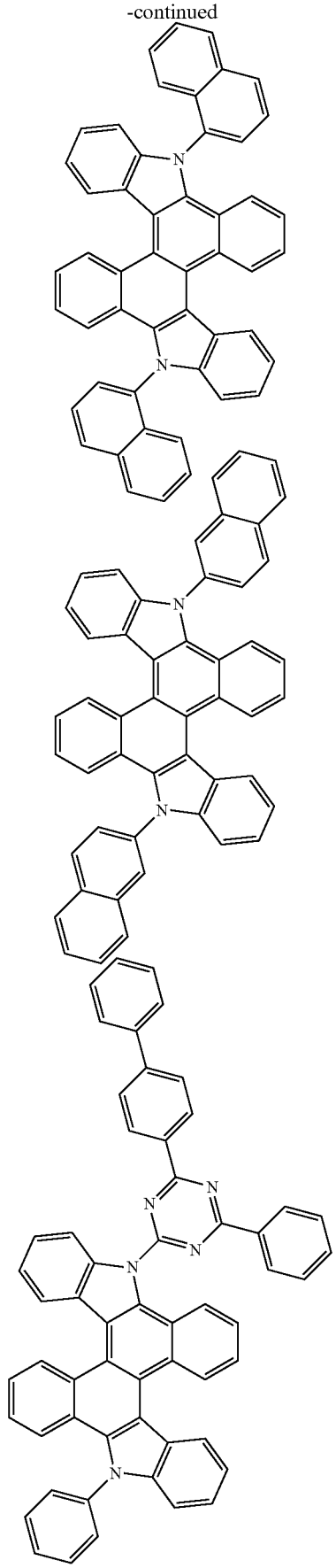
410
-continued
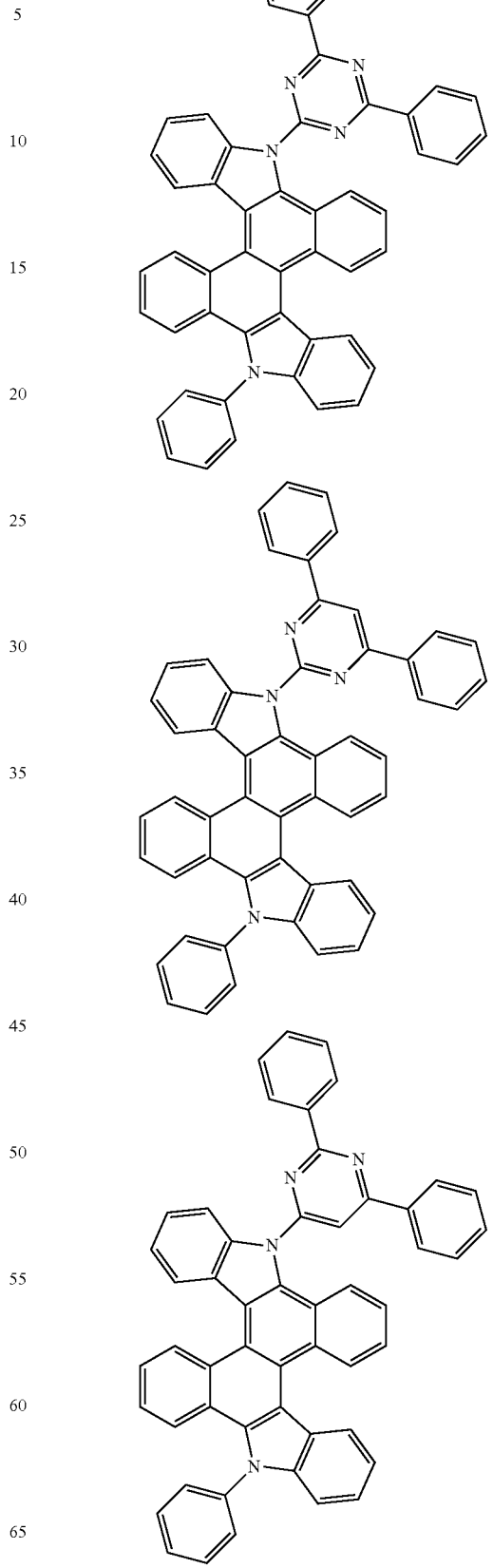

411
-continued
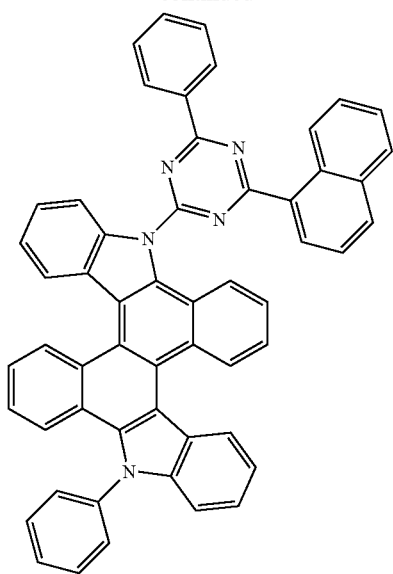
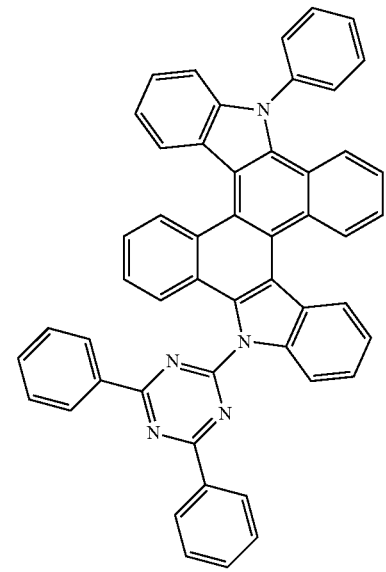
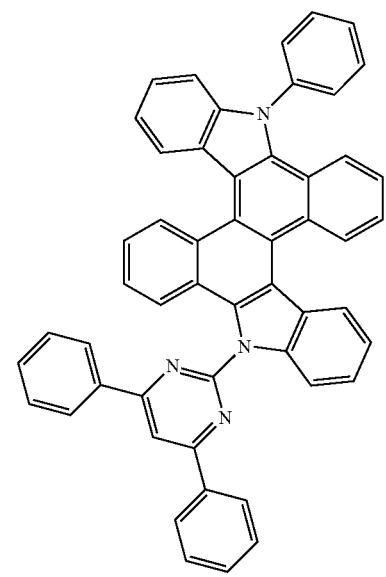
412
-continued
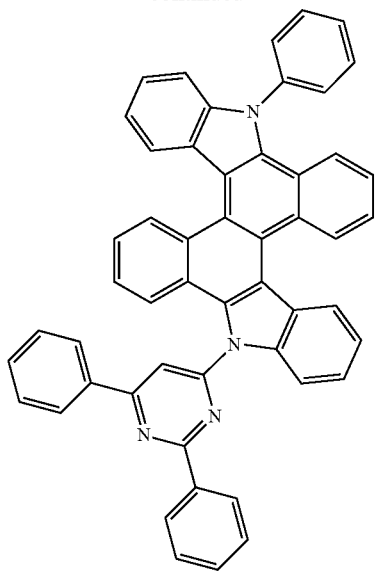
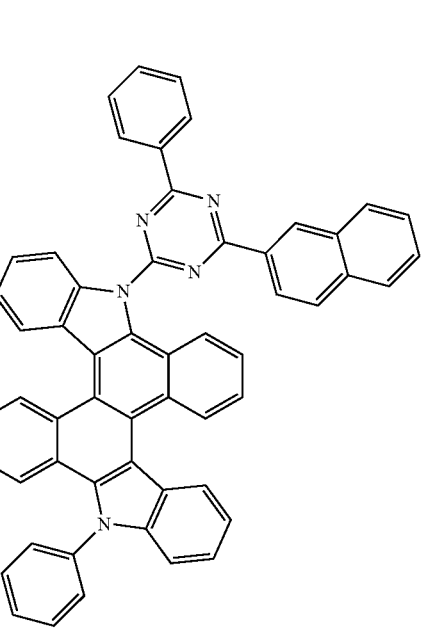
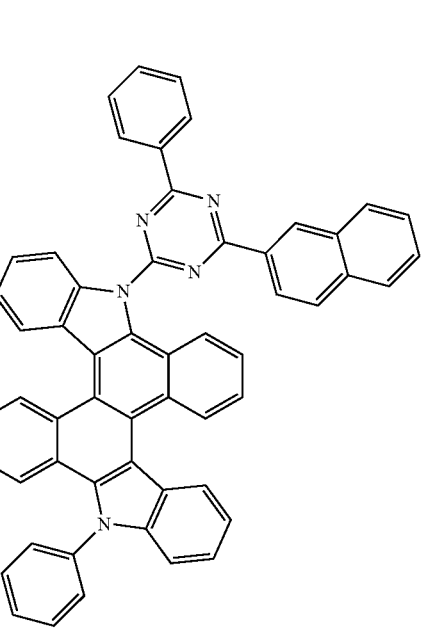

413
-continued
414
-continued
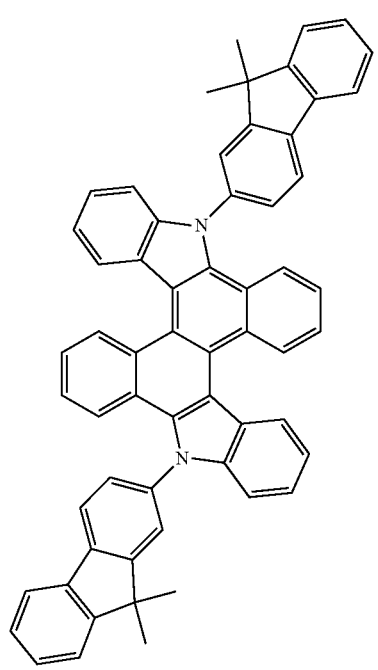
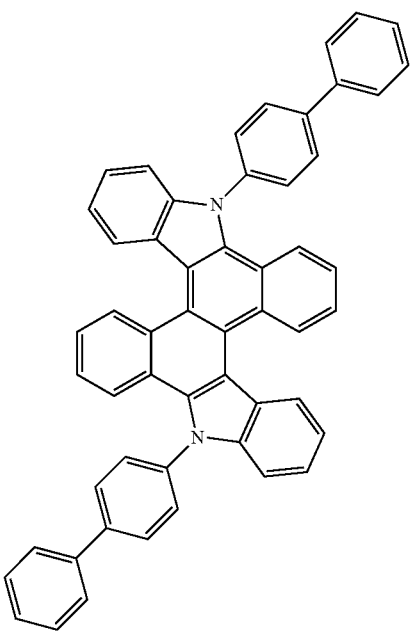
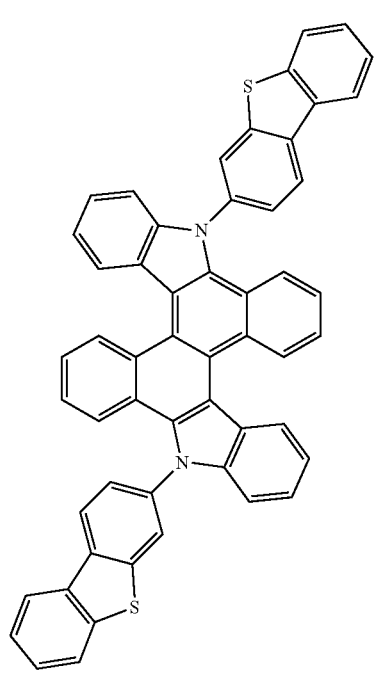

415
-continued
416
-continued
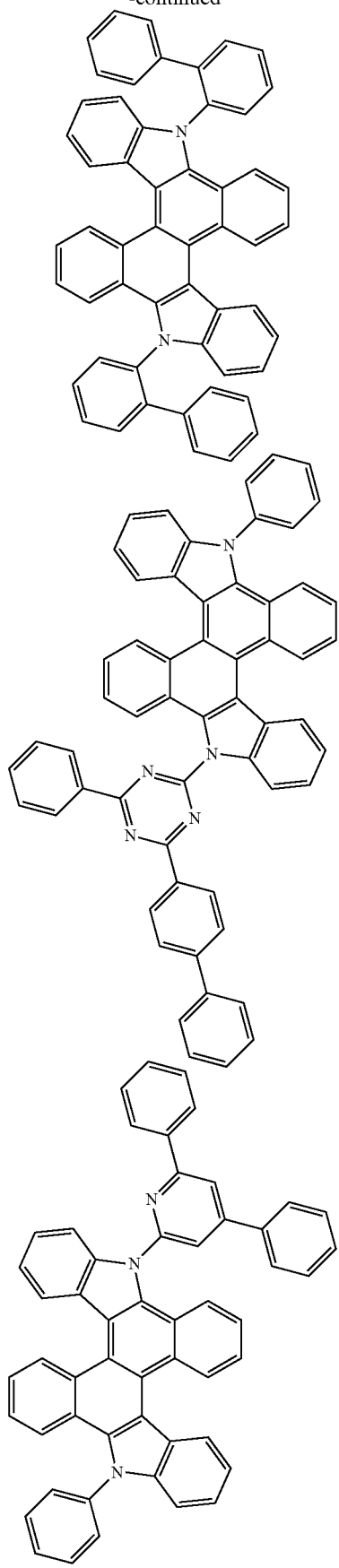
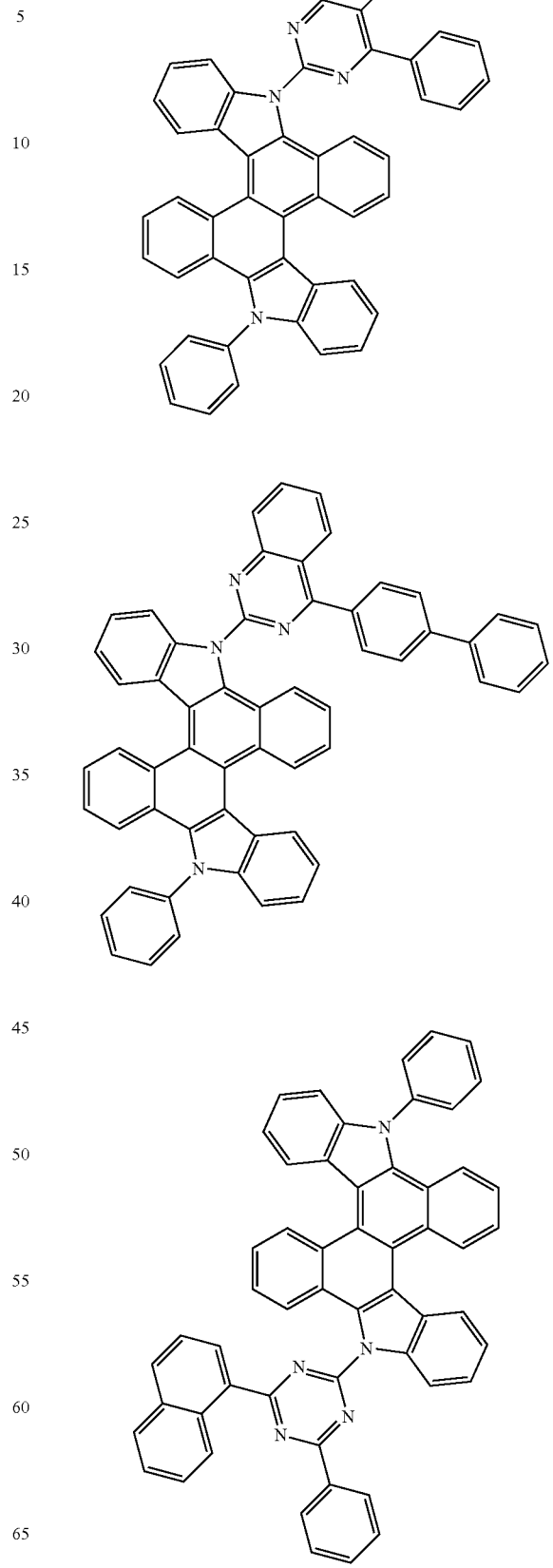

417
-continued
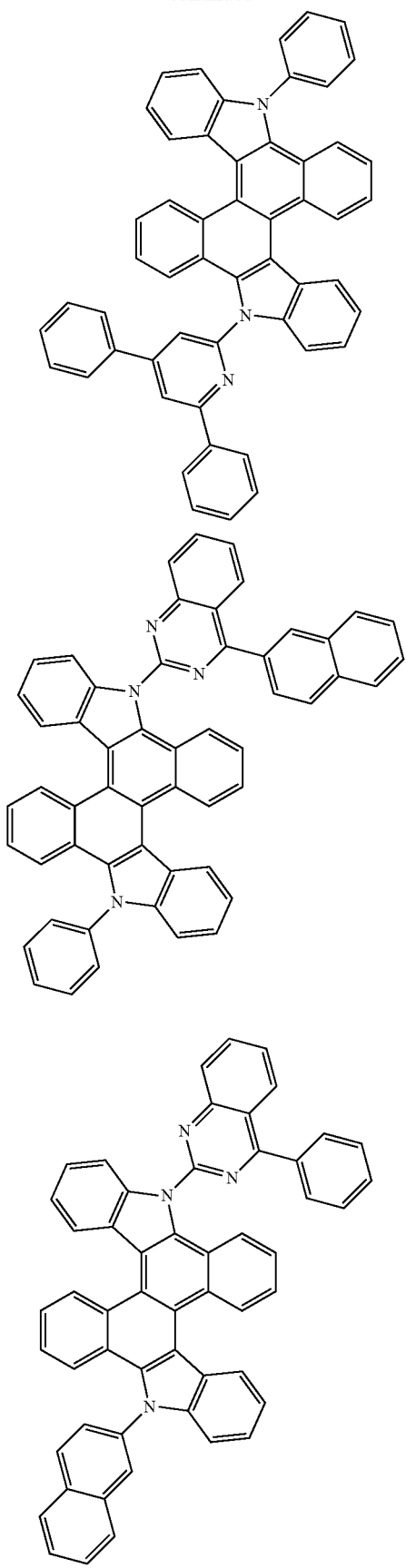
418
-continued
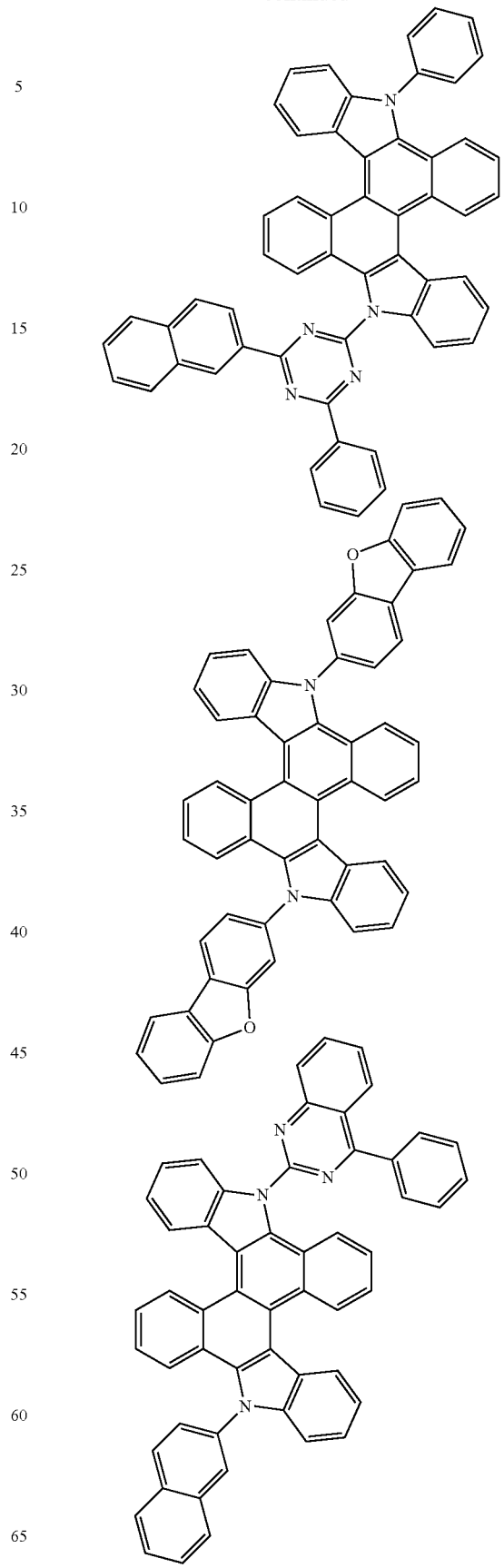

-continued

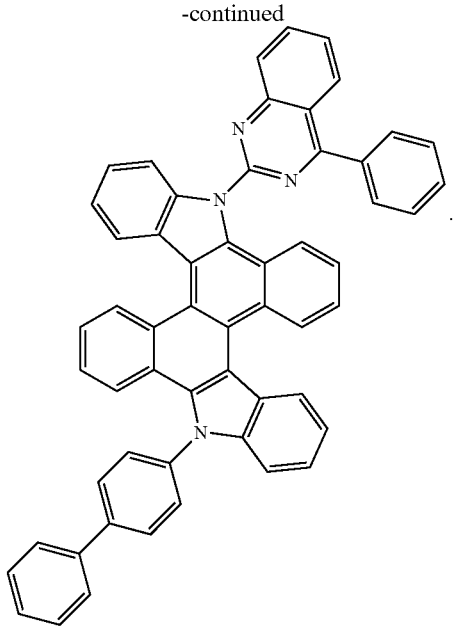

10. An organic electronic device comprising:
a first electrode;
a second electrode provided to face the first electrode; and
one or more organic material layers provided between the first electrode and the second electrode,
wherein one or more layers of the organic material layers comprise the compound of claim 1.

11. The organic electronic device of claim 10, wherein the organic material layer comprises a hole injection layer or a hole transport layer, and the hole injection layer or the hole transport layer comprises the compound.

12. The organic electronic device of claim 10, wherein the organic material layer comprises a light emitting layer, and the light emitting layer comprises the compound.

13. The organic electronic device of claim 10, wherein the organic material layer comprises an electron transport layer or an electron injection layer, and the electron transport layer or the electron injection layer comprises the compound.

14. The organic electronic device of claim 10, wherein the organic material layer comprises an electron blocking layer, and the electron blocking layer comprises the compound.

15. The organic electronic device of claim 10, further comprising:
one or two or more layers selected from a group consisting of a hole injection layer, a hole transport layer, a light emitting layer, an electron transport layer, an electron injection layer, an electron blocking layer, and a hole blocking layer.

16. The organic electronic device of claim 10, wherein the organic electronic device is selected from a group consisting of an organic light emitting device, an organic solar cell, an organic photoconductor (OPC), and an organic transistor.

17. The organic electronic device of claim 10, wherein the organic material layer comprises a light emitting layer, and the light emitting layer comprises a compound represented by the following Chemical Formula A-1:

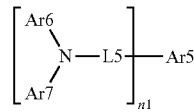

[Chemical Formula A-1]

in Chemical Formula A-1, n1 is an integer of 1 or more, Ar5 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L5 is a direct bond; a substituted or unsubstituted arylene group; or a substituted or unsubstituted heteroarylene group, Ar6 and Ar7 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and when n1 is 2 or more, two or more structures in the parenthesis are the same as or different from each other.

18. The organic electronic device of claim 17, wherein $L_5$ is a direct bond, Ar5 is a divalent pyrene group, Ar6 and Ar7 are the same as or different from each other, and are each independently an aryl group which is unsubstituted or substituted with a germanium group substituted with an alkyl group, and n1 is 2.

19. The organic electronic device of claim 10, wherein the organic material layer comprises a light emitting layer, and the light emitting layer comprises a compound represented by the following Chemical Formula A-2:

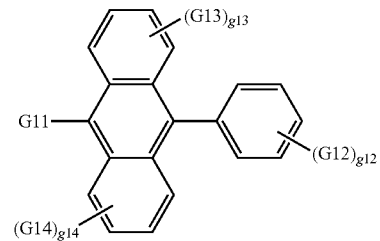

[Chemical Formula A-2]

in Chemical Formula A-2,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

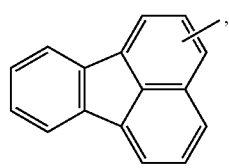

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or more, two or more structures in the parenthesis are the same as or different from each other.

20. The organic electronic device of claim 19, wherein G11 is a phenyl group or a 1-naphthyl group, and G12 is a 2-naphthyl group.

* * * * *